US012655440B2

(12) United States Patent
Malik et al.

(10) Patent No.: US 12,655,440 B2
(45) Date of Patent: Jun. 16, 2026

(54) GENETICALLY MODIFIED PLANTS THAT EXHIBIT AN INCREASE IN SEED YIELD COMPRISING A FIRST BIOTIN ATTACHMENT DOMAIN-CONTAINING (badc) GENE HOMOZYGOUS FOR A WILD-TYPE ALLELE, A SECOND badc GENE HOMOZYGOUS FOR A MUTANT ALLELE, AND HOMOLOGS OF THE FIRST AND SECOND badc GENES

(71) Applicant: NUSEED NUTRITIONAL US INC., West Sacramento, CA (US)

(72) Inventors: Meghna Malik, Saskatoon (CA); Jihong Tang, West Roxbury, MA (US); Yuanyuan Ji, Saskatoon (CA); Venkatesh Bollina, Saskatoon (CA); Lifeng Chen, Saskatoon (CA); Marie Mykytyshyn, Saskatoon (CA); Kristi D. Snell, Belmont, MA (US)

(73) Assignee: NUSEED NUTRITIONAL US INC., West Sacramento, CA (US)

( * ) Notice: Subject to any disclaimer, the term of this patent is extended or adjusted under 35 U.S.C. 154(b) by 294 days.

(21) Appl. No.: 18/005,302

(22) PCT Filed: Aug. 12, 2021

(86) PCT No.: PCT/US2021/045717
§ 371 (c)(1),
(2) Date: Jan. 12, 2023

(87) PCT Pub. No.: WO2022/036078
PCT Pub. Date: Feb. 17, 2022

(65) Prior Publication Data
US 2023/0257759 A1       Aug. 17, 2023

Related U.S. Application Data

(60) Provisional application No. 63/064,796, filed on Aug. 12, 2020.

(51) Int. Cl.
| | |
|---|---|
| *C12N 15/82* | (2006.01) |
| *A01H 5/10* | (2018.01) |
| *A01H 6/20* | (2018.01) |
| *C07K 14/415* | (2006.01) |

(52) U.S. Cl.
CPC ........... *C12N 15/8247* (2013.01); *A01H 5/10* (2013.01); *A01H 6/20* (2018.05); *C07K 14/415* (2013.01); *Y02A 40/146* (2018.01)

(58) Field of Classification Search
CPC .......................... C12N 15/8247; Y02A 40/146
See application file for complete search history.

(56) References Cited

U.S. PATENT DOCUMENTS

| | | | |
|---|---|---|---|
| 9,035,131 B2 | 5/2015 | Hutcheon et al. | |
| 10,883,113 B2 * | 1/2021 | Thelen ................. | C07K 14/415 |
| 11,959,087 B2 | 4/2024 | Thelen et al. | |
| 2003/0110533 A1 | 6/2003 | Cahoon et al. | |
| 2004/0093638 A1 | 5/2004 | Sasaki et al. | |
| 2007/0214517 A1 | 9/2007 | Alexandrov et al. | |
| 2011/0014706 A2 | 1/2011 | Cao et al. | |
| 2012/0102600 A1 | 4/2012 | Nadolska-Orczyk et al. | |
| 2013/0096032 A1 | 4/2013 | Bush et al. | |
| 2014/0230091 A1 | 8/2014 | Shanklin et al. | |
| 2019/0211348 A1 * | 7/2019 | Thelen ............... | C12N 15/8247 |
| 2023/0416760 A1 | 12/2023 | Thelen et al. | |

FOREIGN PATENT DOCUMENTS

| | | | | |
|---|---|---|---|---|
| WO | 1994023027 A2 | 10/1994 | | |
| WO | 1998005758 A1 | 2/1998 | | |
| WO | 2002010210 A2 | 2/2002 | | |
| WO | 2008122980 A2 | 10/2008 | | |
| WO | WO-2010006732 A2 * | 1/2010 | .......... | C07K 14/415 |
| WO | 2013003608 A1 | 1/2013 | | |
| WO | 2015103074 A1 | 7/2015 | | |
| WO | 2016114972 A1 | 7/2016 | | |
| WO | 2017039834 A1 | 3/2017 | | |

(Continued)

OTHER PUBLICATIONS

Keereetaweep et al (Biotin Attachment Domain-Containing Proteins Irreversibly Inhibit Acetyl CoA Carboxylase. Plant Physiology, vol. 177, pp. 208-215, 2018) (Year: 2018).*
Liu et al (The Brassica oleracea genome reveals the asymmetrical evolution of polyploid genomes. Nature. p. 1-11, 2014) (Year: 2014).*
Liu et al (WRINKLED1 Regulates Biotin Attachment Domain-Containing Proteins that Inhibit Fatty Acid Synthesis. Plant Physiology, vol. 181, pp. 55-62, Sep. 2019) (Year: 2019).*
Salie et al (A Family of Negative Regulators Targets the Committed Step of de Novo Fatty Acid Biosynthesis. The Plant Cell, vol. 28: p. 2312-2325, Sep. 2016). (Year: 2016).*
Ye et al (The BADC and BCCP subunits of chloroplast acetyl-CoA carboxylase sense the pH changes of the light-dark cycle. J Biol Chem p. 9901-9916, May 2020). (Year: 2020).*

(Continued)

*Primary Examiner* — Wayne Zhong
(74) *Attorney, Agent, or Firm* — EVENTIDE LAW LLC

(57) ABSTRACT
A genetically modified plant that exhibits an increase in seed yield relative to a progenitor plant is provided. The genetically modified plant includes: (a) a first biotin attachment domain-containing (badc) gene, occurring in its natural position within the genome and being homozygous for a wild-type allele: (b) a second badc gene, occurring in its natural position within the genome and being homozygous for a mutant allele; (c) one or more homologs of the first badc gene, each occurring in its natural position within the genome and being homozygous for a wild-type allele; and (d) one or more homologs of the second badc gene, each occurring in its natural position within the genome, and at least one being homozygous for a wild-type allele. The mutant allele does not encode a functional BADC protein. The increase in seed yield is at least 4%.

11 Claims, 9 Drawing Sheets

Specification includes a Sequence Listing.

(56) References Cited

FOREIGN PATENT DOCUMENTS

WO      2018009626 A2      1/2018
WO      2021016348 A2      1/2021

OTHER PUBLICATIONS

Chao et al., "BrassicaEDB: A Gene Expression Database for Brassica Crops," International Journal of Molecular Sciences, 21, 5831, pp. 1-12, Aug. 13, 2020.

Chen et al., "The Effect of Transparent TESTA2 on Seed Fatty Acid Biosynthesis and Tolerance to Environmental Stresses during Young Seedling Establishment in *Arabidopsis*", Plant Physiology, vol. 160, pp. 1023-1036, Oct. 2012.

Chiu et al., "Engineered GFP as a vital reporter in plants", Current Biology, vol. 6, No. 3, pp. 325-330 (1996).

Del Pozo, et al., "Whole genome duplications in plants: an overview from *Arabidopsis*", Journal of Experimental Botany, vol. 66, No. 22, pp. 6991-7003 (2015).

Dingwall et al., "The Nucleoplasmin Nuclear Location Sequence Is Larger and More Complex than That of S¥-40 Large T Antigen", The Journal of Cell Biology, vol. 107, pp. 841-849, Sep. 1988.

Fastmond, "Sugar-DEPENDENT1 Encodes a Patatin Domain Triacylglycerol Lipase That Initiates Storage Oil Breakdown in Germinating Arabidopsis Seeds", The Plant Cell, vol. 18, pp. 665-675, Mar. 2006.

Glover Et A., "Homoeologs: What Are They and How Do We Infer Them?", Trends in Plant Science, vol. 21, No. 7, pp. 609-621, Jul. 2016, available at https://www.ncbi.nlm.nih.gov/pmc/articles/PMC4920642/?report=printable, pp. 1-22.

Hopp et al., "A Short Polypeptide Marker Sequence Useful for Recombinant Protein Identification and Purification", Bio/Technology, vol. 6, pp. 1204-1210 (1988) (Abstract Only).

Kagale et al., "The developmental transcriptome atlas of the biofuel crop Camelina sativa," The Plant Journal, vol. 38, pp. 879-894 (2016).

Keereetaweep et al., "Biotin Attachment Domain-Containing Proteins Irreversibly Inhibit Acetyl CoA Carboxylase", Plant Physiology, vol. 177, pp. 208-215, May 2018.

Li et al., "Multiplex and Homologous recomination-mediated genome editing in *Arabidopsis* and Nicotiana benthamiana using guide RNA and Cas9", Nature Biotechnology, vol. 31, No. 8, pp. 688-691 (2013).

Liu et al., "The *Brassica oleracea* genome reveals the asymmetrical evolution of polyploid genomes," Nature Communications, 5:3930, pp. 1-11 (2014).

Liu et al., "WRINKLED1 Regulates Biotin Attachment Domain-Containing Proteins that Inhibit Fatty Acid Synthesis," Plant Physiology, vol. 181, pp. 55-62 (2019).

Lu et al., "Generation of transgenic plants of a potential oilseed crop Camelina sativa by Agrobacterium-mediated transformation", Plant Cell Rep., vol. 27, pp. 273-278 (2008).

Lysak et al., "Ancestral Chromosomal Blocks Are Triplicated in *Brassiceae* Species with Varying Chromosome Number and Genome Size," Plant Physiology, vol. 145, pp. 402-410 (2007).

Malik et al., "Production of high levels of poly-3-hydroxybutyrate in plastids of Camelina sativa seeds", Plant Biotechnology Journal; vol. 13; pp. 675-688 (2015).

Malik et al., "Camelina sativa, an oilseed at the nexus between model system and commerical crop", Plant Cell Reports, vol. 37, pp. 1367-1381 (2018).

Matz et al., "Fluorescent proteins from nonbioluminescent *Anthozoa* species", Nature Biotechnology, vol. 17, pp. 969-973, Oct. 1999.

NP_188190.1, Single hybrid motif superfamily protein [*Arabidopsis thaliana*], NCBI, pp. 1-2, available at: https://www.ncbi.nlm.nih.gov/protein/NP_188190.1, last accessed Dec. 21, 2022.

NP_564612.1, "Single hybrid motif superfamily protein [*Arabidopsis thaliana*]," NCBI, pp. 1-2, available at: https://www.ncbi.nlm.nih.gov/protein/NP_564612.1, last accessed Dec. 21, 2022.

NP_567035.1, "biotin/lipoyl attachment domain-containing protein [*Arabidopsis thaliana*]," NCBI, pp. 1-3, available at: https://www.ncbi.nlm.nih.gov/protein/NP_567035.1, last accessed Dec. 21, 2022.

Parkin et al., "Segmental Structure of the Brassica napus Genome Based on Comparative Analysis with *Arabidopsis thaliana*," Genetics, vol. 171, pp. 765-781 (2005).

Salie et al., "A Family of Negative Regulators Targets the Committed Step of de Novo Fatty Acid Biosynthesis", The Plant Cell, vol. 28, pp. 2312-2325, Sep. 2016.

Severin et al., "RNA-Seq Atlas of Glycine max: A guide to the soybean transcriptome," BMC Plant Biology 2010, 10:160, pp. 1-16 (2010).

Shivaiah et al., "Non-Catalytic Subunits Facilitate Quaternary Organization of Plastidic Acetyl-CoA Carboxylase," Plant Physiology, vol. 182, pp. 756-775, Feb. 2020.

Simmonds, "Genetic Transformation of Soybean with Biolistics"; in Molecular Methods of Plant Analysis, eds. J.F. Jackson et al., vol. 23, pp. i-viii, ix-xv, xvii-xix, 159-174 (2003).

Vancanneyt et al., "Construction of an intron-containing marker gene: Splicing of the intron in transgenic plants and its use in monitoring early events in Agrobacterium-mediated plant transformation", Mol Gen Genet, vol. 220, pp. 245-250 (1990).

Woodhouse et al., "Polyploidy", Nature Education (2)(1), pp. 1-4 (2009).

International Search Report and Written Opinion for International Application No. PCT/US2021/045717 dated Jan. 26, 2022, pp. 1-11.

Extended European Search Report for European Appl. No. 21856715.4, mailed Jul. 24, 2024, pp. 1-8.

Ye et al., "The BADC and BCCP subunits of chloroplast acetyl-CoA carboxylase sense the pH changes of the light-dark cycle," Journal of Biological Chemistry, vol. 295, pp. 9901-9916 (2020), Open access version from Science Direct, pp. 1-33.

Andre, C. et al., "Feedback Regulation of Plastidic Acetyl-CoA Carboxylase by 18:1-acyl Carrier Protein in *Brassica napus*," Proceedings of the National Academy of Sciences USA 109(25):10107-10112 (2012).

Arziman et al., "E-RNAi: a web application to design optimized RNAi constructs," Nucleic Acids Research, 33:582-588, 2005.

Baud, S, et al., "WRINKLED1 Specifies the Regulatory Action of Leafy COTYLEDON2 Towards Fatty Acid Metabolism During Seed Maturation in Arabidopsis," The Plant Journal 50(5):825-838 (2007).

Bruening, "Plant gene silencing regularized," Proc. Natl. Acad. Sci. USA, 95:13349-13351, 1998.

Chen et al, The transcriptional response of *Arabidopsis* to genotoxic stress—a high-density colony array study (HDCA), Plant J 35:771-786, 2003 (Year: 2003).

Chen, M., et al., "System Analysis of an *Arabidopsis* Mutant Altered in de Novo Fatty Acid Synthesis Reveals Diverse Changes in Seed Composition and Metabolism," Plant Physiology 150(1):27-41 (2009).

Feria Bourrelier, A.B., et al. "Chloroplast Acetyl-CoA Carboxylase Activity is 2-Oxoglutarate-Regulated by Interaction of PII with the Biotin Carboxyl Carrier Subunit," Proceedings of the National Academy of Sciences USA 107(1):502-507 (2010).

Friedberg, "Automated protein function prediction—The genome challenge," Brief. Bioinformatics 7:225-242 (2006).

Gutterson, "Anthocyanin Biosynthetic Genes and Their Application to Flower Color Modification through Sense Suppression," Hortscience 30:964-966, 1995.

Kozaki, A., et al., "Thiol-Disulfide Exchange Between Nuclear-Encoded and Chloroplast-Encoded Subunits of Pea Acetyla-CoA Carboxylase," The Journal of Biological Chemistry 276(43):39919-39925, 2001.

Li, L., et al., "PlantOrDB: a Genome-Wide Ortholog Database for Land Plants and Green Algae," BMC Plant Biology, vol. 15:161, pp. 1-11, 2015.

Salie et al., "A Family of Negative Regulators Targets the Committed Step of de Novo Fatty Acid Biosynthesis," Plant Cell, 2016, vol. 28, pp. 2312-2325.

Salie, "Discovery and Characterization of Regulatory Mechanisms Affecting the Heteromeric Acetyl-Coenzyme A Carboxylase in *Arabidopsis*," pdf pp. 1-131Retrieved from the Internet: URL:https://

(56)                    References Cited

OTHER PUBLICATIONS mospace.umsystem.edu/xmlui/bitstream/handle/10355/60417/research.pdf?sequence=2&isAllowed=y [retrieved on Jul. 27, 2025] *Chapter II* May 1, 2016.

Sasaki, Y., et al., "Link Between Light and Fatty Acid Synthesis: Thioredoxin-Linked Reductive Activation of Plastidic Acetyl-CoA Carboxylase," Proceedings of the National Academy of Sciences USA 94(20):11096-11101 (1997).

Sasaki et al., "Plant Acetyl-CoA Carboxylase: Structure, Biosynthesis, Regulation, and Gene Manipulation for Plant Breeding," Biosci. Biotechnol. Biochem., 68(6), 1175-1184 (2004).

Thelen, J.J., and Ohlrogge, J.B., "Both Antisense and Sense Expression of Biotin Carboxyl Carrier Protein Isoform 2 Inactivates the Plastid Acetyl-Coenzyme A Carboxylase in *Arabidopsis thaliana*," The Plant Journal 32(4):419-431, Nov. 2002.

Wesley et al., "Construct design for efficient, effective and high-throughput gene silencing in plants," The Plant Journal, 27:581-590, 2001.

Ye at al., "Docking of aectyl-CoA carboxylase to the plastid envelope membrane attenuates fatty acid production in plants," Nature Communications, https://doi.org/10.1038/s41467-020-20014-5, 1-14, 2020 (Year: 2020).

Colliver et al., "Differential modification of flavonoid and isoflavonoid biosynthesis with an antisense chalcone synthase construct in transgenic Lotus corniculatus," Plant Molecular Biology, 35:509-522, 1997.

Dougherty and Parks, "Transgenes and Gene Suppression: Telling Us Something New," Current Opinion in Cell Biology 7:399-405, 1995 (Abstract Only).

Elomaa et al., "Transformation of antisense constructs of the chalcone synthase gene superfamily into Gerbera hybrida: differential effect on the expression of family members," Molecular Breeding,2:41-50, 1996.

Emery et al., "Radial Patterning of Arabidopsis Shoots by Class III HD-ZIP and KANADI Genes," Current Biology 13:1768-1774, 2003.

Fukuda, N., et al., "Expression of the Genes Coding for Plastidic Acetyl-CoA Carboxylase Subunits Is Regulated by a Location-Sensitive Transcription Factor Binding Site," Plant Molecular Biology 82(4-5):473-483 (2013).

Hunter, S.C., and Ohlrogge, J.B., "Regulation of Spinach Chloroplast Acetyl-CoA Carboxylase," Archives of Biochemistry and Biophysics 359(2):170-178, 1998.

Lu and Kang, "Generation of Transgenic Plants of a Potential Oilseed Crop Camelina sativa by Agrobacterium-Mediated Transformation," Plant Cell Reports 27(2):273-278 (2008).

Salie et al., "Regulation and structure of the heteromeric acetyl-CoA-carboxylase," Biochem Biophys Acta., Apr. 16, 2016, vol. 1861, pp. 1207-1213.

Theologis, et al. "Sequence and analysis of chromosome 1 of the plant *Arabidopsis thaliana*," Nature, vol. 408, pp. 816-820 (2000).

Wang, et al., "From Protein Sequence to Protein Function via Mult-Label Linear Discriminant Analysis," IEEE/ACM Transactions on Computational Biology and Bioinformatics, vol. 14, No. 3, 503-513, 2017.

* cited by examiner

SEQUENCE LISTING

```
<160> NUMBER OF SEQ ID NOS: 184

<210> SEQ ID NO 1
<211> LENGTH: 23
<212> TYPE: DNA
<213> ORGANISM: Camelina sativa

<400> SEQUENCE: 1
gctcattccc aagtcctctg agg                                          23

<210> SEQ ID NO 2
<211> LENGTH: 23
<212> TYPE: DNA
<213> ORGANISM: Camelina sativa

<400> SEQUENCE: 2
gctcattccc aagtcctctg agg                                          23

<210> SEQ ID NO 3
<211> LENGTH: 24
<212> TYPE: DNA
<213> ORGANISM: Camelina sativa

<400> SEQUENCE: 3
ccgcctatat gtagcaaggg atct                                         24

<210> SEQ ID NO 4
<211> LENGTH: 24
<212> TYPE: DNA
<213> ORGANISM: Camelina sativa
```

-continued

```
<400> SEQUENCE: 4
ccgcctatat gtagcaaggg atct                                        24

<210> SEQ ID NO 5
<211> LENGTH: 21
<212> TYPE: DNA
<213> ORGANISM: Artificial Sequence
<220> FEATURE:
<223> OTHER INFORMATION: Synthetic construct Camelina sativa badc2 Ch3 2
      base pair deletion

<400> SEQUENCE: 5
gctcattccc aagtcctgag g                                           21

<210> SEQ ID NO 6
<211> LENGTH: 20
<212> TYPE: DNA
<213> ORGANISM: Artificial Sequence
<220> FEATURE:
<223> OTHER INFORMATION: Synthetic construct Camelina sativa badc2 Ch14
      3 base pair deletion

<400> SEQUENCE: 6
gctcattccc aagtctgagg                                             20

<210> SEQ ID NO 7
<211> LENGTH: 13
<212> TYPE: DNA
<213> ORGANISM: Artificial Sequence
<220> FEATURE:
<223> OTHER INFORMATION: Synthetic construct Camelina sativa badc2 Ch3
      10 base pair deletion

<400> SEQUENCE: 7
gctcattctg agg                                                    13

<210> SEQ ID NO 8
<211> LENGTH: 19
<212> TYPE: DNA
<213> ORGANISM: Artificial Sequence
<220> FEATURE:
<223> OTHER INFORMATION: Synthetic construct Camelina sativa badc3 Ch1 4
      base pair deletion

<400> SEQUENCE: 8
ccgcctgtag caagggatc                                              19

<210> SEQ ID NO 9
<211> LENGTH: 16
<212> TYPE: DNA
<213> ORGANISM: Artificial Sequence
<220> FEATURE:
<223> OTHER INFORMATION: Synthetic construct Camelina sativa badc3 Ch15
      22 base pair deletion

<400> SEQUENCE: 9
ggggtttcta actgac                                                 16

<210> SEQ ID NO 10
<211> LENGTH: 18
<212> TYPE: DNA
<213> ORGANISM: Artificial Sequence
<220> FEATURE:
<223> OTHER INFORMATION: Synthetic construct Camelina sativa badc2 Ch3 5
      base pair deletion
```

```
<400> SEQUENCE: 10
gctcattccc aagtgagg                                                   18

<210> SEQ ID NO 11
<211> LENGTH: 16067
<212> TYPE: DNA
<213> ORGANISM: Artificial Sequence
<220> FEATURE:
<223> OTHER INFORMATION: Synthetic construct binary vector pMBXS1200

<400> SEQUENCE: 11
aaactgaagg cgggaaacga caatctgatc caagctcaag ctgctctagc attcgccatt      60
caggctgcgc aactgttggg aagggcgatc ggtgcgggcc tcttcgctat tacgccagct     120
ggcgaaaggg ggatgtgctg caaggcgatt aagttgggta acgccagggt tttcccagtc     180
acgacgttgt aaaacgacgg ccagtgccaa gcttggcgcg cccctaggcg ttgaacaacg     240
gaaactcgac ttgccttccg cacaatacat catttcttct tagctttttt tcttcttctt     300
cgttcataca gttttttttt gtttatcagc ttacattttc ttgaaccgta gctttcgttt     360
tcttcttttt aactttccat tcggagtttt tgtatcttgt ttcatagttt gtcccaggat     420
tagaatgatt aggcatcgaa ccttcaagaa tttgattgaa taaaacatct tcattcttaa     480
gatatgaaga taatcttcaa aaggcccctg ggaatctgaa agaagagaag caggcccatt     540
tatatgggaa agaacaatag tatttcttat ataggcccat ttaagttgaa aacaatcttc     600
aaaagtccca catcgcttag ataagaaaac gaagctgagt ttatatacag ctagagtcga     660
agtagtgatt gatcccttgc tacatatagg gtttttagagc tagaaatagc aagttaaaat     720
aaggctagtc cgttatcaac ttgaaaaagt ggcaccgagt cggtgctttt ttttgcaaaa     780
ttttccagat cgatttcttc ttcctctgtt cttcggcgtt caatttctgg ggttttctct     840 tcgtttctg taactgaaac ctaaaatttg acctaaaaaa aatctcaaat aatatgattc     900
agtggttttg tacttttcag ttagttgagt tttgcagttc cgatgagata aaccaataac     960
taggcgttga acaacggaaa ctcgacttgc cttccgcaca atacatcatt tcttcttagc    1020
tttttttctt cttcttcgtt catacagttt tttttgtttt atcagcttac attttcttga    1080
accgtagctt tcgtttttctt ctttttaact ttccattcgg agtttttgta tcttgtttca    1140
tagtttgtcc caggattaga atgattaggc atcgaaccctt caagaatttg attgaataaa    1200
acatcttcat tcttaagata tgaagataat cttcaaaagg cccctgggaa tctgaaagaa    1260
gagaagcagg cccatttata tgggaaagaa caatagtatt tcttatatag gcccatttaa    1320
gttgaaaaca atcttcaaaa gtcccacatc gcttagataa gaaaacgaag ctgagtttat    1380
atacagctag agtcgaagta gtgattggtt gttgtcgaag ttttaggttt tagagctaga    1440
aatagcaagt taaaataagg ctagtccgtt atcaacttga aaaagtggca ccgagtcggt    1500
gctttttttt gcaaaatttt ccagatcgat ttcttcttcc tctgttcttc ggcgttcaat    1560
ttctggggtt ttctcttcgt tttctgtaac tgaaacctaa aatttgacct aaaaaaaatc    1620
tcaaataata tgattcagtg gttttgtact tttcagttag ttgagttttg cagttccgat    1680
gagataaacc aataactagg cgttgaacaa cggaaactcg acttgccttc cgcacaatac    1740
atcatttctt cttagctttt tttcttcttc ttcgttcata cagttttttt ttgtttatca    1800
gcttacattt tcttgaaccg tagctttcgt tttcttcttt ttaactttcc attcggagtt    1860
tttgtatctt gtttcatagt ttgtcccagg attagaatga ttaggcatcg aaccttcaag    1920
aatttgattg aataaaacat cttcattctt aagatatgaa gataatcttc aaaaggcccc    1980
```

```
tgggaatctg aaagaagaga agcaggccca tttatatggg aaagaacaat agtatttctt    2040
atataggccc atttaagttg aaaacaatct tcaaaagtcc cacatcgctt agataagaaa    2100
acgaagctga gtttatatac agctagagtc gaagtagtga ttgctcattc ccaagtcctc    2160 tggtttttaga gctagaaata gcaagttaaa ataaggctag tccgttatca acttgaaaaa    2220
gtggcaccga gtcggtgctt ttttttgcaa aattttccag atcgatttct tcttcctctg    2280
ttcttcggcg ttcaatttct ggggtttttct cttcgttttc tgtaactgaa acctaaaatt    2340
tgacctaaaa aaaatctcaa ataatatgat tcagtggttt tgtactttttc agttagttga    2400 gttttgcagt tccgatgaga taaaccaata actaggttcg aattaattaa tactccaaga    2460
atatcaaaga tacagtctca gaagaccaaa gggctattga gactttttcaa caaagggtaa    2520 tatcgggaaa cctcctcgga ttccattgcc cagctatctg tcacttcatc aaaaggacag    2580
tagaaaagga aggtggcacc tacaaatgcc atcattgcga taaaggaaag gctatcgttc    2640
aagatgcctc tgccgacagt ggtcccaaag atggaccccc acccacaagg agcatcgtgg    2700
aaaaagaaga cgttccaacc acgtcttcaa agcaagtgga ttgatgtgat atctccactg    2760
acgtaaggga tgacgcacaa tcccactatc cttcgcccca agcttgggcc caagcttggg    2820
tcgcgcccca cggatggtat aagaataaag gcattccgcg tgcaggattc acccgttcgc    2880
ctctcacctt ttcgctgtac tctctcgcca cacacacccc ctctccagct ccgttggagc    2940
tccggacagc agcaggcgcg gggcggtcac gtagtaagca gctctcggct ccctctcccc    3000
ttgctccgtg gatccatgga ttacaaggat gatgatgata aggattacaa ggatgatgat    3060
gataagatgg ctccaaagaa gaagagaaag gttggaatcc acggagttcc agctgctgat    3120
aagaagtact ctatcggact tgacatcgga accaactctg ttggatgggc tgttatcacc    3180
gatgagtaca aggttccatc taagaagttc aaggttcttg gaaacaccga tagacactct    3240
atcaagaaga accttatcgg tgctcttctt ttcgattctg gagagaccgc tgaggctacc    3300
agattgaaga gaaccgctag aagaagatac accagaagaa agaacagaat ctgctacctt    3360
caggaaatct tctctaacga gatggctaag gttgatgatt ctttcttcca cagacttgag    3420
gagtctttcc ttgttgagga ggataagaag cacgagagac acccaatctt cggaaacatc    3480
gttgatgagg ttgcttacca cgagaagtac ccaaccatct accaccttag aaagaagttg    3540
gttgattcta ccgataaggc tgatcttaga cttatctacc ttgctcttgc tcacatgatc    3600
aagttcagag gacacttcct tatcgaggga gaccttaacc cagataactc tgatgttgat    3660
aagttgttca tccagcttgt tcagacctac aaccagcttt tcgaggagaa cccaatcaac    3720
gcttctggag ttgatgctaa ggctatcctt tctgctagac tttctaagtc tcgtagactt    3780
gagaacctta tcgctcagct tccaggagag aagaagaacg gactttttcgg aaaccttatc    3840 gctctttctc ttggacttac cccaaacttc aagtctaact tcgatcttgc tgaggatgct    3900
aagttgcagc tttctaagga tacctacgat gatgatcttg ataaccttct tgctcagatc    3960
ggagatcagt acgctgatct tttccttgct gctaagaacc tttctgatgc tatccttctt    4020
tctgacatcc ttagagttaa caccgagatc accaaggctc cactttctgc ttctatgatc    4080
aagagatacg atgagcacca ccaggatctt acccttttga aggctcttgt tagacagcag    4140
cttccagaga agtacaagga aatcttcttc gatcagtcta gaacggata cgctggatac    4200 atcgatggag gagcttctca ggaggagttc tacaagttca tcaagccaat ccttgagaag    4260
atggatggaa ccgaggagct tcttgttaag ttgaacagag aggatcttct tagaaagcag    4320
```

-continued

```
agaaccttcg ataacggatc tatcccacac cagatccacc ttggagagct tcacgctatc    4380
cttcgtagac aggaggattt ctacccattc ttgaaggata acagagagaa gatcgagaag    4440
atccttacct tcagaatccc atactacgtt ggaccacttg ctagaggaaa ctctcgtttc    4500
gcttggatga ccagaaagtc tgaggagacc atcaccccctt ggaacttcga ggaggtaagt    4560
ttctgcttct acctttgata tatatataat aattatcatt aattagtagt aatataatat    4620
ttcaaatatt tttttcaaaa taaaagaatg tagtatatag caattgcttt tctgtagttt    4680
ataagtgtgt atattttaat ttataacttt tctaatatat gaccaaaatt tgttgatgtg    4740
caggttgttg ataagggagc ttctgctcag tctttcatcg agagaatgac caacttcgat    4800
aagaaccttc caaacgagaa ggttcttcca aagcactctc ttctttacga gtacttcacc    4860
gtttacaacg agcttaccaa ggttaagtac gttaccgagg gaatgagaaa gccagctttc    4920
ctttctggag agcagaagaa ggctatcgtt gatcttcttt tcaagaccaa cagaaaggtt    4980
accgttaagc agttgaagga ggattacttc aagaagatcg agtgcttcga ttctgttgaa    5040
atctctggag ttgaggatag attcaacgct tctcttggaa cctaccacga tcttttgaag    5100
atcatcaagg ataaggattt ccttgataac gaggagaacg aggacatcct tgaggacatc    5160
gttcttaccc ttacccttttt cgaggataga gagatgatcg aggagagact caagacctac    5220 gctcacctttt tcgatgataa ggttatgaag cagttgaaga gaagaagata caccggatgg    5280
ggtagacttt ctcgtaagtt gatcaacgga atcagagata agcagtctgg aaagaccatc    5340
cttgatttct tgaagtctga tggattcgct aacagaaact tcatgcagct tatccacgat    5400
gattctctta ccttcaagga ggacatccag aaggctcagg tttctggaca gggagattct    5460
cttcacgagc acatcgctaa ccttgctgga tctccagcta tcaagaaggg aatccttcag    5520
accgttaagg ttgttgatga gcttgttaag gttatgggta gacacaagcc agagaacatc    5580
gttatcgaga tggctagaga gaaccagacc acccagaagg gacagaagaa ctctcgtgag    5640
agaatgaaga gaatcgagga gggaatcaag gagcttggat ctcaaatctt gaaggagcac    5700
ccagttgaga gacacccagct tcagaacgag aagttgtacc tttactacct tcagaacgga    5760
agagatatgt acgttgatca ggagcttgac atcaacagac tttctgatta cgatgttgat    5820
cacatcgttc cacagtcttt cttgaaggat gattctatcg ataacaaggt tcttacccgt    5880
tctgataaga acagaggaaa gtctgataac gttccatctg aggaggttgt taagaagatg    5940
aagaactact ggagacagct tcttaacgct aagttgatca cccagagaaa gttcgataac    6000
cttaccaagg ctgagagagg aggactttct gagcttgata aggctggatt catcaagaga    6060
cagcttgttg agaccagaca gatcaccaag cacgttgctc agatccttga ttctcgtatg    6120
aacaccaagt acgatgagaa cgataagttg atcagagagg ttaaggttat caccttgaag    6180
tctaagttgg tttctgattt cagaaaggat ttccagttct acaaggttag agagatcaac    6240
aactaccacc acgctcacga tgcttacctt aacgctgttg ttggaaccgc tcttatcaag    6300
aagtacccaa agttggagtc tgagttcgtt tacggagatt acaaggttta cgatgttaga    6360
aagatgatcg ctaagtctga gcaggagatc ggaaaggcta ccgctaagta cttcttctac    6420
tctaacatca tgaacttctt caagaccgag atcaccttg ctaacggaga gatcagaaag    6480
agaccactta tcgagaccaa cggagagacc ggagagatcg tttgggataa gggaagagat    6540
ttcgctaccg ttagaaaggt tctttctatg ccacaggtta acatcgttaa gaaaaccgag    6600
gttcagaccg gaggattctc taaggagtct atccttccaa agagaaactc tgataagttg    6660
atcgctagaa agaaggattg ggacccaaag aagtacggag gattcgattc tccaaccgtt    6720
```

-continued

```
gcttactctg ttcttgttgt tgctaaggtt gagaagggaa agtctaagaa gttgaagtct    6780
gttaaggagc ttcttggaat caccatcatg gagcgttctt ctttcgagaa gaacccaatc    6840
gatttccttg aggctaaggg atacaaggag gttaagaagg atcttatcat caagttgcca    6900
aagtactctc ttttcgagct tgagaacgga agaaagagaa tgcttgcttc tgctggagag    6960
cttcagaagg gaaacgagct tgctcttcca tctaagtacg ttaacttcct ttaccttgct    7020
tctcactacg agaagttgaa gggatctcca gaggataacg agcagaagca gcttttcgtt    7080
gagcagcaca agcactacct tgatgagatc atcgagcaaa tctctgagtt ctctaagaga    7140
gttatccttg ctgatgctaa ccttgataag gttctttctg cttacaacaa gcacagagat    7200
aagccaatca gagagcaggc tgagaacatc atccaccttt tcaccccttac caaccttggt    7260 gctccagctg ctttcaagta cttcgatacc accatcgata gaaaaagata cacctctacc    7320
aaggaggttc ttgatgctac ccttatccac cagtctatca ccggacttta cgagaccaga    7380
atcgatcttt ctcagcttgg aggagataag agaccagctg ctaccaagaa ggctggacag    7440
gctaagaaga agaagtgacc tcaggatcgt tcaaacattt ggcaataaag tttcttaaga    7500
ttgaatcctg ttgccggtct tgcgatgatt atcatataat ttctgttgaa ttacgttaag    7560
catgtaataa ttaacatgta atgcatgacg ttatttatga gatgggtttt tatgattaga    7620
gtcccgcaat tatacattta atacgcgata gaaaacaaaa tatagcgcgc aaactaggat    7680
aaattatcgc gcgcggtgtc atctatgtta ctagatccgg accgctcgag caattgtacg    7740
tagaattcgt aatcatgtca tagctgtttc ctgtgtgaaa ttgttatccg ctcacaattc    7800
cacacaacat acgagccgga agcataaagt gtaaagcctg gggtgcctaa tgagtgagct    7860
aactcacatt aattgcgttg cgctcactgc ccgctttcca gtcgggaaac ctgtcgtgcc    7920
agctgcatta atgaatcggc caacgcgcgg ggagaggcgg tttgcgtatt ggctagagca    7980
gcttgccaac atggtggagc acgacactct cgtctactcc aagaatatca aagatacagt    8040
ctcagaagac caaagggcta ttgagacttt tcaacaaagg gtaatatcgg gaaacctcct    8100
cggattccat tgcccagcta tctgtcactt catcaaaagg acagtagaaa aggaaggtgg    8160
cacctacaaa tgccatcatt gcgataaagg aaaggctatc gttcaagatg cctctgccga    8220
cagtggtccc aaagatggac ccccacccac gaggagcatc gtggaaaaag aagacgttcc    8280
aaccacgtct tcaaagcaag tggattgatg tgaacatggt ggagcacgac actctcgtct    8340
actccaagaa tatcaaagat acagtctcag aagaccaaag ggctattgag acttttcaac    8400
aaagggtaat atcgggaaac ctcctcggat tccattgccc agctatctgt cacttcatca    8460
aaaggacagt agaaaaggaa ggtggcacct acaaatgcca tcattgcgat aaaggaaagg    8520
ctatcgttca agatgcctct gccgacagtg tcccaaaga tggaccccca cccacgagga    8580
gcatcgtgga aaaagaagac gttccaacca cgtcttcaaa gcaagtggat tgatgtgata    8640
tctccactga cgtaagggat gacgcacaat cccactatcc ttcgcaagac ccttcctcta    8700
tataaggaag ttcatttcat ttggagagga cacgctgaaa tcaccagtct ctctctacaa    8760
atctatctct ctcgagaaaa tggcctcctc cgagaacgtc atcaccgagt tcatgcgctt    8820
caaggtgcgc atggagggca ccgtgaacgg ccacagttc gagatcgagg gcgagggcga    8880
gggccgcccc tacgagggcc acaacaccgt gaagctgaag gtgaccaagg gcggccccct    8940
gcccttcgcc tgggacatcc tgtcccccca gttccagtac ggctccaagg tgtacgtgaa    9000
gcaccccgcc gacatccccg actacaagaa gctgtccttc cccgagggct tcaagtggga    9060
```

-continued

```
gcgcgtgatg aacttcgagg acggcggcgt ggcgaccgtg acccaggact cctccctgca      9120
ggacggctgc ttcatctaca aggtgaagtt catcggcgtg aacttcccct ccgacggccc      9180
cgtgatgcag aagaagacca tgggctggga ggcctccacc gagcgcctgt accccgcga      9240 cggcgtgctg aagggcgaga cccacaaggc cctgaagctg aaggacggcg ccactacct      9300 ggtggagttc aagtccatct acatggccaa gaagcccgtg cagctgcccg gctactacta      9360
cgtggacgcc aagctggaca tcacctccca caacgaggac tacaccatcg tggagcagta      9420
cgagcgcacc gagggccgcc accacctgtt cctggtacca atgagctctg tccaacagtc      9480
tcagggttaa ctcgagtttc tccataataa tgtgtgagta gttcccagat aagggaatta      9540
gggttcctat agggtttcgc tcatgtgttg agcatataag aaacccttag tatgtatttg      9600
tatttgtaaa atacttctat caataaaatt tctaattcct aaaaccaaaa tccagtacta      9660
aaatccagat cccccgaatt aattcggcgt taattcagta cattaaaaac gtccgcaatg      9720
tgttattaag ttgtctaagc gtcaatttgt ttacaccaca atatatcctg ccaccagcca      9780
gccaacagct ccccgaccgg cagctcggca caaaatcacc actcgataca ggcagcccat      9840
cagtccggga cggcgtcagc gggagagccg ttgtaaggcg gcagactttg ctcatgttac      9900
cgatgctatt cggaagaacg gcaactaagc tgccgggttt gaaacacgga tgatctcgcg      9960
gagggtagca tgttgattgt aacgatgaca gagcgttgct gcctgtgatc accgcggttt      10020
caaaatcggc tccgtcgata ctatgttata cgccaacttt gaaacaact  ttgaaaaagc      10080 tgttttctgg tatttaaggt tttagaatgc aaggaacagt gaattggagt tcgtcttgtt      10140
ataattagct tcttggggta tctttaaata ctgtagaaaa gaggaaggaa ataataaatg      10200
gctaaaatga gaatatcacc ggaattgaaa aaactgatcg aaaaataccg ctgcgtaaaa      10260
gatacggaag gaatgtctcc tgctaaggta tataagctgg tgggagaaaa tgaaaaccta      10320
tatttaaaaa tgacggacag ccggtataaa gggaccacct atgatgtgga acgggaaaag      10380
gacatgatgc tatggctgga aggaaagctg cctgttccaa aggtcctgca ctttgaacgg      10440
catgatggct ggagcaatct gctcatgagt gaggccgatg gcgtcctttg ctcggaagag      10500
tatgaagatg aacaaagccc tgaaaagatt atcgagctgt atgcggagtg catcaggctc      10560
tttcactcca tcgacatatc ggattgtccc tatacgaata gcttagacag ccgcttagcc      10620
gaattggatt acttactgaa taacgatctg gccgatgtgg attgcgaaaa ctgggaagaa      10680
gacactccat ttaaagatcc gcgcgagctg tatgattttt taaagacgga aaagcccgaa      10740
gaggaacttg tctttttccca cggcgacctg ggagacagca acatctttgt gaaagatggc      10800
aaagtaagtg gctttattga tcttgggaga agcggcaggg cggacaagtg gtatgacatt      10860
gccttctgcg tccggtcgat cagggaggat atcggggaag aacagtatgt cgagctattt      10920
tttgacttac tggggatcaa gcctgattgg gagaaaataa aatattatat tttactggat      10980
gaattgtttt agtacctaga atgcatgacc aaaatccctt aacgtgagtt ttcgttccac      11040
tgagcgtcag accccgtaga aaagatcaaa ggatcttctt gagatccttt ttttctgcgc      11100
gtaatctgct gcttgcaaac aaaaaaacca ccgctaccag cggtggtttg tttgccggat      11160
caagagctac caactctttt tccgaaggta actggcttca gcagagcgca gataccaaat      11220
actgtccttc tagtgtagcc gtagttaggc caccacttca agaactctgt agcaccgcct      11280
acatacctcg ctctgctaat cctgttacca gtggctgctg ccagtggcga taagtcgtgt      11340
cttaccgggt tggactcaag acgatagtta ccggataagg cgcagcggtc gggctgaacg      11400 ggggggttcgt gcacacagcc cagcttggag cgaacgacct acaccgaact gagataccta      11460
```

-continued

```
cagcgtgagc tatgagaaag cgccacgctt cccgaaggga gaaaggcgga caggtatccg  11520
gtaagcggca gggtcggaac aggagagcgc acgagggagc ttccaggggg aaacgcctgg  11580
tatctttata gtcctgtcgg gtttcgccac ctctgacttg agcgtcgatt tttgtgatgc  11640
tcgtcagggg ggcggagcct atggaaaaac gccagcaacg cggccttttt acggttcctg  11700
gccttttgct ggccttttgc tcacatgttc tttcctgcgt tatcccctga ttctgtggat  11760
aaccgtatta ccgcctttga gtgagctgat accgctcgcc gcagccgaac gaccgagcgc  11820
agcgagtcag tgagcgagga agcggaagag cgcctgatgc ggtattttct ccttacgcat  11880
ctgtgcggta tttcacaccg catatggtgc actctcagta caatctgctc tgatgccgca  11940
tagttaagcc agtatacact ccgctatcgc tacgtgactg ggtcatggct gcgccccgac  12000
acccgccaac acccgctgac gcgccctgac gggcttgtct gctcccggca tccgcttaca  12060
gacaagctgt gaccgtctcc gggagctgca tgtgtcagag gttttcaccg tcatcaccga  12120
aacgcgcgag gcagggtgcc ttgatgtggg cgccggcggt cgagtggcga cggcgcggct  12180
tgtccgcgcc ctggtagatt gcctggccgt aggccagcca tttttgagcg gccagcggcc  12240
gcgataggcc gacgcgaagc ggcggggcgt agggagcgca gcgaccgaag ggtaggcgct  12300
ttttgcagct cttcggctgt gcgctggcca gacagttatg cacaggccag gcgggtttta  12360
agagttttaa taagttttaa agagtttag gcggaaaaat cgcctttttt ctcttttata  12420
tcagtcactt acatgtgtga ccggttccca atgtacggct ttgggttccc aatgtacggg  12480
ttccggttcc caatgtacgg ctttgggttc ccaatgtacg tgctatccac aggaaagaga  12540
ccttttcgac ctttttcccc tgctagggca atttgcccta gcatctgctc cgtacattag  12600
gaaccggcgg atgcttcgcc ctcgatcagg ttgcggtagc gcatgactag gatcgggcca  12660
gcctgccccg cctcctcctt caaatcgtac tccggcaggt catttgaccc gatcagcttg  12720
cgcacggtga aacagaactt cttgaactct ccggcgctgc cactgcgttc gtagatcgtc  12780
ttgaacaacc atctggcttc tgccttgcct gcggcgcggc gtgccaggcg gtagagaaaa  12840
cggccgatgc cgggatcgat caaaaagtaa tcggggtgaa ccgtcagcac gtccgggttc  12900
ttgccttctg tgatctcgcg gtacatccaa tcagctagct cgatctcgat gtactccggc  12960
cgcccggttt cgctctttac gatcttgtag cggctaatca aggcttcacc ctcggatacc  13020
gtcaccaggc ggccgttctt ggccttcttc gtacgctgca tggcaacgtg cgtggtgttt  13080
aaccgaatgc aggtttctac caggtcgtct ttctgctttc cgccatcggc tcgccggcag  13140
aacttgagta cgtccgcaac gtgtggacgg aacacgcggc cgggcttgtc tcccttccct  13200
tcccggtatc ggttcatgga ttcggttaga tgggaaaccg ccatcagtac caggtcgtaa  13260
tcccacacac tggccatgcc ggcggccct gcggaaacct ctacgtgccc gtctggaagc  13320
tcgtagcgga tcacctcgcc agctcgtcgg tcacgcttcg acagacggaa aacggccacg  13380
tccatgatgc tgcgactatc gcgggtgccc acgtcataga gcatcggaac gaaaaaatct  13440
ggttgctcgt cgcccttggg cggcttccta atcgacggcg caccggctgc cggcggttgc  13500
cgggattctt tgcggattcg atcagcggcc gcttgccacg attcaccggg gcgtgcttct  13560
gcctcgatgc gttgccgctg ggcggcctgc gcggccttca acttctccac caggtcatca  13620
cccagcgccg cgccgatttg taccgggccg gatggtttgc gaccgctcac gccgattcct  13680
cgggcttggg ggttccagtg ccattgcagg gccggcaggc aacccagccg cttacgcctg  13740
gccaaccgcc cgttcctcca cacatggggc attccacggc gtcggtgcct ggttgttctt  13800
```

-continued

```
gattttccat gccgcctcct ttagccgcta aaattcatct actcatttat tcatttgctc   13860
atttactctg gtagctgcgc gatgtattca gatagcagct cggtaatggt cttgccttgg   13920
cgtaccgcgt acatcttcag cttggtgtga tcctccgccg gcaactgaaa gttgacccgc   13980
ttcatggctg gcgtgtctgc caggctggcc aacgttgcag ccttgctgct gcgtgcgctc   14040
ggacggccgg cacttagcgt gtttgtgctt ttgctcattt tctctttacc tcattaactc   14100
aaatgagttt tgatttaatt tcagcggcca gcgcctggac ctcgcgggca gcgtcgccct   14160
cgggttctga ttcaagaacg gttgtgccgg cggcggcagt gcctgggtag ctcacgcgct   14220
gcgtgatacg ggactcaaga atgggcagct cgtacccggc cagcgcctcg gcaacctcac   14280
cgccgatgcg cgtgcctttg atcgcccgcg acacgacaaa ggccgcttgt agccttccat   14340
ccgtgacctc aatgcgctgc ttaaccagct ccaccaggtc ggcggtggcc catatgtcgt   14400
aagggcttgg ctgcaccgga atcagcacga agtcggctgc cttgatcgcg gacacagcca   14460
agtccgccgc ctggggcgct ccgtcgatca ctacgaagtc gcgccggccg atggccttca   14520
cgtcgcggtc aatcgtcggg cggtcgatgc cgacaacggt tagcggttga tcttcccgca   14580
cggccgccca atcgcgggca ctgccctggg gatcggaatc gactaacaga acatcggccc   14640
cggcgagttg cagggcgcgg gctagatggg ttgcgatggt cgtcttgcct gacccgcctt   14700
tctggttaag tacagcgata accttcatgc gttcccttg cgtatttgtt tatttactca   14760
tcgcatcata tacgcagcga ccgcatgacg caagctgttt tactcaaata cacatcacct   14820
ttttagacgg cggcgctcgg tttcttcagc ggccaagctg gccggccagg ccgccagctt   14880
ggcatcagac aaaccggcca ggatttcatg cagccgcacg gttgagacgt gcgcgggcgg   14940
ctcgaacacg tacccggccg cgatcatctc cgcctcgatc tcttcggtaa tgaaaaacgg   15000
ttcgtcctgg ccgtcctggt gcggtttcat gcttgttcct cttggcgttc attctcggcg   15060
gccgccaggg cgtcggcctc ggtcaatgcg tcctcacgga aggcaccgcg ccgcctggcc   15120
tcggtgggcg tcacttcctc gctgcgctca agtgcgcggt acagggtcga gcgatgcacg   15180
ccaagcagtg cagccgcctc tttcacggtg cggccttcct ggtcgatcag ctcgcgggcg   15240
tgcgcgatct gtgccggggt gagggtaggg cgggggccaa acttcacgcc tcgggccttg   15300
gcggcctcgc gcccgctccg ggtgcggtcg atgattaggg aacgctcgaa ctcggcaatg   15360
ccggcgaaca cggtcaacac catgcggccg gccggcgtgg tggtgtcggc ccacggctct   15420
gccaggctac gcaggcccgc gccggcctcc tggatgcgct cggcaatgtc cagtaggtcg   15480
cgggtgctgc gggccaggcg gtctagcctg gtcactgtca caacgtcgcc agggcgtagg   15540
tggtcaagca tcctggccag ctccgggcgg tcgcgcctgg tgccggtgat cttctcggaa   15600
aacagcttgg tgcagccggc cgcgtgcagt tcggcccgtt ggttggtcaa gtcctggtcg   15660
tcggtgctga cgcgggcata gcccagcagg ccagcggcgg cgctcttgtt catggcgtaa   15720
tgtctccggt tctagtcgca agtattctac tttatgcgac taaaacacgc gacaagaaaa   15780
cgccaggaaa agggcagggc ggcagcctgt cgcgtaactt aggacttgtg cgacatgtcg   15840
ttttcagaag acggctgcac tgaacgtcag aagccgactg cactatagca gcggaggggt   15900
tggatcaaag tactttgatc ccgagggaa ccctgtggtt ggcatgcaca tacaaatgga   15960
cgaacggata aaccttttca cgcccttta aatatccgat tattctaata aacgctcttt   16020
tctcttaggt ttacccgcca atatatcctg tcaaacactg atagttt            16067
```

<210> SEQ ID NO 12
<211> LENGTH: 15331

-continued

```
<212> TYPE: DNA
<213> ORGANISM: Artificial Sequence
<220> FEATURE:
<223> OTHER INFORMATION: Synthetic construct binary vector pMBXS1243

<400> SEQUENCE: 12
aaactgaagg cgggaaacga caatctgatc caagctcaag ctgctctagc attcgccatt      60
caggctgcgc aactgttggg aagggcgatc ggtgcgggcc tcttcgctat tacgccagct     120
ggcgaaaggg ggatgtgctg caaggcgatt aagttgggta acgccagggt tttcccagtc     180
acgacgttgt aaaacgacgg ccagtgccaa gcttggcgcg cccctaggcg ttgaacaacg     240
gaaactcgac ttgccttccg cacaatacat catttcttct tagctttttt tcttcttctt     300
cgttcataca gttttttttt gtttatcagc ttacattttc ttgaaccgta gctttcgttt     360
tcttcttttt aactttccat tcggagtttt tgtatcttgt ttcatagttt gtcccaggat     420
tagaatgatt aggcatcgaa ccttcaagaa tttgattgaa taaaacatct tcattcttaa     480
gatatgaaga taatcttcaa aaggcccctg ggaatctgaa agaagagaag caggcccatt     540
tatatgggaa agaacaatag tatttcttat ataggcccat ttaagttgaa aacaatcttc     600
aaaagtccca catcgcttag ataagaaaac gaagctgagt ttatatacag ctagagtcga     660
agtagtgatt gtacttcttg cgttccacgg gttttagagc tagaaatagc aagttaaaat     720
aaggctagtc cgttatcaac ttgaaaaagt ggcaccgagt cggtgctttt ttttgcaaaa     780
ttttccagat cgatttcttc ttcctctgtt cttcggcgtt caatttctgg ggttttctct     840 tcgtttctg taactgaaac ctaaaatttg acctaaaaaa aatctcaaat aatatgattc     900
agtggttttg tacttttcag ttagttgagt tttgcagttc cgatgagata aaccaataac     960
taggcgttga acaacggaaa ctcgacttgc cttccgcaca atacatcatt tcttcttagc    1020
tttttttctt cttcttcgtt catacagttt tttttgtttt atcagcttac attttcttga    1080
accgtagctt tcgtttttctt cttttttaact ttccattcgg agtttttgta tcttgtttca    1140
tagtttgtcc caggattaga atgattaggc atcgaacctt caagaatttg attgaataaa    1200
acatcttcat tcttaagata tgaagataat cttcaaaagg ccctgggaa tctgaaagaa    1260 gagaagcagg cccatttata tgggaaagaa caatagtatt tcttatatag gcccatttaa    1320
gttgaaaaca atcttcaaaa gtcccacatc gcttagataa gaaaacgaag ctgagtttat    1380
atacagctag agtcgaagta gtgattgtac ttcttgtgta ccacgggttt tagagctaga    1440
aatagcaagt taaaataagg ctagtccgtt atcaacttga aaaagtggca ccgagtcggt    1500
gctttttttt gcaaaatttt ccagatcgat ttcttcttcc tctgttcttc ggcgttcaat    1560
ttctggggtt ttctcttcgt tttctgtaac tgaaacctaa aatttgacct aaaaaaaatc    1620
tcaaataata tgattcagtg gttttgtact tttcagttag ttgagttttg cagttccgat    1680
gagataaacc aataactagg ttcgaattaa ttaatactcc aagaatatca aagatacagt    1740
ctcagaagac caaagggcta ttgagacttt tcaacaaagg gtaatatcgg aaacctcct    1800 cggattccat tgcccagcta tctgtcactt catcaaaagg acagtagaaa aggaaggtgg    1860
cacctacaaa tgccatcatt gcgataaagg aaaggctatc gttcaagatg cctctgccga    1920
cagtggtccc aaagatggac ccccacccac aaggagcatc gtggaaaaag aagacgttcc    1980
aaccacgtct tcaaagcaag tggattgatg tgatatctcc actgacgtaa gggatgacgc    2040
acaatcccac tatccttcgc cccaagcttg ggcccaagct tgggtcgcgc cccacggatg    2100
gtataagaat aaaggcattc cgcgtgcagg attcacccgt cgcctctca cctttttcgct    2160
```

-continued

```
gtactctctc gccacacaca cccctctcc agctccgttg gagctccgga cagcagcagg    2220
cgcggggcgg tcacgtagta agcagctctc ggctccctct ccccttgctc cgtggatcca    2280
tggattacaa ggatgatgat gataaggatt acaaggatga tgatgataag atggctccaa    2340
agaagaagag aaaggttgga atccacggag ttccagctgc tgataagaag tactctatcg    2400
gacttgacat cggaaccaac tctgttggat gggctgttat caccgatgag tacaaggttc    2460
catctaagaa gttcaaggtt cttggaaaca ccgatagaca ctctatcaag aagaacctta    2520
tcggtgctct tctttcgat tctggagaga ccgctgaggc taccagattg aagagaaccg    2580
ctagaagaag atacaccaga agaaagaaca gaatctgcta ccttcaggaa atcttctcta    2640
acgagatggc taaggttgat gattctttct tccacagact tgaggagtct ttccttgttg    2700
aggaggataa gaagcacgag agacacccaa tcttcggaaa catcgttgat gaggttgctt    2760
accacgagaa gtacccaacc atctaccacc ttagaaagaa gttggttgat tctaccgata    2820
aggctgatct tagacttatc taccttgctc ttgctcacat gatcaagttc agaggacact    2880
tccttatcga gggagacctt aacccagata actctgatgt tgataagttg ttcatccagc    2940
ttgttcagac ctacaaccag cttttcgagg agaacccaat caacgcttct ggagttgatg    3000
ctaaggctat cctttctgct agactttcta gtctcgtag acttgagaac cttatcgctc    3060
agcttccagg agagaagaag aacggacttt tcggaaacct tatcgctctt tctcttggac    3120
ttacccaaaa cttcaagtct aacttcgatc ttgctgagga tgctaagttg cagctttcta    3180
aggataccta cgatgatgat cttgataacc ttcttgctca gatcggagat cagtacgctg    3240
atcttttcct tgctgctaag aacctttctg atgctatcct tctttctgac atccttagag    3300
ttaacaccga gatcaccaag gctccacttt ctgcttctat gatcaagaga tacgatgagc    3360
accaccagga tcttacccct ttgaaggctc ttgttagaca gcagcttcca gagaagtaca    3420
aggaaatctt cttcgatcag tctaagaacg gatacgctgg atacatcgat ggaggagctt    3480
ctcaggagga gttctacaag ttcatcaagc caatccttga gaagatggat ggaaccgagg    3540
agcttcttgt taagttgaac agagaggatc ttcttagaaa gcagagaacc ttcgataacg    3600
gatctatccc acaccagatc caccttggag agcttcacgc tatccttcgt agacaggagg    3660
atttctaccc attcttgaag gataacagag agaagatcga gaagatcctt accttcagaa    3720
tcccatacta cgttggacca cttgctagag gaaactctcg tttcgcttgg atgaccagaa    3780
agtctgagga gaccatcacc ccttggaact tcgaggaggt aagtttctgc ttctaccttt    3840
gatatatata taataattat cattaattag tagtaatata atatttcaaa tatttttttc    3900
aaaataaaag aatgtagtat atagcaattg cttttctgta gtttataagt gtgtatattt    3960
taatttataa cttttctaat atatgaccaa aatttgttga tgtgcaggtt gttgataagg    4020
gagcttctgc tcagtctttc atcgagagaa tgaccaactt cgataagaac cttccaaacg    4080
agaaggttct tccaaagcac tctcttcttt acgagtactt caccgtttac aacgagctta    4140
ccaaggttaa gtacgttacc gagggaatga gaaagccagc tttcctttct ggagagcaga    4200
agaaggctat cgttgatctt cttttcaaga ccaacagaaa ggttaccgtt aagcagttga    4260
aggaggatta cttcaagaag atcgagtgct cgattctgt tgaaatctct ggagttgagg    4320
atagattcaa cgcttctctt ggaacctacc acgatctttt gaagatcatc aaggataagg    4380
atttccttga taacgaggag aacgaggaca tccttgagga catcgttctt acccttaccc    4440
ttttcgagga tagagagatg atcgaggaga gactcagac ctacgctcac ctttttcgatg    4500 ataaggttat gaagcagttg aagagaagaa gatacaccgg atgggtaga ctttctcgta    4560
```

```
agttgatcaa cggaatcaga gataagcagt ctggaaagac catccttgat ttcttgaagt    4620
ctgatggatt cgctaacaga aacttcatgc agcttatcca cgatgattct cttaccttca    4680
aggaggacat ccagaaggct caggtttctg gacagggaga ttctcttcac gagcacatcg    4740
ctaaccttgc tggatctcca gctatcaaga agggaatcct tcagaccgtt aaggttgttg    4800
atgagcttgt taaggttatg ggtagacaca agccagagaa catcgttatc gagatggcta    4860
gagagaacca gaccacccag aagggacaga agaactctcg tgagagaatg aagagaatcg    4920
aggagggaat caaggagctt ggatctcaaa tcttgaagga gcacccagtt gagaacaccc    4980
agcttcagaa cgagaagttg tacctttact accttcagaa cggaagagat atgtacgttg    5040
atcaggagct tgacatcaac agactttctg attacgatgt tgatcacatc gttccacagt    5100
ctttcttgaa ggatgattct atcgataaca aggttcttac ccgttctgat aagaacagag    5160
gaaagtctga taacgttcca tctgaggagg ttgttaagaa gatgaagaac tactggagac    5220
agcttcttaa cgctaagttg atcacccaga gaaagttcga taaccttacc aaggctgaga    5280
gaggaggact ttctgagctt gataaggctg gattcatcaa gagacagctt gttgagacca    5340
gacagatcac caagcacgtt gctcagatcc ttgattctcg tatgaacacc aagtacgatg    5400
agaacgataa gttgatcaga gaggttaagg ttatcacctt gaagtctaag ttggtttctg    5460
atttcagaaa ggatttccag ttctacaagg ttagagagat caacaactac caccacgctc    5520
acgatgctta ccttaacgct gttgttggaa ccgctcttat caagaagtac ccaaagttgg    5580
agtctgagtt cgtttacgga gattacaagg tttacgatgt tagaaagatg atcgctaagt    5640
ctgagcagga gatcggaaag gctaccgcta agtacttctt ctactctaac atcatgaact    5700
tcttcaagac cgagatcacc cttgctaacg gagagatcag aaagagacca cttatcgaga    5760
ccaacggaga gaccggagag atcgtttggg ataagggaag agatttcgct accgttagaa    5820
aggttctttc tatgccacag gttaacatcg ttaagaaaac cgaggttcag accggaggat    5880
tctctaagga gtctatcctt ccaaagagaa actctgataa gttgatcgct agaaagaagg    5940
attgggaccc aaagaagtac ggaggattcg attctccaac cgttgcttac tctgttcttg    6000
ttgttgctaa ggttgagaag ggaaagtcta gaagttgaa gtctgttaag gagcttcttg    6060
gaatcaccat catggagcgt tcttctttcg agaagaaccc aatcgatttc cttgaggcta    6120
agggatacaa ggaggttaag aaggatctta tcatcaagtt gccaaagtac tctctttccg    6180
agcttgagaa cggaagaaag agaatgcttg cttctgctgg agagcttcag aagggaaacg    6240
agcttgctct tccatctaag tacgttaact tcctttacct tgcttctcac tacgagaagt    6300
tgaagggatc tccagaggat aacgagcaga agcagctttt cgttgagcag cacaagcact    6360
accttgatga gatcatcgag caaatctctg agttctctaa gagagttatc cttgctgatg    6420
ctaaccttga taaggttctt tctgcttaca caagcacag agataagcca atcagagagc    6480
aggctgagaa catcatccac ctttttcaccc ttaccaacct tggtgctcca gctgctttca    6540
agtacttcga taccaccatc gatagaaaaa gatacacctc taccaaggag gttcttgatg    6600
ctacccttat ccaccagtct atcaccggac tttacgagac cagaatcgat ctttctcagc    6660
ttggaggaga taagagacca gctgctacca agaaggctgg acaggctaag aagaagaagt    6720
gacctcagga tcgttcaaac atttggcaat aaagtttctt aagattgaat cctgttgccg    6780
gtcttgcgat gattatcata taatttctgt tgaattacgt taagcatgta ataattaaca    6840
tgtaatgcat gacgttattt atgagatggg tttttatgat tagagtcccg caattataca    6900
```

-continued

```
tttaatacgc gatagaaaac aaaatatagc gcgcaaacta ggataaatta tcgcgcgcgg    6960
tgtcatctat gttactagat ccggaccgct cgagcaattg tacgtagaat tcgtaatcat    7020
gtcatagctg tttcctgtgt gaaattgtta tccgctcaca attccacaca acatacgagc    7080
cggaagcata aagtgtaaag cctggggtgc ctaatgagtg agctaactca cattaattgc    7140
gttgcgctca ctgcccgctt tccagtcggg aaacctgtcg tgccagctgc attaatgaat    7200
cggccaacgc gcggggagag gcggtttgcg tattggctag agcagcttgc caacatggtg    7260
gagcacgaca ctctcgtcta ctccaagaat atcaaagata cagtctcaga agaccaaagg    7320
gctattgaga cttttcaaca aagggtaata tcgggaaacc tcctcggatt ccattgccca    7380
gctatctgtc acttcatcaa aaggacagta gaaaggaag gtggcaccta caaatgccat    7440
cattgcgata aaggaaaggc tatcgttcaa gatgcctctg ccgacagtgg tcccaaagat    7500
ggacccccac ccacgaggag catcgtggaa aaagaagacg ttccaaccac gtcttcaaag    7560
caagtggatt gatgtgaaca tggtggagca cgacactctc gtctactcca agaatatcaa    7620
agatacagtc tcagaagacc aaagggctat tgagactttt caacaagggg taatatcggg    7680
aaacctcctc ggattccatt gcccagctat ctgtcacttc atcaaaagga cagtagaaaa    7740
ggaaggtggc acctacaaat gccatcattg cgataaagga aaggctatcg ttcaagatgc    7800
ctctgccgac agtggtccca agatggaccc cacccacg aggagcatcg tggaaaaaga    7860
agacgttcca accacgtctt caaagcaagt ggattgatgt gatatctcca ctgacgtaag    7920
ggatgacgca caatcccact atccttcgca agacccttcc tctatataag gaagttcatt    7980
tcatttggag aggacacgct gaaatcacca gtctctctct acaaatctat ctctctcgag    8040
aaaatggcct cctccgagaa cgtcatcacc gagttcatgc gcttcaaggt gcgcatggag    8100
ggcaccgtga acgccacga gttcgagatc gagggcgagg gcgagggccg ccctacgag    8160 ggccacaaca ccgtgaagct gaaggtgacc aagggcggcc ccctgccctt cgcctgggac    8220
atcctgtccc cccagttcca gtacggctcc aaggtgtacg tgaagcaccc cgccgacatc    8280
cccgactaca agaagctgtc cttccccgag ggcttcaagt gggagcgcgt gatgaacttc    8340
gaggacggcg gcgtggcgac cgtgacccag gactcctccc tgcaggacgg ctgcttcatc    8400
tacaaggtga agttcatcgg cgtgaacttc ccctccgacg gccccgtgat gcagaagaag    8460
accatgggct gggaggcctc caccgagcgc ctgtaccccc gcgacggcgt gctgaagggc    8520
gagacccaca aggccctgaa gctgaaggac ggcggccact acctggtgga gttcaagtcc    8580
atctacatgg ccaagaagcc cgtgcagctg cccggctact actacgtgga cgccaagctg    8640
gacatcacct cccacaacga ggactacacc atcgtggagc agtacgagcg caccgagggc    8700
cgccaccacc tgttcctggt accaatgagc tctgtccaac agtctcaggg ttaactcgag    8760
tttctccata ataatgtgtg agtagttccc agataaggga attagggttc ctatagggtt    8820
tcgctcatgt gttgagcata taagaaaccc ttagtatgta tttgtatttg taaaatactt    8880
ctatcaataa aatttctaat tcctaaaacc aaaatccagt actaaaatcc agatcccccg    8940
aattaattcg gcgttaattc agtacattaa aaacgtccgc aatgtgttat taagttgtct    9000
aagcgtcaat ttgtttacac cacaatatat cctgccacca gccagccaac agctccccga    9060
ccggcagctc ggcacaaaat caccactcga tacaggcagc ccatcagtcc gggacggcgt    9120
cagcgggaga gccgttgtaa ggcggcagac tttgctcatg ttaccgatgc tattcggaag    9180
aacggcaact aagctgccgg gtttgaaaca cggatgatct cgcggagggt agcatgttga    9240
ttgtaacgat gacagagcgt tgctgcctgt gatcaccgcg gtttcaaaat cggctccgtc    9300
```

-continued

```
gatactatgt tatacgccaa ctttgaaaac aactttgaaa aagctgtttt ctggtattta    9360 aggtttttaga atgcaaggaa cagtgaattg gagttcgtct tgttataatt agcttcttgg    9420
ggtatcttta aatactgtag aaaagaggaa ggaaataata aatggctaaa atgagaatat    9480
caccggaatt gaaaaaactg atcgaaaaat accgctgcgt aaaagatacg gaaggaatgt    9540
ctcctgctaa ggtatataag ctggtgggag aaaatgaaaa cctatattta aaaatgacgg    9600
acagccggta taaagggacc acctatgatg tggaacggga aaaggacatg atgctatggc    9660
tggaaggaaa gctgcctgtt ccaaaggtcc tgcactttga acggcatgat ggctggagca    9720
atctgctcat gagtgaggcc gatggcgtcc tttgctcgga agagtatgaa gatgaacaaa    9780
gccctgaaaa gattatcgag ctgtatgcgg agtgcatcag gctctttcac tccatcgaca    9840
tatcggattg tccctatacg aatagcttag acagccgctt agccgaattg gattacttac    9900
tgaataacga tctggccgat gtggattgcg aaaactggga agaagacact ccatttaaag    9960
atccgcgcga gctgtatgat tttttaaaga cggaaaagcc cgaagaggaa cttgtctttt    10020
cccacggcga cctgggagac agcaacatct ttgtgaaaga tggcaaagta agtggcttta    10080
ttgatcttgg gagaagcggc agggcggaca agtggtatga cattgccttc tgcgtccggt    10140
cgatcaggga ggatatcggg gaagaacagt atgtcgagct attttttgac ttactgggga    10200
tcaagcctga ttgggagaaa ataaaatatt atattttact ggatgaattg ttttagtacc    10260
tagaatgcat gaccaaaatc ccttaacgtg agttttcgtt ccactgagcg tcagaccccg    10320
tagaaaagat caaaggatct tcttgagatc cttttttttct gcgcgtaatc tgctgcttgc    10380
aaacaaaaaa accaccgcta ccagcggtgg tttgtttgcc ggatcaagag ctaccaactc    10440 ttttttccgaa ggtaactggc ttcagcagag cgcagatacc aaatactgtc cttctagtgt    10500
agccgtagtt aggccaccac ttcaagaact ctgtagcacc gcctacatac ctcgctctgc    10560
taatcctgtt accagtggct gctgccagtg gcgataagtc gtgtcttacc gggttggact    10620
caagacgata gttaccggat aaggcgcagc ggtcgggctg aacggggggt cgtgcacac    10680 agcccagctt ggagcgaacg acctacaccg aactgagata cctacagcgt gagctatgag    10740
aaagcgccac gcttcccgaa gggagaaagg cggacaggta tccggtaagc ggcagggtcg    10800
gaacaggaga gcgcacgagg gagcttccag ggggaaacgc ctggtatctt tatagtcctg    10860
tcgggtttcg ccacctctga cttgagcgtc gatttttgtg atgctcgtca ggggggcgga    10920
gcctatggaa aaacgccagc aacgcggcct ttttacggtt cctggccttt tgctggcctt    10980
ttgctcacat gttctttcct gcgttatccc ctgattctgt ggataaccgt attaccgcct    11040
ttgagtgagc tgataccgct cgccgcagcc gaacgaccga gcgcagcgag tcagtgagcg    11100
aggaagcgga agagcgcctg atgcggtatt ttctccttac gcatctgtgc ggtatttcac    11160
accgcatatg gtgcactctc agtacaatct gctctgatgc cgcatagtta agccagtata    11220
cactccgcta tcgctacgtg actgggtcat ggctgcgccc cgacaccgc caacacccgc     11280 tgacgcgccc tgacgggctt gtctgctccc ggcatccgct tacagacaag ctgtgaccgt    11340
ctccgggagc tgcatgtgtc agaggttttc accgtcatca ccgaaacgcg cgaggcaggg    11400
tgccttgatg tgggcgccgg cggtcgagtg gcgacgcgc ggcttgtccg cgccctggta     11460
gattgcctgg ccgtaggcca gccatttttg agcggccagc ggccgcgata ggccgacgcg    11520
aagcggcggg gcgtagggag cgcagcgacc gaagggtagg cgcttttttgc agctcttcgg    11580 ctgtgcgctg gccagacagt tatgcacagg ccaggcgggt tttaagagtt ttaataagtt    11640
```

-continued

```
ttaaagagtt ttaggcggaa aaatcgcctt ttttctcttt tatatcagtc acttacatgt    11700
gtgaccggtt cccaatgtac ggctttgggt tcccaatgta cgggttccgg ttcccaatgt    11760
acggctttgg gttcccaatg tacgtgctat ccacaggaaa gagacctttt cgaccttttt    11820
cccctgctag ggcaatttgc cctagcatct gctccgtaca ttaggaaccg gcggatgctt    11880
cgccctcgat caggttgcgg tagcgcatga ctaggatcgg gccagcctgc cccgcctcct    11940
ccttcaaatc gtactccggc aggtcatttg acccgatcag cttgcgcacg gtgaaacaga    12000
acttcttgaa ctctccggcg ctgccactgc gttcgtagat cgtcttgaac aaccatctgg    12060
cttctgcctt gcctgcggcg cggcgtgcca ggcggtagga aaaacggccg atgccgggat    12120
cgatcaaaaa gtaatcgggg tgaaccgtca gcacgtccgg gttcttgcct tctgtgatct    12180
cgcggtacat ccaatcagct agctcgatct cgatgtactc cggccgcccg gtttcgctct    12240
ttacgatctt gtagcggcta atcaaggctt caccctcgga taccgtcacc aggcggccgt    12300
tcttggcctt cttcgtacgc tgcatggcaa cgtgcgtggt gtttaaccga atgcaggttt    12360
ctaccaggtc gtctttctgc tttccgccat cggctcgccg gcagaacttg agtacgtccg    12420
caacgtgtgg acggaacacg cggccgggct tgtctccctt cccttccggg tatcggttca    12480
tggattcggt tagatgggaa accgccatca gtaccaggtc gtaatcccac acactggcca    12540
tgccggccgg ccctgcggaa acctctacgt gcccgtctgg aagctcgtag cggatcacct    12600
cgccagctcg tcggtcacgc ttcgacagac ggaaaacggc cacgtccatg atgctgcgac    12660
tatcgcgggt gcccacgtca tagagcatcg gaacgaaaaa atctggttgc tcgtcgccct    12720
tgggcggctt cctaatcgac ggcgcaccgg ctgccggcgg ttgccgggat tctttgcgga    12780
ttcgatcagc ggccgcttgc cacgattcac cggggcgtgc ttctgcctcg atgcgttgcc    12840
gctgggcggc ctgcgcggcc ttcaacttct ccaccaggtc atcacccagc gccgcgccga    12900
tttgtaccgg gccggatggt ttgcgaccgc tcacgccgat tcctcgggct tgggggttcc    12960
agtgccattg cagggccggc aggcaaccca gccgcttacg cctggccaac cgcccgttcc    13020
tccacacatg gggcattcca cggcgtcggt gcctggttgt tcttgatttt ccatgccgcc    13080
tcctttagcc gctaaaattc atctactcat ttattcattt gctcatttac tctggtagct    13140
gcgcgatgta ttcagatagc agctcggtaa tggtcttgcc ttggcgtacc gcgtacatct    13200
tcagcttggt gtgatcctcc gccggcaact gaaagttgac ccgcttcatg gctggcgtgt    13260
ctgccaggct ggccaacgtt gcagccttgc tgctgcgtgc gctcggacgg ccggcactta    13320
gcgtgtttgt gcttttgctc attttctctt tacctcatta actcaaatga gttttgattt    13380
aatttcagcg gccagcgcct ggacctcgcg ggcagcgtcg ccctcgggtt ctgattcaag    13440
aacggttgtg ccggcggcgg cagtgcctgg gtagctcacg cgctgcgtga tacgggactc    13500
aagaatgggc agctcgtacc cggccagcgc ctcggcaacc tcaccgccga tgcgcgtgcc    13560
tttgatcgcc cgcgacacga caaaggccgc ttgtagcctt ccatccgtga cctcaatgcg    13620
ctgcttaacc agctccacca ggtcggcggt ggcccatatg tcgtaagggc ttggctgcac    13680
cggaatcagc acgaagtcgg ctgccttgat cgcggacaca gccaagtccg ccgcctgggg    13740
cgctccgtcg atcactacga agtcgcgccg gccgatggcc ttcacgtcgc ggtcaatcgt    13800
cgggcggtcg atgccgacaa cggttagcgg ttgatcttcc cgcacggccg cccaatcgcg    13860
ggcactgccc tggggatcgg aatcgactaa cagaacatcg gccccggcga gttgcagggc    13920
gcgggctaga tgggttgcga tggtcgtctt gcctgacccg cctttctggt taagtacagc    13980
gataaccttc atgcgttccc cttgcgtatt tgtttatttta ctcatcgcat catatacgca    14040
```

-continued

```
gcgaccgcat gacgcaagct gttttactca aatacacatc accttttag acggcggcgc    14100 tcggtttctt cagcggccaa gctggccggc caggccgcca gcttggcatc agacaaaccg    14160
gccaggattt catgcagccg cacggttgag acgtgcgcgg gcggctcgaa cacgtacccg    14220
gccgcgatca tctccgcctc gatctcttcg gtaatgaaaa acggttcgtc ctggccgtcc    14280
tggtgcggtt tcatgcttgt tcctcttggc gttcattctc ggcggccgcc agggcgtcgg    14340
cctcggtcaa tgcgtcctca cggaaggcac cgcgccgcct ggcctcggtg ggcgtcactt    14400
cctcgctgcg ctcaagtgcg cggtacaggg tcgagcgatg cacgccaagc agtgcagccg    14460
cctctttcac ggtgcggcct tcctggtcga tcagctcgcg ggcgtgcgcg atctgtgccg    14520
gggtgagggt agggcggggg ccaaacttca cgcctcgggc cttggcggcc tcgcgcccgc    14580
tccgggtgcg gtcgatgatt agggaacgct cgaactcggc aatgccggcg aacacggtca    14640
acaccatgcg gccggccggc gtggtggtgt cggcccacgg ctctgccagg ctacgcaggc    14700
ccgcgccggc ctcctggatg cgctcggcaa tgtccagtag gtcgcgggtg ctgcgggcca    14760
ggcggtctag cctggtcact gtcacaacgt cgccagggcg taggtggtca agcatcctgg    14820
ccagctccgg gcggtcgcgc ctggtgccgg tgatcttctc ggaaaacagc ttggtgcagc    14880
cggccgcgtg cagttcggcc cgttggttgg tcaagtcctg gtcgtcggtg ctgacgcggg    14940
catagcccag caggccagcg gcggcgctct tgttcatggc gtaatgtctc cggttctagt    15000
cgcaagtatt ctactttatg cgactaaaac acgcgacaag aaaacgccag gaaaagggca    15060
gggcggcagc ctgtcgcgta acttaggact tgtgcgacat gtcgtttca gaagacggct    15120 gcactgaacg tcagaagccg actgcactat agcagcggag gggttggatc aaagtacttt    15180
gatcccgagg ggaaccctgt ggttggcatg cacatacaaa tggacgaacg gataaacctt    15240
ttcacgccct tttaaatatc cgattattct aataaacgct cttttctctt aggtttaccc    15300
gccaatatat cctgtcaaac actgatagtt t                                   15331
```

```
<210> SEQ ID NO 13
<211> LENGTH: 17655
<212> TYPE: DNA
<213> ORGANISM: Artificial Sequence
<220> FEATURE:
<223> OTHER INFORMATION: Synthetic construct binary vector pMBXS1235

<400> SEQUENCE: 13
```

```
ggccagtgcc aagcttggcg cgcccctagg cgttgaacaa cggaaactcg acttgccttc       60
cgcacaatac atcatttctt cttagctttt tttcttcttc ttcgttcata cagttttttt      120
ttgtttatca gcttacattt tcttgaaccg tagctttcgt tttcttcttt ttaactttcc      180
attcggagtt tttgtatctt gtttcatagt ttgtcccagg attagaatga ttaggcatcg      240
aaccttcaag aatttgattg aataaaacat cttcattctt aagatatgaa gataatcttc      300
aaaaggcccc tgggaatctg aaagaagaga agcaggccca tttatatggg aaagaacaat      360
agtatttctt atataggccc atttaagttg aaaacaatct tcaaaagtcc cacatcgctt      420
agataagaaa acgaagctga gtttatatac agctagagtc gaagtagtga ttgctcgttc      480
ccaagccctc tggtttttaga gctagaaata gcaagttaaa ataaggctag tccgttatca      540
acttgaaaaa gtggcaccga tcggtgcctt tttttttgcaa aatttttccag atcgatttct     600 tcttcctctg ttcttcggcg ttcaatttct ggggtttttct cttcgttttc tgtaactgaa      660
acctaaaatt tgacctaaaa aaaatctcaa ataatatgat tcagtggttt tgtactttttc     720
```

-continued

```
agttagttga gttttgcagt tccgatgaga taaaccaata actaggcgtt gaacaacgga      780
aactcgactt gccttccgca caatacatca tttcttctta gctttttttc ttcttcttcg      840
ttcatacagt tttttttttgt ttatcagctt acattttctt gaaccgtagc tttcgtttttc     900 ttcttttttaa ctttccattc ggagtttttg tatcttgttt catagtttgt cccaggatta      960
gaatgattag gcatcgaacc ttcaagaatt tgattgaata aaacatcttc attcttaaga     1020
tatgaagata atcttcaaaa ggcccctggg aatctgaaag aagagaagca ggcccattta     1080
tatgggaaag aacaatagta tttcttatat aggcccattt aagttgaaaa caatcttcaa     1140
aagtcccaca tcgcttagat aagaaaacga agctgagttt atatacagct agagtcgaag     1200
tagtgattga tttgttcatg ggctcagagt tttagagcta gaaatagcaa gttaaaataa     1260
ggctagtccg ttatcaactt gaaaaagtgg caccgagtcg gtgctttttt ttgcaaaatt     1320
ttccagatcg atttcttctt cctctgttct tcggcgttca atttctgggg ttttctcttc     1380
gttttctgta actgaaacct aaaatttgac ctaaaaaaaa tctcaaataa tatgattcag     1440
tggttttgta ctttttcagtt agttgagttt tgcagttccg atgagataaa ccaataacta     1500
ggcgttgaac aacggaaact cgacttgcct tccgcacaat acatcatttc ttcttagctt     1560 ttttttcttct tcttcgttca tacagttttt ttttgtttat cagcttacat tttcttgaac     1620
cgtagctttc gttttcttct ttttaacttt ccattcggag tttttgtatc ttgtttcata     1680
gtttgtccca ggattagaat gattaggcat cgaaccttca agaatttgat tgaataaaac     1740
atcttcattc ttaagatatg aagataatct tcaaaaggcc cctgggaatc tgaaagaaga     1800
gaagcaggcc catttatatg ggaaagaaca atagtatttc ttatataggc ccatttaagt     1860
tgaaaacaat cttcaaaagt cccacatcgc ttagataaga aaacgaagct gagtttatat     1920
acagctagag tcgaagtagt gattgcttgt cccaagccc tctggtttta gagctagaaa     1980
tagcaagtta aaataaggct agtccgttat caacttgaaa aagtggcacc gagtcggtgc     2040
ttttttttgc aaaattttcc agatcgattt cttcttcctc tgttcttcgg cgttcaattt     2100
ctggggtttt ctcttcgttt tctgtaactg aaacctaaaa tttgacctaa aaaaaatctc     2160
aaataatatg attcagtggt tttgtacttt tcagttagtt gagttttgca gttccgatga     2220
gataaaccaa taactagtcc tcagcttaat taatactcca agaatatcaa agatacagtc     2280
tcagaagacc aaagggctat tgagacttttt caacaaaggg taatatcggg aaacctcctc     2340
ggattccatt gcccagctat ctgtcacttc atcaaaagga cagtagaaaa ggaaggtggc     2400
acctacaaat gccatcattg cgataaagga aaggctatcg ttcaagatgc ctctgccgac     2460
agtggtccca aagatggacc cccacccaca aggagcatcg tggaaaaaga agacgttcca     2520
accacgtctt caaagcaagt ggattgatgt gatatctcca ctgacgtaag ggatgacgca     2580
caatcccact atccttcgcc ccaagcttgg gcccaagctt gggtcgcgcc ccacggatgg     2640
tataagaata aaggcattcc gcgtgcagga ttcacccgtt cgcctctcac cttttcgctg     2700
tactctctcg ccacacacac cccctctcca gctccgttgg agctccggac agcagcaggc     2760
gcggggcggt cacgtagtaa gcagctctcg gctccctctc cccttgctcc gtggatccat     2820
ggattacaag gatgatgatg ataaggatta caaggatgat gatgataaga tggctccaaa     2880
gaagaagaga aaggttggaa tccacggagt tccagctgct gataagaagt actctatcgg     2940
acttgacatc ggaaccaact ctgttggatg ggctgttatc accgatgagt acaaggttcc     3000
atctaagaag ttcaaggttc ttggaaacac cgatagacac tctatcaaga gaaaccttat     3060
cggtgctctt ctttttcgatt ctggagagac cgctgaggct accagattga agagaaccgc     3120
```

-continued

```
tagaagaaga tacaccagaa gaaagaacag aatctgctac cttcaggaaa tcttctctaa   3180
cgagatggct aaggttgatg attctttctt ccacagactt gaggagtctt tccttgttga   3240
ggaggataag aagcacgaga gacacccaat cttcggaaac atcgttgatg aggttgctta   3300
ccacgagaag tacccaacca tctaccacct tagaaagaag ttggttgatt ctaccgataa   3360
ggctgatctt agacttatct accttgctct tgctcacatg atcaagttca gaggacactt   3420
ccttatcgag ggagacctta acccagataa ctctgatgtt gataagttgt tcatccagct   3480
tgttcagacc tacaaccagc ttttcgagga gaacccaatc aacgcttctg gagttgatgc   3540
taaggctatc ctttctgcta gactttctaa gtctcgtaga cttgagaacc ttatcgctca   3600
gcttccagga gagaagaaga acggactttt cggaaacctt atcgctcttt ctcttggact   3660 tacccccaaac ttcaagtcta acttcgatct tgctgaggat gctaagttgc agctttctaa   3720
ggatacctac gatgatgatc ttgataacct tcttgctcag atcggagatc agtacgctga   3780 tcttttccctt gctgctaaga acctttctga tgctatcctt ctttctgaca tccttagagt   3840
taacaccgag atcaccaagg ctccactttc tgcttctatg atcaagagat acgatgagca   3900
ccaccaggat cttacccttt tgaaggctct tgttagacag cagcttccag agaagtacaa   3960
ggaaatcttc ttcgatcagt ctaagaacgg atacgctgga tacatcgatg gaggagcttc   4020
tcaggaggag ttctacaagt tcatcaagcc aatccttgag aagatggatg aaccgagga   4080 gcttcttgtt aagttgaaca gagaggatct tcttagaaag cagagaacct cgataacgg   4140 atctatccca caccagatcc accttggaga gcttcacgct atccttcgta gacaggagga   4200 tttctacccca ttcttgaagg ataacagaga gaagatcgag aagatcctta ccttcagaat   4260
cccatactac gttggaccac ttgctagagg aaactctcgt ttcgcttgga tgaccagaaa   4320
gtctgaggag accatcaccc cttggaactt cgaggaggta agtttctgct tctacctttg   4380
atatatatat aataattatc attaattagt agtaatataa tatttcaaat attttttca   4440 aaataaaaga atgtagtata tagcaattgc ttttctgtag tttataagtg tgtatatttt   4500
aatttataac ttttctaata tatgaccaaa atttgttgat gtgcaggttg ttgataaggg   4560
agcttctgct cagtctttca tcgagagaat gaccaacttc gataagaacc ttccaaacga   4620
gaaggttctt ccaaagcact ctcttcttta cgagtacttc accgtttaca acgagcttac   4680
caaggttaag tacgttaccg agggaatgag aaagccagct ttcctttctg gagagcagaa   4740
gaaggctatc gttgatcttc tttttcaagac caacagaaag gttaccgtta agcagttgaa   4800
ggaggattac ttcaagaaga tcgagtgctt cgattctgtt gaaatctctg gagttgagga   4860
tagattcaac gcttctcttg gaacctacca cgatcttttg aagatcatca aggataagga   4920
tttccttgat aacgaggaga acgaggacat ccttgaggac atcgttctta cccttaccct   4980
tttcgaggat agagagatga tcgaggagag actcaagacc tacgctcacc ttttcgatga   5040
taaggttatg aagcagttga agagaagaag atacaccgga tggggtagac tttctcgtaa   5100
gttgatcaac ggaatcagag ataagcagtc tggaaagacc atccttgatt tcttgaagtc   5160
tgatggattc gctaacagaa acttcatgca gcttatccac gatgattctc ttaccttcaa   5220
ggaggacatc cagaaggctc aggtttctgg acagggagat tctcttcacg agcacatcgc   5280
taaccttgct ggatctccag ctatcaagaa gggaatcctt cagaccgtta aggttgttga   5340
tgagcttgtt aaggttatgg gtagacacaa gccagagaac atcgttatcg agatggctag   5400
agagaaccag accacccaga agggacagaa gaactctcgt gagagaatga gagagaatcga   5460
```

-continued

```
ggagggaatc aaggagcttg gatctcaaat cttgaaggag cacccagttg agaacaccca    5520
gcttcagaac gagaagttgt acctttacta ccttcagaac ggaagagata tgtacgttga    5580
tcaggagctt gacatcaaca gactttctga ttacgatgtt gatcacatcg ttccacagtc    5640
tttcttgaag gatgattcta tcgataacaa ggttcttacc cgttctgata agaacagagg    5700
aaagtctgat aacgttccat ctgaggaggt tgttaagaag atgaagaact actggagaca    5760
gcttcttaac gctaagttga tcacccagag aaagttcgat aaccttacca aggctgagag    5820
aggaggactt tctgagcttg ataaggctgg attcatcaag agacagcttg ttgagaccag    5880
acagatcacc aagcacgttg ctcagatcct tgattctcgt atgaacacca agtacgatga    5940
gaacgataag ttgatcagag aggttaaggt tatcaccttg aagtctaagt tggtttctga    6000
tttcagaaag gatttccagt ctacaaggt tagagagatc aacaactacc accacgctca    6060
cgatgcttac cttaacgctg ttgttggaac cgctcttatc aagaagtacc caaagttgga    6120
gtctgagttc gtttacgag attacaaggt ttacgatgtt agaaagatga tcgctaagtc    6180
tgagcaggag atcggaaagg ctaccgctaa gtacttcttc tactctaaca tcatgaactt    6240
cttcaagacc gagatcaccc ttgctaacgg agagatcaga aagagaccac ttatcgagac    6300
caacggagag accggagaga tcgtttggga taagggaaga gatttcgcta ccgttagaaa    6360
ggttcttctt atgccacagg ttaacatcgt taagaaaacc gaggttcaga ccggaggatt    6420
ctctaaggag tctatccttc aaagagaaa ctctgataag ttgatcgcta gaaagaagga    6480
ttgggaccca aagaagtacg gaggattcga ttctccaacc gttgcttact ctgttcttgt    6540
tgttgctaag gttgagaagg gaaagtctaa gaagttgaag tctgttaagg agcttcttgg    6600
aatcaccatc atggagcgtt cttctttcga gaagaaccca atcgatttcc ttgaggctaa    6660
gggatacaag gaggttaaga aggatcttat catcaagttg ccaaagtact ctctttcga    6720 gcttgagaac ggaagaaaga gaatgcttgc ttctgctgga gagcttcaga agggaaacga    6780
gcttgctctt ccatctaagt acgttaactt cctttacctt gcttctcact acgagaagtt    6840
gaagggatct ccagaggata cgagcagaa gcagcttttc gttgagcagc acaagcacta    6900
ccttgatgag atcatcgagc aaatctctga gttctctaag agagttatcc ttgctgatgc    6960
taaccttgat aaggttcttt ctgcttacaa caagcacaga gataagccaa tcagagagca    7020
ggctgagaac atcatccacc ttttcacct taccaacctt ggtgctccag ctgctttcaa    7080
gtacttcgat accaccatcg atagaaaaag atacacctct accaaggagg ttcttgatgc    7140
tacccttatc caccagtcta tcaccggact ttacgagacc agaatcgatc tttctcagct    7200
tggaggagat aagagaccag ctgctaccaa gaaggctgga caggctaaga agaagaagtg    7260
acctcaggat cgttcaaaca tttggcaata aagtttctta agattgaatc ctgttgccgg    7320
tcttgcgatg attatcatat aatttctgtt gaattacgtt aagcatgtaa taattaacat    7380
gtaatgcatg acgttatta tgagatgggg ttttatgatt agagtcccgc aattatacat    7440
ttaatacgcg atagaaaaca aaatatagcg cgcaaactag gataaattat cgcgcgcggt    7500
gtcatctatg ttactagatc cggaccgctc gagcaattgt acgtagcgta ttggctagag    7560
cagcttgcca acatggtgga gcacgacact ctcgtctact ccaagaatat caaagataca    7620
gtctcagaag accaaagggc tattgagact tttcaacaaa gggtaatatc gggaaacctc    7680
ctcggattcc attgcccagc tatctgtcac ttcatcaaaa ggacagtaga aaaggaaggt    7740
ggcacctaca aatgccatca ttgcgataaa ggaaaggcta tcgttcaaga tgcctctgcc    7800
gacagtggtc ccaaagatgg acccccaccc acgaggagca tcgtggaaaa agaagacgtt    7860
```

-continued

```
ccaaccacgt cttcaaagca agtggattga tgtgaacatg gtggagcacg acactctcgt    7920
ctactccaag aatatcaaag atacagtctc agaagaccaa agggctattg agactttca     7980 acaaagggta atatcgggaa acctcctcgg attccattgc ccagctatct gtcacttcat    8040
caaaaggaca gtagaaaagg aaggtggcac ctacaaatgc catcattgcg ataaaggaaa    8100
ggctatcgtt caagatgcct ctgccgacag tggtcccaaa gatggacccc cacccacgag    8160
gagcatcgtg gaaaaagaag acgttccaac cacgtcttca aagcaagtgg attgatgtga    8220
tatctccact gacgtaaggg atgacgcaca atcccactat ccttcgcaag acccttcctc    8280
tatataagga agttcatttc atttggagag gacacgctga aatcaccagt ctctctctac    8340
aaatctatct ctctcgagtc taccatgagc ccagaacgac gcccggccga catccgccgt    8400
gccaccgagg cggacatgcc ggcggtctgc accatcgtca accactacat cgagacaagc    8460
acggtcaact tccgtaccga gccgcaggaa ccgcaggagt ggacggacga cctcgtccgt    8520
ctgcgggagc gctatccctg gctcgtcgcc gaggtggacg gcgaggtcgc cggcatcgcc    8580
tacgcgggcc cctggaaggc acgcaacgcc tacgactgga cggccgagtc gaccgtgtac    8640
gtctcccccc gccaccagcg gacgggactg ggctccacgc tctacaccca cctgctgaag    8700
tccctggagg cacagggctt caagagcgtg gtcgctgtca tcgggctgcc caacgacccg    8760
agcgtgcgca tgcacgaggc gctcggatat gcccccgcg gcatgctgcg ggcggccggc    8820
ttcaagcacg ggaactggca tgacgtgggt ttctggcagc tggacttcag cctgccggta    8880 ccgcccgtc cggtcctgcc cgtcaccgag atttgactcg agtttctcca taataatgtg     8940
tgagtagttc ccagataagg gaattagggt tcctataggg tttcgctcat gtgttgagca    9000
tataagaaac ccttagtatg tatttgtatt tgtaaaatac ttctatcaat aaaatttcta    9060
attcctaaaa ccaaaatcca gtactaaaat ccagatcccc cgaattaatt cggcgttaat    9120
tcaggtttaa acgaattcgt aatcatgtca tagctgtttc ctgtgtgaaa ttgttatccg    9180
ctcacaattc cacacaacat acgagccgga agcataaagt gtaaagcctg gggtgcctaa    9240
tgagtgagct aactcacatt aattgcgttg cgctcactgc ccgctttcca gtcgggaaac    9300
ctgtcgtgcc agctgcatta atgaatcggc caacgcgcgg ggagaggcgg tttgcgtatt    9360
ggctagagca gcttgccaac atggtggagc acgacactct cgtctactcc aagaatatca    9420
aagatacagt ctcagaagac caaagggcta ttgagacttt tcaacaaagg gtaatatcgg    9480
gaaacctcct cggattccat tgcccagcta tctgtcactt catcaaaagg acagtagaaa    9540
aggaaggtgg cacctacaaa tgccatcatt gcgataaagg aaaggctatc gttcaagatg    9600
cctctgccga cagtggtccc aaagatggac ccccacccac gaggagcatc gtggaaaaag    9660
aagacgttcc aaccacgtct tcaaagcaag tggattgatg tgaacatggt ggagcacgac    9720
actctcgtct actccaagaa tatcaaagat acagtctcag aagaccaaag ggctattgag    9780
acttttcaac aaagggtaat atcgggaaac ctcctcggat tccattgccc agctatctgt    9840
cacttcatca aaaggacagt agaaaaggaa ggtggcacct acaaatgcca tcattgcgat    9900
aaaggaaagg ctatcgttca agatgcctct gccgacagtg gtcccaaaga tggaccccca    9960
cccacgagga gcatcgtgga aaaagaagac gttccaacca cgtcttcaaa gcaagtggat    10020
tgatgtgata tctccactga cgtaagggat gacgcacaat cccactatcc ttcgcaagac    10080
ccttcctcta tataaggaag ttcatttcat ttggagagga cacgctgaaa tcaccagtct    10140
ctctctacaa atctatctct ctcgagaaaa tggcctcctc cgagaacgtc atcaccgagt    10200
```

-continued

```
tcatgcgctt caaggtgcgc atggagggca ccgtgaacgg ccacgagttc gagatcgagg   10260
gcgagggcga gggccgcccc tacgagggcc acaacaccgt gaagctgaag gtgaccaagg   10320 gcggcccccct gcccttcgcc tgggacatcc tgtccccccca gttccagtac ggctccaagg   10380
tgtacgtgaa gcaccccgcc gacatccccg actacaagaa gctgtccttc cccgagggct   10440
tcaagtggga gcgcgtgatg aacttcgagg acggcggcgt ggcgaccgtg acccaggact   10500
cctccctgca ggacggctgc ttcatctaca aggtgaagtt catcggcgtg aacttcccct   10560
ccgacggccc cgtgatgcag aagaagacca tgggctggga ggcctccacc gagcgcctgt   10620
acccccgcga cggcgtgctg aagggcgaaa cccacaaggc cctgaagctg aaggacggcg   10680
gccactacct ggtggagttc aagtccatct acatggccaa gaagcccgtg cagctgcccg   10740
gctactacta cgtggacgcc aagctggaca tcacctccca caacgaggac tacaccatcg   10800
tggagcagta cgagcgcacc gagggccgcc accacctgtt cctggtacca atgagctctg   10860
tccaacagtc tcagggttaa ctcgagtttc tccataataa tgtgtgagta gttcccagat   10920
aagggaatta gggttcctat agggtttcgc tcatgtgttg agcatataag aaacccttag   10980
tatgtatttg tatttgtaaa atacttctat caataaaatt tctaattcct aaaaccaaaa   11040
tccagtacta aaatccagat cccccgaatt aattcggcgt taattcagta cattaaaaac   11100
gtccgcaatg tgttattaag ttgtctaagc gtcaatttgt ttacaccaca atatatcctg   11160
ccaccagcca gccaacagct cccgaccgg cagctcggca caaatcacc actcgataca   11220 ggcagcccat cagtccggga cggcgtcagc gggagagccg ttgtaaggcg gcagactttg   11280
ctcatgttac cgatgctatt cggaagaacg gcaactaagc tgccgggttt gaaacacgga   11340
tgatctcgcg gagggtagca tgttgattgt aacgatgaca gagcgttgct gcctgtgatc   11400
accgcggttt caaaatcggc tccgtcgata ctatgttata cgccaacttt gaaaacaact   11460
ttgaaaaagc tgttttctgg tatttaaggt tttagaatgc aaggaacagt gaattggagt   11520
tcgtcttgtt ataattagct tcttggggta tctttaaata ctgtagaaaa gaggaaggaa   11580
ataataaatg gctaaaatga gaatatcacc ggaattgaaa aaactgatcg aaaaataccg   11640
ctgcgtaaaa gatacggaag gaatgtctcc tgctaaggta tataagctgg tgggagaaaa   11700
tgaaaaccta tatttaaaaa tgacggacag ccggtataaa gggaccacct atgatgtgga   11760 acggaaaag gacatgatgc tatggctgga aggaaagctg cctgttccaa aggtcctgca   11820
ctttgaacgg catgatggct ggagcaatct gctcatgagt gaggccgatg gcgtcctttg   11880
ctcggaagag tatgaagatg aacaaagccc tgaaaagatt atcgagctgt atgcggagtg   11940
catcaggctc tttcactcca tcgacatatc ggattgtccc tatacgaata gcttagacag   12000
ccgcttagcc gaattggatt acttactgaa taacgatctg gccgatgtgg attgcgaaaa   12060
ctgggaagaa gacactccat ttaaagatcc gcgcgagctg tatgattttt aaaagacgga   12120
aaagcccgaa gaggaacttg tcttttccca cggcgacctg ggagacagca acatctttgt   12180
gaaagatggc aaagtaagtg gctttattga tcttgggaga agcggcaggg cggacaagtg   12240
gtatgacatt gccttctgcg tccggtcgat cagggaggat atcggggaag aacagtatgt   12300
cgagctattt tttgacttac tggggatcaa gcctgattgg gagaaaataa aatattatat   12360
tttactggat gaattgtttt agtacctaga atgcatgacc aaaatccctt aacgtgagtt   12420
ttcgttccac tgagcgtcag accccgtaga aaagatcaaa ggatcttctt gagatccttt   12480
ttttctgcgc gtaatctgct gcttgcaaac aaaaaaacca ccgctaccag cggtggtttg   12540
tttgccggat caagagctac caactctttt tccgaaggta actggcttca gcagagcgca   12600
```

```
gataccaaat actgtccttc tagtgtagcc gtagttaggc caccacttca agaactctgt   12660
agcaccgcct acatacctcg ctctgctaat cctgttacca gtggctgctg ccagtggcga   12720
taagtcgtgt cttaccgggt tggactcaag acgatagtta ccggataagg cgcagcggtc   12780
gggctgaacg gggggttcgt gcacacagcc cagcttggag cgaacgacct acaccgaact   12840
gagataccta cagcgtgagc tatgagaaag cgccacgctt cccgaaggga gaaaggcgga   12900
caggtatccg gtaagcggca gggtcggaac aggagagcgc acgagggagc ttccaggggg   12960
aaacgcctgg tatctttata gtcctgtcgg gtttcgccac ctctgacttg agcgtcgatt   13020
tttgtgatgc tcgtcagggg ggcggagcct atggaaaaac gccagcaacg cggccttttt   13080
acggttcctg gccttttgct ggccttttgc tcacatgttc tttcctgcgt tatcccctga   13140
ttctgtggat aaccgtatta ccgcctttga gtgagctgat accgctcgcc gcagccgaac   13200
gaccgagcgc agcgagtcag tgagcgagga agcggaagag cgcctgatgc ggtattttct   13260
ccttacgcat ctgtgcggta tttcacaccg catatggtgc actctcagta caatctgctc   13320
tgatgccgca tagttaagcc agtatacact ccgctatcgc tacgtgactg ggtcatggct   13380
gcgccccgac acccgccaac acccgctgac gcgccctgac gggcttgtct gctcccggca   13440
tccgcttaca gacaagctgt gaccgtctcc gggagctgca tgtgtcagag gttttcaccg   13500
tcatcaccga aacgcgcgag gcagggtgcc ttgatgtggg cgccggcggt cgagtggcga   13560
cggcgcggct tgtccgcgcc ctggtagatt gcctggccgt aggccagcca tttttgagcg   13620
gccagcggcc gcgataggcc gacgcgaagc ggcggggcgt agggagcgca gcgaccgaag   13680
ggtaggcgct ttttgcagct cttcggctgt gcgctggcca gacagttatg cacaggccag   13740
gcgggtttta agagttttaa taagtttaa agagtttag gcggaaaaat cgcctttttt   13800
ctcttttata tcagtcactt acatgtgtga ccggttccca atgtacggct ttgggttccc   13860
aatgtacggg ttccggttcc caatgtacg ctttgggttc ccaatgtacg tgctatccac   13920
aggaaacaga ccttttcgac ctttttcccc tgctagggca atttgcccta gcatctgctc   13980
cgtacattag gaaccggcgg atgcttcgcc ctcgatcagg ttgcggtagc gcatgactag   14040
gatcgggcca gcctgccccg cctcctcctt caaatcgtac tccggcaggt catttgaccc   14100
gatcagcttg cgcacggtga aacagaactt cttgaactct ccggcgctgc cactgcgttc   14160
gtagatcgtc ttgaacaacc atctggcttc tgccttgcct gcggcgcggc gtgccaggcg   14220
gtagagaaaa cggccgatgc cgggatcgat caaaaagtaa tcggggtgaa ccgtcagcac   14280
gtccgggttc ttgccttctg tgatctcgcg gtacatccaa tcagctagct cgatctcgat   14340
gtactccggc cgcccggttt cgctctttac gatcttgtag cggctaatca aggcttcacc   14400
ctcggatacc gtcaccaggc ggccgttctt ggccttcttc gtacgctgca tggcaacgtg   14460
cgtggtgttt aaccgaatgc aggtttctac caggtcgtct ttctgctttc cgccatcggc   14520
tcgccggcag aacttgagta cgtccgcaac gtgtggacgg aacacgcggc cgggcttgtc   14580
tcccttccct tcccggtatc ggttcatgga ttcggttaga tgggaaaccg ccatcagtac   14640
caggtcgtaa tcccacacac tggccatgcc ggccggccct gcggaaacct ctacgtgccc   14700
gtctggaagc tcgtagcgga tcacctcgcc agctcgtcgg tcacgcttcg acagacggaa   14760
aacggccacg tccatgatgc tgcgactatc gcgggtgccc acgtcataga gcatcggaac   14820
gaaaaaatct ggttgctcgt cgcccttggg cggcttccta atcgacggcg caccggctgc   14880
cggcggttgc cgggattctt tgcggattcg atcagcggcc gcttgccacg attcaccggg   14940
```

-continued

```
gcgtgcttct gcctcgatgc gttgccgctg ggcggcctgc gcggccttca acttctccac   15000
caggtcatca cccagcgccg cgccgatttg taccgggccg gatggtttgc gaccgctcac   15060
gccgattcct cgggcttggg ggttccagtg ccattgcagg gccggcaggc aacccagccg   15120
cttacgcctg gccaaccgcc cgttcctcca cacatggggc attccacggc gtcggtgcct   15180
ggttgttctt gattttccat gccgcctcct ttagccgcta aaattcatct actcatttat   15240
tcatttgctc atttactctg gtagctgcgc gatgtattca gatagcagct cggtaatggt   15300
cttgccttgg cgtaccgcgt acatcttcag cttggtgtga tcctccgccg gcaactgaaa   15360
gttgacccgc ttcatggctg gcgtgtctgc caggctggcc aacgttgcag ccttgctgct   15420
gcgtgcgctc ggacggccgg cacttagcgt gtttgtgctt ttgctcattt tctctttacc   15480
tcattaactc aaatgagttt tgatttaatt tcagcggcca gcgcctggac ctcgcgggca   15540
gcgtcgccct cgggttctga ttcaagaacg gttgtgccgg cggcggcagt gcctgggtag   15600
ctcacgcgct gcgtgatacg ggactcaaga atgggcagct cgtacccggc cagcgcctcg   15660
gcaacctcac cgccgatgcg cgtgcctttg atcgcccgcg acacgacaaa ggccgcttgt   15720
agccttccat ccgtgacctc aatgcgctgc ttaaccagct ccaccaggtc ggcggtggcc   15780
catatgtcgt aagggcttgg ctgcaccgga atcagcacga agtcggctgc cttgatcgcg   15840
gacacagcca agtccgccgc ctggggcgct ccgtcgatca ctacgaagtc gcgccggccg   15900
atggccttca cgtcgcggtc aatcgtcggg cggtcgatgc cgacaacggt tagcggttga   15960
tcttcccgca cggccgccca atcgcgggca ctgccctggg gatcggaatc gactaacaga   16020
acatcggccc cggcgagttg cagggcgcgg gctagatggg ttgcgatggt cgtcttgcct   16080
gacccgcctt tctggttaag tacagcgata accttcatgc gttcccttg cgtatttgtt    16140 tatttactca tcgcatcata tacgcagcga ccgcatgacg caagctgttt tactcaaata   16200
cacatcacct ttttagacgg cggcgctcgg tttcttcagc ggccaagctg gccggccagg   16260
ccgccagctt ggcatcagac aaaccggcca ggatttcatg cagccgcacg gttgagacgt   16320
gcgcgggcgg ctcgaacacg tacccggccg cgatcatctc cgcctcgatc tcttcggtaa   16380
tgaaaaacgg ttcgtcctgg ccgtcctggt gcggtttcat gcttgttcct cttggcgttc   16440
attctcggcg gccgccaggg cgtcggcctc ggtcaatgcg tcctcacgga aggcaccgcg   16500
ccgcctggcc tcggtgggcg tcacttcctc gctgcgctca agtgcgcggt acagggtcga   16560
gcgatgcacg ccaagcagtg cagccgcctc tttcacggtg cggccttcct ggtcgatcag   16620
ctcgcgggcg tgcgcgatct gtgccggggt gagggtaggg cgggggccaa acttcacgcc   16680
tcgggccttg gcggcctcgc gcccgctccg ggtgcggtcg atgattaggg aacgctcgaa   16740
ctcggcaatg ccgcgaaca cggtcaacac catcgcggcc gccggcgtgg tggtgtcggc    16800
ccacggctct gccaggctac gcaggcccgc gccggcctcc tggatgcgct cggcaatgtc   16860
cagtaggtcg cgggtgctgc gggccaggcg gtctagcctg gtcactgtca caacgtcgcc   16920
agggcgtagg tggtcaagca tcctggccag ctccgggcgg tcgcgcctgg tgccggtgat   16980
cttctcggaa aacagcttgg tgcagccggc cgcgtgcagt tcggcccgtt ggttggtcaa   17040
gtcctggtcg tcggtgctga cgcgggcata gcccagcagg ccagcggcgg cgctcttgtt   17100
catggcgtaa tgtctccggt tctagtcgca agtattctac tttatgcgac taaaacacgc   17160
gacaagaaaa cgccaggaaa agggcagggc ggcagcctgt cgcgtaactt aggacttgtg   17220
cgacatgtcg ttttcagaag acggctgcac tgaacgtcag aagccgactg cactatagca   17280
gcggaggggt tggatcaaag tactttgatc ccgaggggaa ccctgtggtt ggcatgcaca   17340
```

-continued

```
tacaaatgga cgaacggata aacctttttca cgcccttttta aatatccgat tattctaata    17400
aacgctcttt tctcttaggt ttacccgcca atatatcctg tcaaacactg atagtttaaa    17460
ctgaaggcgg gaaacgacaa tctgatccaa gctcaagctg ctctagcatt cgccattcag    17520
gctgcgcaac tgttgggaag ggcgatcggt gcgggcctct tcgctattac gccagctggc    17580
gaaaggggga tgtgctgcaa ggcgattaag ttgggtaacg ccagggtttt cccagtcacg    17640
acgttgtaaa acgac    17655
```

<210> SEQ ID NO 14
<211> LENGTH: 831
<212> TYPE: DNA
<213> ORGANISM: Camelina sativa

<400> SEQUENCE: 14

```
atggcgtctt ctgcagctct cggatctctt catcagactt tagggtcaca gagtgagctt    60
catttgcttt ctggaaactg gtctgcctct ggtacttctt gcgttccacg gtggagatta    120
tccaacagga gtagcaatta cacgcttgtg ttacgtgcaa aggcctctaa aacttcgaca    180
acaaccaaaa gcgatgattc atctgatgcg actgtgtcaa acgggaagaa atctgttcga    240
cggacaacct tcccgaaaga agtggaggca ctggttcacg agatgtgtga tgagactgag    300
gttgctgtcc tgaaacttaa ggttggagat ttcgagatga acctaaaacg gaagattgga    360
gcggccacaa accccattcc tgtggaggat atatctccaa ccgtagcacc tccgattcct    420
tctgagccca tggataaatc tgtttcttct gctcccagcc catctaaagc aaaaccgtct    480
gaaaaagtat ctccatttat gaatacatca tatgggaaac cagcgaagtt ggtagctttg    540
gaggcatctg gatcaaacaa ttatgttcta gtcaaatctc cctcagttgg cgagtttcac    600
agaagcagaa ctgtaaaagg aaagaaacta tctcctagct gcaaagaggg tgatgaaata    660
aaggaaggcc aagttattgg atacttacat cagttgggaa cagaacttcc agtgacgtcg    720
gatgtagctg gggaagtcct caagcttctt tcagatgacg gagactccgt aggttatggt    780
gatcctctgg ttgcggtctt gccatcgttc cacgatatca acatccagtg a    831
```

<210> SEQ ID NO 15
<211> LENGTH: 827
<212> TYPE: DNA
<213> ORGANISM: Camelina sativa

<400> SEQUENCE: 15

```
atggcgtctt ctgcagctct cggatctctt catcagactt tagggtcaca gagtgagctt    60
cacttgcttt ctggaaattg gtctgcttct ggtacttctt gtgtaccacg gtggagatta    120
tccaacagga gcagcaatta cacgcttgtg ttacgtgcaa aggcctctaa aacttcgaca    180
acaaccaaaa gcgatgattc atctgatgcg actgtgtcaa acgggaagaa atctgttcga    240
cggacaactt tcccgaaaga agtggaggca ctggttcacg agatgtgtga tgagactgag    300
gttgctgtcc tgaaacttaa ggttggagat ttcgagatga acctaaaacg gaagattgaa    360
gcggccacaa accccattcc tgtggaggat atatctccaa ccgtagcacc tccgattcct    420
tctgagccca tgaatcaatc ggtttcctct attcctagcc catctaaagc aaaaccttct    480
gaaaaagtat ctccatttat aaatacatca tatgggaaac cagcaaagtt ggcagctttg    540
gaggcatctg gatcaaataa ttatgttcta gtcaaatctc cctcagttgg cgagtttcac    600
agaagcagaa ctgtaaaagg aaagaaacta tctcctagct gcaaagaggg tgatgaaata    660
```

```
aaggaagggc aagttattgg atacttacat cagttgggaa cagaacttcc agtgacgtcg      720
gatgtagctg gggaagtcct caagcttctt tcagatgacg gagactccgt aggttatggt      780
gatcctctgg ttgcggtctt gccatcgttc cacgatatca acatcca                   827

<210> SEQ ID NO 16
<211> LENGTH: 831
<212> TYPE: DNA
<213> ORGANISM: Camelina sativa

<400> SEQUENCE: 16
atggcgtctt ctgcagctct cggatctctt catcagactt tagggtcaca gagtgagctt       60
cacttgcttt ctggaaattg gtctgcttct ggtacttctt gtgtaccacg gtggagatta      120
tccaacagga gcagcaatta cacgcttgtg ttacgtgcaa aggcctctaa aacttcgaca      180
acaaccaaaa gcgatgattc atctgatgca actgtgtcaa acgggaagaa atctgttcga      240
aggacaactt tcccgaaaga agtggagaca ctggttcacg agatgtgtga tgagactgag      300
gttgctgtcc tgaaactcaa ggttggagat ttcgagatga acctaaaacg gaagattgga      360
gctaccacaa accccattcc tgtggaggat atatctccaa ccgtagcacc tccaattcct      420
tctgagccca tgaatcaatc ggtttcctct gctcccagcc catctacagc aaaaccgtct      480
gaaaaagtat ctccatttat gaatacatca tatgggaaac cagcaaagtt ggcagctttg      540
gaggcatctg gatcaaacaa ttatgttcta gtcaaatctc cctcagttgg cgagtttcac      600
agaagcagaa ctgtaaaagg aaagaaacta tctcctagct gcaaagaggg tgatgaaata      660
aaggaaggcc aagtgattgg atacttacat cagttgggaa cagaacttcc agtgacgtcg      720
gatgtagctg gggaagtcct caagcttctt tcagatgacg gagactccat aggttatggt      780
gatcctctgg ttgcggtctt gccatcgttc cacgatatca acatccagtg a              831

<210> SEQ ID NO 17
<211> LENGTH: 831
<212> TYPE: DNA
<213> ORGANISM: Camelina sativa

<400> SEQUENCE: 17
atgaattcct gtagtttagg agctccaaaa gttagaattg ctgcagcaaa tttcagtaga       60
ttaagatgtg gaaacttgct gatacccaac aatcaaagac tttttattga ccaaagccaa      120
agccaaagcc ccatcaagta tccgagtctg aggacaactc tgcgagctgt gaaagctgtc      180
caattgtcta ctgtcccacc tgcagatata gcagctgttg cagacgtaga ggattctcaa      240
gagaccgaat caactgttgt gaatactcag ctcattccca agtcctctga ggtggaagca      300
cttatcaaag aaatcacaga ttcctcatcg attgcagagt ttgaactgaa actgggaggt      360
ttccgcctat atgtagcaag gaaattagct gaccaaagta gtccaccgcc tcagcaaatt      420
ccacctgtgg ttgctgcaag ctcagcccct gagggggttc atactaatgg ctcagccact      480
tcctcgtcat tggctatcac aaaatcagca tctccatcag acagaccaca aacactcgct      540
aacaaagctg ctgatcaggg tttagtgatt ctccaatctc caacggttgg ttatttcagg      600
agatccaaga ccataaaagg caaacgcact cctacaatct gtaaagagaa agacatagtg      660
aaagaaggtc aagttctatg ctacattgaa caactcggtg gccagatccc agttgagtct      720
gatgtttccg gtgagattgt caaaatactc cgggaagatg gcgagcctgt aggatacaac      780
gatgctctca ttaccgttct tccttcattt cctggcatca agaagcttta g              831
```

```
<210> SEQ ID NO 18
<211> LENGTH: 810
<212> TYPE: DNA
<213> ORGANISM: Camelina sativa

<400> SEQUENCE: 18
atgaattcct gtactttagg agctccaaaa gttcggattt ctgcagcaaa tttcagtaga       60
ttaagatgtg gaaacttgct gatacccaac aatcaaagac tactaattgg ccaaagcccc      120
atcaagtatc cgagtctgag gacaactctg cgagctgtcc aattgtctac tgtcccacct      180
gcagcaatag cagctgttgc agacgtagag gattctgaag agaccgaatc aactgttgtg      240
aatactcagc tcattcccaa gtcctctgag gtggaagcac ttattaaaga aatcacagat      300
tcctcatcga ttgcagagtt tgaactgaaa ctgggaggtt ccgcctata tgtagcaagg       360 aaattagctg accaaagtag tccaccgcct cagcaaattc cacctgtggt tgctgcaagc      420
tcagctcctg aggggggttca tactaatggc tcagccactt cctcgtcatt ggctatcaca      480
aaatcagcat ctccatcaga cagaccacaa acactcgcta acaaagctgc tgatcagggt      540
ttagtgattc tccaatctcc aacggttggt tatttcagga gatccaagac cataaaaggc      600
aaacgcactc ctacaatctg taaagagaaa gacacagtaa aagaaggtca agttctatgc      660
tacattgaac aactcggtgg ccagatccca gttgagtctg atgtttccgg tgagattgtc      720
aaaatactcc gggaagatgg cgagcctgta ggatacaacg atgctctcat caccgttctt      780
ccttcatttc ctggcatcaa gaagctttag                                      810

<210> SEQ ID NO 19
<211> LENGTH: 810
<212> TYPE: DNA
<213> ORGANISM: Camelina sativa

<400> SEQUENCE: 19
atgaattcct gtagtttagg agctccaaaa gttcggattt ctgcagcata tttcagtaga       60
ttaagatgtg gaaacttgct gatacccaac aatcaaagac tactaattgg ccaaagcccc      120
atcaagtatc agagtctgag gacaactctg cgagctgtcc aattgtctac tgtcccacct      180
gcagaaatag cagctgttgc agacgtagag gattctgaag agaccgaatc aactgttgtg      240
aatactcagc tcattcccaa gtcctctgag gtggaagcac ttatcaaaga aatcacagat      300
tcctcatcga ttgcagagtt tgaactgaaa ctgggaggtt ccgcctata tgtagcaagg       360 aaattagctg accaaagtag tccaccgcct cagcaaattc cacctgtggt tgctgcaagc      420
tcagctcctg aggggggttca tactaatggc tcagccactt cctcgtcatt ggctatcaca      480
aaatcagcat ctccatcaga cagaccacaa acactcgcta acaaagctgc tgatcagggt      540
ttagtgattc tccaatctcc aacggttggt tatttcagga gatccaagac cataaaaggc      600
aaacgcactc ctacaatctg taaagagaaa gacacagtga aagaaggtca agttctatgc      660
tacattgaac aactcggtgg ccagatccca gttgagtctg atgtttccgg tgagattgtc      720
aaaatactcc gggaagatgg cgagcctgta ggatacaacg atgctctcat taccgttctt      780
ccttcatttc ctggcatcaa gaagctttag                                      810

<210> SEQ ID NO 20
<211> LENGTH: 792
<212> TYPE: DNA
<213> ORGANISM: Camelina sativa

<400> SEQUENCE: 20
```

-continued

```
atggcttcct gtagcctagg agttcctaaa attaaaatct cagcagtaga ccttagtaga        60
gtaagttctg gaagcttact gataccattc agccaaagat cattgcttgg acaaaggccg       120
gtgaagtact tgagtctcag gacaactttt ggatctgtga aagctgtcca agtatctact       180
gtcccaaccg cagaaacatc agctactata gaagtagaag attctgaaga aaccaagtca       240
tctccattga acgctcagct agttcccaag ccatctgagg tggaagctct tgtcactgaa       300
atatgcgatt cctcatcaat tgcagagttt gaattgaaac tgggggggttt ccgcctatat       360 gtagcaaggg atctaactga caaaagtagt ccgcagcctc atccagttcc tgctgtggct       420
gctgccagtg aaactaccaa gagtcctgat tcgaatggat caactccttc tacttcattg       480
gctatcacaa gaccagcatc ctcagctgct gatcacggtt tgatgattct ccaatctcca       540
aaagtagggt tcttcaggag atccaaaact ataaagggta aacgcatgcc ttcgtcatgt       600
aaagagaaag accaagtgaa agaaggtcaa attctgtgct acattgaaca actcggtggc       660
caattcccaa tagagtctga tgtcagcggc gaggttgtca aaatactccg agaagatgga       720
gagcctgtag gatacaatga tgctctcatc tcgatccttc cctctttccc tgggatcaag       780
aagcttcagt aa                                                            792
```

```
<210> SEQ ID NO 21
<211> LENGTH: 792
<212> TYPE: DNA
<213> ORGANISM: Camelina sativa

<400> SEQUENCE: 21
```

```
atggcatcct gtagcctagg agttcctaaa attaaaatct cagcagtaga ccttagtaga        60
gtaagttctg gaagcttact gataccattc agtcaaagat cattgcttgg acaaaggccg       120
gtgaagtact tgagtctgag gacaactttt ggatctgtga aagctgtaca agtatctact       180
gtcccagctg cagaaacatc agctactgta ggagtagaag attctgaaga aaccaagtca       240
tccccattga acgctcagct agttcccaag cgatctgagg tggaagctct tgtcactgaa       300
atatgcgact cctcatcaat tgcagagttt gaactgaaac tgggggggttt ccgcctatat       360 gtagcaaggg atctagctga caaaagtagt ccgcagcctc atccaattcc tgctgtggct       420
gctgcaagtg aaactaccaa gagtcctgat tcgaatggat caacaccttc tacttcattg       480
gctatcacaa gaccagcatc ttcagctgct gatcagggtt tgatgattct ccaatctcca       540
aaagtagggt tctttaggag atccaaaacc ataaagggta aacgcatgcc ttcgtcatgt       600
aaagagaaag accaagtgaa agaaggtcaa attctgtgct acattgaaca actcggtggc       660
caattcccaa tagagtctga tgtcagcggt gaggttgtca aaatactccg cgaagatgga       720
gaacctgtag gatacaatga tgctctcatc tcgatccttc cctctttccc tgggatcaag       780
aagcttcagt aa                                                            792
```

```
<210> SEQ ID NO 22
<211> LENGTH: 792
<212> TYPE: DNA
<213> ORGANISM: Camelina sativa

<400> SEQUENCE: 22
```

```
atggcttcct gtagcctagg agttcctaaa attaaaatct cagcagtaga ccttagtaga        60
gtaagttctg gaagcttgct ggtaccattc agtcaaagat cattgcttgg acaaaggacg       120
gtgaagtact tgagtctgag gaaaactttt ggatctgtga aagctgtaca actatctact       180
gtcccagctg cagaaacatc agctactgta ggagtagaag attctgaaga aaccaagtca       240
```

-continued

```
tctccattga acgctcagct agttcccaat ccatctgagg tggaagctct tgtcactgaa        300
atatgcgact cctcatcaat tgcagagttt gaactgaaac tgggggggttt ccgcctatat        360 gtagcaaggg atctagctga caaaagtagt ccgcagcctc atccaattcc tgctgtggct        420
gctgcaagtg aaactaccaa gagtcctgat tcgaatggat caacaccttc tacttcattg        480
gctatcacaa gaccagcatc ttcagctgct gatcagggtt tgatgattct ccaatctcca        540
aaagtagggt tctttaggag atccaaaacc ataaagggta aacgcatgcc ttcgtcatgt        600
aaagagaaag accaagtgaa agaaggtcaa attctgtgct acattgaaca actcggtggc        660
caattcccaa tagagtctga tgtcagcggc gaggttgtca aaatactccg agaagatgga        720
gagcctgtag ggtacaatga tgctctcatc tcgatccttc cctctttccc tgggatcaag        780
aagcttcagt aa                                                           792
```

```
<210> SEQ ID NO 23
<211> LENGTH: 17
<212> TYPE: PRT
<213> ORGANISM: Artificial Sequence
<220> FEATURE:
<223> OTHER INFORMATION: Synthetic construct nuclear localization
      sequence

<400> SEQUENCE: 23

Met Ala Pro Lys Lys Lys Arg Lys Val Gly Ile His Gly Val Pro Ala
1               5                   10                  15

Ala
```

```
<210> SEQ ID NO 24
<211> LENGTH: 20
<212> TYPE: DNA
<213> ORGANISM: Artificial Sequence
<220> FEATURE:
<223> OTHER INFORMATION: Synthetic construct guide target sequence
      CsC1-69

<400> SEQUENCE: 24
ggttgttgtc gaagttttag                                                    20
```

```
<210> SEQ ID NO 25
<211> LENGTH: 20
<212> TYPE: DNA
<213> ORGANISM: Artificial Sequence
<220> FEATURE:
<223> OTHER INFORMATION: Synthetic construct guide target sequence
      CsC2-33

<400> SEQUENCE: 25
gctcattccc aagtcctctg                                                    20
```

```
<210> SEQ ID NO 26
<211> LENGTH: 20
<212> TYPE: DNA
<213> ORGANISM: Artificial Sequence
<220> FEATURE:
<223> OTHER INFORMATION: Synthetic construct guide target sequence
      CsC3-52

<400> SEQUENCE: 26
gatcccttgc tacatatagg                                                    20
```

```
<210> SEQ ID NO 27
<211> LENGTH: 20
```

-continued

```
<212> TYPE: DNA
<213> ORGANISM: Artificial Sequence
<220> FEATURE:
<223> OTHER INFORMATION: Synthetic construct guide target sequence
      C1-29A

<400> SEQUENCE: 27
gtacttcttg tgtaccacgg                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic construct guide target sequence
      C1-29B

<400> SEQUENCE: 28
gtacttcttg cgttccacgg                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic construct guide target sequence C1-66

<400> SEQUENCE: 29
gatatatcct ccacaggaat                                                20

<210> SEQ ID NO 30
<211> LENGTH: 20
<212> TYPE: DNA
<213> ORGANISM: Artificial Sequence
<220> FEATURE:
<223> OTHER INFORMATION: Synthetic construct guide target sequence
      C12-75

<400> SEQUENCE: 30
gatttgttca tgggctcaga                                                20

<210> SEQ ID NO 31
<211> LENGTH: 20
<212> TYPE: DNA
<213> ORGANISM: Artificial Sequence
<220> FEATURE:
<223> OTHER INFORMATION: Synthetic construct guide target sequence C3-58

<400> SEQUENCE: 31
gctcgttccc aagccctctg                                                20

<210> SEQ ID NO 32
<211> LENGTH: 20
<212> TYPE: DNA
<213> ORGANISM: Artificial Sequence
<220> FEATURE:
<223> OTHER INFORMATION: Synthetic construct guide target sequence C5-66

<400> SEQUENCE: 32
gcttgttccc aagccctctg                                                20

<210> SEQ ID NO 33
<211> LENGTH: 2106
<212> TYPE: DNA
<213> ORGANISM: Camelina sativa

<400> SEQUENCE: 33
```

-continued

```
atgaattcct gtaagttttg atgttcacat tcgatcctca agtttcagtt tttatatttt      60
cttttgtaaa attgatcctg aatgattttg ttgttctcca tttacgttaa atcgttattt     120
taattgggtc aacttgcagt tcggaattac ttttatgtga ttggtgtatt tattagagag     180
gggaaaaata aaaattgagt cttgattcta tcatcttgat cttaggggtt gttgatgcgt     240
cttcgtttca agagtaatgc atttaaagct tgttccttta tataatgcta ttgttcctct     300
actcgtttca agactatata tatgataact tgcaaaaaac aagtacatca gttttcaaaa     360
cattctcctt tttttttttt ttttttttgtt gtttgtggag tttataggta atgaaacatg     420
tagtttactt aagatcaatg ctgtattgag gagtattgat aagatttttg attctatttc     480
aggtacttta ggagctccaa aagttcggat ttctgcagca aatttcagta gattaagatg     540
tggaaacttg ctgatacccca acaatcaaag actactaatt ggccaaagcc ccatcaagta     600
tccgagtctg aggacaactc tgcgagctgt ccaattgtct actgtcccac ctgcagcaat     660
agcaggtata tattgttgtt atcttatcac ttgattttgt tttactgttt gtcaccaaaa     720
ccattctgac aatgcttaaa gttttttggct tatggaatga catttaaatc tggaataata     780
ctgtagctgt tgcagacgta gaggattctg aagagaccga atcaactgtt gtgaatactc     840
agctcattcc caagtcctct gaggttggtc ttaccttcct tttaaatctc ttattccaat     900
gtattgttgt tactgctgtg cttattatga tattcctaga gaaggaagga tgtgtgtcct     960
cgttgagcca gcgtggacat cagttatgtg aattgagcca ttatttttct tttccatttt    1020
ctaggtggaa gcacttatta aagaaatcac agattcctca tcgattgcag agtttgaact    1080
gaaagtaagt aagcccctct tctgatttct gaactcgtaa ctatgttatt tgttataggc    1140
ttgtagctca gttcattaga ttactaagat ttctaagttt cctataagat tgtgtctaat    1200
acttttgctc tctcccattt tgcatatatc taatagctgg gaggtttccg cctatatgta    1260
gcaaggaaat tagctgacca aagtagtcca ccgcctcagc aaattccacc tgtggttgct    1320
gcaagctcag ctcctgaggg ggttcatact aatggctcag ccacttcctc gtcattggct    1380
atcacaaaat cagcatcgcc atcagacaga ccacaaacac tcgctaacaa agctgctgat    1440
cagggtttag tgattctcca atctccaacg gttagaatcc agatttaact ttgaggctca    1500
acgctagata attttcttga aactgacatt ggcatcacta aaatttggga tccctcgatt    1560
ggatggattt ttgttgttgc aggttggtta tttcaggaga tccaagacca taaaaggcaa    1620
acgcactcct acaatctgta aagaggtacc tcttctctta tgtttaaac aagtctttga    1680 aaattttcca tcttcatgga gttttttggaa tgtctcaatt gattatgtat ttgcttttgg    1740
ttactcatca gaaagacaca gtaaaagaag gtcaagttct atgctacatt gaacaactcg    1800
gtggccagat cccagttgag gtaataacag taaatcctat tcggtttctt tgcgtttttt    1860
tttctctctt tctatctctt cttattttcc tttttcttct tccagtctga tgtttccggt    1920
gagattgtca aaatactccg ggaagatggc ggtaagacct ttttacttaa tgttgttgaa    1980
tctttcctca taccagcatg atatttatct tctgactttg gtattttttt atctgcagag    2040
cctgtaggat acaacgatgc tctcatcacc gttcttcctt catttcctgg catcaagaag    2100
ctttag                                                               2106
```

<210> SEQ ID NO 34
<211> LENGTH: 21
<212> TYPE: DNA
<213> ORGANISM: Artificial Sequence
<220> FEATURE:

<223> OTHER INFORMATION: Synthetic construct Camelina sativa badc1 Ch6 1
      base pair insertion

<400> SEQUENCE: 34
gtacttcttg tgtaccaacg g                                                  21

<210> SEQ ID NO 35
<211> LENGTH: 21
<212> TYPE: DNA
<213> ORGANISM: Artificial Sequence
<220> FEATURE:
<223> OTHER INFORMATION: Synthetic construct Camelina sativa badc1 Ch4 1
      base pair insertion

<400> SEQUENCE: 35
gtacttcttg cgttccaacg g                                                  21

<210> SEQ ID NO 36
<211> LENGTH: 21
<212> TYPE: DNA
<213> ORGANISM: Artificial Sequence
<220> FEATURE:
<223> OTHER INFORMATION: Synthetic construct Camelina sativa badc1 Ch4 1
      base pair insertion

<400> SEQUENCE: 36
gtacttcttg cgttccaacg g                                                  21

<210> SEQ ID NO 37
<211> LENGTH: 21
<212> TYPE: DNA
<213> ORGANISM: Artificial Sequence
<220> FEATURE:
<223> OTHER INFORMATION: Synthetic construct Camelina sativa badc1 Ch4 1
      base pair insertion

<400> SEQUENCE: 37
gtacttcttg cgttccagcg g                                                  21

<210> SEQ ID NO 38
<211> LENGTH: 15
<212> TYPE: DNA
<213> ORGANISM: Artificial Sequence
<220> FEATURE:
<223> OTHER INFORMATION: Synthetic construct Camelina sativa badc1 Ch6 5
      base pair deletion

<400> SEQUENCE: 38
gtacttcttg tgtag                                                         15

<210> SEQ ID NO 39
<211> LENGTH: 21
<212> TYPE: DNA
<213> ORGANISM: Artificial Sequence
<220> FEATURE:
<223> OTHER INFORMATION: Synthetic construct Camelina sativa badc1 Ch9 1
      base pair insertion

<400> SEQUENCE: 39
gtacttcttg tgtaccagcg g                                                  21

<210> SEQ ID NO 40
<211> LENGTH: 21
<212> TYPE: DNA
<213> ORGANISM: Artificial Sequence
<220> FEATURE:
<223> OTHER INFORMATION: Synthetic construct Camelina sativa badc1 Ch9 1

-continued

```
base pair insertion

<400> SEQUENCE: 40
gtacttcttg tgtaccatcg g                                              21

<210> SEQ ID NO 41
<211> LENGTH: 21
<212> TYPE: DNA
<213> ORGANISM: Artificial Sequence
<220> FEATURE:
<223> OTHER INFORMATION: Synthetic construct Camelina sativa badc1 Ch4 1
      base pair insertion

<400> SEQUENCE: 41
gtacttcttg cgttccaccg g                                              21

<210> SEQ ID NO 42
<211> LENGTH: 21
<212> TYPE: DNA
<213> ORGANISM: Artificial Sequence
<220> FEATURE:
<223> OTHER INFORMATION: Synthetic construct Camelina sativa badc1 Ch6 1
      base pair insertion

<400> SEQUENCE: 42
gtacttcttg tgtaccaacg g                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetic construct Camelina sativa badc1 Ch9 1
      base pair insertion

<400> SEQUENCE: 43
gtacttcttg tgtaccatcg g                                              21

<210> SEQ ID NO 44
<211> LENGTH: 21
<212> TYPE: DNA
<213> ORGANISM: Artificial Sequence
<220> FEATURE:
<223> OTHER INFORMATION: Synthetic construct Camelina sativa badc1 Ch4 1
      base pair insertion

<400> SEQUENCE: 44
gtacttcttg cgttccaacg g                                              21

<210> SEQ ID NO 45
<211> LENGTH: 21
<212> TYPE: DNA
<213> ORGANISM: Artificial Sequence
<220> FEATURE:
<223> OTHER INFORMATION: Synthetic construct Camelina sativa badc1 Ch6 1
      base pair insertion

<400> SEQUENCE: 45
gtacttcttg tgtaccagcg g                                              21

<210> SEQ ID NO 46
<211> LENGTH: 18
<212> TYPE: DNA
<213> ORGANISM: Artificial Sequence
<220> FEATURE:
<223> OTHER INFORMATION: Synthetic construct Camelina sativa badc1 Ch9 2
      base pair deletion
```

-continued

<400> SEQUENCE: 46
gtacttcttg tgtaccgg                                                                18

<210> SEQ ID NO 47
<211> LENGTH: 21
<212> TYPE: DNA
<213> ORGANISM: Artificial Sequence
<220> FEATURE:
<223> OTHER INFORMATION: Synthetic construct Camelina sativa badc1 Ch4 1
      base pair insertion

<400> SEQUENCE: 47
gtacttcttg cgttccaacg g                                                            21

<210> SEQ ID NO 48
<211> LENGTH: 19
<212> TYPE: DNA
<213> ORGANISM: Artificial Sequence
<220> FEATURE:
<223> OTHER INFORMATION: Synthetic construct Camelina sativa badc1 Ch6 1
      base pair deletion

<400> SEQUENCE: 48
gtacttcttg tgtacccgg                                                               19

<210> SEQ ID NO 49
<211> LENGTH: 19
<212> TYPE: DNA
<213> ORGANISM: Artificial Sequence
<220> FEATURE:
<223> OTHER INFORMATION: Synthetic construct Camelina sativa badc1 Ch9 1
      base pair deletion

<400> SEQUENCE: 49
gtacttcttg tgtacccgg                                                               19

<210> SEQ ID NO 50
<211> LENGTH: 19
<212> TYPE: DNA
<213> ORGANISM: Artificial Sequence
<220> FEATURE:
<223> OTHER INFORMATION: Synthetic construct Camelina sativa badc1 Ch4 1
      base pair deletion

<400> SEQUENCE: 50
gtacttcttg cgttcccgg                                                               19

<210> SEQ ID NO 51
<211> LENGTH: 21
<212> TYPE: DNA
<213> ORGANISM: Artificial Sequence
<220> FEATURE:
<223> OTHER INFORMATION: Synthetic construct Camelina sativa badc1 Ch6 1
      base pair insertion

<400> SEQUENCE: 51
gtacttcttg tgtaccaacg g                                                            21

<210> SEQ ID NO 52
<211> LENGTH: 21
<212> TYPE: DNA
<213> ORGANISM: Artificial Sequence
<220> FEATURE:
<223> OTHER INFORMATION: Synthetic construct Camelina sativa badc1 Ch6 1
      base pair insertion

<400> SEQUENCE: 52
gtacttcttg tgtaccatcg g                                              21

<210> SEQ ID NO 53
<211> LENGTH: 21
<212> TYPE: DNA
<213> ORGANISM: Artificial Sequence
<220> FEATURE:
<223> OTHER INFORMATION: Synthetic construct Camelina sativa badc1 Ch9 1
      base pair insertion

<400> SEQUENCE: 53
gtacttcttg tgtaccaacg g                                              21

<210> SEQ ID NO 54
<211> LENGTH: 21
<212> TYPE: DNA
<213> ORGANISM: Artificial Sequence
<220> FEATURE:
<223> OTHER INFORMATION: Synthetic construct Camelina sativa badc1 Ch4 1
      base pair insertion

<400> SEQUENCE: 54
gtacttcttg cgttccatcg g                                              21

<210> SEQ ID NO 55
<211> LENGTH: 21
<212> TYPE: DNA
<213> ORGANISM: Artificial Sequence
<220> FEATURE:
<223> OTHER INFORMATION: Synthetic construct Camelina sativa badc1 Ch6 1
      base pair insertion

<400> SEQUENCE: 55
gtacttcttg tgtaccaacg g                                              21

<210> SEQ ID NO 56
<211> LENGTH: 21
<212> TYPE: DNA
<213> ORGANISM: Artificial Sequence
<220> FEATURE:
<223> OTHER INFORMATION: Synthetic construct Camelina sativa badc1 Ch9 1
      base pair insertion

<400> SEQUENCE: 56
gtacttcttg tgtaccatcg g                                              21

<210> SEQ ID NO 57
<211> LENGTH: 21
<212> TYPE: DNA
<213> ORGANISM: Artificial Sequence
<220> FEATURE:
<223> OTHER INFORMATION: Synthetic construct Camelina sativa badc1 Ch9 1
      base pair insertion

<400> SEQUENCE: 57
gtacttcttg tgtaccaacg g                                              21

<210> SEQ ID NO 58
<211> LENGTH: 21
<212> TYPE: DNA
<213> ORGANISM: Artificial Sequence
<220> FEATURE:
<223> OTHER INFORMATION: Synthetic construct Camelina sativa badc1 Ch4 1
      base pair insertion

<400> SEQUENCE: 58

-continued

```
gtacttcttg cgttccagcg g                                              21

<210> SEQ ID NO 59
<211> LENGTH: 21
<212> TYPE: DNA
<213> ORGANISM: Artificial Sequence
<220> FEATURE:
<223> OTHER INFORMATION: Synthetic construct Camelina sativa badc1 Ch6 1
      base pair insertion

<400> SEQUENCE: 59
gtacttcttg tgtaccatcg g                                              21

<210> SEQ ID NO 60
<211> LENGTH: 21
<212> TYPE: DNA
<213> ORGANISM: Artificial Sequence
<220> FEATURE:
<223> OTHER INFORMATION: Synthetic construct Camelina sativa badc1 Ch9 1
      base pair insertion

<400> SEQUENCE: 60
gtacttcttg tgtaccatcg g                                              21

<210> SEQ ID NO 61
<211> LENGTH: 19
<212> TYPE: DNA
<213> ORGANISM: Artificial Sequence
<220> FEATURE:
<223> OTHER INFORMATION: Synthetic construct Camelina sativa badc1 Ch9 2
      base pair deletion

<400> SEQUENCE: 61
gtacttcttg tgtaccagg                                                 19

<210> SEQ ID NO 62
<211> LENGTH: 813
<212> TYPE: DNA
<213> ORGANISM: Brassica napus

<400> SEQUENCE: 62
atggagtctt ctgcagctct cggatctctc cgtcagagtt taggatccgc cgtaaatgtt       60
cactcgcttt ctggtaactg gtctccctct ggtaattctt gtgcgccacg gtggagtttg      120
ttcaacagga acatgcttgt attgcgtgca gactcctcta aatcttcaac aacaacaacc      180
aaaactgatg aatcatctga tgcctcaaac gggactaaaa ctaaaactgt tcgaaggaca      240
actttcccta aagaagtgga ggcactggtt cacgagatgt gtgatgagac tgaggttgga      300
gattttgaga tgaaccttaa gcggaagatt ggactggccg aaactcccat tcccgtgcct      360
gatatttctc catctgtagc tcctccaatt ccttctgagc ccatgaacaa atcagtttct      420
gcttctgctg atgctagccc atccaaagca aagcctgcct ctgaaaaagt gtctccgttc      480
ataaatgctg cataccggaa atcatcaaag ctggctgctt tggaggcagc tggatctaac      540
aactatgttc tagtcacatc tccgtcagtg ggtaagtttc agagaagcag aactgtaaaa      600
ggaaagaaac aaggtcctac ctgtaaagag ggtgatgcaa taaaggaagg ccaagtgatt      660
ggatacttac atcagttggg aaaagaactt ccagtgacgt cagatgtagc tggggaagtt      720
ctcaagcttc tttcagatga tggagactct gtaggttatg gggagcctct ggttgccgtc      780
ttgccatcgt tccatgatat caacatccag tga                                 813
```

-continued

```
<210> SEQ ID NO 63
<211> LENGTH: 777
<212> TYPE: DNA
<213> ORGANISM: Brassica napus

<400> SEQUENCE: 63
atggagtctc tcggatctct ccatcagagt ttaggatccg ccgtaaatgt tcactcgctt      60
tctggtaaat cttgtgcgcc gccacggtgg agtttgttca acaggaacac gcttgtgttg     120
cgtgcagagt cctctaaatc ttccacaaca accaaaactg atgaatcatc tgatgcctca     180
aacgggacta aaactgttcg gaggacaact ttccctaaag aagtggaggc actggttcac     240
gagatgtgtg atgagactga ggttggagat ttcgagatga acctgaagcg gaagattgga     300
cttgctgaaa ctcccattcc cgtgcctgat atctctccat ctgtagctcc tccgattcct     360
tctgagccca tgaacaaatc agtttcttct tctgctgctg ctgctaccag cccatccaaa     420
gcaaaacctg cagtgtctcc gttcataaac gctgcatatc gaaaatcatc aaagctggct     480
gctttggatg catctggatc taacaactat gttctcgtca catctccctc agtgggaaag     540
tttcagagaa gcagaactgt aaaaggaaag aaacaaggtc ctacctgtaa agagggtgat     600
gcaataaagg aaggccaagt gattggatac ttacatcagt tgggaaaaga acttccagta     660
acgtcagatg tagctgggga agttctcaag cttctttcag atgatggaga ctctgtaggt     720
tatggagagc tctggttgc agtcttgcca tcgttccatg atatcaacat ccagtga        777
```

```
<210> SEQ ID NO 64
<211> LENGTH: 750
<212> TYPE: DNA
<213> ORGANISM: Brassica napus

<400> SEQUENCE: 64
atggcttcct gtagcctagg agttccgaag attaaaatct cagcggtaga cgtgagtaga      60
gtaagatctg gaaggttaca gattccatac agtcagagat cattgtttgc tcaaaggcag     120
gttaagtact tgagtctgag acaagtgtt ggatctttga aagctctcca agtgtctact      180
gtcacagctg tggaaacatc agctactgtt gaagtagaag atgctgaaaa gaccaagtca     240
tctccgttga acgctcagct cgttcccaag ccctctgagg tggaagctct tgtcactgag     300
atatgtgatt cctcatcaat tgcagagttt gaactgaaac taggggggttt ccgcctatat     360 gtagcaagga acttagctga caacaacatt agtccaccac aacctcagcc aactcctgct     420
gccctttctg caaatgccgt taccgagagt gctgattcta atggatcagc ttcctctact     480
tcattagcca tcacaaaacc agcatcttca gctgctgatc agggtttgat tattctccaa     540
tctccaaaag taggattctt caggagatcc aaaaccataa agggtaaacg cactccttcc     600
tcctgtaaag agaagaccaa agtgaaagaa ggtcaagttc tttgctacat tgagcaactc     660
ggtggccagt tccctatcga gtctgatgtt actggagagg ttgtcaagat actccgagag     720
gatggaggca agtcttatct tcttctttaa                                      750
```

```
<210> SEQ ID NO 65
<211> LENGTH: 762
<212> TYPE: DNA
<213> ORGANISM: Brassica napus

<400> SEQUENCE: 65
atggcttcct gtagcctggc agttcctaag attaaaatct cagcagcagt agacctcagt      60
ttagtaagat ctgggaggtt tcagatacca tgcaatcaaa gagtgttgtt gattggtcaa     120
```

```
aggccggtta agtacttgag tctcagggca actcttggtt ctgtccaagc gtctactgtc          180
acagctgctg aatctgcagc aactgtagaa gtagaagata ctgagacgac gaagccatct          240
ccgttgaacg ctcagctcgt tcccaagccc tctgaggtgg aagctcttgt cactgagata          300
tgcgattcct catcaattgc agagtttgaa ctgaaactgg ggggtttccg cctatatgta          360
gcgaggaact tagctgacaa caacagtagt ccaccacaac ctcagccaat tcctgctgcc          420
gtggctgcaa gtgcaaccac tgagagtgtt gattcgaatg gatcagcttc ctctacttca          480
ctggctatca caaaaccaac atcctcagct gctgatcagg gtttggtgat tctccaatct          540
ccaaaggtag ggttcttcag gagatccaaa accataaagg gtaaacgcac tccttcgtca          600
tgtaaagaga aagaccaagt gaaagaaggt caagttctgt gctatattga acagctcggt          660
ggccaatttc caatcgagtc tgatgttacc ggcgaggttg tcaaaatact cagagaggat          720
ggaggcaagt ctttcttctt attattcttt aacctttctt aa                             762
```

```
<210> SEQ ID NO 66
<211> LENGTH: 771
<212> TYPE: DNA
<213> ORGANISM: Brassica napus

<400> SEQUENCE: 66
atggcttcct gtagcctagg agttcctaag attaaaatct cagcagtaga cctcagtaga           60
gtaagatctg gaagcttaca gttacagata ccatgcaatc aaagagtgtt gattggtcaa          120
aggctggtta agtacttgag tctcagggca actcttggtt ctgtgaaagc tccccaagcg          180
tctactgtca cagctgccga atctgcagct actgttgaag tagaagatgc tgaaatgacc          240
aagccatctc cattgaacgc tcagcttgtt cccagccct ctgaggtgga agctcttgta          300
actgaaatat gcgactcctc atcaattgca gagtttgaat tgaaactggg gggtttccgc          360
ctgtatgtag caacgaactt agctgacaac aacagtagtc caccacaacc tcagccaatt          420
cctgctgccg ttgctgcaag tgcaaccacg gagggtgttg attcgaatgg atcagcttcc          480
tctacttcac tggctatcac aaaaccaaca tcctcagctg ctgatcaggg tttggtgatt          540
ctccaatctc aaaagtagg gttcttcagg agatccaaaa ccttaaaggg taaacgcact          600
ccttcgtcat gtaaagagaa agaccaagtg aaagaaggtc aagttctgtg ctacattgaa          660
caactcggtg ccagtttcc aatcgagtct gatgttaccg gcgaggttgt caaaatactc          720
agagaggatg gaggcaagtc tttcttctta ttattcttta acctttctta a                   771
```

```
<210> SEQ ID NO 67
<211> LENGTH: 765
<212> TYPE: DNA
<213> ORGANISM: Brassica napus

<400> SEQUENCE: 67
atggcttcct gtagcctagg agttccgaag attaaaatct cagcggtaga cgtgagtaga           60
ttaagatctg gaagcttaca gattccatac agtcagagat cattgtttgt tcaaaggcag          120
gttaagtact ttagtctgag acaagtgtt ggatctttga aagctctcca agtgtctact          180
gtcacagctg cggaaacagc agctagtgca gaagtagaag atgctgaaaa gaccaagtca          240
tctccgttga acgctcagct cgttcccaag ccctctgagg tggaagctct tgtcactgag          300
atatgtgatt cctcatcaat tgcagagttt gaactgaaac tagggggttt ccgcctatat          360
gtagcaagga acttagctga caacaacatt agtccaccac aacctcagcc aattcctgct          420
gccttttctg cagctaatga aagtgctggt tcgaatggat cagcttcctc tacttcattg          480
```

-continued

```
gctatcacga aaccagcatc ttcagctgct gatcagggtt tgattattct ccagtctcca      540
aaagtaggat tcttcaggag atccaaaacc ataaagggta aacgcactcc ttcctcctgt      600
aaagagaaag accaagtgaa agaaggtcaa gttctgtgct acattgaaca gctcggtggc      660
cagttcccta tcgagtctga tgttacgggc gaggttgtca agatactccg agaggatgga      720
ggcaagtctt tcttcttctt taacctttc atgttttttt cttaa                      765
```

```
<210> SEQ ID NO 68
<211> LENGTH: 270
<212> TYPE: PRT
<213> ORGANISM: Brassica napus

<400> SEQUENCE: 68

Met Glu Ser Ser Ala Ala Leu Gly Ser Leu Arg Gln Ser Leu Gly Ser
1               5                   10                  15

Ala Val Asn Val His Ser Leu Ser Gly Asn Trp Ser Pro Ser Gly Asn
                20                  25                  30

Ser Cys Ala Pro Arg Trp Ser Leu Phe Asn Arg Asn Met Leu Val Leu
            35                  40                  45

Arg Ala Asp Ser Ser Lys Ser Ser Thr Thr Thr Thr Lys Thr Asp Glu
        50                  55                  60

Ser Ser Asp Ala Ser Asn Gly Thr Lys Thr Lys Thr Val Arg Arg Thr
65                  70                  75                  80

Thr Phe Pro Lys Glu Val Glu Ala Leu Val His Glu Met Cys Asp Glu
                85                  90                  95

Thr Glu Val Gly Asp Phe Glu Met Asn Leu Lys Arg Lys Ile Gly Leu
            100                 105                 110

Ala Glu Thr Pro Ile Pro Val Pro Asp Ile Ser Pro Ser Val Ala Pro
        115                 120                 125

Pro Ile Pro Ser Glu Pro Met Asn Lys Ser Val Ser Ala Ser Ala Asp
    130                 135                 140

Ala Ser Pro Ser Lys Ala Lys Pro Ala Ser Glu Lys Val Ser Pro Phe
145                 150                 155                 160

Ile Asn Ala Ala Tyr Arg Lys Ser Ser Lys Leu Ala Ala Leu Glu Ala
                165                 170                 175

Ala Gly Ser Asn Asn Tyr Val Leu Val Thr Ser Pro Ser Val Gly Lys
            180                 185                 190

Phe Gln Arg Ser Arg Thr Val Lys Gly Lys Lys Gln Gly Pro Thr Cys
        195                 200                 205

Lys Glu Gly Asp Ala Ile Lys Glu Gly Gln Val Ile Gly Tyr Leu His
    210                 215                 220

Gln Leu Gly Lys Glu Leu Pro Val Thr Ser Asp Val Ala Gly Glu Val
225                 230                 235                 240

Leu Lys Leu Leu Ser Asp Asp Gly Asp Ser Val Gly Tyr Gly Glu Pro
                245                 250                 255

Leu Val Ala Val Leu Pro Ser Phe His Asp Ile Asn Ile Gln
                260                 265                 270
```

```
<210> SEQ ID NO 69
<211> LENGTH: 258
<212> TYPE: PRT
<213> ORGANISM: Brassica napus

<400> SEQUENCE: 69

Met Glu Ser Leu Gly Ser Leu His Gln Ser Leu Gly Ser Ala Val Asn
```

-continued

```
1               5                   10                  15
Val His Ser Leu Ser Gly Lys Ser Cys Ala Pro Pro Arg Trp Ser Leu
            20                  25                  30

Phe Asn Arg Asn Thr Leu Val Leu Arg Ala Glu Ser Ser Lys Ser Ser
            35                  40                  45

Thr Thr Thr Lys Thr Asp Glu Ser Ser Asp Ala Ser Asn Gly Thr Lys
    50                  55                  60

Thr Val Arg Arg Thr Thr Phe Pro Lys Glu Val Glu Ala Leu Val His
65                  70                  75                  80

Glu Met Cys Asp Glu Thr Glu Val Gly Asp Phe Glu Met Asn Leu Lys
                85                  90                  95

Arg Lys Ile Gly Leu Ala Glu Thr Pro Ile Pro Val Pro Asp Ile Ser
                100                 105                 110

Pro Ser Val Ala Pro Pro Ile Pro Ser Glu Pro Met Asn Lys Ser Val
                115                 120                 125

Ser Ser Ser Ala Ala Ala Ala Thr Ser Pro Ser Lys Ala Lys Pro Ala
    130                 135                 140

Val Ser Pro Phe Ile Asn Ala Ala Tyr Arg Lys Ser Ser Lys Leu Ala
145                 150                 155                 160

Ala Leu Asp Ala Ser Gly Ser Asn Asn Tyr Val Leu Val Thr Ser Pro
                165                 170                 175

Ser Val Gly Lys Phe Gln Arg Ser Arg Thr Val Lys Gly Lys Lys Gln
                180                 185                 190

Gly Pro Thr Cys Lys Glu Gly Asp Ala Ile Lys Glu Gly Gln Val Ile
                195                 200                 205

Gly Tyr Leu His Gln Leu Gly Lys Glu Leu Pro Val Thr Ser Asp Val
                210                 215                 220

Ala Gly Glu Val Leu Lys Leu Leu Ser Asp Asp Gly Asp Ser Val Gly
225                 230                 235                 240

Tyr Gly Glu Pro Leu Val Ala Val Leu Pro Ser Phe His Asp Ile Asn
                245                 250                 255

Ile Gln
```

<210> SEQ ID NO 70
<211> LENGTH: 249
<212> TYPE: PRT
<213> ORGANISM: Brassica napus

<400> SEQUENCE: 70

```
Met Ala Ser Cys Ser Leu Gly Val Pro Lys Ile Lys Ile Ser Ala Val
1               5                   10                  15

Asp Val Ser Arg Val Arg Ser Gly Arg Leu Gln Ile Pro Tyr Ser Gln
            20                  25                  30

Arg Ser Leu Phe Ala Gln Arg Gln Val Lys Tyr Leu Ser Leu Arg Thr
            35                  40                  45

Ser Val Gly Ser Leu Lys Ala Leu Gln Val Ser Thr Val Thr Ala Val
    50                  55                  60

Glu Thr Ser Ala Thr Val Glu Val Glu Asp Ala Glu Lys Thr Lys Ser
65                  70                  75                  80

Ser Pro Leu Asn Ala Gln Leu Val Pro Lys Pro Ser Glu Val Glu Ala
                85                  90                  95

Leu Val Thr Glu Ile Cys Asp Ser Ser Ser Ile Ala Glu Phe Glu Leu
                100                 105                 110

Lys Leu Gly Gly Phe Arg Leu Tyr Val Ala Arg Asn Leu Ala Asp Asn
```

-continued

```
              115                 120                 125
Asn Ile Ser Pro Pro Gln Pro Gln Pro Thr Pro Ala Ala Leu Ser Ala
    130                 135                 140
Asn Ala Val Thr Glu Ser Ala Asp Ser Asn Gly Ser Ala Ser Ser Thr
145                 150                 155                 160
Ser Leu Ala Ile Thr Lys Pro Ala Ser Ser Ala Ala Asp Gln Gly Leu
                165                 170                 175
Ile Ile Leu Gln Ser Pro Lys Val Gly Phe Phe Arg Arg Ser Lys Thr
                180                 185                 190
Ile Lys Gly Lys Arg Thr Pro Ser Ser Cys Lys Glu Lys Asp Gln Val
                195                 200                 205
Lys Glu Gly Gln Val Leu Cys Tyr Ile Glu Gln Leu Gly Gly Gln Phe
    210                 215                 220
Pro Ile Glu Ser Asp Val Thr Gly Glu Val Val Lys Ile Leu Arg Glu
225                 230                 235                 240
Asp Gly Gly Lys Ser Tyr Leu Leu Leu
                245
```

```
<210> SEQ ID NO 71
<211> LENGTH: 253
<212> TYPE: PRT
<213> ORGANISM: Brassica napus

<400> SEQUENCE: 71

Met Ala Ser Cys Ser Leu Ala Val Pro Lys Ile Lys Ile Ser Ala Ala
1               5                  10                  15
Val Asp Leu Ser Leu Val Arg Ser Gly Arg Phe Gln Ile Pro Cys Asn
                20                  25                  30
Gln Arg Val Leu Leu Ile Gly Gln Arg Pro Val Lys Tyr Leu Ser Leu
            35                  40                  45
Arg Ala Thr Leu Gly Ser Val Gln Ala Ser Thr Val Thr Ala Ala Glu
    50                  55                  60
Ser Ala Ala Thr Val Glu Val Glu Asp Thr Glu Thr Thr Lys Pro Ser
65                  70                  75                  80
Pro Leu Asn Ala Gln Leu Val Pro Lys Pro Ser Glu Val Glu Ala Leu
                85                  90                  95
Val Thr Glu Ile Cys Asp Ser Ser Ser Ile Ala Glu Phe Glu Leu Lys
                100                 105                 110
Leu Gly Gly Phe Arg Leu Tyr Val Ala Arg Asn Leu Ala Asp Asn Asn
            115                 120                 125
Ser Ser Pro Pro Gln Pro Gln Pro Ile Pro Ala Ala Val Ala Ala Ser
    130                 135                 140
Ala Thr Thr Glu Ser Val Asp Ser Asn Gly Ser Ala Ser Ser Thr Ser
145                 150                 155                 160
Leu Ala Ile Thr Lys Pro Thr Ser Ser Ala Ala Asp Gln Gly Leu Val
                165                 170                 175
Ile Leu Gln Ser Pro Lys Val Gly Phe Phe Arg Arg Ser Lys Thr Ile
            180                 185                 190
Lys Gly Lys Arg Thr Pro Ser Ser Cys Lys Glu Lys Asp Gln Val Lys
            195                 200                 205
Glu Gly Gln Val Leu Cys Tyr Ile Glu Gln Leu Gly Gly Gln Phe Pro
    210                 215                 220
Ile Glu Ser Asp Val Thr Gly Glu Val Val Lys Ile Leu Arg Glu Asp
225                 230                 235                 240
```

-continued

```
Gly Gly Lys Ser Phe Phe Leu Leu Phe Phe Asn Leu Ser
            245                 250

<210> SEQ ID NO 72
<211> LENGTH: 256
<212> TYPE: PRT
<213> ORGANISM: Brassica napus

<400> SEQUENCE: 72

Met Ala Ser Cys Ser Leu Gly Val Pro Lys Ile Lys Ile Ser Ala Val
1               5                   10                  15

Asp Leu Ser Arg Val Arg Ser Gly Ser Leu Gln Leu Gln Ile Pro Cys
            20                  25                  30

Asn Gln Arg Val Leu Ile Gly Gln Arg Leu Val Lys Tyr Leu Ser Leu
        35                  40                  45

Arg Ala Thr Leu Gly Ser Val Lys Ala Pro Gln Ala Ser Thr Val Thr
    50                  55                  60

Ala Ala Glu Ser Ala Ala Thr Val Glu Val Glu Asp Ala Glu Met Thr
65                  70                  75                  80

Lys Pro Ser Pro Leu Asn Ala Gln Leu Val Pro Lys Pro Ser Glu Val
                85                  90                  95

Glu Ala Leu Val Thr Glu Ile Cys Asp Ser Ser Ser Ile Ala Glu Phe
            100                 105                 110

Glu Leu Lys Leu Gly Gly Phe Arg Leu Tyr Val Ala Thr Asn Leu Ala
        115                 120                 125

Asp Asn Asn Ser Ser Pro Pro Gln Pro Gln Pro Ile Pro Ala Ala Val
    130                 135                 140

Ala Ala Ser Ala Thr Thr Glu Gly Val Asp Ser Asn Gly Ser Ala Ser
145                 150                 155                 160

Ser Thr Ser Leu Ala Ile Thr Lys Pro Thr Ser Ser Ala Ala Asp Gln
                165                 170                 175

Gly Leu Val Ile Leu Gln Ser Pro Lys Val Gly Phe Phe Arg Arg Ser
            180                 185                 190

Lys Thr Leu Lys Gly Lys Arg Thr Pro Ser Ser Cys Lys Glu Lys Asp
        195                 200                 205

Gln Val Lys Glu Gly Gln Val Leu Cys Tyr Ile Glu Gln Leu Gly Gly
    210                 215                 220

Gln Phe Pro Ile Glu Ser Asp Val Thr Gly Glu Val Val Lys Ile Leu
225                 230                 235                 240

Arg Glu Asp Gly Gly Lys Ser Phe Phe Leu Leu Phe Phe Asn Leu Ser
            245                 250                 255

<210> SEQ ID NO 73
<211> LENGTH: 254
<212> TYPE: PRT
<213> ORGANISM: Brassica napus

<400> SEQUENCE: 73

Met Ala Ser Cys Ser Leu Gly Val Pro Lys Ile Lys Ile Ser Ala Val
1               5                   10                  15

Asp Val Ser Arg Leu Arg Ser Gly Ser Leu Gln Ile Pro Tyr Ser Gln
            20                  25                  30

Arg Ser Leu Phe Val Gln Arg Gln Val Lys Tyr Phe Ser Leu Arg Thr
        35                  40                  45

Ser Val Gly Ser Leu Lys Ala Leu Gln Val Ser Thr Val Thr Ala Ala
    50                  55                  60
```

-continued

```
Glu Thr Ala Ala Ser Ala Glu Val Glu Asp Ala Glu Lys Thr Lys Ser
65                  70                  75                  80

Ser Pro Leu Asn Ala Gln Leu Val Pro Lys Pro Ser Glu Val Glu Ala
                85                  90                  95

Leu Val Thr Glu Ile Cys Asp Ser Ser Ser Ile Ala Glu Phe Glu Leu
            100                 105                 110

Lys Leu Gly Gly Phe Arg Leu Tyr Val Ala Arg Asn Leu Ala Asp Asn
        115                 120                 125

Asn Ile Ser Pro Pro Gln Pro Gln Pro Ile Pro Ala Ala Phe Ser Ala
        130                 135                 140

Ala Asn Glu Ser Ala Gly Ser Asn Gly Ser Ala Ser Ser Thr Ser Leu
145                 150                 155                 160

Ala Ile Thr Lys Pro Ala Ser Ser Ala Ala Asp Gln Gly Leu Ile Ile
            165                 170                 175

Leu Gln Ser Pro Lys Val Gly Phe Phe Arg Arg Ser Lys Thr Ile Lys
            180                 185                 190

Gly Lys Arg Thr Pro Ser Ser Cys Lys Glu Lys Asp Gln Val Lys Glu
        195                 200                 205

Gly Gln Val Leu Cys Tyr Ile Glu Gln Leu Gly Gly Gln Phe Pro Ile
        210                 215                 220

Glu Ser Asp Val Thr Gly Glu Val Val Lys Ile Leu Arg Glu Asp Gly
225                 230                 235                 240

Gly Lys Ser Phe Phe Phe Phe Asn Leu Phe Met Phe Phe Ser
                245                 250
```

<210> SEQ ID NO 74
<211> LENGTH: 876
<212> TYPE: DNA
<213> ORGANISM: Glycine max

<400> SEQUENCE: 74

```
atggaatcct ccgctgccat tcgatctttt cactatccca taggcactat gtcccatgtg      60
cgagcctccc ttgagaagca ggctgtagtt cccattcata atgccggatg gaactctaaa     120
agtaggcttt tcatccagca tttggcatat ggtcagaagc acattaattc ccacacgaag     180
gggaaaaaca cactaatttc atgtggaaaa acagctgaag ctatcaacgc atccaaatct     240
gatgcttctt cagataacac tccacaaggc tcattggaga aaaagccttt gcaaactgct     300
acttttccta atggatttga ggctttggta ttagaggtct gtgatgagac tgaaattgct     360
gaactgaaag taaaggttgg agattttgaa atgcatatta agcgaaacat tggagcaaca     420
aaggttcctt tgtctaacat ttcaccaact acaccaccac ctattccaag taaacctatg     480
gatgaatcag cacccggtag cctgccacct tcaccaccaa aatcatctcc agaaaagaac     540
aacccatttg caaatgtttc caaagagaaa tcaccaagat tggcagcatt ggaggcttct     600
ggtaccaata cctatgtctt agtatcatct cccacggttg gcttattccg aagaggtaga     660
acagtgaaag ggaagaagca acctcctatc tgtaaagagg gtgatgtaat caaagaaggg     720
caagtcatag ggtatttgga tcaatttggc actggacttc ctattaagtc tgatgtggct     780
ggagaagtgt tgaaactact tgttgaggat ggagagcctg ttggttatgg agaccctctt     840
attgctgtgt tgccatcttt tcatgacatc aagtga                             876
```

<210> SEQ ID NO 75
<211> LENGTH: 291
<212> TYPE: PRT
<213> ORGANISM: Glycine max

<400> SEQUENCE: 75

```
Met Glu Ser Ser Ala Ala Ile Arg Ser Phe His Tyr Pro Ile Gly Thr
1               5                   10                  15

Met Ser His Val Arg Ala Ser Leu Glu Lys Gln Ala Val Val Pro Ile
                20                  25                  30

His Asn Ala Gly Trp Asn Ser Lys Ser Arg Leu Phe Ile Gln His Leu
            35                  40                  45

Ala Tyr Gly Gln Lys His Ile Asn Ser His Thr Lys Gly Lys Asn Thr
        50                  55                  60

Leu Ile Ser Cys Gly Lys Thr Ala Glu Ala Ile Asn Ala Ser Lys Ser
65                  70                  75                  80

Asp Ala Ser Ser Asp Asn Thr Pro Gln Gly Ser Leu Glu Lys Lys Pro
                85                  90                  95

Leu Gln Thr Ala Thr Phe Pro Asn Gly Phe Glu Ala Leu Val Leu Glu
                100                 105                 110

Val Cys Asp Glu Thr Glu Ile Ala Glu Leu Lys Val Lys Val Gly Asp
            115                 120                 125

Phe Glu Met His Ile Lys Arg Asn Ile Gly Ala Thr Lys Val Pro Leu
        130                 135                 140

Ser Asn Ile Ser Pro Thr Thr Pro Pro Ile Pro Ser Lys Pro Met
145                 150                 155                 160

Asp Glu Ser Ala Pro Gly Ser Leu Pro Pro Ser Pro Pro Lys Ser Ser
                165                 170                 175

Pro Glu Lys Asn Asn Pro Phe Ala Asn Val Ser Lys Glu Lys Ser Pro
                180                 185                 190

Arg Leu Ala Ala Leu Glu Ala Ser Gly Thr Asn Thr Tyr Val Leu Val
            195                 200                 205

Ser Ser Pro Thr Val Gly Leu Phe Arg Arg Gly Arg Thr Val Lys Gly
        210                 215                 220

Lys Lys Gln Pro Pro Ile Cys Lys Glu Gly Asp Val Ile Lys Glu Gly
225                 230                 235                 240

Gln Val Ile Gly Tyr Leu Asp Gln Phe Gly Thr Gly Leu Pro Ile Lys
                245                 250                 255

Ser Asp Val Ala Gly Glu Val Leu Lys Leu Leu Val Glu Asp Gly Glu
                260                 265                 270

Pro Val Gly Tyr Gly Asp Pro Leu Ile Ala Val Leu Pro Ser Phe His
            275                 280                 285

Asp Ile Lys
    290
```

<210> SEQ ID NO 76
<211> LENGTH: 876
<212> TYPE: DNA
<213> ORGANISM: Glycine max

<400> SEQUENCE: 76

```
atggaatcct cgcctgccat tcgttccttt cactatccca tgggcactat gtcccatgtg      60
cgagcctgcc ttgagaagca agctgtactc cccatccata atgccagatg gaactctaaa     120
cgtaggcttt tcatccagca tttggcatat ggtcagaagc acattaattc ccacatgaag     180
gggaaaagca cactagtctc atctgcaaaa acagctgaag ctatcaacac atccaattct     240
gatgcttctt cagataacac cccccaaggc tcattggaga aaaagccttt gcaaactgct     300
acttttccta atggatttga ggctttggta ttagaggtct gtgatgagac tgaaattgct     360
```

-continued

```
gaactgaaag taaaggttgg agattttgaa atgcatatta agcgaaacat tggagcaaca    420
aaggttcctt tgtctaacat ttcaccgact acaccaccac ctatcccaag taaacctatg    480
gatgaatcag cacccaatag cctgccacca tcaccaccaa aatcatctcc tgaaaagaac    540
aacccatttg caaatgtttc caaagagaaa tcaccaaaat tggcagcatt ggaggcttct    600
gggaccaata cctatgtctt agtaacatct cccacggttg gcttattccg aagaggtaga    660
acagtgaaag ggaagaagca acctcctatc tgtaaagagg gtgatgtaat caaagaaggg    720
caagtcatag ggtatttgga tcagtttggc actggacttc ctatcaggtc tgatgtggct    780
ggagaagtgt tgaagctact tgttgaggat ggagagcctg ttggttatgg agaccgtctt    840
attgctgtct tgccttcttt tcatgatatc aagtga                              876
```

```
<210> SEQ ID NO 77
<211> LENGTH: 291
<212> TYPE: PRT
<213> ORGANISM: Glycine max

<400> SEQUENCE: 77

Met Glu Ser Ser Pro Ala Ile Arg Ser Phe His Tyr Pro Met Gly Thr
1               5                   10                  15

Met Ser His Val Arg Ala Cys Leu Glu Lys Gln Ala Val Leu Pro Ile
                20                  25                  30

His Asn Ala Arg Trp Asn Ser Lys Arg Arg Leu Phe Ile Gln His Leu
            35                  40                  45

Ala Tyr Gly Gln Lys His Ile Asn Ser His Met Lys Gly Lys Ser Thr
        50                  55                  60

Leu Val Ser Ser Ala Lys Thr Ala Glu Ala Ile Asn Thr Ser Asn Ser
65                  70                  75                  80

Asp Ala Ser Ser Asp Asn Thr Pro Gln Gly Ser Leu Glu Lys Lys Pro
                85                  90                  95

Leu Gln Thr Ala Thr Phe Pro Asn Gly Phe Glu Ala Leu Val Leu Glu
            100                 105                 110

Val Cys Asp Glu Thr Glu Ile Ala Glu Leu Lys Val Lys Val Gly Asp
        115                 120                 125

Phe Glu Met His Ile Lys Arg Asn Ile Gly Ala Thr Lys Val Pro Leu
    130                 135                 140

Ser Asn Ile Ser Pro Thr Thr Pro Pro Ile Pro Ser Lys Pro Met
145                 150                 155                 160

Asp Glu Ser Ala Pro Asn Ser Leu Pro Pro Ser Pro Pro Lys Ser Ser
                165                 170                 175

Pro Glu Lys Asn Asn Pro Phe Ala Asn Val Ser Lys Glu Lys Ser Pro
            180                 185                 190

Lys Leu Ala Ala Leu Glu Ala Ser Gly Thr Asn Thr Tyr Val Leu Val
        195                 200                 205

Thr Ser Pro Thr Val Gly Leu Phe Arg Arg Gly Arg Thr Val Lys Gly
    210                 215                 220

Lys Lys Gln Pro Pro Ile Cys Lys Glu Gly Asp Val Ile Lys Glu Gly
225                 230                 235                 240

Gln Val Ile Gly Tyr Leu Asp Gln Phe Gly Thr Gly Leu Pro Ile Arg
                245                 250                 255

Ser Asp Val Ala Gly Glu Val Leu Lys Leu Leu Val Glu Asp Gly Glu
            260                 265                 270

Pro Val Gly Tyr Gly Asp Arg Leu Ile Ala Val Leu Pro Ser Phe His
```

-continued

```
                275               280               285

Asp Ile Lys
    290

<210> SEQ ID NO 78
<211> LENGTH: 897
<212> TYPE: DNA
<213> ORGANISM: Glycine max

<400> SEQUENCE: 78 atgctttca ccttcttcac ttcactaccc tttacccttc tctgtgacac acactctttc       60
tgcttcacgt tttcaatggc ttcatgtagt atagggaccc caaatattaa agtattgaac      120
ttgcactttg gtggaaaaaa agttggcctc tcacgacaat ttggtacaag aagctggatc      180
agtaggctgc agtatactag tttggttatg tcacgacaga cagttaggtt tttagcatca      240
tccaatggcc catcgacaga gatccaattt gctgcaaggt cagaaggttc tgaagagatt      300
agatcttcag gtctgacaag tgagcttatt cctaatatta tgaggtgga gttcctgctc       360 acaaaattat gcgacacaag ttcaattggg gagttagatt taaaacttgc tggatttcac      420
ctgcatgtag tgagggattt gactgaaaaa actaaaactc tacctcctct gattcctgct      480
tctgtaagta taattaatgt cacagaaaca cctaaaacaa atggatcagt tcctacaact      540
tcgttggctg tctcgaagcc agtagaccca gtaccttctt cagggtccat ccagagattc      600
ctagacaaag ctgctgatga aggcttggta ataattcagt ctccaaaggt gggtttcttt      660
aggagatcac ggacgataaa ggggaagcgt gctccaccat catgtaaaga gaagcaaaat      720
gttgaggagg ggcaagtgat ttgttatatt gaacagcttg gtggtgagct gccaattgag      780
tccgatgtgt cgggagaggt catcaagata ctacgacagg atggcgaccc tgttggatat      840
ggtgatgcac ttgttgcaat attgccatca tttcctggaa taaagaagct tcaataa        897

<210> SEQ ID NO 79
<211> LENGTH: 298
<212> TYPE: PRT
<213> ORGANISM: Glycine max

<400> SEQUENCE: 79

Met Leu Phe Thr Phe Phe Thr Ser Leu Pro Phe Thr Leu Leu Cys Asp
1               5                   10                  15

Thr His Ser Phe Cys Phe Thr Phe Ser Met Ala Ser Cys Ser Ile Gly
            20                  25                  30

Thr Pro Asn Ile Lys Val Leu Asn Leu His Phe Gly Gly Lys Lys Val
        35                  40                  45

Gly Leu Ser Arg Gln Phe Gly Thr Arg Ser Trp Ile Ser Arg Leu Gln
    50                  55                  60

Tyr Thr Ser Leu Val Met Ser Arg Gln Thr Val Arg Phe Leu Ala Ser
65                  70                  75                  80

Ser Asn Gly Pro Ser Thr Glu Ile Gln Phe Ala Ala Arg Ser Glu Gly
                85                  90                  95

Ser Glu Glu Ile Arg Ser Ser Gly Leu Thr Ser Glu Leu Ile Pro Asn
            100                 105                 110

Ile Asn Glu Val Glu Phe Leu Leu Thr Lys Leu Cys Asp Thr Ser Ser
        115                 120                 125

Ile Gly Glu Leu Asp Leu Lys Leu Ala Gly Phe His Leu His Val Val
    130                 135                 140

Arg Asp Leu Thr Glu Lys Thr Lys Thr Leu Pro Pro Leu Ile Pro Ala
```

-continued

```
145                150                155                160
Ser Val Ser Ile Ile Asn Val Thr Glu Thr Pro Lys Thr Asn Gly Ser
                165                170                175

Val Pro Thr Thr Ser Leu Ala Val Ser Lys Pro Val Asp Pro Val Pro
            180                185                190

Ser Ser Gly Ser Ile Gln Arg Phe Leu Asp Lys Ala Ala Asp Glu Gly
            195                200                205

Leu Val Ile Ile Gln Ser Pro Lys Val Gly Phe Phe Arg Arg Ser Arg
        210                215                220

Thr Ile Lys Gly Lys Arg Ala Pro Pro Ser Cys Lys Glu Lys Gln Asn
225                230                235                240

Val Glu Glu Gly Gln Val Ile Cys Tyr Ile Glu Gln Leu Gly Gly Glu
                245                250                255

Leu Pro Ile Glu Ser Asp Val Ser Gly Glu Val Ile Lys Ile Leu Arg
            260                265                270

Gln Asp Gly Asp Pro Val Gly Tyr Gly Asp Ala Leu Val Ala Ile Leu
        275                280                285

Pro Ser Phe Pro Gly Ile Lys Lys Leu Gln
    290                295
```

```
<210> SEQ ID NO 80
<211> LENGTH: 831
<212> TYPE: DNA
<213> ORGANISM: Glycine max

<400> SEQUENCE: 80 atggttatt  tgtgtcattaa  ttcaatggca  ggtagtatag  ggaccccaaa  tattaaagca       60
ttgaacttgc  actttggtgg  aaaaaaagtt  ggcctttcac  aacaatttgg  tacaagaagc      120
tggatcagta  agcagtcact  gcagtacact  agtttggtta  tgtcacgaca  gaaagttagg      180
ttttcaccga  cagagatcca  atttgttaca  aggtcagaag  gttctgaaga  ggttaaatct      240
tcaggtttga  caagtgagct  tattcctaat  cttattgagg  tggagttcct  gctcacaaaa      300
ttatgcgaca  caagttcaat  tggggagtta  gatttaaaac  ttgctgggtt  tcacctgcat      360
gtagtgaggg  atttgactga  aaaaactaaa  actctacctc  ctccaattcc  tgcttctgaa      420
agtataatta  atgtcacaga  aacacctaaa  acaaatggat  cagtttctac  aacttcgttg      480
gctgtctcga  agccagtaga  cccaatacct  tcttctgggt  ccatccagag  attcctaaac      540
aaagctgctg  atgaaggctt  ggtaataatt  cagtctccaa  aggtgggttt  ctttaggaga      600
tcacggacga  taaagggggag  gcgtgctcca  ccatcatgta  aagagaaaca  aaatgttgag      660
gaggggcaag  tgatttgtta  tattgaacag  cttggtggtg  agctgccaat  tgagtctgat      720
gtgtcgggag  aggtcatcaa  gatcctacaa  aaggacggcg  atcctgttgg  atatggtgac      780
gcacttgttg  caatattgcc  atcatttcct  ggaataaaga  agcttcaata  g                831
```

```
<210> SEQ ID NO 81
<211> LENGTH: 276
<212> TYPE: PRT
<213> ORGANISM: Glycine max

<400> SEQUENCE: 81

Met Val Ile Cys Val Ile Asn Ser Met Ala Gly Ser Ile Gly Thr Pro
1                5                10                15

Asn Ile Lys Ala Leu Asn Leu His Phe Gly Gly Lys Lys Val Gly Leu
            20                25                30
```

```
Ser Gln Gln Phe Gly Thr Arg Ser Trp Ile Ser Lys Gln Ser Leu Gln
    35                  40                  45

Tyr Thr Ser Leu Val Met Ser Arg Gln Lys Val Arg Phe Ser Pro Thr
    50                  55                  60

Glu Ile Gln Phe Val Thr Arg Ser Glu Gly Ser Glu Glu Val Lys Ser
65                  70                  75                  80

Ser Gly Leu Thr Ser Glu Leu Ile Pro Asn Leu Ile Glu Val Glu Phe
                85                  90                  95

Leu Leu Thr Lys Leu Cys Asp Thr Ser Ser Ile Gly Glu Leu Asp Leu
            100                 105                 110

Lys Leu Ala Gly Phe His Leu His Val Val Arg Asp Leu Thr Glu Lys
            115                 120                 125

Thr Lys Thr Leu Pro Pro Pro Ile Pro Ala Ser Glu Ser Ile Ile Asn
    130                 135                 140

Val Thr Glu Thr Pro Lys Thr Asn Gly Ser Val Ser Thr Thr Ser Leu
145                 150                 155                 160

Ala Val Ser Lys Pro Val Asp Pro Ile Pro Ser Ser Gly Ser Ile Gln
                165                 170                 175

Arg Phe Leu Asn Lys Ala Ala Asp Glu Gly Leu Val Ile Ile Gln Ser
            180                 185                 190

Pro Lys Val Gly Phe Phe Arg Arg Ser Arg Thr Ile Lys Gly Arg Arg
            195                 200                 205

Ala Pro Pro Ser Cys Lys Glu Lys Gln Asn Val Glu Glu Gly Gln Val
    210                 215                 220

Ile Cys Tyr Ile Glu Gln Leu Gly Gly Glu Leu Pro Ile Glu Ser Asp
225                 230                 235                 240

Val Ser Gly Glu Val Ile Lys Ile Leu Gln Lys Asp Gly Asp Pro Val
                245                 250                 255

Gly Tyr Gly Asp Ala Leu Val Ala Ile Leu Pro Ser Phe Pro Gly Ile
                260                 265                 270

Lys Lys Leu Gln
        275

<210> SEQ ID NO 82
<211> LENGTH: 287
<212> TYPE: PRT
<213> ORGANISM: Amborella trichopoda

<400> SEQUENCE: 82

Met Glu Ala Ala Ala Thr Leu Arg Ser Ile His Val Ser Gly Ala Thr
1               5                   10                  15

Ile Ala His Ala Gln Ser Phe Cys Asp Thr Ser Asp Ala Val Lys Ile
            20                  25                  30

Phe Arg Val Val Ser Cys Arg Ser Phe Ser His Arg His Arg Val
            35                  40                  45

Phe Pro Ser Pro Val Asn Arg Lys Val Pro Leu Val Pro Tyr Ile Lys
    50                  55                  60

Ala Ser Lys Thr Val Leu Ala Val Ala Ser Asp Ser Val Thr Ser Glu
65                  70                  75                  80

Ser Ser Ser Asp Gly Lys Leu Glu Lys Lys Ser Leu His Lys Thr Thr
                85                  90                  95

Phe Pro Asp Gly Phe Glu Ala Trp Val Ser Asp Ile Cys Asp Glu Thr
            100                 105                 110

Glu Val Ala Glu Leu Lys Leu Lys Val Gly Asp Phe Glu Met His Leu
            115                 120                 125
```

```
Arg Arg Asn Ile Gly Asn Thr Lys Ala Pro Ala Pro Ser Pro Ile Val
    130             135             140
```

```
Ser Pro Ser Thr Pro Pro Pro Val Pro Thr Lys Pro Met Val Glu Ser
145             150             155             160
```

```
Ala Pro Ala Thr Ala Pro Ser Val Thr Gln Lys Ala Pro Pro Val Ala
            165             170             175
```

```
Ser Ser Pro Phe Ser Asn Val Ser Ala Lys Ala Ser Lys Leu Ala Ser
            180             185             190
```

```
Leu Asp Ser Asp Gly Ala Asn Ala Tyr Val Ile Val Ala Ser Pro Thr
            195             200             205
```

```
Val Gly Lys Phe Arg Thr Gly Arg Thr Val Lys Gly Lys Arg Gln Pro
    210             215             220
```

```
Pro Val Ala Lys Glu Gly Asp Val Ile Lys Glu Asp Gln Ile Ile Gly
225             230             235             240
```

```
Tyr Leu Asp Gln Phe Gly Ser Glu Leu Pro Val Lys Ser Asp Val Ala
            245             250             255
```

```
Gly Glu Val Leu Lys Ile Leu Phe Arg Asp Gly Glu Ala Val Gly Tyr
            260             265             270
```

```
Gly Asp Pro Leu Ile Ala Val Leu Pro Ser Phe His Gly Ile Lys
            275             280             285
```

<210> SEQ ID NO 83
<211> LENGTH: 281
<212> TYPE: PRT
<213> ORGANISM: Amborella trichopoda

<400> SEQUENCE: 83

```
Met Ala Leu Ser Ala Ser Ser Ser Phe Gly Pro Leu Ala Lys Val Glu
1               5               10              15
```

```
Leu Ser Thr Leu Asn Leu Pro Asn His Ser Thr Cys Lys Tyr Ile Gly
            20              25              30
```

```
Pro Pro Asp Leu Arg Met Met Arg Arg Arg Cys Thr Gly Pro Gln Ser
            35              40              45
```

```
Leu His Tyr Glu Gly Phe Arg Met Gln Ser Arg Asn Leu Val Lys Pro
    50              55              60
```

```
Val Ser Leu Leu Ser Gly Pro Ser Ala Glu Ala Met Ser Thr Ser Asp
65              70              75              80
```

```
Asp Gly Ser Lys Glu Asp Pro Lys Gly Lys Ser Ser Pro Ile Val Pro
            85              90              95
```

```
Asn Ser Leu Glu Val Gln Ser Leu Val Lys Glu Ile Cys Glu Thr Thr
            100             105             110
```

```
Ser Ile Ala Glu Phe Glu Leu Lys Leu Asp Gly Phe Arg Leu Tyr Val
            115             120             125
```

```
Ala Arg Asp Ile Asn Gly Lys Asp Met Pro Pro Pro Thr Ser Pro Ser
    130             135             140
```

```
Ser Pro Ile His Thr Thr Thr Asn Val Ala Glu Glu Thr Leu Asp Ser
145             150             155             160
```

```
Asn Gly Ser Ala Ser Pro Pro Pro Thr Ile Ser Lys Pro Glu Pro Pro
            165             170             175
```

```
Leu Thr Arg Ile Gln Arg Leu Leu Glu Ala Ala Ala Asp Glu Gly Leu
            180             185             190
```

```
Val Ile Ile Asn Ser Pro Lys Val Gly Tyr Phe Arg Arg Ala Arg Thr
            195             200             205
```

```
Val Lys Gly Lys Arg Gly Pro Ala Ala Cys Lys Glu Lys Gln Ile Val
```

-continued

```
            210                 215                 220

Lys Glu Gly Gln Val Ile Cys Tyr Val Glu Gln Leu Gly Gly Glu Val
225                 230                 235                 240

Pro Val Glu Ser Asp Val Ala Gly Glu Val Ile Lys Ile Leu Arg Glu
                245                 250                 255

Asp Gly Glu Pro Val Gly Tyr Gly Asp Pro Leu Ile Ala Ile Leu Pro
                260                 265                 270

Ser Phe Pro Gly Ile Lys Lys Leu Gln
        275                 280

<210> SEQ ID NO 84
<211> LENGTH: 281
<212> TYPE: PRT
<213> ORGANISM: Arabidopsis thaliana

<400> SEQUENCE: 84

Met Ala Ser Ser Ala Ala Leu Gly Ser Leu His Gln Thr Leu Gly Ser
1               5                   10                  15

Ala Ile Asn Ser Gln Ser Glu Val His Ser Leu Ser Gly Asn Trp Ser
                20                  25                  30

Ala Ser Gly Asn Ser Cys Val Pro Arg Trp Arg Leu Ser Asn Arg Asn
        35                  40                  45

Ser Asn Tyr Arg Leu Val Leu Arg Ala Lys Ala Ala Lys Ser Ser Thr
    50                  55                  60

Thr Thr Ile Ser Asp Gly Ser Ser Asp Ala Ser Val Ser Asp Gly Lys
65                  70                  75                  80

Lys Thr Val Arg Arg Ile Thr Phe Pro Lys Glu Val Glu Ala Leu Val
                85                  90                  95

His Glu Met Cys Asp Glu Thr Glu Val Ala Val Leu Gln Leu Lys Val
                100                 105                 110

Gly Asp Phe Glu Met Asn Leu Lys Arg Lys Ile Gly Ala Ala Thr Asn
        115                 120                 125

Pro Ile Pro Val Ala Asp Ile Ser Pro Thr Val Ala Pro Pro Ile Pro
    130                 135                 140

Ser Glu Pro Met Asn Lys Ser Ala Ser Ser Ala Pro Ser Pro Ser Gln
145                 150                 155                 160

Ala Lys Pro Ser Ser Glu Lys Val Ser Pro Phe Lys Asn Thr Ser Tyr
                165                 170                 175

Gly Lys Pro Ala Lys Leu Ala Ala Leu Glu Ala Ser Gly Ser Thr Asn
        180                 185                 190

Tyr Val Leu Val Thr Ser Pro Ala Val Gly Lys Phe Gln Arg Ser Arg
        195                 200                 205

Thr Val Lys Gly Lys Lys Gln Ser Pro Ser Cys Lys Glu Gly Asp Ala
    210                 215                 220

Ile Lys Glu Gly Gln Val Ile Gly Tyr Leu His Gln Leu Gly Thr Glu
225                 230                 235                 240

Leu Pro Val Thr Ser Asp Val Ala Gly Glu Val Leu Lys Leu Leu Ser
                245                 250                 255

Asp Asp Gly Asp Ser Val Gly Tyr Gly Asp Pro Leu Val Ala Val Leu
                260                 265                 270

Pro Ser Phe His Asp Ile Asn Ile Gln
        275                 280

<210> SEQ ID NO 85
<211> LENGTH: 274
```

<212> TYPE: PRT
<213> ORGANISM: Arabidopsis thaliana

<400> SEQUENCE: 85

Met Asn Ser Cys Ser Leu Gly Ala Pro Lys Val Arg Ile Phe Ala Thr
1               5                   10                  15

Asn Phe Ser Arg Leu Arg Cys Gly Asn Leu Leu Ile Pro Asn Asn Gln
                20                  25                  30

Arg Leu Phe Val Asp Gln Ser Pro Met Lys Tyr Leu Ser Leu Arg Thr
            35                  40                  45

Thr Leu Arg Ser Val Lys Ala Ile Gln Leu Ser Thr Val Pro Pro Ala
        50                  55                  60

Glu Thr Glu Ala Ile Ala Asp Val Lys Asp Ser Asp Glu Thr Lys Ser
65                  70                  75                  80

Thr Val Val Asn Thr His Leu Met Pro Lys Ser Ser Glu Val Glu Ala
                85                  90                  95

Leu Ile Ser Glu Ile Thr Asp Ser Ser Ser Ile Ala Glu Phe Glu Leu
            100                 105                 110

Lys Leu Gly Gly Phe Arg Leu Tyr Val Ala Arg Lys Leu Thr Asp Glu
        115                 120                 125

Ser Ser Pro Pro Pro Gln Gln Ile Gln Pro Val Val Ala Ala Ser Ala
        130                 135                 140

Thr Pro Glu Gly Val His Thr Asn Gly Ser Ala Thr Ser Ser Ser Leu
145                 150                 155                 160

Ala Ile Thr Lys Thr Ser Ser Ser Ser Ala Asp Arg Pro Gln Thr Leu
                165                 170                 175

Ala Asn Lys Ala Ala Asp Gln Gly Leu Val Ile Leu Gln Ser Pro Thr
            180                 185                 190

Val Gly Tyr Phe Arg Arg Ser Lys Thr Ile Lys Gly Lys Arg Thr Pro
            195                 200                 205

Thr Ile Cys Lys Glu Lys Asp Ile Val Lys Glu Gly Gln Val Leu Cys
        210                 215                 220

Tyr Ile Glu Gln Leu Gly Gly Gln Ile Pro Val Glu Ser Asp Val Ser
225                 230                 235                 240

Gly Glu Ile Val Lys Ile Leu Arg Glu Asp Gly Glu Pro Val Gly Tyr
                245                 250                 255

Asn Asp Ala Leu Ile Thr Val Leu Pro Ser Phe Pro Gly Ile Lys Lys
            260                 265                 270

Leu Gln

<210> SEQ ID NO 86
<211> LENGTH: 263
<212> TYPE: PRT
<213> ORGANISM: Arabidopsis thaliana

<400> SEQUENCE: 86

Met Ala Ser Cys Ser Leu Gly Val Pro Lys Ile Lys Ile Ser Ala Val
1               5                   10                  15

Asp Leu Ser Arg Val Arg Ser Gly Ser Leu Leu Ile Pro Tyr Asn Gln
                20                  25                  30

Arg Ser Leu Leu Arg Gln Arg Pro Val Lys Tyr Leu Ser Leu Lys Thr
            35                  40                  45

Thr Phe Gly Ser Val Lys Ala Val Gln Val Ser Thr Val Pro Thr Ala
        50                  55                  60

Glu Thr Ser Ala Thr Ile Glu Val Lys Asp Ser Lys Glu Ile Lys Ser

-continued

```
65                70                75                80

Ser Arg Leu Asn Ala Gln Leu Val Pro Lys Pro Ser Glu Val Glu Ala
                85                90                95

Leu Val Thr Glu Ile Cys Asp Ser Ser Ile Ala Glu Phe Glu Leu
            100               105               110

Lys Leu Gly Gly Phe Arg Leu Tyr Val Ala Arg Asn Ile Ala Asp Asn
            115               120               125

Ser Ser Leu Gln Pro Pro Thr Pro Ala Val Thr Ala Ser Asn Ala
        130               135               140

Thr Thr Glu Ser Pro Glu Ser Asn Gly Ser Ala Ser Ser Thr Ser Leu
145               150               155               160

Ala Ile Ser Lys Pro Ala Ser Ser Ala Ala Asp Gln Gly Leu Met Ile
                165               170               175

Leu Gln Ser Pro Lys Val Gly Phe Phe Arg Arg Ser Lys Thr Ile Lys
            180               185               190

Gly Lys Arg Leu Pro Ser Ser Cys Lys Glu Lys Asp Gln Val Lys Glu
            195               200               205

Gly Gln Ile Leu Cys Tyr Ile Glu Gln Leu Gly Gly Gln Phe Pro Ile
        210               215               220

Glu Ser Asp Val Thr Gly Glu Val Val Lys Ile Leu Arg Glu Asp Gly
225               230               235               240

Glu Pro Val Gly Tyr Asn Asp Ala Leu Ile Ser Ile Leu Pro Ser Phe
                245               250               255

Pro Gly Ile Lys Lys Leu Gln
                260

<210> SEQ ID NO 87
<211> LENGTH: 277
<212> TYPE: PRT
<213> ORGANISM: Arabis alpina

<400> SEQUENCE: 87

Met Ala Ser Ser Ala Thr Leu Gly Ser Leu His Gln Thr Leu Gly Ser
1                 5                10                15

Val Ser Lys Val His Ser Ile Ser Gly Asn Trp Ser Ala Ser Gly Asn
                20                25                30

Ser Cys Leu Pro Arg Trp Arg Leu Cys Asn Lys Asn Arg Asn Ser Met
            35                40                45

Phe Val Leu Ser Thr Lys Ala Ser Lys Ser Ser Thr Thr Thr Lys Ser
        50                55                60

Asp Asp Ser Ser Asp Thr Ser Val Ser Asn Gly Lys Asn Ala Val Arg
65                70                75                80

Arg Ile Thr Phe Pro Lys Glu Val Glu Ala Leu Val His Glu Met Cys
                85                90                95

Asp Glu Thr Glu Val Ala Val Leu Gln Leu Lys Val Gly Asp Phe Glu
            100               105               110

Met Asn Leu Lys Arg Lys Ile Gly Gln Ala Ala Asn His Ile Pro Val
            115               120               125

Asp Asp Ile Ser Pro Thr Ile Ala Pro Pro Ile Pro Ser Glu Pro Met
        130               135               140

Asn Lys Ser Val Ser Ala Ala Pro Thr Pro Ser Gln Thr Lys Ala Ser
145               150               155               160

Ser Glu Arg Val Ser Pro Phe Ile Asn Thr Ser Tyr Arg Lys Ser Ser
                165               170               175
```

-continued

```
Thr Leu Ala Ala Leu Glu Ala Ser Gly Ile Asn Asn Tyr Val Leu Val
            180                 185                 190

Thr Ser Pro Ser Val Gly Lys Phe Glu Arg Ser Arg Thr Val Lys Gly
            195                 200                 205

Lys Lys Gln Pro Pro Ser Cys Lys Glu Gly Asp Ala Ile Lys Glu Gly
            210                 215                 220

Gln Val Ile Gly Tyr Leu His Gln Leu Gly Thr Glu Leu Pro Val Thr
225                 230                 235                 240

Ser Asp Val Ala Gly Glu Val Leu Lys Leu Leu Ser Asn Asp Gly Asp
            245                 250                 255

Ser Val Gly Tyr Gly Glu Pro Leu Val Ala Val Leu Pro Ser Phe His
            260                 265                 270

Asp Ile Asn Ile Gln
            275

<210> SEQ ID NO 88
<211> LENGTH: 263
<212> TYPE: PRT
<213> ORGANISM: Arabis alpina

<400> SEQUENCE: 88

Met Ala Ser Cys Ser Leu Gly Val Pro Lys Ile Lys Ile Ser Ala Val
1               5                   10                  15

Asp Leu Ser Ile Val Arg Ser Val Ser Leu Gln Ile Pro Cys Ser Gln
            20                  25                  30

Arg Ser Leu Val Lys Gln Arg Pro Val Lys Tyr Leu Ser Leu Arg Thr
            35                  40                  45

Ser Leu Gly Ser Val Arg Ala Val Gln Val Ser Thr Val Pro Ala Ala
        50                  55                  60

Glu Ala Ser Ala Thr Val Glu Ile Glu Asp Ser Glu Glu Thr Lys Ser
65                  70                  75                  80

Tyr Pro Leu Asn Ala Gln Leu Val Pro Lys Pro Ser Glu Val Glu Ala
                85                  90                  95

Leu Val Thr Glu Ile Cys Asp Ser Ser Ser Ile Ala Glu Phe Glu Leu
            100                 105                 110

Lys Leu Gly Gly Phe Arg Leu Tyr Val Ala Arg Asp Leu Ala Asp Lys
        115                 120                 125

Ser Ser Pro Gln Pro Gln Pro Ile Ser Ala Ala Val Thr Val Asn Ala
        130                 135                 140

Thr Thr Glu Ser Ser Asp Ser Asn Gly Ser Ala Ser Ser Thr Ser Leu
145                 150                 155                 160

Ala Ile Ile Lys Pro Ala Ser Ser Ala Ala Asp Gln Gly Leu Met Ile
                165                 170                 175

Leu Gln Ser Pro Lys Val Gly Phe Phe Arg Arg Ser Lys Thr Ile Lys
            180                 185                 190

Gly Lys Arg Thr Pro Ser Ser Cys Lys Glu Lys Asp Gln Val Lys Glu
        195                 200                 205

Gly Gln Val Leu Cys Tyr Ile Glu Gln Leu Gly Gly Gln Phe Pro Ile
        210                 215                 220

Glu Ser Asp Val Thr Gly Glu Val Val Lys Ile Leu Arg Glu Asp Gly
225                 230                 235                 240

Glu Pro Val Gly Tyr Asn Asp Ala Leu Ile Ser Ile Leu Pro Ser Phe
                245                 250                 255

Pro Gly Ile Lys Lys Leu Gln
                260
```

-continued

```
<210> SEQ ID NO 89
<211> LENGTH: 286
<212> TYPE: PRT
<213> ORGANISM: Arachis duranensis

<400> SEQUENCE: 89

Met Glu Ala Ser Ala Ala Ile Arg Ser Leu Asn Tyr Pro Ile Gly Ser
1               5                   10                  15

Met Ala Pro Met Arg Cys Ser Leu Glu Lys Pro Ala Ile Val Pro Ser
            20                  25                  30

His Asn Ile Arg Trp Asn Ser Lys Ser Arg Leu Phe Val Gln Arg Leu
        35                  40                  45

Val Asn Gly Glu Lys Tyr Lys Gly Asn Lys Thr Leu Val Leu Cys Ala
    50                  55                  60

Lys Thr Ala Asp Thr Ile Asn Thr Thr Lys Ser Glu Ala Ser Ser Asp
65                  70                  75                  80

Thr Thr Leu Gln Asp Ser Leu Glu Lys Lys Pro Leu Gln Asn Ala Thr
                85                  90                  95

Phe Pro Asn Gly Phe Glu Ala Leu Val Leu Glu Val Cys Asp Glu Thr
            100                 105                 110

Glu Ile Ala Glu Leu Lys Val Lys Val Gly Glu Phe Glu Met His Leu
        115                 120                 125

Lys Arg Asn Ile Gly Ala Thr Lys Ala Pro Leu Ser Asn Ile Ser Pro
    130                 135                 140

Thr Thr Pro Pro Pro Ile Pro Ser Glu Pro Met Val Glu Leu Ala Ala
145                 150                 155                 160

Gly Thr Pro Pro Pro Ser Pro Pro Lys Ser Ser Pro Glu Lys Thr Asn
                165                 170                 175

Pro Phe Val Asn Val Ser Leu Glu Lys Ser Ser Lys Leu Ala Ala Leu
            180                 185                 190

Glu Ala Ser Gly Asn Asn Thr Tyr Val Leu Val Ser Ser Pro Thr Val
        195                 200                 205

Gly Leu Phe Arg Arg Gly Arg Thr Val Lys Gly Lys Lys Gln Pro Pro
    210                 215                 220

Ile Cys Lys Glu Gly Asp Phe Ile Lys Glu Gly Gln Val Ile Gly Tyr
225                 230                 235                 240

Leu Asp Gln Phe Gly Thr Gly Leu Pro Val Lys Ser Asp Val Ala Gly
                245                 250                 255

Glu Val Leu Lys Leu Leu Val Glu Asp Gly Glu Pro Val Gly Tyr Gly
            260                 265                 270

Asp Pro Leu Ile Ala Val Leu Pro Ser Phe His Asp Ile Lys
        275                 280                 285

<210> SEQ ID NO 90
<211> LENGTH: 274
<212> TYPE: PRT
<213> ORGANISM: Arachis duranensis

<400> SEQUENCE: 90

Met Ala Ser Cys Ser Leu Gly Ala Pro Asn Asn Lys Leu Leu Asn Leu
1               5                   10                  15

Gln Phe Gly Gly Arg Arg Val Gly Phe Leu Gln Gly Phe Gly Ala Arg
            20                  25                  30

Ser Trp Ile Ser Arg Lys Pro Val Gln His Thr Ala Leu Val Met Gln
        35                  40                  45
```

```
Gln Gln Ser Val Lys Ser Leu Thr Glu Ser Thr Ala Gln Ser Ile Glu
    50              55              60

Ile Gln Ser Ile Thr Arg Ser Glu Asp Ser Ser Glu Asp Ile His Ser
65              70              75              80

Ser Gly Val Ser Ser Glu Leu Val Pro Lys Phe His Glu Val Glu Phe
                85              90              95

Leu Leu Asn Thr Ile Cys Asp Ser Ser Ser Val Gly Glu Phe Glu Leu
            100             105             110

Lys Leu Asp Gly Phe His Leu Arg Val Val Arg Gly Leu Ser Glu Lys
        115             120             125

Asn Lys Thr Val Pro Pro Leu Thr Pro Ala Ser Thr Ser Val Asn Thr
    130             135             140

Ile Thr Glu Ala Pro Lys Ser Asn Gly Leu Ala Ser Asn Ser Ala Leu
145             150             155             160

Ser Leu Ala Ile Ser Lys Pro Leu Pro Ser Pro Glu Ser Ile Gln Arg
            165             170             175

Phe Leu Asp Lys Ala Thr Asp Glu Gly Leu Val Ile Ile Gln Ser Pro
            180             185             190

Lys Val Gly Phe Phe Arg Arg Ser Arg Thr Ile Lys Gly Lys Arg Thr
        195             200             205

Pro Pro Ala Cys Lys Glu Asn Gln Lys Val Glu Glu Gly Gln Val Ile
    210             215             220

Cys Phe Ile Glu Gln Leu Gly Gly Glu Leu Pro Ile Glu Ser Asp Val
225             230             235             240

Ser Gly Glu Ile Ile Lys Ile Leu Arg Lys Asp Gly Glu Pro Val Gly
            245             250             255

Tyr Gly Asp Pro Val Ile Ala Val Leu Pro Ser Phe Pro Gly Ile Lys
            260             265             270

Ile Gln
```

```
<210> SEQ ID NO 91
<211> LENGTH: 291
<212> TYPE: PRT
<213> ORGANISM: Arachis ipaensis

<400> SEQUENCE: 91
```

```
Met Glu Ala Ser Ala Ala Ile Arg Ser Leu Asn Tyr Pro Ile Gly Ser
1               5               10              15

Met Ala Pro Met Arg Cys Ser Leu Glu Lys Pro Ala Ile Val Pro Ser
            20              25              30

His Asn Ile Arg Trp Asn Ser Lys Ser Arg Leu Phe Val Gln Arg Leu
        35              40              45

Val Asn Gly Val Lys Tyr Ile Asn Tyr His Ser Lys Gly Asn Lys Thr
    50              55              60

Leu Val Leu Cys Ala Lys Thr Ala Asp Thr Ile Asn Thr Thr Lys Ser
65              70              75              80

Glu Ala Ser Ser Asp Thr Thr Ser Gln Asp Ser Leu Glu Lys Lys Pro
                85              90              95

Leu Gln Asn Ala Thr Phe Pro Asn Gly Phe Glu Ala Leu Val Leu Glu
            100             105             110

Val Cys Asp Glu Thr Glu Ile Ala Glu Leu Lys Val Lys Val Gly Glu
        115             120             125

Phe Glu Met His Leu Lys Arg Asn Ile Gly Ala Thr Lys Ala Pro Leu
    130             135             140
```

```
Ser Asn Ile Ser Pro Thr Thr Pro Pro Pro Ile Pro Ser Glu Pro Met
145                 150             155             160

Val Glu Leu Ala Ala Gly Thr Pro Pro Ser Pro Pro Lys Ser Ser
            165             170             175

Pro Glu Lys Thr Asn Pro Phe Val Asn Val Ser Leu Glu Lys Ser Ser
            180             185             190

Lys Leu Ala Ala Leu Glu Ala Ser Gly Asn Asn Thr Tyr Val Leu Val
            195             200             205

Ser Ser Pro Thr Val Gly Leu Phe Arg Arg Gly Arg Thr Val Lys Gly
    210             215             220

Lys Lys Gln Pro Pro Ile Cys Lys Glu Gly Asp Phe Ile Lys Glu Gly
225             230             235             240

Gln Val Ile Gly Tyr Leu Asp Gln Phe Gly Thr Gly Leu Pro Val Lys
            245             250             255

Ser Asp Val Ala Gly Glu Val Leu Lys Leu Leu Val Glu Asp Gly Glu
            260             265             270

Pro Val Gly Tyr Gly Asp Pro Leu Ile Ala Val Leu Pro Ser Phe His
            275             280             285

Asp Ile Lys
    290

<210> SEQ ID NO 92
<211> LENGTH: 274
<212> TYPE: PRT
<213> ORGANISM: Arachis ipaensis

<400> SEQUENCE: 92

Met Ala Ser Cys Ser Leu Gly Ala Pro Asn Asn Lys Leu Leu Asn Leu
1               5               10              15

Gln Phe Gly Gly Arg Arg Val Gly Phe Leu Gln Gly Phe Gly Ala Arg
            20              25              30

Ser Trp Ile Ser Arg Lys Pro Val Gln Tyr Thr Thr Leu Val Met Gln
        35              40              45

Gln Gln Ser Val Lys Ser Leu Thr Glu Ser Thr Ala Gln Ser Ile Glu
    50              55              60

Ile Gln Ser Ile Thr Arg Ser Glu Asp Ser Ser Glu Asp Ile His Ser
65              70              75              80

Ser Gly Val Thr Ser Glu Leu Val Pro Lys Phe His Glu Val Glu Phe
            85              90              95

Leu Leu Asn Thr Ile Cys Asp Ser Ser Ser Val Gly Glu Phe Glu Leu
            100             105             110

Lys Leu Asp Gly Phe His Leu Arg Val Val Arg Gly Leu Ser Glu Lys
            115             120             125

Asn Lys Thr Val Pro Pro Leu Thr Pro Ala Ser Thr Ser Val Asn Thr
    130             135             140

Ile Pro Glu Ala Pro Lys Ser Asn Gly Leu Ala Ser Asn Ser Ala Leu
145             150             155             160

Ser Leu Ala Ile Ser Arg Pro Leu Pro Ser Pro Glu Ser Ile Gln Arg
            165             170             175

Phe Leu Asp Lys Ala Thr Asp Glu Gly Leu Val Ile Ile Gln Ser Pro
            180             185             190

Lys Val Gly Phe Phe Arg Arg Ser Arg Thr Ile Lys Gly Lys Arg Thr
            195             200             205

Pro Pro Ala Cys Lys Glu Asn Gln Lys Val Glu Glu Gly Gln Val Ile
```

```
        210             215             220

Cys Phe Ile Glu Gln Leu Gly Gly Glu Val Pro Ile Glu Ser Asp Val
225                 230             235                 240

Ser Gly Glu Ile Ile Lys Ile Leu Arg Lys Asp Gly Glu Pro Val Gly
                245             250             255

Tyr Gly Asp Ala Val Ile Ala Val Leu Pro Ser Phe Pro Gly Ile Lys
            260             265             270

Ile Gln

<210> SEQ ID NO 93
<211> LENGTH: 274
<212> TYPE: PRT
<213> ORGANISM: Beta vulgaris

<400> SEQUENCE: 93

Met Glu Thr Ala Ala Phe Arg Phe Ser Ala Gly Ser Ile Ser His Pro
1               5                   10                  15

Cys Ser Ser Phe Glu Lys Pro Gly Leu Ala Ala Trp Pro Ala Val Val
                20                  25                  30

Gln Ser Arg Cys Arg Ala Leu Thr Ala Gly Lys Leu Thr Ser Phe Ser
            35                  40                  45

Arg Gln Ala Arg Ile Val Val Ser Cys Ala Lys Thr Pro Glu Lys Thr
        50                  55                  60

Ala Pro Ser Lys Ser Asp Val Ser Leu Asp Asn Ile Ser Lys Gly Ser
65                  70                  75                  80

Ile Glu Lys His Ala Leu Arg Thr Thr Phe Pro Ser Ala Phe Glu Ala
                85                  90                  95

Leu Leu Leu Glu Val Cys Asp Glu Thr Ser Val Ala Glu Val Gln Leu
            100             105             110

Lys Val Gly Asp Phe Glu Met His Leu Lys Arg Asn Val Gly Ala Val
        115             120             125

Asn Ala Pro Val Pro Val Ala Pro Pro Val Pro Thr Glu Pro Met Leu
        130             135             140

Gln Ser Thr Pro Ala Val Pro Ser Thr Ser Ser Pro Lys Pro Ser Pro
145             150             155             160

Glu Lys Ser Ser Leu Phe Ala Ser Ala Ser Ser Ala Val Ser Ser Lys
                165             170             175

Leu Ala Ser Leu Glu Ala Ser Gly Val Asn Gly Phe Lys Leu Val Thr
            180             185             190

Ser Pro Thr Val Gly Ser Phe Arg Arg Gly Arg Thr Val Lys Gly Lys
        195             200             205

Arg Gln Pro Pro Asn Cys Lys Gln Gly Asp Val Ile Lys Glu Gly Gln
        210             215             220

Val Ile Gly Tyr Ile Asp Gln Phe Gly Thr Glu Leu Pro Val Lys Ser
225             230             235             240

Asp Val Ala Gly Glu Val Leu Lys Leu Leu Phe Glu Glu Gly Glu Ala
                245             250             255

Ile Gly Tyr Gly Asp Pro Leu Ile Ala Val Leu Pro Ser Phe His Gly
            260             265             270

Leu Ser

<210> SEQ ID NO 94
<211> LENGTH: 281
<212> TYPE: PRT
<213> ORGANISM: Beta vulgaris
```

<400> SEQUENCE: 94

Met Ala Ala Ser Ser Leu Ser Phe Ser Asn Ala Gln Ile Leu Ser Ser
1               5                   10                  15

Lys Leu Asn His Lys Ser Ser Tyr Cys Met Pro Ser Phe Arg Cys Val
                20                  25                  30

Ile Gln Ala Gly Ser Arg Gln Lys Leu Trp Arg His Ser Ala Leu Val
            35                  40                  45

Met Ser Gln Ser Ser His Arg Glu Ser Ser Ile Cys Cys Ala Gln Ser
        50                  55                  60

Ser Ser Val Thr Glu Asn Glu Pro Ala Ala Leu Gly Leu Glu Val Arg
65                  70                  75                  80

Glu Glu Gln Arg Gly Phe Ser Gly Ser Val Val Ser Gln Leu Ile Pro
                85                  90                  95

Asn Ser Asp Gln Val Asn Phe Leu Leu Thr Glu Ile Cys Asp Thr Thr
            100                 105                 110

Ser Ile Ala Glu Phe Glu Leu Lys Leu Asn Gly Phe His Leu His Val
            115                 120                 125

Thr Arg Ala Leu Ser Ala Gly Val Glu Pro Pro Pro Pro Pro Pro Asp
    130                 135                 140

Tyr Val Ser Thr Ser Ala Asn Thr Ile Ala Glu Thr Pro Ser Leu Asn
145                 150                 155                 160

Gly Pro Val Ser Pro Ser Ser Leu Ala Ile Thr Lys Ala Gly Pro Leu
                165                 170                 175

Glu Leu Thr Ser Ser Thr Leu Leu Glu Arg Ala Ala Asp Glu Gly Phe
            180                 185                 190

Ala Ile Ile Gln Ser Pro Lys Val Gly Phe Phe Arg Arg Ser Arg Thr
            195                 200                 205

Ile Lys Gly Lys Arg Ala Pro Pro Ala Cys Lys Glu Lys Gln Val Val
    210                 215                 220

Lys Glu Gly Gln Val Ile Cys Tyr Ile Glu Gln Leu Gly Gly Glu Ile
225                 230                 235                 240

Pro Val Glu Ser Asp Val Ser Gly Glu Ile Thr Lys Ile Leu Cys Lys
                245                 250                 255

Glu Gly Glu Pro Val Gly Tyr Gly Asp Ala Ile Ile Ala Ile Leu Pro
                260                 265                 270

Ser Phe Pro Gly Ile Lys Lys Leu Ser
                275                 280

<210> SEQ ID NO 95
<211> LENGTH: 268
<212> TYPE: PRT
<213> ORGANISM: Brassica oleracea

<400> SEQUENCE: 95

Met Glu Ser Leu Gly Ser Leu His Gln Ser Leu Gly Ser Ala Val Asn
1               5                   10                  15

Val His Ser Leu Ser Gly Lys Ser Cys Ala Pro Pro Arg Trp Ser Leu
                20                  25                  30

Phe Asn Arg Asn Thr Leu Val Leu Arg Ala Glu Ser Ser Lys Ser Ser
            35                  40                  45

Thr Thr Thr Lys Thr Asp Glu Ser Ser Asp Ala Ser Asn Gly Thr Lys
        50                  55                  60

Thr Val Arg Arg Thr Thr Phe Pro Lys Glu Val Glu Ala Leu Val His
65                  70                  75                  80

-continued

Glu Met Cys Asp Glu Thr Glu Val Ala Val Leu Lys Leu Lys Val Gly
                85                      90                      95

Asp Phe Glu Met Asn Leu Lys Arg Lys Ile Gly Leu Ala Glu Thr Pro
                100                     105                     110

Ile Pro Val Pro Asp Ile Ser Pro Ser Val Ala Pro Pro Ile Pro Ser
                115                     120                     125

Glu Pro Met Asn Lys Ser Val Ser Ser Ser Ala Ala Ala Ala Thr Ser
        130                     135                     140

Pro Ser Lys Ala Lys Pro Ala Ser Glu Lys Val Ser Pro Phe Ile Asn
145                     150                     155                     160

Ala Ala Tyr Arg Lys Ser Ser Lys Leu Ala Ala Leu Asp Ala Ser Gly
                165                     170                     175

Ser Asn Asn Tyr Val Leu Val Thr Ser Pro Ser Val Gly Lys Phe Gln
                180                     185                     190

Arg Ser Arg Thr Val Lys Gly Lys Lys Gln Gly Pro Thr Cys Lys Glu
                195                     200                     205

Gly Asp Ala Ile Lys Glu Gly Gln Val Ile Gly Tyr Leu His Gln Leu
        210                     215                     220

Gly Lys Glu Leu Pro Val Thr Ser Asp Val Ala Gly Glu Val Leu Lys
225                     230                     235                     240

Leu Leu Ser Asp Asp Gly Asp Ser Val Gly Tyr Gly Glu Pro Leu Val
                245                     250                     255

Ala Val Leu Pro Ser Phe His Asp Ile Asn Ile Gln
                260                     265

<210> SEQ ID NO 96
<211> LENGTH: 265
<212> TYPE: PRT
<213> ORGANISM: Brassica oleracea

<400> SEQUENCE: 96

Met Ala Ser Cys Ser Leu Gly Val Pro Lys Ile Lys Ile Ser Ala Val
1               5                       10                      15

Asp Leu Ser Arg Val Arg Ser Gly Ser Leu Gln Ile Pro Cys Asn Gln
                20                      25                      30

Arg Val Leu Ile Gly Gln Arg Pro Val Lys Tyr Leu Ser Leu Arg Ala
        35                      40                      45

Thr Leu Gly Ser Val Lys Ala Pro Gln Ala Ser Thr Val Thr Ala Ala
        50                      55                      60

Glu Ser Ala Ala Thr Val Glu Val Glu Asp Ala Glu Met Thr Lys Pro
65                      70                      75                      80

Ser Pro Leu Asn Ala Gln Leu Val Pro Lys Pro Ser Glu Val Glu Ala
                85                      90                      95

Leu Val Thr Glu Ile Cys Asp Ser Ser Ser Ile Ala Glu Phe Glu Leu
                100                     105                     110

Lys Leu Gly Gly Phe Arg Leu Tyr Val Ala Arg Asn Leu Ala Asp Asn
        115                     120                     125

Asn Ser Ser Pro Pro Gln Pro Gln Pro Ile Pro Ala Ala Val Ala Ala
        130                     135                     140

Ser Ala Thr Thr Glu Gly Val Asp Ser Asn Gly Ser Ala Ser Ser Thr
145                     150                     155                     160

Ser Leu Ala Ile Thr Lys Pro Thr Ser Ser Ala Ala Asp Gln Gly Leu
                165                     170                     175

Val Ile Leu Gln Ser Pro Lys Val Gly Phe Phe Arg Arg Ser Lys Thr

-continued

```
              180             185             190

Ile Lys Gly Lys Arg Thr Pro Ser Ser Cys Lys Glu Lys Asp Gln Val
        195             200             205

Lys Glu Gly Gln Val Leu Cys Tyr Ile Glu Gln Leu Gly Gly Gln Phe
    210             215             220

Pro Ile Glu Ser Asp Val Thr Gly Glu Val Val Lys Ile Leu Arg Glu
225             230             235             240

Asp Gly Glu Pro Val Gly Tyr Asn Asp Ala Leu Ile Ser Ile Leu Pro
                245             250             255

Ser Phe Pro Gly Ile Lys Lys Leu Gln
                260             265

<210> SEQ ID NO 97
<211> LENGTH: 277
<212> TYPE: PRT
<213> ORGANISM: Brassica rapa

<400> SEQUENCE: 97

Met Glu Ser Ser Ala Ala Leu Gly Ser Leu Arg Gln Ser Leu Gly Ser
1               5               10              15

Ala Val Asn Val His Ser Leu Ser Gly Asn Trp Ser Pro Ser Gly Asn
                20              25              30

Ser Cys Val Pro Arg Trp Ser Leu Phe Asn Arg Asn Met Leu Val Leu
            35              40              45

Arg Ala Asp Ser Ser Lys Ser Ser Thr Thr Thr Thr Lys Thr Asp Glu
    50              55              60

Ser Ser Asp Ala Ser Asn Gly Thr Lys Thr Lys Thr Val Arg Arg Thr
65              70              75              80

Thr Phe Pro Lys Glu Val Glu Ala Leu Val His Glu Met Cys Asp Glu
                85              90              95

Thr Glu Val Ala Val Leu Lys Leu Lys Val Gly Asp Phe Glu Met Asn
                100             105             110

Leu Lys Arg Lys Ile Gly Leu Ala Glu Thr Pro Ile Pro Val Pro Asp
            115             120             125

Ile Ser Pro Ser Val Ala Pro Pro Ile Pro Ser Glu Pro Met Asn Lys
    130             135             140

Ser Val Ser Ala Ser Ala Asp Ala Ser Pro Ser Lys Ala Lys Pro Ala
145             150             155             160

Ser Glu Lys Val Ser Pro Phe Ile Asn Ala Ala Tyr Arg Lys Ser Ser
                165             170             175

Lys Leu Ala Ala Leu Glu Ala Ala Gly Ser Asn Asn Tyr Val Leu Val
            180             185             190

Thr Ser Pro Ser Val Gly Lys Phe Gln Arg Ser Arg Thr Val Lys Gly
            195             200             205

Lys Lys Gln Gly Pro Thr Cys Lys Glu Gly Asp Ala Ile Lys Glu Gly
    210             215             220

Gln Val Ile Gly Tyr Leu His Gln Leu Gly Lys Glu Leu Pro Val Thr
225             230             235             240

Ser Asp Val Ala Gly Glu Val Leu Lys Leu Leu Ser Asp Asp Gly Asp
                245             250             255

Ser Val Gly Tyr Gly Glu Pro Leu Val Ala Val Leu Pro Ser Phe His
            260             265             270

Asp Ile Asn Ile Gln
    275
```

<210> SEQ ID NO 98
<211> LENGTH: 265
<212> TYPE: PRT
<213> ORGANISM: Brassica rapa

<400> SEQUENCE: 98

Met Ala Ser Cys Ser Leu Gly Val Pro Lys Ile Lys Ile Ser Ala Val
1               5                   10                  15

Asp Val Ser Arg Val Arg Ser Gly Arg Leu Gln Ile Pro Tyr Ser Gln
            20                  25                  30

Arg Ser Leu Phe Ala Gln Arg Gln Val Lys Tyr Leu Ser Leu Arg Thr
        35                  40                  45

Ser Val Gly Ser Leu Lys Ala Leu Gln Val Ser Thr Val Thr Ala Val
    50                  55                  60

Glu Thr Ser Ala Thr Val Glu Val Glu Asp Ala Glu Lys Thr Lys Ser
65                  70                  75                  80

Ser Pro Leu Asn Ala Gln Leu Val Pro Lys Pro Ser Glu Val Glu Ala
                85                  90                  95

Leu Val Thr Glu Ile Cys Asp Ser Ser Ser Ile Ala Glu Phe Glu Leu
            100                 105                 110

Lys Leu Gly Gly Phe Arg Leu Tyr Val Ala Arg Asn Leu Ala Asp Asn
        115                 120                 125

Asn Ile Ser Pro Pro Gln Pro Gln Pro Thr Pro Ala Ala Leu Ser Ala
    130                 135                 140

Asn Ala Val Thr Glu Ser Ala Asp Ser Asn Gly Ser Ala Ser Ser Thr
145                 150                 155                 160

Ser Leu Ala Ile Thr Lys Pro Ala Ser Ser Ala Ala Asp Gln Gly Leu
                165                 170                 175

Ile Ile Leu Gln Ser Pro Lys Val Gly Phe Phe Arg Arg Ser Lys Thr
            180                 185                 190

Ile Lys Gly Lys Arg Thr Pro Ser Ser Cys Lys Glu Lys Asp Gln Val
        195                 200                 205

Lys Glu Gly Gln Val Leu Cys Tyr Ile Glu Gln Leu Gly Gly Gln Phe
    210                 215                 220

Pro Ile Glu Ser Asp Val Thr Gly Glu Val Val Lys Ile Leu Arg Glu
225                 230                 235                 240

Asp Gly Glu Pro Val Gly Tyr Asn Asp Ala Leu Ile Ser Ile Leu Pro
                245                 250                 255

Ser Phe Pro Gly Ile Lys Lys Leu Gln
            260                 265

<210> SEQ ID NO 99
<211> LENGTH: 275
<212> TYPE: PRT
<213> ORGANISM: Cajanus cajan

<400> SEQUENCE: 99

Met Ser His Met Arg Pro Ser Leu Gly Lys Gln Val Leu Val Pro Ile
1               5                   10                  15

His Asn Val Arg Ser Asn Ser Lys Thr Arg Leu Phe Ile Gln His Phe
            20                  25                  30

Ser Tyr Gly Gln Lys His Ile Asn Phe His Thr Lys Gly Lys Asn Thr
        35                  40                  45

Leu Val Ser Cys Ala Lys Thr Ala Glu Ala Ile Asn Lys Ser Lys Ser
    50                  55                  60

-continued

```
Asp Val Thr Ser Asn Ser Thr Pro Gln Asp Ser Leu Glu Lys Lys Pro
65              70                  75                  80

Leu Gln Ile Ala Thr Phe Pro Asn Gly Phe Glu Ala Leu Val Leu Glu
                85                  90                  95

Val Cys Asp Glu Thr Glu Ile Ala Glu Leu Lys Val Lys Val Gly Asp
            100                 105                 110

Phe Glu Met His Ile Lys Arg Asn Ile Gly Ala Thr Lys Ala Pro Leu
            115                 120                 125

Ser Asn Ile Ser Pro Thr Thr Pro Pro Pro Ile Pro Ser Lys Pro Met
        130                 135                 140

Asp Ala Ala Ala Pro Ala Thr Leu Pro Pro Ser Pro Pro Lys Ser Ser
145                 150                 155                 160

Pro Gln Lys Thr Asn Pro Phe Ser Asn Ala Ser Lys Glu Lys Ser Pro
                165                 170                 175

Arg Leu Ala Ala Leu Glu Ala Ser Gly Ile Asn Asn Tyr Val Leu Val
                180                 185                 190

Ser Ser Pro Arg Val Gly Leu Phe Arg Arg Gly Arg Thr Val Lys Gly
            195                 200                 205

Lys Arg Gln Pro Pro Ile Cys Lys Glu Gly Asp Phe Ile Lys Glu Gly
        210                 215                 220

Gln Val Val Gly Tyr Leu Asp Gln Phe Gly Thr Gly Leu Pro Ile Lys
225                 230                 235                 240

Ser Glu Val Ser Gly Glu Val Leu Lys Leu Leu Val Val Asp Gly Glu
                245                 250                 255

Pro Val Gly Tyr Ala Asp Pro Leu Ile Ala Val Leu Pro Ser Phe His
                260                 265                 270

Asp Ile Lys
        275

<210> SEQ ID NO 100
<211> LENGTH: 273
<212> TYPE: PRT
<213> ORGANISM: Cajanus cajan

<400> SEQUENCE: 100

Met Ala Ser Cys Ser Leu Gly Thr Ser Asn Ile Lys Leu Leu Asn Leu
1               5                   10                  15

His Phe Gly Gly Ile Lys Phe Gly Leu Ser Gln Gln Tyr Gly Thr Arg
            20                  25                  30

Ser Trp Ile Ser Arg Gln Ser Leu Gln Tyr Thr Ser Leu Val Met Ser
        35                  40                  45

Arg Gln Thr Val Arg Phe Leu Ala Ser Pro Asn Asp Pro Ser Pro Asp
    50                  55                  60

Ile Glu Phe Val Thr Lys Ser Glu Glu Asp Ser Glu Glu Asn Lys Ser
65              70                  75                  80

Ser Gly Leu Thr Ser Glu Leu Ile Pro Asn Phe Asn Glu Val Glu Phe
                85                  90                  95

Leu Leu Thr Lys Leu Cys Asp Thr Ser Ser Ile Gly Glu Leu Asp Leu
            100                 105                 110

Lys Leu Ala Gly Phe His Leu His Val Val Arg Asp Leu Gly Glu Asn
        115                 120                 125

Ile Lys Thr Leu Pro Ser Ala Ser Pro Ala Ser Val Ser Ile Asn Asn
        130                 135                 140

Val Pro Glu Thr Pro Lys Thr Asn Gly Ser Val Ser Thr Thr Ser Leu
145                 150                 155                 160
```

Ala Ile Ser Asn Pro Val Pro Ser Leu Gly Ser Ile Gln Arg Phe Leu
                165                 170                 175

Asp Lys Ala Ala Asp Glu Gly Leu Val Ile Ile Gln Ser Pro Lys Val
            180                 185                 190

Gly Phe Phe Arg Arg Ser Arg Thr Ile Lys Gly Lys Arg Ala Pro Pro
            195                 200                 205

Ser Cys Lys Glu Lys Gln Asn Val Glu Glu Gly Gln Val Ile Cys Tyr
        210                 215                 220

Ile Glu Gln Leu Gly Gly Glu Leu Pro Ile Glu Ser Asp Val Thr Gly
225                 230                 235                 240

Glu Val Ile Lys Ile Leu Arg Lys Asp Gly Asp Pro Val Gly Tyr Gly
                245                 250                 255

Asp Ala Leu Val Ala Ile Leu Pro Ser Phe Pro Gly Ile Lys Lys Leu
            260                 265                 270

Gln

<210> SEQ ID NO 101
<211> LENGTH: 272
<212> TYPE: PRT
<213> ORGANISM: Capsella rubella

<400> SEQUENCE: 101

Met Asn Ser Cys Ser Leu Gly Ala Pro Lys Leu Arg Ile Ser Leu Ala
1               5                   10                  15

Asn Phe Ser Arg Leu Arg Cys Gly Asn Leu Leu Ile Pro Asn Asn Gln
            20                  25                  30

Arg Leu Phe Ile Asp Gln Gly Gln Ser Pro Ile Lys Phe Pro Ser Leu
        35                  40                  45

Arg Thr Thr Leu Arg Ala Val Lys Ala Val Gln Leu Ser Thr Val Pro
    50                  55                  60

Pro Ala Glu Thr Ser Asp Val Glu Asp Ser Glu Glu Thr Glu Pro Thr
65                  70                  75                  80

Ile Val Asn Thr Gln Leu Ile Pro Asn Ser Ser Glu Val Glu Ala Leu
                85                  90                  95

Ile Ser Glu Ile Thr Asp Ser Ser Ser Ile Ala Glu Phe Glu Leu Lys
            100                 105                 110

Leu Gly Gly Phe Arg Leu Tyr Val Ala Arg Lys Leu Ala Asp Gln Ser
        115                 120                 125

Ser Pro Pro Pro Gln Gln Ile Pro Asn Val Val Ala Ala Ser Ala Ala
    130                 135                 140

Pro Glu Gly Val His Thr Asn Gly Ser Ala Thr Ser Ser Ser Leu Ala
145                 150                 155                 160

Ile Thr Lys Ser Ser Ser Ser Ser Asp Arg Pro Gln Thr Leu Ser Asn
                165                 170                 175

Lys Ala Ala Asp Gln Gly Leu Val Ile Leu Gln Ser Pro Thr Val Gly
            180                 185                 190

Tyr Phe Arg Arg Ser Lys Thr Ile Lys Gly Lys Arg Thr Pro Thr Ile
        195                 200                 205

Cys Lys Glu Lys Asp Ile Val Lys Glu Gly Gln Val Leu Cys Tyr Ile
        210                 215                 220

Glu Gln Leu Gly Gly Gln Ile Pro Val Glu Ser Asp Val Ser Gly Glu
225                 230                 235                 240

Ile Val Lys Ile Leu Arg Glu Asp Gly Glu Pro Val Gly Tyr Asn Asp
                245                 250                 255

-continued

```
Ala Leu Ile Thr Val Leu Pro Ser Phe Pro Gly Ile Lys Lys Leu Gln
            260                 265                 270

<210> SEQ ID NO 102
<211> LENGTH: 263
<212> TYPE: PRT
<213> ORGANISM: Capsella rubella

<400> SEQUENCE: 102

Met Ala Ser Cys Ser Leu Gly Val Pro Lys Ile Lys Ile Ser Ala Val
1               5                   10                  15

Asp Leu Ser Arg Val Arg Ser Gly Ser Leu Leu Ile Pro Phe Asn Gln
            20                  25                  30

Arg Ser Leu Leu Gly Gln Lys Pro Val Lys Tyr Leu Ser Leu Arg Thr
        35                  40                  45

Thr Phe Gly Thr Val Lys Ala Val Gln Val Ser Thr Val Pro Ala Pro
    50                  55                  60

Glu Thr Ser Ala Thr Ile Glu Val Glu Asp Ser Asp Glu Thr Lys Ser
65                  70                  75                  80

Ser Lys Leu Asn Ala Gln Leu Val Pro Lys Pro Ser Glu Val Glu Ala
                85                  90                  95

Leu Val Thr Glu Ile Cys Asp Thr Ser Ser Ile Ala Glu Phe Glu Leu
            100                 105                 110

Lys Leu Gly Gly Phe Arg Leu Tyr Val Ala Arg Asp Leu Ala Asp Lys
        115                 120                 125

Ser Ser Pro Gln Pro His Ala Thr Pro Ala Val Ala Ala Thr Ser Glu
    130                 135                 140

Thr Thr Asn Ser Thr Asp Ser Asn Gly Ser Ala Pro Ser Thr Ser Leu
145                 150                 155                 160

Ala Ile Thr Arg Pro Ala Ser Ser Ala Ala Asp Lys Gly Leu Met Ile
                165                 170                 175

Leu Gln Ser Pro Lys Val Gly Phe Phe Arg Arg Ser Lys Thr Ile Lys
            180                 185                 190

Gly Lys Arg Met Pro Ser Ser Cys Lys Glu Lys Asp Gln Val Lys Glu
        195                 200                 205

Gly Gln Ile Leu Cys Tyr Ile Glu Gln Leu Gly Gly Gln Phe Pro Ile
    210                 215                 220

Glu Ser Asp Val Thr Gly Glu Val Val Lys Ile Leu Arg Glu Asp Gly
225                 230                 235                 240

Glu Pro Val Gly Tyr Asn Asp Ala Leu Ile Ser Ile Leu Pro Ser Phe
                245                 250                 255

Pro Gly Ile Lys Lys Leu Gln
            260

<210> SEQ ID NO 103
<211> LENGTH: 295
<212> TYPE: PRT
<213> ORGANISM: Capsicum annuum

<400> SEQUENCE: 103

Met Glu Ser Ala Val Val Leu Arg Ser Phe His His Ser Val Gly Thr
1               5                   10                  15

Thr Ser His Val Arg Ser Gly Ile Glu Met Pro Gly Val Ile Pro Thr
            20                  25                  30

Asn Ser Ile Ala Phe Ser Lys Phe Thr Lys Leu Thr Leu Lys Asp Ser
        35                  40                  45
```

-continued

```
Ser Asn Gly Ala Arg Phe Met Ser Ser Pro Asn Lys His Gly Arg Leu
    50                  55                  60

Met Leu Ser Cys Ala Lys Thr Ser Glu Thr Thr Val Thr Ala Lys Ser
65                  70                  75                  80

Asp Gly Ala Val Leu Ala Asp Ser His Lys Lys Val Pro Thr Glu Ser
                85                  90                  95

Ser Pro Leu Pro Thr Thr Thr Phe Pro Lys Gly Phe Glu Ala Leu Ile
                100                 105                 110

Thr Glu Val Cys Asp Asp Thr Glu Val Ala Glu Leu Lys Leu Lys Val
            115                 120                 125

Gly Gly Phe Glu Leu His Leu Lys Arg Asn Ile Glu Ala Pro Val Val
        130                 135                 140

Pro Ala Pro Val Val Ser Thr Pro Thr Pro Thr Pro Pro Ser Ala
145                 150                 155                 160

Ser Lys Pro Ser Ile Ser Ser Thr Ala Thr Ala Pro Ala Ala Ser Leu
                165                 170                 175

Arg Lys Ser Ser Ser Glu Lys Val Ser Pro Phe Thr Asn Ile Ala Ala
                180                 185                 190

Glu Lys Ser Ala Lys Leu Ala Ala Leu Glu Ala Thr Gly Ala Ser Gly
                195                 200                 205

Tyr Val Leu Val Ser Cys Pro Thr Val Gly Ser Leu Arg Arg Ala Arg
    210                 215                 220

Thr Leu Lys Gly Lys Lys Gln Pro Pro Ala Cys Lys Glu Gly Asp Ile
225                 230                 235                 240

Ile Lys Glu Gly Gln Ile Ile Gly Phe Leu Asp Gln Phe Gly Thr Glu
                245                 250                 255

Leu Pro Val Arg Ser Asp Ala Ala Gly Glu Val Leu Lys Ile Leu Phe
                260                 265                 270

Asn Asp Gly Glu Ala Ala Gly Tyr Gly Asp Pro Leu Ile Ala Val Leu
                275                 280                 285

Pro Ser Phe Arg Gly Ile Asn
    290                 295
```

```
<210> SEQ ID NO 104
<211> LENGTH: 274
<212> TYPE: PRT
<213> ORGANISM: Capsicum annuum

<400> SEQUENCE: 104
```

```
Met Ala Ala Cys Gly Phe Gly Ala Ser Gly Leu Lys Leu Thr Thr Leu
1               5                   10                  15

Asn Leu Gly Ser Thr Lys Pro Lys Phe Ser Ala Trp His Asn Leu Lys
                20                  25                  30

Thr Lys Lys Leu Val Gln Thr Asp Gly Leu Leu Leu Thr Thr Lys Ser
            35                  40                  45

Arg Lys Thr Phe Ser Cys Arg Cys Ser Thr Val Glu Ala Glu Pro Ala
    50                  55                  60

Ala Ala Ala Ala Ile Pro Asn Ser Asp Asp Ser Ser Arg Lys Val Val
65                  70                  75                  80

Ser Ser Glu Thr Ala Ser Pro Leu Ile Pro Asn Ser Tyr Glu Val Glu
                85                  90                  95

Ser Leu Leu Thr Glu Ile Cys Asp Thr Thr Ser Ile Ala Glu Val Asp
                100                 105                 110

Leu Lys Leu Gly Gly Phe Arg Leu Tyr Val Lys Arg Asn Leu Thr Gly
```

-continued

```
            115                 120                 125

Gln Thr Thr Thr Ser Leu Pro Ala Ile Ser Ser Pro Val Ser Ile Pro
    130                 135                 140

Ser Pro Val Glu Val Ala Asp Ser Asn Gly Ser Ala Ser Ser Thr Ser
145                 150                 155                 160

Leu Ala Ile Thr Lys Ser Ser Pro Pro Ser Asp Gly Ile Gln Thr Met
                165                 170                 175

Ile Asp Lys Ala Ala Asp Glu Gly Leu Val Ile Ile Gln Ser Pro Arg
            180                 185                 190

Val Gly Tyr Phe Arg Arg Ser Arg Thr Ile Lys Gly Lys Arg Ala Pro
            195                 200                 205

Pro Ser Cys Lys Glu Lys Gln Gln Val Lys Glu Gly Gln Val Val Phe
    210                 215                 220

Phe Ile Glu Gln Leu Gly Gly Glu Leu Pro Val Glu Ser Asp Val Ser
225                 230                 235                 240

Gly Glu Val Ile Lys Ile Leu Arg Glu Asp Gly Asp Pro Val Gly Tyr
                245                 250                 255

Gly Asp Pro Leu Ile Ser Ile Leu Pro Ser Phe Pro Gly Ile Lys Lys
            260                 265                 270

Leu Gln

<210> SEQ ID NO 105
<211> LENGTH: 292
<212> TYPE: PRT
<213> ORGANISM: Cicer arietinum

<400> SEQUENCE: 105

Met Asp Ser Ser Leu Ala Ile Arg Ser Phe Gln Tyr Pro Ile Gly Thr
1               5                   10                  15

Met Pro Gln Val Arg Ser Pro Ile Glu Arg Ala Thr Val Ile Pro Cys
                20                  25                  30

His Lys Val Arg Trp Asn Ser Asn Ser Gly Ile Phe Gln His Leu Thr
            35                  40                  45

His Ser Glu Asn His Ile Tyr Phe His Thr Arg Gly Lys Lys Thr Leu
    50                  55                  60

Val Ser Cys Ala Lys Thr Val Glu Ala Ile Asn Thr Thr Lys Ser Asp
65                  70                  75                  80

Ala Ser Ser Asp Ser Thr Leu Gln Asn Ser Leu Glu Lys Glu Gln Leu
                85                  90                  95

Gln Ile Ala Ala Phe Pro Asn Gly Phe Glu Ala Leu Val Leu Glu Val
            100                 105                 110

Cys Asp Glu Thr Glu Ile Ala Glu Leu Lys Leu Lys Val Gly Glu Phe
            115                 120                 125

Glu Met His Leu Lys Arg Asn Ile Gly Ala Thr Lys Ala Pro Leu Ser
    130                 135                 140

Asn Ile Ser Pro Thr Ile Pro Pro Ile Pro Ser Lys Pro Met Asp
145                 150                 155                 160

Glu Ser Ala Pro Ala Thr Pro Gln Pro Leu Leu Pro Lys Ser Ser Ser
                165                 170                 175

Glu Lys Thr Asn Pro Phe Ala Asn Val Ser Ser Gln Lys Ser Ser Lys
            180                 185                 190

Leu Thr Ala Leu Glu Ala Ser Gly Ser Asn Thr Tyr Val Leu Val Ser
            195                 200                 205

Ser Pro Thr Val Gly Leu Phe Arg Arg Gly Arg Thr Val Lys Gly Lys
```

```
            210                 215                 220
Lys His Pro Pro Leu Cys Lys Glu Gly Asp Val Ile Lys Glu Gly Gln
225                 230                 235                 240

Val Ile Gly Tyr Leu Asp Gln Phe Ser Thr Ser Leu Pro Val Lys Ser
                245                 250                 255

Asp Val Ala Gly Glu Val Leu Lys Leu Leu Glu Asp Gly Glu Pro
                260                 265                 270

Val Gly Tyr Gly Asp Pro Leu Leu Ala Val Leu Pro Ser Phe His Asp
                275                 280                 285

Ile Asn Ile Met
        290

<210> SEQ ID NO 106
<211> LENGTH: 276
<212> TYPE: PRT
<213> ORGANISM: Cicer arietinum

<400> SEQUENCE: 106

Met Ala Ser Ser Ser Cys Asn Leu Gly Thr Gln Asn Val Glu Val Leu
1               5                   10                  15

Asn Leu His Phe Gly Gln Lys Arg Ile Gly Leu Ser Gln Gln Phe Gly
                20                  25                  30

Thr Lys Asn Trp Ile Ser Arg Lys Ser Leu Gln Tyr Thr Ser Leu Val
                35                  40                  45

Thr Ser Gln Gln Arg Val Arg Ser Leu Thr Ser Thr Asn Gly Gln Leu
        50                  55                  60

Ala Glu Ile Gln Ser Val Ser Ser Ser Glu Glu Asp Ser Glu Glu Ile
65                  70                  75                  80

Lys Ser Ser Gly Leu Ala Ser Glu Leu Ile Pro Asn Phe Asn Glu Val
                85                  90                  95

Glu Phe Leu Leu Thr Asn Leu Cys Asp Thr Thr Ser Ile Ala Glu Leu
                100                 105                 110

Glu Leu Lys Leu Asp Gly Phe His Leu His Val Val Arg Asp Leu Thr
        115                 120                 125

Glu Lys Thr Thr Thr Leu Pro Pro Pro Ile Pro Thr Pro Ala Ser Thr
        130                 135                 140

Ser Ile Ala Ala Glu Ala Pro Lys Pro Asn Gly Leu Val Ser Thr Leu
145                 150                 155                 160

Ser Ser Leu Ala Ile Ser Lys Ser Gly Pro Ser Ser Val Ser Met Gln
                165                 170                 175

Gly Phe Leu Asp Lys Ala Ala Asp Glu Gly Leu Val Ile Ile Gln Ser
                180                 185                 190

Pro Lys Val Gly Phe Phe Arg Arg Ser Arg Thr Ile Lys Gly Lys Arg
        195                 200                 205

Ala Arg Pro Ser Cys Lys Glu Met Gln Lys Val Glu Glu Gly Gln Val
        210                 215                 220

Ile Cys Tyr Ile Glu Gln Leu Gly Gly Glu Leu Pro Ile Glu Cys Asp
225                 230                 235                 240

Val Ser Gly Glu Val Ile Lys Ile Leu Arg Lys Asp Gly Asp Pro Val
                245                 250                 255

Gly Tyr Gly Asp Ala Leu Val Ala Val Leu Pro Ser Phe Pro Gly Ile
                260                 265                 270

Lys Lys Leu Gln
        275
```

<210> SEQ ID NO 107
<211> LENGTH: 287
<212> TYPE: PRT
<213> ORGANISM: Citrus clementina

<400> SEQUENCE: 107

Met Ala Ser Ser Ala Ala Leu Arg Ser Phe His Tyr Ser Val Gly Ala
1               5                   10                  15

Val Ala Lys Ser Gly Ser Ser Phe Glu Arg Pro Gly Ile Val Leu Pro
            20                  25                  30

Val Arg Asn Ser Ser Trp Pro Ser Ala Ala Ser Lys Ser Phe Asn Leu
        35                  40                  45

Val Thr Pro Pro Val Trp Arg Gly Val Thr Val Val Val Ser Ser Ala
    50                  55                  60

Lys Thr Ser Glu Asn Thr Ser Thr Ala Lys Thr Asp Glu Ser Thr Glu
65                  70                  75                  80

Glu Ser Ser Ser Glu Lys Ser Thr Leu Arg Ser Pro Ile Phe Pro Ser
                85                  90                  95

Gly Phe Glu Ala Leu Met Leu Glu Val Cys Asp Glu Thr Glu Ile Ala
            100                 105                 110

Glu Leu Lys Leu Lys Val Gly Asp Phe Glu Met His Leu Lys Arg Asn
            115                 120                 125

Val Gly Ala Pro Lys Ala Pro Ala Pro Leu Ser Asn Ile Ser Pro Thr
        130                 135                 140

Thr Pro Pro Pro Ile Pro Thr Glu Pro Met Glu Val Ser Asp Pro Val
145                 150                 155                 160

Ser Pro Pro Pro Pro Pro Ser Pro Pro Lys Pro Tyr Ser Glu Lys Ala
                165                 170                 175

Ala Pro Phe Ile Asn His Ser Phe Gly Lys Ser Ser Lys Leu Ala Ala
            180                 185                 190

Leu Glu Ala Ser Gly Ser Asn Gly Tyr Val Leu Val Phe Ser Pro Thr
            195                 200                 205

Val Gly Ser Phe Arg Arg Asn Arg Thr Val Lys Gly Lys Lys Gln Ser
        210                 215                 220

Pro Ile Cys Lys Glu Gly Asp Val Ile Lys Glu Gly Gln Ile Ile Gly
225                 230                 235                 240

Tyr Leu Asp Gln Phe Gly Thr Glu Leu Pro Val Lys Ser Asp Val Ala
                245                 250                 255

Gly Glu Val Leu Lys Leu Leu Phe Asp Asp Gly Asp Ala Val Gly Phe
            260                 265                 270

Gly Asp Pro Leu Ile Ala Val Leu Pro Ser Phe His Asp Ile Lys
            275                 280                 285

<210> SEQ ID NO 108
<211> LENGTH: 270
<212> TYPE: PRT
<213> ORGANISM: Citrus clementina

<400> SEQUENCE: 108

Met Ala Ser Tyr Ser Leu Gly Ala Ser Asn Ile Lys Ile Pro Lys Gly
1               5                   10                  15

Asn Leu Gly Arg Ala Arg Val Gly Asp Leu Gln Pro Arg Ser Asp Val
            20                  25                  30

Arg Lys Trp Met Gly Arg Lys Pro Phe Gln Tyr Ala Gly Leu Ala Met
            35                  40                  45

-continued

```
Ser Gln Pro Leu Glu Lys Ala Phe Thr Val Phe Cys Gly Gln Ser Ser
    50                  55                  60

Glu Ala Glu Ser Thr Arg Asn Ala Arg Asp Gly His Glu Asp Met Lys
65                  70                  75                  80

Ser Thr Gln Leu Ile Pro Asp Ser Ser Glu Val Glu Ser Leu Val Thr
                85                  90                  95

Asp Ile Cys Asn Thr Thr Ser Val Ala Glu Phe Glu Leu Lys Leu Asp
                100                 105                 110

Gly Phe Arg Leu Tyr Val Thr Arg Asp Ile Ala Gly Ala Ser Ser Pro
            115                 120                 125

Leu Leu Pro Ser Ser Pro Ala Pro Val Thr Val Asn Lys Pro Ala Asp
    130                 135                 140

Arg Pro Asp Ser Asn Gly Ser Val Pro Thr Pro Ser Leu Ala Ile Thr
145                 150                 155                 160

Lys Pro Val Ser Ser Ser Gly Gly Ile Gln Thr Leu Leu Asp Lys Ala
                165                 170                 175

Ala Asp Glu Gly Leu Val Ile Leu Glu Ser Pro Lys Val Gly Tyr Phe
            180                 185                 190

Arg Arg Ser Arg Thr Ile Lys Gly Lys Arg Ala Pro Pro Ser Cys Lys
            195                 200                 205

Glu Lys Gln Thr Val Arg Glu Gly Gln Val Leu Cys Tyr Ile Glu Gln
    210                 215                 220

Leu Gly Gly Glu Ile Pro Ile Glu Ser Asp Ile Ala Gly Glu Val Ile
225                 230                 235                 240

Lys Ile Leu Arg Lys Asp Gly Asp Pro Ile Gly Tyr Gly Asp Pro Leu
                245                 250                 255

Ile Val Ile Leu Pro Ser Phe Pro Gly Ile Lys Leu Leu Gln
                260                 265                 270
```

<210> SEQ ID NO 109
<211> LENGTH: 287
<212> TYPE: PRT
<213> ORGANISM: Citrus sinensis

<400> SEQUENCE: 109

```
Met Ala Ser Ser Ala Ala Leu Arg Ser Phe His Tyr Ser Val Gly Ala
1               5                   10                  15

Val Ala Lys Ser Gly Ser Ser Phe Glu Arg Pro Gly Ile Val Leu Pro
            20                  25                  30

Val Arg Asn Ser Ser Trp Pro Ser Ala Ala Ser Lys Ser Phe Asn Leu
        35                  40                  45

Val Thr Pro Pro Val Trp Arg Gly Val Thr Val Val Val Ser Ser Ala
    50                  55                  60

Lys Thr Ser Glu Asn Thr Ser Thr Ala Lys Thr Asp Glu Ser Thr Glu
65                  70                  75                  80

Glu Ser Ser Ser Glu Lys Ser Thr Leu Arg Ser Pro Ile Phe Pro Ser
                85                  90                  95

Gly Phe Glu Ala Leu Met Leu Glu Val Cys Asp Glu Thr Glu Ile Ala
                100                 105                 110

Glu Leu Lys Leu Lys Val Gly Asp Phe Glu Met His Leu Lys Arg Asn
            115                 120                 125

Val Gly Ala Pro Lys Ala Pro Ala Pro Leu Ser Asn Ile Ser Pro Thr
    130                 135                 140

Thr Pro Pro Pro Ile Pro Thr Glu Pro Met Glu Val Ser Asp Pro Val
145                 150                 155                 160
```

Ser Pro Pro Pro Pro Pro Ser Pro Pro Lys Pro Tyr Ser Glu Lys Ala
            165             170             175

Ala Pro Phe Ile Asn His Ser Phe Gly Lys Ser Ser Lys Leu Ala Ala
            180             185             190

Leu Glu Ala Ser Gly Ser Asn Gly Tyr Val Leu Val Phe Ser Pro Thr
        195             200             205

Val Gly Ser Phe Arg Arg Asn Arg Thr Val Lys Gly Lys Lys Gln Ser
    210             215             220

Pro Ile Cys Lys Glu Gly Asp Val Ile Lys Glu Gly Gln Ile Ile Gly
225             230             235             240

Tyr Leu Asp Gln Phe Gly Thr Glu Leu Pro Val Lys Ser Asp Val Ala
            245             250             255

Gly Glu Val Leu Lys Leu Leu Phe Asp Asp Gly Asp Ala Val Gly Phe
            260             265             270

Gly Asp Pro Leu Ile Ala Val Leu Pro Ser Phe His Asp Ile Lys
        275             280             285

<210> SEQ ID NO 110
<211> LENGTH: 271
<212> TYPE: PRT
<213> ORGANISM: Citrus sinensis

<400> SEQUENCE: 110

Met Ala Ser Tyr Ser Leu Gly Ala Ser Asn Ile Lys Ile Pro Lys Gly
1               5               10              15

Asn Leu Gly Arg Ala Arg Val Gly Asp Leu Gln Pro Arg Ser Asp Val
            20              25              30

Arg Lys Trp Met Gly Arg Lys Pro Phe Gln Tyr Ala Gly Leu Ala Met
        35              40              45

Ser Gln Pro Leu Glu Lys Ala Phe Thr Val Phe Cys Gly Gln Ser Ser
    50              55              60

Glu Ala Glu Ser Thr Arg Asn Ala Arg Asp Gly His Glu Asp Met Lys
65              70              75              80

Ser Pro Gln Leu Ile Pro Asp Ser Ser Glu Val Glu Ser Leu Val Thr
            85              90              95

Asp Ile Cys Asn Thr Thr Ser Val Ala Glu Phe Glu Leu Lys Leu Asp
            100             105             110

Gly Phe Arg Leu Tyr Val Thr Arg Asp Ile Ala Gly Asp Ser Ile Pro
        115             120             125

Pro Leu Pro Pro Ser Ser Pro Ala Pro Val Thr Val Asn Lys Pro Ala
    130             135             140

Asp Arg Pro Asp Ser Asn Gly Ser Val Pro Thr Ser Ser Leu Ala Ile
145             150             155             160

Thr Lys Pro Val Ser Ser Ser Gly Gly Ile Gln Thr Leu Leu Asp Lys
            165             170             175

Ala Ala Asp Glu Gly Leu Val Ile Leu Glu Ser Pro Lys Val Gly Tyr
            180             185             190

Phe Arg Arg Ser Arg Thr Ile Lys Gly Lys Arg Ala Pro Pro Ser Cys
        195             200             205

Lys Glu Lys Gln Thr Val Arg Glu Gly Gln Val Leu Cys Tyr Ile Glu
    210             215             220

Gln Leu Gly Gly Glu Ile Pro Ile Glu Ser Asp Ile Ala Gly Glu Val
225             230             235             240

Ile Lys Ile Leu Arg Lys Asp Gly Asp Pro Ile Gly Tyr Gly Asp Pro

-continued

```
                245                250                255
Leu Ile Val Ile Leu Pro Ser Phe Pro Gly Ile Lys Leu Leu Gln
            260                265                270

<210> SEQ ID NO 111
<211> LENGTH: 278
<212> TYPE: PRT
<213> ORGANISM: Cucumis melo

<400> SEQUENCE: 111

Met Glu Ser Ser Ala Ser Leu Arg Ser Phe His Tyr Phe Ala Gly Gly
1               5                10                15

Ser Arg Leu Gln Leu Val Asp Lys Pro Ser Lys Ile Tyr Val Ala Ser
            20                25                30

Thr Asn Lys Ser Ser Ile Gln Arg Leu Ser Ile Phe Gly Lys Pro Ile
        35                40                45

His Ser Pro Thr Ser Gln Lys Lys Ile Val Val Ser Cys Ile Lys Thr
    50                55                60

Pro Glu Val Ser Glu Ala Ala Lys Pro Lys Asp Ser Ala Gln Gly Ser
65                70                75                80

Leu Gln Lys Lys Pro Ala Ser Asn Ala Thr Phe Pro Asn Gly Phe Glu
                85                90                95

Ala Leu Val Leu Glu Val Cys Asp Glu Thr Glu Ile Ala Glu Leu Lys
            100                105                110

Leu Lys Val Gly Glu Phe Glu Met His Leu Lys Arg Asn Ile Gly Val
            115                120                125

Val Arg Ala Pro Leu Ser Ser Ile Ser Pro Thr Val Pro Pro Pro Ile
    130                135                140

Pro Ser Lys Pro Met Val Glu Ser Ala Pro Thr Ala Pro Ala Pro Pro
145                150                155                160

Lys Pro Ser Pro Glu Lys Ala Ala Ala Phe Thr Asn Ile Pro Leu Gln
            165                170                175

Lys Ser Ser Lys Leu Ala Ala Leu Glu Ser Ser Gly Ala Lys Gly Tyr
            180                185                190

Val Leu Val Pro Ser Pro Thr Val Gly Ser Phe Arg Ser Gly Arg Thr
            195                200                205

Ile Lys Gly Lys Lys Gln Pro Pro Ile Cys Lys Glu Asn Asp Leu Ile
    210                215                220

Lys Glu Gly Gln Val Ile Gly Tyr Val Asp Gln Phe Gly Thr Glu Leu
225                230                235                240

Pro Val Lys Ser Asp Val Ala Gly Glu Val Leu Arg Val Leu Phe Lys
            245                250                255

Asp Gly Glu Ala Val Gly Tyr Gly Asp Pro Leu Ile Ala Val Leu Pro
            260                265                270

Glu Phe His Gly Ile Arg
        275

<210> SEQ ID NO 112
<211> LENGTH: 276
<212> TYPE: PRT
<213> ORGANISM: Cucumis melo

<400> SEQUENCE: 112

Met Ala Ser Cys Ser Leu Arg Ala Val Asp Ile Lys Val Ser Lys Leu
1               5                10                15

Asp Ile Arg Arg Gly Arg Val Ser Thr Leu Gln Pro Cys Ser Leu Arg
```

-continued

```
              20                  25                  30

Asn Trp Ile Gly Arg Thr Pro His Gln Tyr Ser Thr Leu Val Ile Ser
        35                  40                  45

His Ser Ser Gln Lys Ala Leu His Ala Cys Ser Ser Ala Ser Pro Glu
    50                  55                  60

Thr Gln Thr Val Ile Lys Ser Glu Thr Gly Ser Glu Glu Ile Lys Pro
65                  70                  75                  80

Ser Asn Leu Val Ser Gln Leu Ile Pro Asn Leu His Glu Val Glu Thr
                85                  90                  95

Leu Leu Thr Asn Ile Cys Asp Thr Ser Ser Ile Ala Glu Phe Glu Leu
                100                 105                 110

Lys Leu Ser Gly Phe Asn Leu Arg Met Val Arg Ser Leu Lys Ser Glu
            115                 120                 125

Asn Leu Pro Leu Pro Pro Ala Pro Ala Pro Ala Pro Asp Ile Gln Asn
        130                 135                 140

Thr Ser Ser Ile Pro Ser Asp Ser Asn Gly Leu Val Lys Thr Ser Leu
145                 150                 155                 160

Ala Leu Val Lys Pro Glu Pro Val Ser Ser Ser Pro Glu Gly Ile Ser
                165                 170                 175

Arg Tyr Val Glu Lys Ala Thr Asp Gly Gly Leu Ser Ile Leu Val Ser
                180                 185                 190

Pro Lys Val Gly Val Phe Arg Arg Ser Arg Thr Ile Lys Gly Lys Arg
            195                 200                 205

Ala Pro Pro Ser Cys Glu Glu Asn Gln Val Val Lys Glu Gly Lys Val
        210                 215                 220

Leu Cys Tyr Ile Asp Gln Leu Gly Ala Glu Ile Pro Ile Glu Ser Asp
225                 230                 235                 240

Ile Ser Gly Glu Ile Val Lys Ile Leu Arg Lys Asp Gly Glu Pro Val
                245                 250                 255

Gly Tyr Gly Asp Pro Leu Ile Ala Val Leu Pro Ser Phe Pro Gly Ile
                260                 265                 270

Lys Lys Leu Leu
        275

<210> SEQ ID NO 113
<211> LENGTH: 274
<212> TYPE: PRT
<213> ORGANISM: Cucumis sativus

<400> SEQUENCE: 113

Met Glu Ser Ser Ala Ser Leu Arg Ser Phe His Tyr Phe Ala Gly Gly
1               5                   10                  15

Ser Arg Leu Gln Leu Ile Glu Lys Pro Ser Arg Ile Tyr Val Ser Ser
            20                  25                  30

Thr Asn Lys Thr Ser Ile Gln Arg Leu Ser Ile Phe Gly Lys Pro Ile
        35                  40                  45

His Asn Pro Thr Ser Gln Lys Lys Ile Ala Val Ser Cys Thr Lys Thr
    50                  55                  60

Pro Glu Val Thr Glu Thr Asp Ser Ala Lys Gly Ser Leu Gln Lys Lys
65                  70                  75                  80

Pro Ala Ser Asn Val Thr Phe Pro Asn Gly Phe Glu Glu Leu Leu Leu
                85                  90                  95

Glu Val Cys Asp Asp Thr Glu Ile Ala Glu Leu Lys Leu Lys Val Gly
            100                 105                 110
```

-continued

Glu Phe Glu Met His Val Lys Arg Asn Ile Gly Val Val Ser Ala Pro
            115                 120                 125

Leu Ser Ala Ile Ser Pro Thr Val Pro Pro Pro Ile Pro Ser Lys Pro
    130                 135                 140

Met Val Glu Ser Ala Leu Ala Ala Pro Ala Pro Pro Ile Pro Ser Pro
145                 150                 155                 160

Glu Lys Ala Asn Ala Phe Thr Asp Val Pro Phe Lys Lys Ser Ser Lys
                165                 170                 175

Leu Ala Ala Leu Glu Ala Ser Gly Ala Lys Gly Tyr Val Leu Val Thr
            180                 185                 190

Ser Pro Thr Val Gly Ser Phe Arg Ser Gly Arg Thr Val Lys Gly Arg
            195                 200                 205

Arg Met Pro Pro Ile Cys Lys Glu Asn Asp Leu Ile Arg Glu Gly Gln
    210                 215                 220

Val Val Ala Tyr Val Asp Gln Phe Gly Ser Gln Leu Pro Val Lys Ser
225                 230                 235                 240

Asp Val Ala Gly Glu Val Leu Arg Ile Leu Phe Lys Glu Asp Glu Pro
                245                 250                 255

Val Gly Phe Gly Asp Pro Leu Ile Ala Val Leu Pro Ile Phe His Gly
            260                 265                 270

Ile Arg

<210> SEQ ID NO 114
<211> LENGTH: 277
<212> TYPE: PRT
<213> ORGANISM: Cucumis sativus

<400> SEQUENCE: 114

Met Ala Phe Cys Ser Leu Arg Ala Ala Asp Ile Lys Phe Ser Lys Leu
1               5                   10                  15

Asp Ile Arg Arg Gly Arg Val Ser Thr Leu Gln Pro Cys Ser Leu Arg
            20                  25                  30

Asn Trp Ile Gly Arg Thr Pro His Gln Tyr Ser Ser Leu Val Ile Ser
            35                  40                  45

His Ser Ser Gln Lys Ala Leu His Ala Cys Ser Gly Ala Ser Pro Lys
    50                  55                  60

Ala Gln Thr Val Ile Lys Ser Glu Thr Gly Ser Glu Glu Ile Lys Pro
65                  70                  75                  80

Ser Ser Leu Gly Ser Gln Leu Ile Pro Asn Phe His Glu Val Glu Thr
                85                  90                  95

Leu Leu Thr Asn Val Cys Asp Thr Ser Ser Ile Ala Glu Phe Glu Leu
            100                 105                 110

Lys Leu Ser Gly Phe Asn Leu Arg Met Val Arg Ser Leu Lys Ser Lys
            115                 120                 125

Asn Leu Pro Leu Pro Pro Val Pro Ala Pro Ala Pro Asp Ile Gln Asn
    130                 135                 140

Thr Ser Ser Ile Pro Ser Asp Ser Asn Gly Leu Val Lys Thr Thr Ser
145                 150                 155                 160

Leu Ala Leu Val Lys Pro Glu Pro Val Ser Ser Ser Pro Arg Gly Ile
                165                 170                 175

Ser Arg Tyr Val Glu Lys Ala Arg Asp Gly Gly Val Thr Ile Leu Ser
            180                 185                 190

Ser Pro Asn Val Gly Val Phe Arg Arg Ser Arg Thr Ile Lys Gly Lys
            195                 200                 205

-continued

Arg Ala Pro Pro Ser Cys Ala Glu Asp Gln Val Val Arg Glu Gly Gln
    210             215             220

Val Leu Cys Tyr Ile Glu Gln Leu Gly Gly Gln Ile Pro Val Lys Ser
225             230             235             240

Asp Thr Pro Gly Glu Ile Leu Lys Ile Leu Arg Lys Asp Gly Glu Pro
            245             250             255

Val Gly Tyr Gly Asp Ala Leu Ile Ala Val Leu Pro Ser Phe Pro Gly
            260             265             270

Ile Lys Lys Leu Arg
        275

<210> SEQ ID NO 115
<211> LENGTH: 261
<212> TYPE: PRT
<213> ORGANISM: Daucus carota

<400> SEQUENCE: 115

Met Arg Ser Ser Leu Glu Lys Ala Thr Trp Ser Ile Ser Asn Arg Cys
1               5               10              15

Pro Ile Gln Gly Leu Thr Val Gly Arg Asn Phe Val Ser Ser Pro Ser
            20              25              30

Lys Arg Glu Leu Arg Val Ile Ala Cys Val Lys Thr Ser Asp Ser Ala
        35              40              45

Ile Val Ala Lys Ser Glu Asp Ser Cys Ser Gln Gly Ser Val Glu Lys
    50              55              60

Thr Pro Phe Arg Gly Ala Thr Phe Pro Gly Gly Phe Glu Ala Leu Val
65              70              75              80

Lys Glu Val Cys Asp Glu Thr Gln Ile Ala Glu Leu Lys Leu Lys Ile
            85              90              95

Gly Asp Phe Glu Met His Leu Lys Arg Asn Ile Glu Ser Pro Val Ala
            100             105             110

Val Ala Pro Pro Val Ala Pro Ala Pro Val Pro Thr Ala Pro Lys Thr
            115             120             125

Glu Ser Thr Pro Ala Ser Ser Ala Pro Ser Pro Thr Lys Ala Ser Pro
    130             135             140

Val Lys Thr Asn Pro Phe Thr Asn Ile Pro Val Glu Lys Ser Arg Lys
145             150             155             160

Leu Ala Ala Leu Glu Ala Ser Gly Ala Ser Gly Tyr Val Leu Val Ala
            165             170             175

Ser Pro Thr Val Gly Ser Phe Arg Lys Gly Arg Thr Leu Lys Gly Lys
            180             185             190

Lys Gln Pro Pro Ser Cys Lys Glu Gly Asp Leu Ile Lys Glu Gly Gln
        195             200             205

Val Ile Gly Phe Leu Asp Gln Phe Gly Thr Glu Leu Pro Val Lys Lys
    210             215             220

Leu Leu Val Met Glu Ile Pro Leu Leu Leu Ser Cys His His Phe Met
225             230             235             240

Glu Ser Gly Ile Gly Met Cys Lys Thr Val Leu Ala Thr Ser Gly Met
            245             250             255

Gly Tyr Thr Asn Pro
            260

<210> SEQ ID NO 116
<211> LENGTH: 195
<212> TYPE: PRT
<213> ORGANISM: Daucus carota

<400> SEQUENCE: 116

```
Met Lys Leu Ala Asn Ser His Leu Trp Arg Ser Asn Gln Val Lys Tyr
1               5                   10                  15

Val Glu Ser Leu Leu Glu Glu Ile Cys Asp Thr Thr Ser Ile Ala Glu
            20                  25                  30

Phe Glu Leu Lys Phe Gly Gly Phe Arg Leu Tyr Val Ser Arg Asp Leu
        35                  40                  45

Ser Gly Lys Asn Glu Ala Pro Gln Leu Pro Val Ser Ala Pro Leu Thr
    50                  55                  60

Ser Thr Ala Val Ser Val Pro Glu Leu Asn Gly Ser Ala Thr Ser Thr
65                  70                  75                  80

Ser Leu Ala Ile Ser Lys Pro Ala Leu Thr Ser Gly Gly Ile Gln Ser
                85                  90                  95

Phe Leu Asp Arg Ala Gly Asp Asp Gly Leu Val Ile Leu Pro Ser Pro
            100                 105                 110

Lys Val Gly Tyr Phe Arg Arg Cys Arg Thr Ile Lys Gly Lys Arg Ala
        115                 120                 125

Pro Pro Ala Cys Lys Glu Lys Gln Thr Val Lys Glu Gly Gln Val Leu
    130                 135                 140

Cys Phe Ile Glu Gln Leu Gly Gly Glu Ile Pro Ile Glu Ser Glu Thr
145                 150                 155                 160

Ser Gly Glu Val Ile Arg Ile Leu Arg Glu Asp Gly Asp Pro Val Gly
                165                 170                 175

Tyr Gly Asp Ala Leu Ile Ala Ile Leu Pro Ser Phe Pro Gly Ile Lys
            180                 185                 190

Lys Leu Gln
        195
```

<210> SEQ ID NO 117
<211> LENGTH: 292
<212> TYPE: PRT
<213> ORGANISM: Dorcoceras hygrometricum

<400> SEQUENCE: 117

```
Met Glu Ser Ala Ala Val Asn His Arg Ser Phe Leu Tyr Ala Ala Ser
1               5                   10                  15

Pro Gly Ser His Ser Asn Ala Thr Phe Glu Arg Pro Gly Val Ile Thr
            20                  25                  30

Met Asn Asn Gly Val Phe Ser Asn Ala Ser Arg Leu Asn Leu Cys Asp
        35                  40                  45

Gly Lys Ile Phe Ser Ser Thr Asn Arg His Arg Ala Leu Ser Val Ser
    50                  55                  60

Cys Val Lys Thr Ser Glu Thr Ala Leu Ala Ala Lys Ser Asn Gly Asp
65                  70                  75                  80

Pro Asn Gly Ala Ile Val Pro Glu Ser Gln Gln His Asp Leu Leu Glu
                85                  90                  95

Lys Lys Ser Asn Phe Arg Ala Thr Phe Pro Asn Gly Phe Glu Asp Leu
            100                 105                 110

Leu Lys Glu Val Cys Asp Glu Thr Gln Ile Ala Glu Leu Lys Val Lys
        115                 120                 125

Phe Gly Ala Phe Glu Ile His Met Lys Arg Asn Ile Asp Val Pro Thr
    130                 135                 140

Ala Pro Val Pro Val Phe Pro Gln Glu Thr Ser Pro Pro Val Pro Ser
145                 150                 155                 160
```

-continued

```
Lys Pro Val Asp Val Pro Thr Ser Ala Pro Pro Pro Pro Lys Ser
            165                 170                 175

Ser Val Glu Lys Val Ser Pro Phe Thr Asn Val Ser Val Glu Lys Thr
            180                 185                 190

Thr Lys Leu Ala Ala Val Glu Ala Ile Arg Ser Asp Gly Tyr Val Ile
            195                 200                 205

Val Ser Ser Pro Thr Val Gly Ser Phe Arg Arg Ala Arg Thr Leu Lys
        210                 215                 220

Gly Lys Lys Gln Pro Pro Ala Cys Lys Glu Gly Asp Val Ile Lys Glu
225                 230                 235                 240

Gly Gln Val Ile Gly Phe Leu Asp Gln Phe Gly Thr Glu Leu Pro Val
                245                 250                 255

Lys Ser Asp Val Ser Gly Glu Val Leu Lys Val Leu Tyr Ser Asp Gly
            260                 265                 270

Glu Ala Val Gly Tyr Gly Asp Pro Leu Ile Ala Val Leu Pro Ser Phe
            275                 280                 285

Pro Gly Ile Lys
    290

<210> SEQ ID NO 118
<211> LENGTH: 284
<212> TYPE: PRT
<213> ORGANISM: Elaeis guineensis

<400> SEQUENCE: 118

Met Glu Ala Ala Ala Val Leu Arg Ser Phe Gln Gly Gly Val Trp Thr
1               5                   10                  15

Lys Gln Pro Ser Glu Ser Phe Leu Glu Lys Pro Ala Val Ala Ser Val
            20                  25                  30

Ser Asn Val Ala Leu Lys Val Lys Pro Ile Ser Gly Val Leu Met Val
            35                  40                  45

Ala Gln Gly Trp Lys Arg Ser Phe Leu Pro Tyr Leu Lys Ala Ser Glu
        50                  55                  60

Thr Asn Ser Ala Leu Thr Ser Glu Val Thr Ser Asp Arg Ser Ser Gln
65                  70                  75                  80

Glu Pro Leu Glu Glu Ser Val Gln Asn Ser Thr Phe Pro Asn Gly Phe
                85                  90                  95

Glu Ala Leu Ile Leu Glu Val Cys Asp Glu Thr Asn Ile Ala Glu Phe
            100                 105                 110

Lys Ile Lys Ile Gly Asp Phe Glu Met His Leu Lys Arg Asp Ile Glu
            115                 120                 125

Ser Pro Arg Ala Pro Ser Pro Ser Thr His Ile Val Ser Pro Thr Thr
        130                 135                 140

Ala Pro Pro Ile Pro Ser Glu Pro Met Asn Glu Ser Gly Ala Ala Ala
145                 150                 155                 160

Gln Pro Ala Val Ser Arg Lys Ser Pro Pro Ala Ala Thr Ser Pro Phe
                165                 170                 175

Ala Asn Ile Ser Ser Ala Lys Ala Leu Lys Leu Ala Ala Leu Glu Ala
            180                 185                 190

Ser Val Ser Asn Ala Tyr Val Leu Ile Ser Ser Pro Thr Val Gly Thr
            195                 200                 205

Phe Gln Arg Gly Gly Thr Phe Lys Gly Lys Lys Gln Pro Pro Ser Cys
        210                 215                 220

Lys Glu Gly Asp Ile Ile Lys Glu Gly Gln Ile Ile Gly Phe Leu Asp
```

-continued

```
225                 230                 235                 240

Gln Phe Gly Asn Glu Leu Pro Val Lys Ser Asp Val Ala Gly Glu Val
                245                 250                 255

Leu Lys Val Leu Tyr Gln Asp Gly Glu Ala Val Gly Tyr Gly Asp Pro
                260                 265                 270

Leu Val Ala Val Leu Pro Ala Phe His Gly Ile Glu
                275                 280
```

<210> SEQ ID NO 119
<211> LENGTH: 282
<212> TYPE: PRT
<213> ORGANISM: Elaeis guineensis

<400> SEQUENCE: 119

```
Met Ala Thr Cys Ser Gln Gly Ser Thr Phe Asn Val Thr Leu Leu Asn
1               5                   10                  15

Phe His Pro Glu Phe Arg Lys Leu Arg Cys Thr Ala Leu Phe Thr Pro
                20                  25                  30

Cys Lys Thr Lys Ser Gly Arg Leu Glu Ala Leu Asn Gly Leu Lys Gly
                35                  40                  45

Thr Gln Ile Trp Gln Glu Pro Val Arg Ala Ala Gly Phe Asp Lys Gln
    50                  55                  60

Ala Gln Arg Pro Thr Asn Ser Leu Val Ala Arg Cys Arg Leu Ser Ser
65                  70                  75                  80

Gly Thr Glu Asn Asn Ser Glu Ala Ile Lys Leu Glu Glu Asn Lys Ser
                85                  90                  95

Lys Gly Glu Gln Ile Ile Pro Val Ser Leu Glu Val Glu Pro Leu Leu
                100                 105                 110

Thr Ala Ile Cys Asp Thr Thr Ser Ile Ser Glu Phe Lys Leu Asp Leu
                115                 120                 125

Ala Gly Phe Cys Leu Tyr Val Lys Arg Asp Leu Val Glu Lys Asn Val
                130                 135                 140

Pro Pro Pro Val Pro Ser Leu Leu Gln Thr Asn Thr Thr Asn Gln Thr
145                 150                 155                 160

Pro Asp Ser Asn Gly Ser Ala Ala Thr Ala Ser Leu Val Ile Ser Lys
                165                 170                 175

Pro Lys Pro Ser Thr Gly Gly Ile Gln Arg Thr Ala Ser Asp Glu Gly
                180                 185                 190

Leu Val Met Leu Pro Ser Pro Lys Val Gly Phe Phe Arg Thr Ser Cys
                195                 200                 205

Thr Ile Lys Gly Arg Arg Ala Pro Pro Leu Cys Lys Glu Lys Gln Glu
                210                 215                 220

Val Lys Glu Gly Gln Val Leu Cys Tyr Ile Glu Gln Leu Gly Gly Glu
225                 230                 235                 240

Ile Pro Ile Glu Ser Asp Val Ser Gly Glu Ile Val Lys Ile Leu Arg
                245                 250                 255

Glu Asp Gly Glu Pro Val Gly Tyr Gly Asp Ala Leu Ile Ala Ile Leu
                260                 265                 270

Pro Ser Phe Ser Gly Ile Lys Lys Leu Gln
                275                 280
```

<210> SEQ ID NO 120
<211> LENGTH: 292
<212> TYPE: PRT
<213> ORGANISM: Erythranthe guttata -continued

```
<400> SEQUENCE: 120

Met Glu Ser Ala Ala Val Leu Arg Ser Phe Gln Tyr Ala Val Gly Ser
1               5                   10                  15

Ser Ser His Leu Lys Ser Gly Val Glu Arg Pro Ala Met Ile Thr Met
            20                  25                  30

Asn Asn Ala Ala Phe Tyr Asn Leu Ser Arg Leu Pro Val Phe Gly Gly
        35                  40                  45

Asn Thr Val Ser Ser Thr Asn Arg His Gly Ala Leu Leu Val Ser Cys
    50                  55                  60

Val Lys Thr Ser Glu Ala Thr Val Thr Ala Lys Ser Lys Gly Asp Pro
65                  70                  75                  80

Asn Gly Ala Val Leu Ala Asp Ser Pro Gln Asn Gly Ser Pro Glu Lys
                85                  90                  95

Lys Ser Pro Ile Asn Ala Thr Phe Pro Asn Gly Phe Glu Asn Leu Leu
            100                 105                 110

Ser Glu Val Cys Asp Glu Thr Lys Ile Ala Glu Leu Lys Val Lys Ile
            115                 120                 125

Gly Gly Phe Glu Leu His Met Lys Arg Asn Ile Asp Gly Pro Ala Ile
    130                 135                 140

Ser Ala Pro Val Val Ser Gln Thr Thr Val Pro Ser Leu Pro Ser Lys
145                 150                 155                 160

Pro Ala Asn Glu Leu Ser Pro Ser Ala Pro Pro Pro Ser Lys Ser
                165                 170                 175

Ser Ala Glu Lys Val Asn Pro Phe Ala Asn Val Ser Val Glu Lys Ala
            180                 185                 190

Ala Lys Leu Ala Ala Leu Asp Ala Ser Gly Ser Ser Gly Tyr Val Ile
            195                 200                 205

Val Ser Ser Pro Thr Val Gly Ser Phe Arg Arg Ala Arg Thr Leu Lys
    210                 215                 220

Gly Lys Lys Gln Pro Pro Ala Cys Lys Glu Gly Asp Leu Ile Lys Glu
225                 230                 235                 240

Gly Gln Val Ile Gly Tyr Leu Asp Gln Phe Gly Thr Glu Leu Pro Val
                245                 250                 255

Asn Ser Asp Val Ala Gly Glu Val Leu Lys Leu Leu Tyr Asn Asp Gly
            260                 265                 270

Glu Ala Val Gly Tyr Gly Asp Pro Leu Ile Ala Val Leu Pro Ser Phe
            275                 280                 285

His Gly Ile Arg
    290

<210> SEQ ID NO 121
<211> LENGTH: 273
<212> TYPE: PRT
<213> ORGANISM: Erythranthe guttata

<400> SEQUENCE: 121

Met Ala Ala Cys Gly Phe Gly Ala Ser Gly Ile Lys Ile Lys Ser Leu
1               5                   10                  15

Asp Phe Gly Ser Val Arg Pro Lys Leu Arg Thr Leu Gln Pro Leu His
            20                  25                  30

Gly Leu Lys Thr Pro Ser Ile Val Arg Phe Asp Gly Leu Val Leu Ser
        35                  40                  45

Asn Arg Ser Lys Lys Met Leu Ile Gly Cys Arg Ser Ser Ser Leu Glu
    50                  55                  60
```

-continued

```
Ser Asp Ser Asn Ala Ser Ile Glu Asp Ile Ser Lys Glu Thr Glu Ser
65                  70                  75                  80

Pro Glu Ala Val Ser Thr Leu Ile Pro Asn Ala Phe Glu Val Glu Ser
                85                  90                  95

Leu Leu Thr Val Leu Cys Asp Thr Thr Ser Ile Ala Glu Ile Glu Leu
            100                 105                 110

Lys Leu Gly Gly Phe Arg Leu Tyr Val Ser Arg Asp Leu Ala Glu Gln
        115                 120                 125

Asn Ala Pro Pro Gln Pro Pro Ala Pro Ala His Val Ile Ala His Ser
        130                 135                 140

Val Val Glu Thr Pro Ser Ser Asn Gly Ser Ala Ser Ser Pro Ser Leu
145                 150                 155                 160

Ala Leu Ser Lys Pro Thr Ser Ser Ser Ala Gly Ile Gln Thr Met Leu
                165                 170                 175

Asp Lys Ala Ala Asp Glu Gly Leu Val Ile Leu Gln Ser Pro Arg Val
            180                 185                 190

Gly Tyr Phe Lys Arg Cys Arg Thr Ile Lys Gly Lys Lys Ala Pro Pro
        195                 200                 205

Ser Cys Lys Glu Lys Asp Thr Val Lys Glu Gly Gln Val Leu Cys Phe
    210                 215                 220

Ile Glu Gln Leu Gly Gly Glu Ile Pro Ile Glu Ser Asp Ile Ser Gly
225                 230                 235                 240

Glu Val Val Lys Ile Leu Arg Glu Asp Gly Ala Pro Val Gly Tyr Gly
                245                 250                 255

Asp Ala Leu Ile Ala Ile Leu Pro Ser Phe Pro Gly Ile Lys Lys Leu
            260                 265                 270

Gln
```

```
<210> SEQ ID NO 122
<211> LENGTH: 222
<212> TYPE: PRT
<213> ORGANISM: Eucalyptus grandis

<400> SEQUENCE: 122
```

```
Met Arg Thr Ser Asp Ser Ala Ile Ser Thr Asp Thr Asn Glu Cys Ile
1               5                   10                  15

Gly Arg Ser Val Glu Lys Gly Pro Leu Glu Asp Ala Thr Phe Pro Ser
                20                  25                  30

Gly Phe Gln Thr Leu Leu Leu Glu Val Cys Asp Glu Thr Gln Ile Ala
        35                  40                  45

Glu Leu Lys Leu Lys Val Gly Asn Phe Glu Met His Val Lys Arg Asn
    50                  55                  60

Val Gly Ala Ala Glu Val Pro Ala Pro Val Ile Ala Ser Pro Val Thr
65                  70                  75                  80

Pro Pro Pro Ile Pro Ala Glu Pro Val Asn Lys Ser Ser Ser Gly Val
                85                  90                  95

Ser Pro Pro Ser Ala Leu Lys Pro Ser Ser Glu Lys Ala Ala Pro Phe
            100                 105                 110

Met Asn Val Thr Phe Gly Lys Ser Ala Lys Val Lys Ala Leu Glu Ala
        115                 120                 125

Ser Gly Ser Ser Gly Tyr Ala Leu Val Ser Ser Pro Thr Val Gly Ser
    130                 135                 140

Phe Gln Lys Gly Arg Thr Val Lys Gly Lys Lys Gln Gly Pro Ser Cys
145                 150                 155                 160
```

```
Lys Glu Gly Asp Leu Ile Lys Glu Gly Gln Val Ile Gly Trp Leu Asp
                165                 170                 175

Gln Phe Gly Thr Glu Leu Pro Val Lys Ser Asp Val Ser Gly Glu Val
                180                 185                 190

Leu Lys Leu Leu Ile Asp Asp Gly Glu Ala Val Gly Tyr Gly Asp Pro
            195                 200                 205

Leu Leu Ala Val Leu Pro Ser Phe Pro Gly Val Gly Val Gln
        210                 215                 220

<210> SEQ ID NO 123
<211> LENGTH: 276
<212> TYPE: PRT
<213> ORGANISM: Eucalyptus grandis

<400> SEQUENCE: 123

Met Leu Leu Ser Met Ala Ser Cys Ser Leu Gly Ala Ser Asn Val Lys
1               5                   10                  15

Ile Ala Asn Leu Asn Ser Gly Arg Pro Lys Ile Gly Glu Ser Arg Leu
                20                  25                  30

Ser Tyr Gly Arg Ser Trp Ile Val Leu Lys Thr Pro Lys Tyr Ala Gly
            35                  40                  45

Leu Thr Leu Phe Gln Gln Leu Asp Lys Ile Cys Pro Val Cys Cys His
        50                  55                  60

Pro Ser Ser Gly Ser Pro Ser Thr Ser Ser Leu Leu Asp Asp Ser Glu
65                  70                  75                  80

Asp Ser Glu Pro Ser Ser Leu Thr Ser Gln Leu Ile Pro Asn Ser Ser
                85                  90                  95

Glu Val Glu Ser Leu Leu Thr Asp Ile Cys Glu Thr Ser Ile Ala Glu
                100                 105                 110

Phe Glu Leu Lys Leu Asn Gly Phe Arg Leu Tyr Val Ala Arg Asp Val
            115                 120                 125

Ser Gly Gly His Lys Pro Leu Pro Pro Phe Ser Pro Ala Pro Thr Pro
        130                 135                 140

Val His Ser Asn Val Glu Ala Thr Asp Thr Asn Gly Ser Leu Ser Lys
145                 150                 155                 160

Pro Ser Leu Ala Ile Ser Lys Ala Leu Thr Ser Ser Asp Gly Gly Pro
                165                 170                 175

Thr Trp Leu Asp Lys Ala Ala Asp Ala Gly Leu Val Ile Leu Gln Ser
            180                 185                 190

Pro Arg Val Gly Phe Phe Arg Arg Ser Arg Thr Ile Lys Gly Lys Arg
            195                 200                 205

Ala Pro Pro Ala Cys Lys Glu Lys Gln Ile Val Lys Glu Gly Gln Val
        210                 215                 220

Val Cys Tyr Ile Glu Gln Leu Gly Gly Glu Leu Pro Ile Glu Ser Asp
225                 230                 235                 240

Val Ser Gly Glu Val Val Lys Ile Leu Arg Glu Asp Gly Asp Pro Val
                245                 250                 255

Gly Tyr Gly Asp Ala Leu Ile Ser Ile Leu Pro Ser Phe Pro Gly Ile
            260                 265                 270

Lys Lys Leu Gln
        275

<210> SEQ ID NO 124
<211> LENGTH: 291
<212> TYPE: PRT
<213> ORGANISM: Fragaria vesca
```

-continued

<400> SEQUENCE: 124

```
Met Glu Ser Ser Ala Val Leu Arg Ser Leu Asn Cys Ser Val Gly Thr
1               5                   10                  15

Val Ser Gln Ile Arg Ser Phe Ile Asp Lys Pro Gly Val Leu Pro Val
            20                  25                  30

Tyr Asn Ala Arg Arg Pro Thr Tyr Ser Arg Ser Tyr Phe Gln Gly Met
        35                  40                  45

Met Val Ser Glu Lys Phe Ile Tyr Ser Pro Gln Lys Arg Lys Gly Val
    50                  55                  60

Leu Ile Ser Cys Val Lys Thr Thr Glu Ala Ala Lys Thr Glu Asn Ser
65                  70                  75                  80

Ser Val Leu Leu Asp Thr Lys Ser Glu Ser Thr Ser Glu Gly Ser Pro
                85                  90                  95

Gln Ser Thr Val Phe Pro Ser Gly Tyr Glu Ala Leu Met Leu Glu Val
            100                 105                 110

Cys Asp Glu Thr Glu Ile Ala Glu Leu Lys Leu Lys Ile Gly Asp Phe
            115                 120                 125

Gln Met His Ile Lys Arg Asn Ile Gly Ala Thr Ser Ala Pro Val Ser
    130                 135                 140

Asn Ile Ser Pro Thr Val Ala Pro Pro Ile Pro Ser Pro Pro Met Ala
145                 150                 155                 160

Ala Ser Ala Pro Ala Pro Pro Ala Ala Pro Lys Ser Ser Pro Ala
                165                 170                 175

Lys Ala Thr Pro Phe Asn Asn Gly Ser Val Ala Lys Ser Ser Lys Leu
            180                 185                 190

Ala Ala Leu Glu Ala Ser Gly Ser Asn Gly Tyr Val Leu Val Thr Ser
            195                 200                 205

Pro Thr Val Gly Ser Phe Arg Arg Gly Arg Thr Val Lys Gly Lys Lys
    210                 215                 220

Gln Pro Pro Ile Phe Asn Glu Gly Asp Leu Ile Lys Glu Gly Gln Val
225                 230                 235                 240

Ile Gly Tyr Val Asp Gln Phe Gly Thr Glu Leu Pro Val Lys Thr Asp
            245                 250                 255

Val Gly Gly Glu Val Leu Lys Leu Leu Phe Asn Asp Gly Asp Ala Val
            260                 265                 270

Gly Tyr Gly Asp Ala Leu Ile Ala Val Leu Pro Ser Phe Arg Gly Ile
        275                 280                 285

Gly Val Leu
    290
```

<210> SEQ ID NO 125
<211> LENGTH: 272
<212> TYPE: PRT
<213> ORGANISM: Fragaria vesca

<400> SEQUENCE: 125

```
Met Ala Ser Cys Ser Leu Gly Thr Ser Tyr Pro Lys Ile Thr Asn Leu
1               5                   10                  15

Asn Leu Gly Arg Thr Arg Val Gly Ile Ser Gln Ser Tyr Gly Val Arg
            20                  25                  30

Thr Trp Thr Leu Gln Arg Pro Gln Leu Tyr Ser Gly Leu Ser Ile Ser
        35                  40                  45

Arg Arg Ser Glu Lys Val Ser His Val His Ser Ala Pro Ser Leu Glu
    50                  55                  60
```

```
Ile Ile Ser Ala Thr Ser Ser Asp Asp Gly Ser Lys Glu Ser Asp Ser
65                  70                  75                  80

Gly Ser Ala Ser Pro Arg Ile Pro Asn Phe Asp Glu Ile Gln Ser Leu
                85                  90                  95

Leu Thr Thr Ile Cys Asp Thr Thr Ser Val Ala Glu Val Gln Leu Lys
            100                 105                 110

Leu Gly Gly Phe Arg Leu His Val Val Arg Glu Leu Thr Glu Asn Val
        115                 120                 125

Ser Thr Pro Pro Pro Ser Ile Pro Ala Pro Val Ser Val Ser Thr Pro
    130                 135                 140

Ala Glu Val Pro Glu Ser Asn Gly Ser Val Pro Thr Gln Ser Leu Ala
145                 150                 155                 160

Ile Thr Arg Ala Glu Ser Ser Ser Arg Asp Ile Gln Thr Leu Leu Asp
                165                 170                 175

Lys Ala Ala Asp Glu Gly Leu Val Leu Ile Gln Ser Pro Arg Val Gly
            180                 185                 190

Ser Phe Arg Arg Ser Arg Thr Ile Lys Gly Lys Arg Ala Pro Pro Ser
        195                 200                 205

Cys Lys Glu Lys Gln Ile Val Lys Glu Gly Gln Val Ile Cys Tyr Ile
    210                 215                 220

Glu Gln Leu Gly Gly Glu Leu Pro Ile Glu Ser Asp Val Ala Gly Glu
225                 230                 235                 240

Val Ile Lys Ile Leu Arg Glu Asp Gly Glu Pro Val Gly Tyr Gly Asp
                245                 250                 255

Ala Leu Val Ala Val Leu Pro Ser Phe Pro Gly Ile Lys Lys Leu Gln
            260                 265                 270
```

<210> SEQ ID NO 126
<211> LENGTH: 252
<212> TYPE: PRT
<213> ORGANISM: Genlisea aurea

<400> SEQUENCE: 126

```
Leu Glu Met Ala Ala Cys Gly Phe Gly Ala Ser Gly Leu Lys His Val
1               5                   10                  15

His Leu Asn Ser Ser Ile Ile Gly Pro Lys Leu Ser Ile Leu Ala Pro
            20                  25                  30

Phe His Gly Leu Lys Thr Pro Lys Thr Ile Arg Phe Gly Gly Met Val
        35                  40                  45

Leu Leu Arg Arg Glu Asn Asn Gly Thr Thr Asn Cys Arg Ser Leu Lys
    50                  55                  60

Ser Glu Asn Asp Ser Ser Ala Gln Leu Glu Asp Asp Ser Lys Gly Thr
65                  70                  75                  80

Val Ser Ser Asp Ala Val Arg Thr Leu Leu Pro Asn Ser Leu Glu Val
                85                  90                  95

Glu Ser Leu Leu Lys Thr Val Cys Asp Thr Thr Ser Ile Ala Glu Leu
            100                 105                 110

Glu Leu Lys Leu Gly Gly Phe Arg Leu His Val Arg Arg Ser Leu Thr
        115                 120                 125

Glu Gln Gly Leu Pro Leu Gln Leu Pro Ser Pro Ala Pro Val Val Ala
    130                 135                 140

His Ser Val Val Ala Ala Thr Pro Ala Asn Gly Ser Ala Ser Ser Thr
145                 150                 155                 160

Ser Leu Ala Ile Ala Asn Ala Gly Pro Ser Ser Asp Gly Ala Arg Ser
```

-continued

```
                 165                 170                 175

Phe Leu Asp Lys Ala Ser Asp Glu Gly Leu Thr Ile Leu Gln Ser Pro
            180                 185                 190

Arg Val Gly Phe Phe Arg Arg Ser Arg Thr Ile Lys Gly Lys Arg Ala
            195                 200                 205

Pro Pro Ser Cys Lys Glu Lys Asp Thr Val Lys Glu Gly Gln Val Leu
    210                 215                 220

Cys Phe Ile Glu Gln Leu Gly Gly Glu Ile Pro Val Glu Ser Asp Thr
225                 230                 235                 240

Ser Gly Glu Val Val Lys Ile Leu Lys Asp Glu Gly
            245                 250

<210> SEQ ID NO 127
<211> LENGTH: 291
<212> TYPE: PRT
<213> ORGANISM: Glycine soja

<400> SEQUENCE: 127

Met Glu Ser Ser Ala Ala Ile Arg Ser Phe His Tyr Pro Ile Gly Thr
1               5                   10                  15

Met Ser His Val Arg Ala Ser Leu Glu Lys Gln Ala Val Val Pro Ile
            20                  25                  30

His Asn Ala Gly Trp Asn Ser Lys Ser Arg Leu Phe Ile Gln His Leu
        35                  40                  45

Ala Tyr Gly Gln Lys His Ile Asn Ser His Thr Lys Gly Lys Asn Thr
    50                  55                  60

Leu Ile Ser Cys Gly Lys Thr Ala Glu Ala Ile Asn Ala Ser Lys Ser
65                  70                  75                  80

Asp Ala Ser Ser Asp Asn Thr Pro Gln Gly Ser Leu Glu Lys Lys Pro
            85                  90                  95

Leu Gln Thr Ala Thr Phe Pro Asn Gly Phe Glu Ala Leu Val Leu Glu
            100                 105                 110

Val Cys Asp Glu Thr Glu Ile Ala Glu Leu Lys Val Lys Val Gly Asp
        115                 120                 125

Phe Glu Met His Ile Lys Arg Asn Ile Gly Ala Thr Glu Val Pro Leu
    130                 135                 140

Ser Asn Ile Ser Pro Thr Thr Pro Pro Ile Pro Ser Lys Pro Met
145                 150                 155                 160

Asp Glu Ser Ala Pro Gly Ser Leu Pro Pro Ser Pro Pro Lys Ser Ser
            165                 170                 175

Pro Glu Lys Asn Asn Pro Phe Ala Asn Val Ser Lys Glu Lys Ser Pro
            180                 185                 190

Arg Leu Ala Ala Leu Glu Ala Ser Gly Thr Asn Thr Tyr Val Leu Val
            195                 200                 205

Ser Ser Pro Thr Val Gly Leu Phe Arg Arg Gly Arg Thr Val Lys Gly
    210                 215                 220

Lys Lys Gln Pro Pro Ile Cys Lys Glu Gly Asp Val Ile Lys Glu Gly
225                 230                 235                 240

Gln Val Ile Gly Tyr Leu Asp Gln Phe Gly Thr Gly Leu Pro Ile Lys
            245                 250                 255

Ser Asp Val Ala Gly Glu Val Leu Lys Leu Leu Val Glu Asp Gly Glu
            260                 265                 270

Pro Val Gly Tyr Gly Asp Pro Leu Ile Ala Val Leu Pro Ser Phe His
            275                 280                 285
```

-continued

Asp Ile Lys
    290

<210> SEQ ID NO 128
<211> LENGTH: 298
<212> TYPE: PRT
<213> ORGANISM: Glycine soja

<400> SEQUENCE: 128

Met Leu Phe Thr Phe Phe Thr Ser Leu Pro Phe Thr Leu Leu Cys Asp
1               5                   10                  15

Thr His Ser Phe Cys Ser Thr Phe Pro Met Ala Ser Cys Ser Ile Gly
            20                  25                  30

Thr Pro Asn Ile Lys Val Leu Asn Leu His Phe Gly Gly Lys Lys Val
        35                  40                  45

Gly Leu Ser Arg Gln Phe Gly Thr Arg Ser Trp Ile Ser Arg Leu Gln
    50                  55                  60

Tyr Thr Ser Leu Val Met Ser Arg Gln Thr Val Arg Phe Leu Ala Ser
65                  70                  75                  80

Ser Asn Gly Pro Ser Thr Glu Ile Gln Phe Ala Ala Arg Ser Glu Gly
            85                  90                  95

Ser Glu Glu Ile Arg Ser Ser Cys Leu Thr Ser Glu Leu Ile Pro Asn
            100                 105                 110

Ile Asn Glu Val Glu Phe Leu Leu Thr Lys Leu Cys Asp Thr Ser Ser
        115                 120                 125

Ile Gly Glu Leu Asp Leu Lys Leu Ala Gly Phe His Leu His Val Val
    130                 135                 140

Arg Asp Leu Thr Glu Lys Thr Lys Thr Leu Pro Pro Leu Ile Pro Ala
145                 150                 155                 160

Ser Val Ser Ile Ile Asn Val Thr Glu Thr Pro Lys Thr Asn Gly Ser
            165                 170                 175

Val Pro Thr Thr Ser Leu Ala Val Ser Lys Pro Val Asp Pro Val Pro
            180                 185                 190

Ser Ser Gly Ser Ile Gln Arg Phe Leu Asp Lys Ala Ala Asp Glu Gly
            195                 200                 205

Leu Val Ile Ile Gln Ser Pro Lys Val Gly Phe Phe Arg Arg Ser Arg
    210                 215                 220

Thr Ile Lys Gly Lys Arg Ala Pro Pro Ser Cys Lys Glu Lys Gln Asn
225                 230                 235                 240

Val Glu Glu Gly Gln Val Ile Cys Tyr Ile Glu Gln Leu Gly Gly Glu
            245                 250                 255

Leu Pro Ile Glu Ser Asp Val Ser Gly Glu Val Ile Lys Ile Leu Arg
            260                 265                 270

Gln Asp Gly Asp Pro Val Gly Tyr Gly Asp Ala Leu Val Ala Ile Leu
        275                 280                 285

Pro Ser Phe Pro Gly Ile Lys Lys Leu Gln
    290                 295

<210> SEQ ID NO 129
<211> LENGTH: 78
<212> TYPE: PRT
<213> ORGANISM: Gossypium arboreum

<400> SEQUENCE: 129

Met Arg Ser Gln Thr Ile Lys Val Lys His Ala Pro Pro Ser Cys Lys
1               5                   10                  15

-continued

```
Glu Lys Gln Ile Val Lys Glu Gly Lys Val Leu Cys Tyr Ile Glu Gln
            20                  25                  30

Leu Gly Cys Glu Ile Pro Ile Ala Ser Asp Val Ser Gly Glu Val Ile
            35                  40                  45

Lys Ile Leu Arg Glu Asp Gly Asp Ser Ile Gly Tyr Gly Asp Ala Phe
    50                  55                  60

Ile Ala Ile Leu Pro Ser Phe Pro Gly Ile Lys Lys Leu Gln
65                  70                  75

<210> SEQ ID NO 130
<211> LENGTH: 290
<212> TYPE: PRT
<213> ORGANISM: Gossypium hirsutum

<400> SEQUENCE: 130

Met Glu Ser Ser Ala Ala Leu Arg Ser Phe His Tyr Ser Val Ser Ala
1               5                   10                  15

Val Ser Gln Ala Cys Cys Met Leu Glu Lys Pro Ser Thr Phe His Met
            20                  25                  30

Ser Ser Ser Cys Trp Pro Asn Ser Arg Lys Ser Cys Val Pro Gly Leu
            35                  40                  45

Met Phe Gly Gly Lys Asn Asn Ser Ser Thr Arg Arg Ala Val Val Leu
    50                  55                  60

Ala Ser Ser Ala Lys Thr Pro Glu Ala Thr Ala Thr Ala Lys Ser Asn
65                  70                  75                  80

Val Pro Pro Glu Ser Thr Lys Lys Gly Ser Leu Glu Lys Lys Ser Ser
                85                  90                  95

Arg Asn Ala Thr Phe Pro Asn Gly Phe Glu Ala Leu Ile Leu Glu Val
            100                 105                 110

Cys Asp Glu Thr Glu Val Ala Glu Leu Gln Met Lys Ile Gly Asp Phe
            115                 120                 125

Glu Met His Leu Lys Arg Asn Val Gly Ala Thr Lys Ala Pro Met Ser
    130                 135                 140

Asn Ile Ser Pro Thr Thr Ala Pro Ser Ile Pro Thr Glu Pro Met Asn
145                 150                 155                 160

Glu Ala Ala Ala Ala Thr Pro Pro Pro Ser Pro Pro Lys Pro Ser Pro
                165                 170                 175

Glu Lys Pro Ser Pro Phe Lys Ser Ser Ala Phe Gly Lys Ser Ser Lys
            180                 185                 190

Leu Ala Ala Leu Glu Ala Ser Gly Ser Ser Asn Tyr Ile Leu Val Pro
            195                 200                 205

Ser Pro Val Val Gly Leu Phe Gln Arg Gly Arg Thr Val Lys Gly Lys
    210                 215                 220

Arg Gln Pro Pro Ile Cys Lys Glu Gly Asp Leu Ile Lys Glu Gly Gln
225                 230                 235                 240

Val Ile Gly Phe Leu Asn Gln Phe Gly Phe Glu Leu Pro Val Lys Ser
                245                 250                 255

Asp Met Ala Gly Thr Val Leu Lys Ile Leu Phe Glu Asp Gly Asp Ala
            260                 265                 270

Val Gly Tyr Gly Asp Pro Leu Phe Ala Val Leu Pro Ser Phe His Gly
        275                 280                 285

Ile Asp
    290

<210> SEQ ID NO 131
```

-continued

```
<211> LENGTH: 290
<212> TYPE: PRT
<213> ORGANISM: Gossypium raimondii

<400> SEQUENCE: 131

Met Glu Ser Ser Ala Ala Leu Arg Ser Phe His Tyr Ser Val Ser Ala
1               5                   10                  15

Val Ser Lys Ala Cys Cys Thr His Glu Arg Pro Gly Thr Phe His Met
            20                  25                  30

Ser Ser Ser Cys Trp Pro Asn Ser Arg Lys Ala Cys Val Pro Gly Leu
        35                  40                  45

Met Phe Gly Gly Lys Asn Asn Ser Ser Thr Arg Arg Thr Val Val Leu
    50                  55                  60

Ala Ser Ser Ala Lys Thr Pro Glu Ala Thr Ala Thr Ala Lys Ser Asn
65                  70                  75                  80

Val Pro Pro Glu Ser Thr Lys Lys Gly Ser Leu Glu Lys Lys Pro Ser
                85                  90                  95

Arg Asn Ala Thr Phe Pro Asn Gly Phe Glu Ala Leu Ile Leu Glu Val
            100                 105                 110

Cys Asp Glu Thr Glu Val Ala Glu Leu Lys Met Lys Ile Gly Asp Phe
        115                 120                 125

Glu Met His Leu Lys Arg Asn Val Ala Ser Thr Lys Ala Pro Met Ser
    130                 135                 140

Asn Ile Ser Pro Thr Thr Ala Pro Ser Ile Pro Thr Glu Pro Met Asn
145                 150                 155                 160

Glu Ala Ala Ala Ala Thr Pro Pro Ser Pro Pro Lys Pro Ser Pro
                165                 170                 175

Glu Lys Pro Ser Pro Phe Lys Ser Ser Ala Phe Gly Gln Ser Ser Lys
            180                 185                 190

Leu Ala Ala Leu Glu Ala Ser Gly Ser Ser Asn Tyr Val Leu Val Pro
        195                 200                 205

Ser Pro Val Val Gly Ile Phe Gln Arg Gly Arg Thr Ile Lys Gly Lys
    210                 215                 220

Arg Gln Pro Pro Ile Cys Lys Glu Gly Asp Leu Ile Lys Glu Gly Gln
225                 230                 235                 240

Val Ile Gly Phe Leu Asn Gln Phe Gly Phe Glu Leu Pro Val Lys Ser
                245                 250                 255

Asp Ile Ala Gly Thr Val Leu Lys Ile Leu Phe Glu Asp Gly Asp Ala
            260                 265                 270

Val Gly Tyr Gly Asp Pro Leu Phe Ala Val Leu Pro Ser Phe His Gly
        275                 280                 285

Ile Gly
    290

<210> SEQ ID NO 132
<211> LENGTH: 195
<212> TYPE: PRT
<213> ORGANISM: Gossypium raimondii
<220> FEATURE:
<221> NAME/KEY: misc_feature
<222> LOCATION: (55)..(55)
<223> OTHER INFORMATION: Xaa can be any naturally occurring amino acid

<400> SEQUENCE: 132

Met Ser Gly Ser Thr Ser Gln Leu Ile Pro Asn Ser Ser Gly Val Glu
1               5                   10                  15

Ser Leu Val Arg Asp Ile Cys Ser Thr Thr Ser Ile Ala Glu Phe Glu
```

-continued

```
                20                  25                  30

Leu Lys Leu Gly Gly Phe Arg Leu Tyr Met Val Trp Asn Leu Ala Gly
        35                  40                  45

Lys Ser Glu Pro Pro Pro Xaa Gln Pro Pro Pro Val Ser Val Ser Thr
    50                  55                  60

Asn Lys Thr Val Glu Ala Pro Lys Ser Asn Glu Thr Val Ser Thr Pro
65                  70                  75                  80

Ser Leu Val Ile Thr Arg Pro Leu Ser Ser Ser Gly Arg Ile Glu Ser
                85                  90                  95

Phe Leu Asp Lys Ala Ala Asp Glu Gly Leu Val Ile Leu Gln Ser Pro
            100                 105                 110

Lys Val Gly Phe Phe Met Ile Ser Arg Thr Ile Lys Gly Lys Arg Ala
        115                 120                 125

Pro Pro Ser Cys Lys Glu Lys Gln Ile Val Lys Glu Gly Gln Val Leu
    130                 135                 140

Cys Tyr Ile Glu Gln Leu Gly Cys Glu Ile Pro Ile Val Ser Asp Val
145                 150                 155                 160

Ser Gly Glu Val Ile Lys Ile Leu Gln Glu Asn Gly Asp Ser Ile Gly
                165                 170                 175

Tyr Gly Asp Ala Leu Ile Ala Ile Leu Pro Ser Phe Pro Gly Ile Lys
            180                 185                 190

Lys Leu Gln
        195

<210> SEQ ID NO 133
<211> LENGTH: 260
<212> TYPE: PRT
<213> ORGANISM: Jatropha curcas

<400> SEQUENCE: 133

Met Glu Ser Ser Ile Ala Leu Gln Ser Phe Arg Cys Asn Ile Tyr Gly
1               5                   10                  15

Gln Arg Leu Thr Val Ser Arg Lys Met Val Ser Ser Pro Val Lys Arg
            20                  25                  30

Asn Val Ala Leu Val Ser Cys Val Lys Ala Pro Glu Ala Ala Glu Thr
        35                  40                  45

Val Lys Ser Asp Ala Gly Gly Ala Lys Gly Ser Leu Glu Asn Ser Asn
    50                  55                  60

Leu Arg Ser Ala Thr Phe Pro Asn Gly Phe Glu Ala Leu Val Leu Glu
65                  70                  75                  80

Val Cys Asp Glu Thr Glu Ile Ala Glu Leu Lys Leu Lys Val Gly Asp
                85                  90                  95

Phe Glu Met His Leu Arg Arg Asn Val Gly Ala Ile Thr Ala Pro Leu
            100                 105                 110

Ser His Ile Ser Pro Thr Glu Pro Pro Ile Pro Thr Glu Pro Met
        115                 120                 125

Asn Val Ser Ala Pro Val Thr Pro Pro Pro Ala Pro Pro Lys Pro Ser
    130                 135                 140

Thr Glu Lys Ser Thr Pro Phe Lys Asn Val Ser Phe Gly Lys Ser Ser
145                 150                 155                 160

Lys Leu Ala Ala Leu Glu Ala Ser Gly Ala Thr Gly Tyr Val Leu Val
            165                 170                 175

Thr Ser Pro Thr Val Gly Ser Phe Arg Arg Asn Arg Thr Val Lys Gly
        180                 185                 190
```

```
Lys Arg Gln Pro Pro Ile Phe Lys Glu Gly Asp Leu Ile Lys Glu Gly
        195                 200             205

Gln Val Ile Gly Tyr Leu Asp Gln Phe Gly Thr Glu Leu Pro Val Lys
        210                 215             220

Ser Asp Val Ala Gly Glu Val Leu Lys Leu Leu Phe Asp Asp Gly Asp
225                 230                 235                 240

Ala Val Gly Tyr Gly Asp Pro Leu Ile Ala Val Leu Pro Ser Phe His
                245                 250                 255

Asp Ile Asn Lys
        260
```

<210> SEQ ID NO 134
<211> LENGTH: 285
<212> TYPE: PRT
<213> ORGANISM: Jatropha curcas

<400> SEQUENCE: 134

```
Met Ala Ser Cys Ser Leu Gly Ala Ser Asn Ile Lys Leu Ser Lys Leu
1               5                   10                  15

Asn Phe Gly Arg Glu Arg Ala Gly Asn Ile Gln Gln Trp Ser Gly Met
            20                  25                  30

Arg Thr Ser Ile Gly Trp Arg Gln Leu Gln Tyr Thr Gly Leu Thr Val
            35                  40                  45

Ile Tyr Lys Pro Lys Glu Thr Phe Ser Val Arg Cys Cys Pro Thr Leu
        50                  55                  60

Glu Lys Glu Thr Ser Thr Asn Arg Val Asp Ser Ile Lys Gln Thr Lys
65                  70                  75                  80

Ser Ser Gly Leu Thr Ser Gln Leu Ile Pro Asn Ser Ser Glu Ile Glu
                85                  90                  95

Phe Leu Val Thr Glu Val Cys Asn Ala Thr Ser Ile Ala Glu Phe Glu
            100                 105                 110

Leu Lys Val Gly Gly Phe Trp Leu Tyr Leu Thr Arg Asn Leu Thr Gln
            115                 120                 125

Lys Ser Lys Pro Ser Pro Val Pro Thr Leu Ala Pro Leu Pro Pro Asp
        130                 135                 140

Pro Ala Pro Ala Pro Asp Pro Leu Thr Ala Asp Lys Thr Ile Lys Ala
145                 150                 155                 160

Pro Glu Leu Asn Gly Ser Val Ser Ser Thr Ser Phe Ala Ile Ser Lys
                165                 170                 175

Pro Ala Pro Phe Ser Gly Gly Ile Gln Ser Phe Leu Asp Lys Ala Val
            180                 185                 190

Asp Glu Gly Leu Met Ile Leu Gln Ser Pro Arg Val Gly Phe Phe Arg
        195                 200                 205

Arg Ser Arg Thr Ile Lys Gly Lys Arg Ala Pro Pro Ser Cys Lys Glu
        210                 215                 220

Lys Gln Ile Val Lys Glu Gly Gln Val Leu Cys Tyr Ile Glu Gln Leu
225                 230                 235                 240

Gly Gly Glu Leu Pro Ile Glu Ser Asp Val Ser Gly Glu Val Ile Lys
                245                 250                 255

Ile Leu Arg Glu Asp Gly Asp Pro Val Gly Tyr Gly Asp Ala Leu Ile
            260                 265                 270

Ala Ile Leu Pro Ser Phe Pro Gly Ile Lys Lys Leu Gln
        275                 280                 285
```

<210> SEQ ID NO 135

-continued

```
<211> LENGTH: 278
<212> TYPE: PRT
<213> ORGANISM: Klebsormidium flaccidum

<400> SEQUENCE: 135

Met Ala Ala Ala Leu Ser Arg Thr Ser Val Ala Ser Val Ala Ser Arg
1               5                   10                  15

Leu Ala Gly Ser Ala Gly Cys Ser Arg Cys Lys Ala Val Gly Val Asn
                20                  25                  30

Ala Pro Leu Ala Lys Ala Trp Ala Gly Arg Arg Leu Val Pro Cys Ala
            35                  40                  45

Thr Asn Ala Arg Gln His Val Pro Asn Phe Arg Gln Ala Gly Val Arg
        50                  55                  60

Cys Ala Ala Ala Val Glu Ala Ala Glu Ala Ile Glu Ala Glu Asp Glu
65                  70                  75                  80

Ala Glu Glu Ser Phe Leu Glu Ser Ala Leu Ser Pro Asn Ala Leu Glu
                85                  90                  95

Val Gln Gln Leu Leu Val Glu Leu Cys Asp Glu Thr Ser Ile Ala Glu
            100                 105                 110

Leu Lys Leu Lys Val Gly Ser Phe Arg Leu His Val Leu Arg Asp Val
        115                 120                 125

Ser Gly Glu Arg Ala Ala His His Ala Ala His Gln Ala Ser Leu Leu
        130                 135                 140

Glu Ile Pro Thr Pro Pro Val Pro Pro His Val Ser Met Glu Glu Val
145                 150                 155                 160

Leu Arg Ala Arg Gln Thr Thr Pro Ala Glu Ala Pro Lys Lys Glu Ala
                165                 170                 175

Pro Leu Ala Glu Asp Glu Ile Arg Pro Asp Glu Gly Leu Asp Phe Val
            180                 185                 190

Leu Ala Pro Arg Val Gly Val Leu Arg Arg Gly Arg Ala Arg Lys Gly
        195                 200                 205

Lys Gln Gly Arg Ser Val Ala Asn Glu Gly Gln Val Val Lys Glu Gly
        210                 215                 220

Gln Val Ile Cys Tyr Val Glu Gln Leu Gly Thr Gln Gln Pro Ile Glu
225                 230                 235                 240

Ser Thr Val Ser Gly Glu Ile Ile Asn Phe Leu Val Glu Asp Gly Asp
                245                 250                 255

Ala Val Gly Phe Gly Glu Pro Ile Val Glu Val Arg Pro Ser Phe Val
            260                 265                 270

Gly Ile Lys Lys Leu Ala
        275

<210> SEQ ID NO 136
<211> LENGTH: 288
<212> TYPE: PRT
<213> ORGANISM: Malus domestica

<400> SEQUENCE: 136

Met Glu Ser Ser Ala Ala Leu Arg Ser Phe Asn Cys Ser Val Gly Thr
1               5                   10                  15

Val Ser His Val Arg Ser Leu Leu Asp Lys Pro Gly Met Leu Pro Val
                20                  25                  30

His Asn Thr Arg Arg Pro Ala Pro Ser Arg Ser Tyr Phe Gln Gly Leu
        35                  40                  45

Met Val Ser Glu Lys Phe Ile Tyr Ser Ser Gln Lys Arg Asn Gly Val
        50                  55                  60
```

```
Leu Val Ser Cys Val Lys Thr Ser Asp Ala Thr Lys Ser Glu Asn Ser
65                  70                  75                  80

Ser Asp Ser Ala Asp Ser Lys Pro Gln Gly Ser Ser Lys Lys Ala Thr
                85                  90                  95

Gln Pro Thr Ile Phe Pro Ser Gly Phe Glu Ala Leu Met Leu Glu Val
            100                 105                 110

Cys Asp Glu Thr Glu Val Ala Glu Leu Lys Leu Lys Val Gly Asp Phe
            115                 120                 125

Glu Met His Leu Lys Arg Asn Ile Gly Gly Thr Ser Ala Pro Val Pro
        130                 135                 140

Ser Ile Ser Pro Ala Thr Pro Pro Ile Pro Ser Ala Pro Met Asp
145                 150                 155                 160

Ser Thr Pro Ala Pro Pro Pro Ala Ser Pro Pro Lys Ser Ser Glu Lys
                165                 170                 175

Thr Thr Pro Phe Thr Asn Val Ser Ala Asp Lys Ser Ser Arg Leu Ala
            180                 185                 190

Ala Leu Glu Ala Ser Gly Ala Asn Gly Tyr Gly Leu Val Ser Ser Pro
        195                 200                 205

Thr Val Gly Ser Phe Arg Arg Gly Arg Thr Val Lys Gly Lys Lys Gln
    210                 215                 220

Pro Pro Ile Cys Lys Glu Gly Asp Leu Ile Lys Gln Gly Gln Val Ile
225                 230                 235                 240

Gly Tyr Val Asp Gln Phe Gly Thr Glu Leu Pro Val Lys Thr Asp Leu
                245                 250                 255

Gly Gly Glu Val Leu Lys Leu Leu Phe Asn Asp Gly Glu Ala Val Gly
            260                 265                 270

Phe Gly Asp Pro Leu Ile Ala Val Leu Pro Ser Phe Pro Gly Ile Gln
        275                 280                 285
```

```
<210> SEQ ID NO 137
<211> LENGTH: 301
<212> TYPE: PRT
<213> ORGANISM: Marchantia polymorpha

<400> SEQUENCE: 137
```

```
Met His Leu Leu Cys Asp Ala Gly Ser Leu Ser Ser Arg Phe Gly Pro
1               5                   10                  15

His Val Cys Val Gly Arg Ile Asp Ala Phe Ser Gly Pro Val Thr Ala
                20                  25                  30

Tyr Val Pro Ser Pro Arg Ser Thr Ala Gly Gly Ser Ser Ala Ala Gln
            35                  40                  45

Ala Gln Pro Ser Phe Ser Thr Ser Arg Arg Gln Thr Thr Ser Thr Arg
        50                  55                  60

Gln His Arg Pro Leu Val Thr Cys Val Ala Val Ser Ser Asp Lys Leu
65                  70                  75                  80

Phe Leu Phe Leu Arg His Asp Ala Leu Val Asp Val Glu Asp Glu Gln
                85                  90                  95

Ser Ala Pro Glu Glu Glu Ile Ser Pro Leu Thr Pro Thr Ser Phe Glu
            100                 105                 110

Val Gln Ser Leu Leu Met Glu Leu Cys Asp Glu Thr Ser Ile Ala Glu
            115                 120                 125

Leu Gln Leu Lys Val Gly Ala Phe Lys Leu Ser Val Lys Arg Asp Val
        130                 135                 140

Gly Lys Ile Lys Ser Thr Thr Ala Thr Pro Gln Ala Thr Pro Pro Pro
```

```
                 145                150                155                160

Val Pro Ser Arg Pro Met Val Asp Ser Leu Pro Ala Ala Pro Pro Ala
                 165                170                175

Pro Ala Ser Ala Pro Lys Thr Ser Thr Ser Thr Ser Met Leu Ser Ser
                 180                185                190

Val Ser Lys Pro Leu Ser Ser Val Phe Ala Leu Leu Glu Ser Ala Ala
                 195                200                205

Asp Glu Gly Leu Leu Phe Val Lys Ser Pro Lys Val Gly Tyr Phe Arg
             210                215                220

Lys Gly Arg Val Val Lys Gly Lys Ser Gly Pro Pro Leu Cys Glu Glu
225                230                235                240

Gly Gln Ser Ile Lys Glu Gly His Val Val Cys Tyr Leu Glu Gln Leu
                 245                250                255

Gly Thr Gln Gln Pro Val Glu Ser Asp Ile Ser Gly Glu Val Val Lys
                 260                265                270

Val Leu Trp Asp Asp Gly Glu Pro Val Gly Tyr Gly Asp Pro Leu Ile
                 275                280                285

Ala Ile Arg Pro Ser Phe Pro Gly Ile Lys Lys Leu Thr
             290                295                300

<210> SEQ ID NO 138
<211> LENGTH: 276
<212> TYPE: PRT
<213> ORGANISM: Musa acuminata

<400> SEQUENCE: 138

Met Ala Leu Arg Leu Phe Pro Gly Ala Ser Lys Thr Ile Leu Gln Val
1                5                  10                 15

Asp Ser Ser Leu Asn Ser Lys Ser Leu Leu Trp Arg Val Pro Glu Glu
                 20                 25                 30

Pro Gln Arg Leu Ile Ser Ser Gly Ala Phe Gln Lys Gln Phe Leu His
             35                 40                 45

Val Lys Ala Ser Gln Asn Thr Ser Ser Leu Thr Thr Asn Ala Asp Ile
         50                 55                 60

Asn Lys Lys Asn Ala Thr Ala Thr Leu Gln Lys Lys Asn Val Tyr Lys
65                 70                 75                 80

Ser Thr Phe Pro Ser Gly Phe Gln Thr Leu Val Glu Glu Val Cys Asp
                 85                 90                 95

Gln Thr Asp Val Ala Glu Leu Lys Leu Lys Val Gly Asp Phe Glu Met
                 100                105                110

Leu Leu Lys Arg Asp Thr Gly Asn Ser Lys Ala Pro Ile Ser Val Ser
             115                120                125

Ala Pro Ile Glu Ser Pro Thr Thr Ala Pro Pro Ile Pro Ser Lys Pro
         130                135                140

Met Val Glu Thr Ile Ser Ser Pro Ser Pro Val Ala Glu Gln Glu Ser
145                150                155                160

Ala Ala Ala Thr Phe Gly Ser Phe Thr Asn Thr Ser Ala Ala Lys Thr
                 165                170                175

Ser Lys Leu Ala Ala Leu Asp Ala Ser Gly Gln Asn Ala Tyr Val Leu
             180                185                190

Val Ser Ser Ser Thr Val Gly Leu Phe Gln Arg Gly Arg Thr Leu Lys
             195                200                205

Glu Lys Arg Gln Pro Pro Ser Cys Lys Glu Gly Asp Ile Ile Lys Glu
         210                215                220
```

```
Gly Gln Ile Ile Gly Phe Leu Asp Gln Phe Gly Asn Glu Leu Pro Val
225             230             235             240

Arg Ser Asp Val Ala Gly Glu Val Leu Lys Ile Ile Tyr Glu Asp Gly
            245             250             255

Glu Ala Val Gly Tyr Gly Asp Pro Leu Val Ala Val Leu Pro Ser Phe
            260             265             270

His Gly Ile Lys
        275

<210> SEQ ID NO 139
<211> LENGTH: 288
<212> TYPE: PRT
<213> ORGANISM: Nelumbo nucifera

<400> SEQUENCE: 139

Met Val Ser Val Thr Val Phe Arg Ser Phe His Gly Ala Ile Asp Ser
1               5               10              15

Ile Thr His Leu Gln Ser Leu Ser Glu Arg Pro Gly Ala Val Pro Ile
            20              25              30

Tyr Asn Ala Asn Ala Lys Lys Leu Ser Phe Ala Gln Gly Leu Ala Leu
        35              40              45

Gly Ser Arg Ile Thr Ser Ala Asn Glu Lys Arg Ala Phe Val Pro Cys
    50              55              60

Leu Lys Ala Ser Glu Ser Thr Thr Glu Ile Thr Ser Val Val Tyr Leu
65              70              75              80

Asp Gly Lys Ser Gln Glu Pro Leu Glu Lys Arg Ser Leu Gln Ser Thr
            85              90              95

Thr Phe Pro Asn Gly Phe Glu Ala Leu Val Leu Glu Val Cys Asp Glu
            100             105             110

Thr Asn Val Ala Glu Leu Lys Leu Lys Val Gly Asp Phe Glu Met His
            115             120             125

Leu Lys Arg Asn Ile Asp Thr Thr Lys His Thr Thr Pro Ile Ile Ser
    130             135             140

Pro Thr Pro Pro His Leu Ser Ser Glu Pro Met Val Lys Ala Thr Pro
145             150             155             160

Val Ala Pro Pro Ser Ser Ser Pro Lys Ser Ser Ser Glu Thr Ala Ser
            165             170             175

Pro Phe Lys Asn Lys Ser Ser Thr Lys Ser Ser Lys Leu Ala Ala Leu
            180             185             190

Glu Ala Ser Gly Ala Asn Ser Tyr Val Leu Val Ser Ser Pro Lys Val
            195             200             205

Gly Ser Phe Arg Arg Gly Lys Thr Val Lys Gly Lys Lys Gln Pro Pro
    210             215             220

Ile Cys Lys Glu Gly Asp Val Ile Lys Glu Gly Gln Thr Ile Gly Tyr
225             230             235             240

Leu Asn Gln Phe Gly Ser Glu Leu Pro Val Met Ser Asp Val Ala Gly
            245             250             255

Glu Val Leu Lys Phe Leu Tyr Asn Asp Gly Asp Ala Val Gly Tyr Gly
            260             265             270

Asp Pro Leu Val Ala Ile Leu Pro Ser Phe His Asp Ile Asn Ile Asn
        275             280             285

<210> SEQ ID NO 140
<211> LENGTH: 275
<212> TYPE: PRT
<213> ORGANISM: Nelumbo nucifera
```

<400> SEQUENCE: 140

Met Ala Ala Cys Asn Leu Gly Cys Val Ser Asn Ala Arg Leu Ser Ser
1               5                   10                  15

Phe Tyr Met Asp Phe Gly Arg Thr Arg Ser Ala Ser Met Gln Thr Ser
            20                  25                  30

Tyr Ala Ile Arg Ser Trp Gly Arg Gln Lys Gln Pro Gln Tyr Ala Gly
        35                  40                  45

Phe Ile Ser Thr Lys Gln Lys Lys Pro Leu Ser Val Ser Cys Ser Ser
        50                  55                  60

Ser Ser Glu Val Glu Thr Ala Ala Asp Leu Asp Ser Leu Gln Glu Lys
65                  70                  75                  80

Lys Ser Asn Gly Ile Thr Arg Gln Ile Ile Pro Asn Ser Thr Glu Val
                85                  90                  95

Gln Ala Leu Leu Thr Glu Ile Cys Asp Thr Thr Tyr Ile Ala Glu Phe
            100                 105                 110

Glu Leu Lys Leu Ala Gly Phe Arg Leu Tyr Val Thr Arg Asp Val Ala
            115                 120                 125

Gly Lys Ser Ala Pro Pro Pro Pro Ser Ser Leu Pro Ala Asn Val
        130                 135                 140

Ser Thr Thr Ser Asp Ala Pro Ala Leu Asn Gly Ser Val Ser Thr Pro
145                 150                 155                 160

Ser Leu Ala Ile Ala Lys Ala Val Pro Ser Ser Gly Glu Ile Gln Arg
                165                 170                 175

Met Leu Asn Lys Asp Thr Asp Glu Ser Leu Val Ile Leu Gln Ser Pro
            180                 185                 190

Lys Val Gly Tyr Phe Arg Arg Ser Arg Thr Ile Lys Gly Lys Arg Ala
            195                 200                 205

Pro Pro Ser Cys Gln Glu Lys Gln Val Val Lys Glu Gly Gln Val Leu
        210                 215                 220

Cys Phe Ile Glu Gln Leu Gly Gly Gln Ile Pro Ile Glu Ser Asp Val
225                 230                 235                 240

Ser Gly Glu Val Ile Lys Ile Leu Arg Asp Asp Gly Glu Pro Val Gly
                245                 250                 255

Tyr Gly Asp Ala Leu Ile Ala Ile Leu Pro Ser Phe Pro Gly Ile Lys
            260                 265                 270

Lys Leu Gln
        275

<210> SEQ ID NO 141
<211> LENGTH: 285
<212> TYPE: PRT
<213> ORGANISM: Nicotiana sylvestris

<400> SEQUENCE: 141

Met Glu Ser Ala Ala Val Leu Arg Ser Phe His His Ser Val Gly Thr
1               5                   10                  15

Thr Ser His Met Arg Ser Val Ile Glu Met Pro Gly Val Ile Pro Met
            20                  25                  30

Asn Asn Val Ala Phe Ser Lys Pro Thr Lys Leu Pro Leu Lys Gly Ser
        35                  40                  45

Ser Asn Gly Ala Lys Leu Val Ser Ser Thr Asn Lys His Ser Arg Leu
        50                  55                  60

Ile Leu Ser Cys Ala Lys Thr Ser Glu Thr Thr Val Thr Thr Lys Ser
65                  70                  75                  80

-continued

```
Asp Ser His Gln Lys Val Ser Thr Glu Lys Ser Pro Leu Pro Thr Ala
                85                  90                  95

Thr Phe Pro Lys Gly Phe Glu Ala Leu Ile Thr Glu Val Cys Asp Asp
               100                 105                 110

Thr Glu Val Ala Glu Leu Lys Leu Lys Ile Gly Asp Phe Glu Leu His
               115                 120                 125

Leu Lys Arg Asn Ile Glu Ala Pro Ile Val Pro Ala Pro Val Val Ser
       130                 135                 140

Thr Pro Pro Pro Pro Ser Ala Ser Lys Pro Ser Thr Ala Ser Thr Ala
145                 150                 155                 160

Ala Ala Pro Ala Thr Ser Pro Gly Lys Ser Ser Ser Glu Lys Ile Ser
               165                 170                 175

Pro Phe Thr Asn Val Ala Ala Glu Lys Ser Met Lys Leu Ala Glu Leu
               180                 185                 190

Gln Thr Thr Gly Ala Ser Gly Tyr Val Leu Val Ser Cys Pro Thr Val
               195                 200                 205

Gly Ser Phe Arg Arg Ala Arg Thr Leu Lys Gly Lys Lys Gln Pro Pro
       210                 215                 220

Ala Cys Lys Glu Gly Asp Val Ile Lys Glu Gly Gln Ile Ile Gly Phe
225                 230                 235                 240

Leu Asp Gln Phe Gly Thr Glu Leu Pro Val Arg Ser Asp Ala Ala Gly
               245                 250                 255

Glu Val Leu Lys Ile Leu Phe Asn Asp Gly Glu Ala Val Gly Tyr Gly
               260                 265                 270

Asp Pro Leu Ile Ala Val Leu Pro Ser Phe Arg Gly Ile
       275                 280                 285
```

```
<210> SEQ ID NO 142
<211> LENGTH: 360
<212> TYPE: PRT
<213> ORGANISM: Nicotiana sylvestris

<400> SEQUENCE: 142
```

```
Met Ser Leu Phe Leu Arg Val Phe Ser Arg Thr Val Arg Ala Arg Leu
1               5                   10                  15

Cys Trp Glu His Gly Ser Gly Phe Ala Ala Arg Leu Leu Leu Pro Val
                20                  25                  30

Glu Leu Ala Thr Phe Gln Arg Leu Leu Ala Ile Ile Arg Glu Thr Phe
                35                  40                  45

Ser Phe Leu Leu Ser Asn Phe Phe Val Cys Ile Asp Asn Glu Gln Ser
       50                  55                  60

Phe Lys Leu Tyr Gln Gln Leu Ser Ala Leu Leu Cys Ser Ser Arg Arg
65                  70                  75                  80

Val Leu Pro Leu Leu Met Ala Ala Cys Gly Phe Gly Ala Ser Gly Phe
                85                  90                  95

Lys Leu Thr Asn Leu Asn Leu Gly Ser Ser Lys Pro Lys Leu Thr Ala
               100                 105                 110

Leu His Asn Leu Arg Thr Lys Lys Leu Ser Gln Ser Asp Gly Leu Leu
               115                 120                 125

Leu Thr Thr Lys Ser Arg Lys Thr Leu Phe Gly Cys Trp Cys Ser Thr
       130                 135                 140

Ala Glu Val Glu Ser Ala Ala Ala Ala Val Ser His Ser Ser Asp Asp
145                 150                 155                 160

Ser Ser Arg Lys Ile Ile Ser Ser Glu Thr Ala Ser Pro Leu Ile Pro
```

-continued

```
                165                170                175

Ser Ser Tyr Glu Val Glu Ser Leu Leu Thr Glu Ile Cys Asp Thr Thr
            180                185                190

Ser Ile Ala Glu Val Asp Leu Lys Leu Gly Gly Phe His Leu Tyr Val
            195                200                205

Lys Arg Asp Leu Thr Gly Pro Ser Thr Thr Ser Leu Pro Ala Ile Ser
    210                215                220

Asn Pro Val Asn Ile His Ser Ser Val Glu Val Ala Asp Ser Asn Gly
225                230                235                240

Ser Ala Ser Ser Pro Ser Leu Ala Ile Thr Lys Ser Ser Pro Pro Ser
                245                250                255

Asp Gly Ile Arg Thr Ile Ile Asp Lys Ala Ala Asp Glu Gly Leu Val
            260                265                270

Ile Ile Gln Ser Pro Arg Val Gly Tyr Phe Arg Arg Ser Arg Thr Ile
            275                280                285

Lys Gly Lys Arg Ala Pro Pro Ser Cys Lys Glu Lys Gln Gln Val Lys
    290                295                300

Glu Gly Gln Val Val Cys Phe Ile Glu Gln Leu Gly Gly Glu Leu Pro
305                310                315                320

Val Glu Ser Asp Val Ser Gly Glu Val Ile Lys Ile Leu Gln Lys Asp
                325                330                335

Gly Asp Pro Val Gly Tyr Gly Asp Pro Leu Ile Ser Ile Leu Pro Ser
            340                345                350

Phe Pro Gly Ile Lys Lys Leu Gln
            355                360

<210> SEQ ID NO 143
<211> LENGTH: 285
<212> TYPE: PRT
<213> ORGANISM: Nicotiana tabacum

<400> SEQUENCE: 143

Met Glu Ser Ala Ala Val Leu Arg Ser Phe His His Ser Val Gly Thr
1               5               10              15

Thr Ser His Met Arg Ser Val Ile Glu Met Pro Gly Val Ile Pro Met
            20              25              30

Asn Asn Val Ala Phe Ser Lys Pro Thr Lys Leu Pro Leu Lys Gly Ser
            35              40              45

Ser Asn Gly Ala Lys Leu Val Ser Ser Thr Asn Lys His Ser Arg Leu
    50              55              60

Ile Leu Ser Cys Ala Lys Thr Ser Glu Thr Thr Val Thr Thr Lys Ser
65              70              75              80

Asp Ser His Gln Lys Val Ser Thr Glu Lys Ser Pro Leu Pro Thr Ala
            85              90              95

Thr Phe Pro Lys Gly Phe Glu Ala Leu Ile Thr Glu Val Cys Asp Asp
            100             105             110

Thr Glu Val Ala Glu Leu Lys Leu Lys Ile Gly Asp Phe Glu Leu His
            115             120             125

Leu Lys Arg Asn Ile Glu Ala Pro Ile Val Pro Ala Pro Val Val Ser
    130             135             140

Thr Pro Pro Leu Pro Ser Ala Ser Lys Pro Ser Thr Ala Ser Thr Ala
145             150             155             160

Ala Ala Pro Ala Thr Ser Pro Gly Lys Ser Ser Ser Glu Lys Ile Ser
            165             170             175
```

Pro Phe Thr Asn Val Ala Ala Glu Lys Ser Met Lys Leu Ala Glu Leu
            180                 185                 190

Gln Thr Thr Gly Ala Ser Gly Tyr Val Leu Val Ser Cys Pro Thr Val
            195                 200                 205

Gly Ser Phe Arg Arg Ala Arg Thr Leu Lys Gly Lys Lys Gln Pro Pro
    210                 215                 220

Ala Cys Lys Glu Gly Asp Val Ile Lys Glu Gly Gln Ile Ile Gly Phe
225                 230                 235                 240

Leu Asp Gln Phe Gly Thr Glu Leu Pro Val Arg Ser Asp Ala Ala Gly
                245                 250                 255

Glu Val Leu Lys Ile Leu Phe Asn Asp Gly Glu Ala Val Gly Tyr Gly
            260                 265                 270

Asp Pro Leu Ile Ala Val Leu Pro Ser Phe Arg Gly Ile
            275                 280                 285

<210> SEQ ID NO 144
<211> LENGTH: 274
<212> TYPE: PRT
<213> ORGANISM: Nicotiana tabacum

<400> SEQUENCE: 144

Met Ala Ala Cys Gly Phe Gly Ala Ala Gly Phe Lys Leu Thr Asn Leu
1               5                   10                  15

Asn Leu Gly Ser Thr Lys Pro Lys Phe Leu Leu His Asn Leu Arg Thr
            20                  25                  30

Lys Lys Leu Ile Gln Asn Asp Gly Leu Leu Leu Thr Lys Lys Ser Arg
            35                  40                  45

Lys Thr Leu Phe Gly Cys Arg Cys Ser Thr Val Glu Ala Glu Ser Ala
    50                  55                  60

Ala Ala Val Val Ser Asp Asn Ser Asp Asp Ser Leu Arg Lys Ile Ile
65                  70                  75                  80

Ser Ser Glu Ala Ala Ser Pro Leu Ile Pro Asn Ser Tyr Glu Val Glu
                85                  90                  95

Ser Leu Leu Thr Glu Ile Cys Asp Thr Thr Ser Ile Ala Glu Val Glu
            100                 105                 110

Leu Lys Leu Gly Gly Phe His Leu Tyr Val Lys Arg Asp Leu Thr Gly
        115                 120                 125

Pro Ser Thr Thr Ser Leu Pro Ala Ile Ser Asn Pro Val Asn Ile His
    130                 135                 140

Ser Ser Val Glu Val Ala Asp Ser Asn Gly Ser Ala Ser Ser Ser Ser
145                 150                 155                 160

Leu Ala Ile Thr Lys Ser Ser Pro Pro Ser Asp Gly Ile Gln Thr Met
            165                 170                 175

Ile Asp Lys Ala Ala Asp Glu Gly Leu Val Ile Ile Gln Ser Pro Arg
            180                 185                 190

Val Gly Tyr Phe Arg Arg Ser Arg Thr Ile Lys Gly Lys Arg Ala Pro
            195                 200                 205

Pro Ser Cys Lys Glu Lys Gln Gln Val Lys Glu Gly Gln Val Val Cys
    210                 215                 220

Phe Ile Glu Gln Leu Gly Gly Glu Leu Pro Val Glu Ser Asp Val Ser
225                 230                 235                 240

Gly Glu Val Ile Lys Ile Leu Gln Lys Asp Gly Glu Pro Val Gly Tyr
                245                 250                 255

Gly Asp Pro Leu Ile Ser Ile Leu Pro Ser Phe Pro Gly Ile Lys Lys
            260                 265                 270

Leu Gln

<210> SEQ ID NO 145
<211> LENGTH: 289
<212> TYPE: PRT
<213> ORGANISM: Phaseolus vulgaris

<400> SEQUENCE: 145

Met Glu Ser Ser Ala Ala Ile Arg Ser Phe His Tyr Pro Met Gly Thr
1               5                   10                  15

Met Ser His Met Arg Pro Ser Tyr Asp Lys Gln Val Val Val Pro Ile
                20                  25                  30

His Asn Val Arg Trp Asn Ser Lys Ser Arg Leu Phe Ile Gln His Leu
            35                  40                  45

Ala Tyr Asp Arg Lys His Ile Asn Ser His Met Lys Gly Ser Thr Thr
        50                  55                  60

Leu Val Ser Cys Ala Lys Thr Ala Glu Pro Ile Asn Thr Ser Asn Ser
65                  70                  75                  80

Asp Asp Ala Ser Pro Gly Ser Thr Pro Gln Gly Ser Leu Glu Lys Lys
                85                  90                  95

Pro Leu Gln Ala Ala Thr Phe Pro Asn Gly Phe Glu Asp Leu Val Leu
            100                 105                 110

Glu Val Cys Asp Glu Thr Glu Ile Ala Glu Leu Lys Val Lys Val Gly
            115                 120                 125

Asp Phe Glu Met His Ile Lys Arg Asn Ile Gly Ala Thr Thr Val Pro
        130                 135                 140

Leu Ser Asn Ile Ser Pro Thr Thr Pro Pro Ile Pro Ser Lys Pro
145                 150                 155                 160

Met Asp Ser Ala Pro Gly Thr Leu Pro Pro Ser Pro Pro Lys Ser Ser
                165                 170                 175

Pro Glu Lys Lys Asn Pro Ile Ile Asp Ala Ser Arg Lys Lys Ser Pro
                180                 185                 190

Ile Leu Thr Ala Leu Glu Ala Ser Glu Ser Gly Thr Tyr Val Leu Ile
            195                 200                 205

Pro Ser Pro Thr Val Gly Phe Phe Arg Arg Gly Arg Thr Val Lys Gly
        210                 215                 220

Lys Arg Gln Pro Pro Ile Cys Lys Glu Gly Asp Phe Val Gln Glu Gly
225                 230                 235                 240

Gln Val Ile Gly Tyr Leu Asp Gln Leu Gly Ser Gly Asn Pro Val Lys
                245                 250                 255

Thr Asp Val Thr Gly Gln Val Leu Lys Leu Leu Val Glu Asp Gly Glu
                260                 265                 270

Pro Val Gly Tyr Gly Asp Pro Leu Ile Ala Val Phe Pro Leu Asp Leu
        275                 280                 285

Lys

<210> SEQ ID NO 146
<211> LENGTH: 277
<212> TYPE: PRT
<213> ORGANISM: Phaseolus vulgaris

<400> SEQUENCE: 146

Met Ala Ser Cys Cys Leu Gly Thr Pro Lys Ile Lys Val Leu Asn Leu
1               5                   10                  15

Arg Phe Ser Gly Lys Asn Val Gly Leu Ser Gln Gln Val Gly Thr Arg

-continued

```
                  20                    25                    30

Ser Trp Arg Arg Gln Ser Leu Gln Tyr Thr Ser Leu Val Met Ser Arg
          35                    40                    45

Gln Thr Asp Arg Phe Leu Ala Ser Ala Asn Ala Pro Ser Ser Glu Thr
      50                    55                    60

Gln Ile Ile Thr Arg Ser Glu Glu Gly Ser Glu Gly Thr Lys Ser Ser
65                    70                    75                    80

Val Leu Thr Ser Gln Leu Ile Pro Asn Phe Asn Glu Val Glu Phe Leu
                  85                    90                    95

Val Thr Lys Leu Cys Asp Ser Ser Ile Gly Glu Ile Asp Leu Lys
              100                   105                   110

Leu Ala Gly Phe His Leu His Ile Val Arg Asp Leu Thr Glu Gln Asn
          115                   120                   125

Glu Thr Leu Pro Pro Pro Thr Pro Ile Pro Ala Ser Val Ser Val Asn
      130                   135                   140

Asp Val Val Glu Thr Pro Lys Thr Asn Gly Ser Val Ser Thr Thr Ser
145                   150                   155                   160

Leu Ala Ile Ser Asn Pro Leu Gly Gln Val Tyr Phe Pro Gly Ser Ile
                  165                   170                   175

Gln Arg Phe Leu Asp Lys Ala Lys Asp Glu Gly Leu Val Ile Ile Pro
              180                   185                   190

Cys Pro Lys Val Gly Tyr Phe Arg Arg Ser Arg Thr Ile Lys Gly Lys
              195                   200                   205

Arg Ala Pro Pro Ser Cys Lys Glu Lys Gln Ile Val Glu Glu Gly Gln
      210                   215                   220

Val Ile Cys Tyr Ile Glu Met Leu Gly Val Glu Val Ala Ile Glu Ala
225                   230                   235                   240

Asp Val Ser Gly Glu Ile Ile Lys Ile Leu Arg Lys Asp Gly Glu Pro
                  245                   250                   255

Val Ala Tyr Gly Asp Ala Leu Ile Ala Ile Leu Pro Ser Phe Pro Gly
                  260                   265                   270

Ile Lys Lys Leu Gln
              275

<210> SEQ ID NO 147
<211> LENGTH: 284
<212> TYPE: PRT
<213> ORGANISM: Phoenix dactylifera

<400> SEQUENCE: 147

Met Glu Ala Ala Ala Val Leu Arg Ser Phe Arg Gly Gly Val Arg Thr
1                 5                     10                    15

Lys Gln Pro Ser Glu Ser Phe Leu Glu Lys Pro Ala Val Ala His Val
              20                    25                    30

Ser Asn Val Ser Asn Val Ala Leu Lys Thr Pro Phe Ser Gly Gly Phe
          35                    40                    45

Met Val Ala Gln Gly Trp Asn Arg Thr Phe Leu Pro Tyr Leu Lys Ala
      50                    55                    60

Ser Lys Thr Asn Ser Val Leu Thr Ser Glu Asp Arg Ser Ser Gln Glu
65                    70                    75                    80

Pro Leu Glu Lys Ile Ser Val Gln Asn Ser Thr Phe Pro Ile Gly Phe
                  85                    90                    95

Glu Ala Leu Ile Leu Glu Val Cys Asp Glu Thr Asn Ile Ala Glu Phe
              100                   105                   110
```

-continued

```
Lys Ile Lys Ile Gly Asp Phe Glu Met His Leu Lys Arg Asp Ile Glu
        115                 120                 125

Ser Pro Arg Ala Pro Ser Pro Gly Thr His Ile Val Ser Pro Thr Thr
        130                 135                 140

Ala Pro Pro Ile Pro Ser Gln Pro Met Asn Glu Ser Gly Ala Ala Ala
145                 150                 155                 160

Gln Pro Val Val Ser Gln Lys Ser Pro Thr Ala Ala Thr Ser Pro Phe
                165                 170                 175

Ala Asn Ile Ser Ser Ala Lys Ala Ser Lys Leu Val Ala Leu Glu Ala
                180                 185                 190

Ser Ala Ser Asn Ala Tyr Val Leu Val Ser Ser Pro Thr Val Gly Thr
                195                 200                 205

Phe Gln Arg Gly Arg Thr Leu Lys Gly Lys Lys Gln Pro Pro Ser Cys
        210                 215                 220

Lys Glu Gly Asp Val Ile Lys Glu Gly Gln Ile Ile Gly Phe Leu Asp
225                 230                 235                 240

Gln Phe Gly Asn Glu Leu Pro Val Lys Ser Asp Val Ala Gly Glu Val
                245                 250                 255

Val Lys Val Leu Cys Gln Asp Gly Glu Ala Val Gly Tyr Gly Asp Pro
                260                 265                 270

Leu Val Ala Val Leu Pro Ser Phe His Gly Ile Glu
        275                 280
```

<210> SEQ ID NO 148
<211> LENGTH: 289
<212> TYPE: PRT
<213> ORGANISM: Phoenix dactylifera

<400> SEQUENCE: 148

```
Met Ala Thr Cys Gly Leu Gly Ser Thr Ser Asn Val Lys Leu Leu Ser
1                   5                   10                  15

Phe Tyr Pro Asp Phe Lys Lys Leu Arg Ser Thr Ala Leu Leu Thr Pro
                20                  25                  30

His Asn Leu Lys Cys Gly Gly Leu Glu Thr Leu Asn Gly Ser Lys Gly
        35                  40                  45

Thr Gln Ile Trp Lys Glu Pro Val His Ala Ala Gly Phe Asp Lys Gln
        50                  55                  60

Ala Gln Arg Phe Ser Asn Ser Leu Val Ala Arg Cys Cys Ile Ser Pro
65                  70                  75                  80

Gly Lys Asn Asp Ser Lys Val Ile Glu Leu Glu Glu Asn Lys Ser Asn
                85                  90                  95

Gly Asp Gln Ile Ile Pro Val Ser Leu Glu Val Glu Pro Leu Leu Thr
                100                 105                 110

Ala Val Cys Asp Thr Thr Ser Ile Ala Glu Phe Lys Leu Asp Phe Ala
                115                 120                 125

Gly Phe Arg Leu Tyr Val Lys Arg Asp Leu Val Glu Lys Asn Val Pro
        130                 135                 140

Pro Pro Ile Pro Thr Leu Pro Pro Thr Gln Thr Asn Thr Thr Asn Gln
145                 150                 155                 160

Thr Thr Asp Ser Asn Gly Ser Ala Ala Thr Ala Ser Leu Ala Ile Ser
                165                 170                 175

Lys Pro Lys Pro Ser Thr Gly Gly Ile Gln Arg Thr Ala Ser Asp Glu
                180                 185                 190

Gly Leu Met Met Leu Pro Ser Pro Lys Val Gly Phe Phe Arg Arg Ser
        195                 200                 205
```

-continued

```
Arg Thr Ile Lys Gly Lys Gln Ala Pro Pro Ser Cys Lys Glu Gly Gln
    210             215             220

Asp Val Arg Glu Asp Gln Val Leu Cys Tyr Ile Glu Gln Leu Gly Gly
225             230             235             240

Glu Val Pro Val Glu Ser Asp Val Ser Gly Glu Val Ile Lys Ile Leu
            245             250             255

Arg Glu Asp Gly Glu Pro Val Gly Tyr Gly Asp Ala Ile Ile Ala Ile
            260             265             270

Leu Pro Ser Phe Pro Gly Ile Lys Lys Leu Gln Gln Ala Gly Ser Phe
            275             280             285

Pro

<210> SEQ ID NO 149
<211> LENGTH: 260
<212> TYPE: PRT
<213> ORGANISM: Populus euphratica

<400> SEQUENCE: 149

Met Glu Ser Ser Val Leu Leu Arg Ser Phe Gln Cys Asn Leu Leu Ala
1               5               10              15

Gln Gly Gln Gly Leu Thr Val Gly Arg Lys Leu Ile Ser Tyr Pro Ser
            20              25              30

Lys Arg Asn Leu Arg Leu Val Ser Cys Val Lys Thr Ser Glu Ala Pro
            35              40              45

Ala Ile Ala Lys Ser Asp Asp Gly Asn Lys Gln Gly Ser Leu Glu Lys
    50              55              60

Asn Ser Leu Arg Asn Ala Thr Phe Pro Asn Gly Phe Glu Ala Leu Val
65              70              75              80

Leu Glu Val Cys Asp Glu Thr Glu Ile Ala Glu Leu Lys Leu Lys Val
            85              90              95

Gly Asp Phe Glu Met His Leu Lys Arg Asn Val Gly Ala Val Lys Ala
            100             105             110

Pro Leu Ile Ser Ser Thr Pro Leu Pro Pro Ile Pro Thr Pro Pro Met
            115             120             125

Glu Val Ser Ala Ala Val Ser Pro Ser Pro Ser Pro Ser Lys Ser Ser
    130             135             140

Val Glu Lys Ser Thr Pro Phe Thr Asn Val Ser Phe Gly Lys Ser Ser
145             150             155             160

Lys Leu Ala Ala Leu Glu Ala Ser Gly Ala Ser Gly Tyr Val Leu Val
            165             170             175

Ala Ser Pro Thr Val Gly Ser Phe Arg Arg Asn Arg Thr Val Lys Gly
            180             185             190

Lys Lys Gln Pro Pro Ile Cys Lys Glu Gly Asp Val Ile Lys Glu Gly
            195             200             205

Gln Val Ile Gly Tyr Leu Asp Gln Phe Gly Thr Glu Leu Pro Val Lys
    210             215             220

Ser Asp Val Ala Gly Glu Val Leu Lys Leu Leu Phe Asn Asp Gly Asp
225             230             235             240

Ala Val Gly Tyr Gly Asp Pro Leu Ile Ala Val Leu Pro Ser Phe His
            245             250             255

Gly Ile Asn Asn
            260

<210> SEQ ID NO 150
```

-continued

<211> LENGTH: 269
<212> TYPE: PRT
<213> ORGANISM: Populus euphratica

<400> SEQUENCE: 150

Met Ala Ser Cys Arg Leu Gly Ala Leu Asn Val Lys Leu Ser Lys Leu
1               5                   10                  15

Asp Phe Gly Arg Gly Lys Phe Gly Asn Leu Gln Gln Arg Ser Gly Val
                20                  25                  30

Arg Val Trp Met Gly Arg Gly Gln Leu Gln Tyr Ala Gly Met Ala Ile
            35                  40                  45

Ser His Glu Ser Gly Lys Ala Phe Arg Cys Cys Gly Ser Ala Ser Glu
        50                  55                  60

Thr Glu Trp Thr Thr Lys Glu Thr Thr Ser Leu Gly Leu Thr Ser Gln
65                  70                  75                  80

Leu Ile Pro Asn Ser Ser Glu Ile Glu Ser Leu Val Thr Glu Ile Cys
                85                  90                  95

Asn Thr Thr Ser Ile Ala Glu Phe Glu Leu Lys Leu Gly Gly Phe Arg
                100                 105                 110

Leu Tyr Val Met Arg Tyr Leu Thr Glu Lys Asn Glu Pro Thr Pro Gln
            115                 120                 125

Pro Leu Ser Pro Pro Pro Leu Val Val Thr Val Lys Thr Thr Thr Asp
        130                 135                 140

Ala Ser Asp Leu Asn Gly Ser Ala Ser Thr Ser Leu Ala Ile Ser Lys
145                 150                 155                 160

Gln Glu Pro Ser Phe Gly Gly Ile Val Ser Phe Leu Asp Arg Ala Ala
                165                 170                 175

Asp Glu Gly Leu Met Ile Leu Gln Ser Pro Arg Val Gly Phe Phe Arg
            180                 185                 190

Arg Ser Arg Thr Ile Lys Gly Lys Arg Ala Pro Pro Ser Cys Lys Glu
            195                 200                 205

Lys Gln Ile Ile Lys Glu Gly Gln Val Leu Cys Tyr Ile Glu Gln Leu
        210                 215                 220

Gly Gly Glu Leu Pro Ile Glu Ser Asp Ile Ser Gly Glu Val Ile Lys
225                 230                 235                 240

Ile Leu Leu Glu Asp Gly Glu Pro Val Gly Tyr Gly Asp Ala Leu Ile
                245                 250                 255

Ala Ile Leu Pro Ser Phe Pro Gly Ile Lys Lys Leu Gln
                260                 265

<210> SEQ ID NO 151
<211> LENGTH: 260
<212> TYPE: PRT
<213> ORGANISM: Populus trichocarpa

<400> SEQUENCE: 151

Met Glu Ser Ser Val Leu Leu Arg Ser Phe Gln Cys Asn Leu Leu Ala
1               5                   10                  15

Gln Gly Gln Gly Leu Thr Val Gly Arg Lys Leu Ile Ser Tyr Pro Ser
                20                  25                  30

Lys Arg Asn Leu Arg Leu Val Ser Cys Val Lys Thr Ser Glu Ala Pro
        35                  40                  45

Ala Ile Ala Lys Ser Asp Asp Gly Asn Lys Gln Gly Ser Leu Glu Lys
        50                  55                  60

Asn Ser Leu Arg Asn Ala Thr Phe Pro Asn Gly Phe Glu Ala Leu Val
65                  70                  75                  80

-continued

```
Leu Glu Val Cys Asp Glu Thr Glu Ile Ala Glu Leu Lys Leu Lys Val
                85                  90                  95

Gly Asp Phe Glu Met His Leu Lys Arg Asn Val Gly Ala Ala Lys Ala
            100                 105                 110

Pro Leu Ile Ser Ser Thr Pro Leu Pro Pro Ile Pro Thr Pro Pro Met
            115                 120                 125

Glu Val Ser Ala Ala Val Ser Pro Ser Pro Ser Pro Ser Lys Ser Ser
            130                 135                 140

Val Glu Lys Thr Thr Pro Phe Thr Asn Val Ser Phe Gly Lys Ser Ser
145                 150                 155                 160

Lys Leu Ala Ala Leu Glu Ala Ser Gly Ala Ser Gly Tyr Val Leu Val
                165                 170                 175

Ala Ser Pro Thr Val Gly Ser Phe Arg Arg Asn Arg Thr Val Lys Gly
            180                 185                 190

Lys Lys Gln Pro Pro Ile Cys Lys Glu Gly Asp Val Ile Lys Glu Gly
            195                 200                 205

Gln Val Ile Gly Tyr Leu Asp Gln Phe Gly Thr Glu Leu Pro Val Lys
            210                 215                 220

Ser Asp Val Ala Gly Glu Val Leu Lys Leu Leu Phe Asn Asp Gly Asp
225                 230                 235                 240

Ala Val Gly Tyr Gly Asp Pro Leu Ile Ala Val Leu Pro Ser Phe His
                245                 250                 255

Gly Ile Asn Thr
            260

<210> SEQ ID NO 152
<211> LENGTH: 271
<212> TYPE: PRT
<213> ORGANISM: Populus trichocarpa

<400> SEQUENCE: 152

Met Ala Ser Cys Ser Leu Gly Ala Ser Asn Met Lys Leu Ser Lys Leu
1               5                   10                  15

Asp Phe Gly Arg Ala Thr Val Val Asn Leu Gln Lys Gln Ser Gly Leu
            20                  25                  30

Ile Ala Trp Arg Gly Arg Gly Arg Leu Gln His Ala Gly Val Ala Ile
            35                  40                  45

Ser His Lys Ser Arg Glu Ala Phe Arg Cys Arg Gly Ser Ala Ser Glu
        50                  55                  60

Thr Glu Leu Thr Thr Lys Glu Thr Lys Ser Ser Gly Leu Thr Ser Gln
65                  70                  75                  80

Leu Ile Pro Asn Ser Ser Glu Ile Glu Ser Leu Val Thr Glu Ile Cys
                85                  90                  95

Asn Thr Thr Ser Val Ala Glu Leu Glu Leu Lys Leu Gly Gly Phe Arg
            100                 105                 110

Leu Tyr Val Arg Arg Asp Leu Thr Glu Lys Asn Lys Asp Thr His Gln
            115                 120                 125

Pro Leu Pro Ala Pro Pro Ala Ser Leu Ala Val Thr Val Lys Thr Thr
            130                 135                 140

Thr Asp Ala Ser Asp Leu Asn Gly Ser Val Ser Thr Ser Leu Ala Ile
145                 150                 155                 160

Ser Lys Gln Glu Pro Ser Ser Gly Gly Ile Ile Ser Phe Leu Asp Arg
                165                 170                 175

Ala Ala Asp Glu Gly Leu Met Ile Leu Gln Ser Pro Arg Val Gly Phe
```

-continued

```
                  180              185              190

Phe Arg Arg Ser Arg Thr Ile Lys Gly Lys Arg Ala Pro Pro Ser Cys
            195              200              205

Lys Glu Lys Gln Ile Val Lys Glu Gly Gln Val Leu Cys Phe Ile Glu
        210              215              220

Gln Leu Gly Gly Glu Leu Pro Ile Glu Thr Asp Ile Ser Gly Glu Val
225              230              235              240

Ile Arg Ile Leu Arg Glu Asp Gly Glu Pro Val Gly Tyr Gly Asp Ala
                245              250              255

Leu Ile Ala Ile Leu Pro Ser Phe Pro Gly Ile Lys Lys Leu Gln
            260              265              270

<210> SEQ ID NO 153
<211> LENGTH: 289
<212> TYPE: PRT
<213> ORGANISM: Prunus mume

<400> SEQUENCE: 153

Met Glu Ser Ser Ala Val Phe Arg Ser Phe Asn Cys Ser Val Gly Thr
1               5               10              15

Val Ser His Val Arg Ser Ser Leu Asp Lys Pro Gly Met Leu Ala Ala
            20              25              30

Tyr Asn Thr Ala Arg Pro Thr Val Ser Arg Ser Tyr Phe Gln Gly Leu
        35              40              45

Met Val Ser Glu Lys Phe Ile Tyr Ser Pro Gln Lys Arg Arg Gly Val
        50              55              60

Pro Val Ser Cys Val Lys Thr Ser Glu Ala Ala Lys Ser Glu Lys Ser
65              70              75              80

Ser Asp Ser Lys Pro Gln Val Ser Ser Glu Arg Thr Thr Gln Pro Ala
                85              90              95

Thr Phe Pro Ser Gly Phe Glu Ala Leu Met Leu Glu Val Cys Asp Glu
            100             105             110

Thr Glu Val Ala Glu Leu Lys Leu Lys Val Gly Asp Phe Glu Met His
        115             120             125

Leu Lys Arg Asn Ile Gly Ala Thr Ser Ala Pro Val Ser Ser Ile Ser
        130             135             140

Pro Ala Val Ala Pro Pro Ile Pro Ser Lys Pro Met Val Glu Ser Ala
145             150             155             160

Ser Ala Pro Pro Pro Ala Pro Ala Pro Lys Ser Ser Ser Glu Lys Ala
                165             170             175

Thr Pro Phe Thr Asn Thr Ser Val Asp Lys Ser Ser Arg Leu Ala Ala
            180             185             190

Leu Glu Ala Ser Gly Ala Asn Gly Tyr Val Leu Val Ser Ser Pro Thr
        195             200             205

Val Gly Ser Phe Arg Arg Gly Arg Thr Val Lys Gly Lys Lys Gln Pro
        210             215             220

Pro Ile Cys Lys Glu Gly Asp Leu Ile Lys Gly Gly Gln Val Val Gly
225             230             235             240

Tyr Val Asp Gln Phe Gly Thr Glu Leu Pro Val Lys Ser Asp Val Gly
                245             250             255

Gly Glu Val Leu Lys Leu Leu Phe Asn Asp Gly Glu Ala Val Gly Tyr
            260             265             270

Gly Asp Pro Leu Ile Ala Val Leu Pro Ser Phe His Gly Ile Asn Ile
        275             280             285
```

-continued

Lys

<210> SEQ ID NO 154
<211> LENGTH: 273
<212> TYPE: PRT
<213> ORGANISM: Prunus mume

<400> SEQUENCE: 154

Met Ala Ser Cys Ser Leu Gly Thr Leu Asn Ala Lys Ile Thr Asn Leu
1               5                   10                  15

Asn Phe Gly Arg Thr Arg Val Gly Ile Leu Gln Ser Ser Gly Leu Lys
            20                  25                  30

Thr Trp Thr Gly Gln Lys Pro Gln Leu Tyr Ser Cys Leu Ser Met Ser
            35                  40                  45

Arg Arg Pro Asp Lys Val Leu Arg Ala His Ser Gly Pro Ser Leu Glu
    50                  55                  60

Thr Leu Pro Thr Thr Ser Leu Glu Asp Gly Pro Ala Glu Ser Arg Asp
65                  70                  75                  80

Ser Gly Ser Thr Asn Gln Leu Ile Pro Asn Phe Asp Glu Val Glu Ser
                85                  90                  95

Leu Val Thr Thr Ile Cys Asp Thr Thr Ser Val Ala Glu Phe Glu Leu
            100                 105                 110

Lys Ile Gly Gly Phe Arg Leu His Val Leu Arg Glu Leu Thr Glu Lys
            115                 120                 125

Ile Ser Thr Leu Pro Pro Pro Ser Pro Ala Pro Val Ser Val Asn Ala
        130                 135                 140

Thr Ala Glu Ala Pro Ala Ser Asn Gly Thr Val Pro Thr Gln Ser Leu
145                 150                 155                 160

Ala Ile Ile Arg Gln Glu His Ser Ser Arg Asn Ile Gln Thr Leu Leu
                165                 170                 175

Asp Arg Ala Ala Asp Asp Gly Leu Val Leu Ile His Ser Pro Arg Val
            180                 185                 190

Gly Leu Phe Arg Arg Ser Arg Thr Ile Lys Gly Lys Arg Ala Pro Pro
            195                 200                 205

Ser Cys Lys Glu Lys Gln Ile Val Lys Glu Gly Gln Val Ile Cys Tyr
        210                 215                 220

Ile Glu Gln Leu Gly Gly Glu Leu Pro Ile Glu Ser Asp Val Ser Gly
225                 230                 235                 240

Glu Val Ile Lys Ile Leu Arg Glu Asp Gly Asp Pro Val Gly Tyr Gly
                245                 250                 255

Asp Ala Leu Ile Ala Val Leu Pro Ser Phe Pro Gly Ile Lys Lys Leu
            260                 265                 270

Gln

<210> SEQ ID NO 155
<211> LENGTH: 291
<212> TYPE: PRT
<213> ORGANISM: Prunus persica

<400> SEQUENCE: 155

Met Glu Ser Ser Ala Val Phe Arg Ser Phe Asn Cys Ser Val Gly Thr
1               5                   10                  15

Val Ser His Val Arg Ser Ser Leu Asp Lys Pro Gly Met Leu Pro Ala
            20                  25                  30

Tyr Asn Thr Ala Arg Pro Thr Val Ser Arg Ser Tyr Phe Gln Gly Leu
            35                  40                  45

-continued

```
Met Val Ser Glu Lys Phe Ile Tyr Ser Pro Gln Lys Arg Arg Gly Val
    50                  55                  60

Gln Val Ser Cys Val Lys Thr Ser Glu Ala Ala Lys Ser Glu Lys Ser
65                  70                  75                  80

Ser Asp Ser Lys Pro Gln Val Ser Ser Glu Arg Thr Thr Gln Pro Ala
                85                  90                  95

Thr Phe Pro Asn Gly Phe Glu Ala Leu Met Leu Glu Val Cys Asp Glu
                100                 105                 110

Thr Glu Val Ala Glu Leu Lys Leu Lys Val Gly Asp Phe Glu Met His
                115                 120                 125

Leu Lys Arg Asn Ile Gly Ala Thr Ser Ala Pro Val Ser Ser Ile Ser
    130                 135                 140

Pro Ala Ala Ala Pro Pro Ile Pro Ser Lys Pro Met Val Glu Ser Ala
145                 150                 155                 160

Pro Ala Pro Pro Pro Ala Pro Ala Pro Ala Pro Lys Ser Ser Ser Glu
                165                 170                 175

Lys Ala Thr Pro Phe Thr Asn Thr Ser Val Asp Lys Ser Ser Arg Leu
                180                 185                 190

Ala Ala Leu Glu Ala Ser Gly Ala Asn Gly Tyr Val Leu Val Ser Ser
                195                 200                 205

Pro Thr Val Gly Ser Phe Arg Arg Gly Arg Thr Val Lys Gly Lys Lys
    210                 215                 220

Gln Pro Pro Ile Cys Lys Glu Gly Asp Leu Ile Lys Gly Gly Gln Val
225                 230                 235                 240

Ile Gly Tyr Val Asp Gln Phe Gly Thr Glu Leu Pro Val Lys Ser Asp
                245                 250                 255

Val Gly Gly Glu Val Leu Lys Leu Leu Phe Asn Asp Gly Glu Ala Val
                260                 265                 270

Gly Tyr Gly Asp Pro Leu Ile Ala Val Leu Pro Ser Phe His Gly Ile
    275                 280                 285

Asn Ile Asn
    290

<210> SEQ ID NO 156
<211> LENGTH: 273
<212> TYPE: PRT
<213> ORGANISM: Prunus persica

<400> SEQUENCE: 156

Met Ala Ser Cys Ser Leu Gly Thr Leu Asn Ala Lys Ile Thr Asn Leu
1               5                   10                  15

Asn Phe Gly Arg Thr Arg Val Gly Ile Leu Gln Ser Ser Gly Leu Lys
                20                  25                  30

Pro Trp Thr Gly Gln Lys Pro Gln Leu Tyr Ser Cys Leu Ser Ile Ser
    35                  40                  45

Arg Arg Pro Asp Asn Val Leu Arg Ala His Ser Gly Pro Ser Leu Glu
    50                  55                  60

Thr Leu Pro Thr Thr Ser Leu Glu Asp Gly Pro Ala Glu Ser Arg Asp
65                  70                  75                  80

Ser Gly Ser Thr Asn Gln Leu Ile Pro Asn Phe Asp Glu Val Glu Ser
                85                  90                  95

Leu Val Thr Thr Ile Cys Asp Thr Thr Ser Val Ala Glu Phe Glu Leu
                100                 105                 110

Lys Ile Gly Gly Phe Arg Leu His Val Leu Arg Glu Leu Thr Glu Lys
```

-continued

```
                115                 120                 125

Ile Ser Thr Leu Pro Pro Pro Ser Pro Ala Pro Val Ser Val Asn Ala
    130                 135                 140

Thr Ser Glu Ala Pro Ala Ser Asn Gly Ser Val Pro Thr Gln Ser Leu
145                 150                 155                 160

Ala Val Ile Arg Gln Glu His Ser Ser Arg Asn Ile Gln Thr Leu Leu
                165                 170                 175

Asp Arg Ala Ala Asp Asp Gly Leu Val Leu Ile His Ser Pro Arg Val
                180                 185                 190

Gly Leu Phe Arg Arg Ser Arg Thr Ile Lys Gly Lys Arg Ala Pro Pro
                195                 200                 205

Ser Cys Lys Glu Lys Gln Ile Val Lys Glu Gly Gln Val Ile Cys Tyr
    210                 215                 220

Ile Glu Gln Leu Gly Gly Glu Leu Pro Ile Glu Ser Asp Val Ser Gly
225                 230                 235                 240

Glu Val Ile Lys Ile Leu Arg Glu Asp Gly Asp Pro Val Gly Tyr Gly
                245                 250                 255

Asp Ala Leu Ile Ala Val Leu Pro Ser Phe Pro Gly Ile Lys Lys Leu
                260                 265                 270

Gln

<210> SEQ ID NO 157
<211> LENGTH: 288
<212> TYPE: PRT
<213> ORGANISM: Pyrus bretschneideri

<400> SEQUENCE: 157

Met Glu Ser Ser Ala Ala Leu Arg Ser Phe Asn Cys Ser Val Gly Thr
1               5                   10                  15

Val Ser His Val Gly Ser Leu Leu Asp Lys Arg Gly Met Leu Pro Val
                20                  25                  30

Tyr Asn Thr Arg Arg Pro Thr Pro Ser Arg Ser Tyr Phe Gln Gly Leu
    35                  40                  45

Met Val Ser Glu Lys Phe Ile Tyr Ser Ser Gln Lys Arg Lys Gly Val
    50                  55                  60

Leu Val Ser Cys Val Asn Thr Ser Glu Ala Ala Lys Thr Glu Asn Ser
65                  70                  75                  80

Ser Val Ser Ala Asp Ser Lys Pro Gln Cys Ser Ser Glu Lys Ala Ala
                85                  90                  95

His Pro Thr Ile Phe Pro Ser Gly Phe Glu Ala Leu Met Leu Glu Val
                100                 105                 110

Cys Asp Glu Thr Glu Val Ala Glu Leu Lys Leu Lys Val Gly Asp Phe
                115                 120                 125

Glu Met Tyr Leu Lys Arg Asn Ile Ala Val Thr Ser Ala Pro Val Pro
    130                 135                 140

Ser Ile Ser Pro Ala Thr Pro Pro Val Pro Ser Lys Pro Met Asp
145                 150                 155                 160

Ser Thr Pro Ala Pro Pro Ala Ser Pro Pro Lys Thr Ser Glu Lys
                165                 170                 175

Thr Thr Pro Phe Thr Asn Val Ser Val Asp Lys Leu Ser Arg Leu Ala
                180                 185                 190

Ala Leu Glu Ala Ser Gly Ala Lys Gly Tyr Asp Leu Val Ser Ser Pro
                195                 200                 205

Thr Val Gly Ser Phe Arg Arg Gly Arg Thr Val Lys Gly Lys Lys Gln
```

-continued

```
        210             215             220
Pro Pro Ile Phe Lys Glu Gly Asp Leu Ile Lys Lys Gly Gln Val Ile
225             230             235             240

Gly Tyr Val Asp Gln Phe Gly Thr Glu Leu Pro Val Lys Thr Asp Val
            245             250             255

Gly Gly Glu Val Leu Lys Leu Leu Phe Asn Asp Gly Glu Ala Val Gly
            260             265             270

Phe Gly Asp Pro Leu Ile Ala Val Leu Pro Ser Phe Ala Gly Ile Gln
            275             280             285

<210> SEQ ID NO 158
<211> LENGTH: 273
<212> TYPE: PRT
<213> ORGANISM: Pyrus bretschneideri

<400> SEQUENCE: 158

Met Ala Ser Ser Ser Leu Gly Thr Leu Asn Ala Lys Ile Thr Asn Leu
1               5               10              15

Asn Phe Ser Arg Ala Arg Val Gly Val Leu Arg Ser Tyr Gly Ile Ile
            20              25              30

Thr Trp Thr Gly Arg Lys Pro Gln Leu Tyr Ser Cys Leu Ser Ile Ser
        35              40              45

Arg Gln Ser Glu Lys Val Leu His Ala Arg Ser Val Pro Ser Leu Glu
    50              55              60

Ile Leu Ser Ala Lys Ser Leu Glu Glu Val Ser Glu Glu Ser Gly Asp
65              70              75              80

Ser Gly Pro Thr Asn Gln Leu Ile Gln Asn Phe Asp Glu Val Gln Ser
            85              90              95

Leu Leu Thr Ala Ile Cys Asp Thr Thr Thr Val Ala Glu Val Lys Leu
            100             105             110

Lys Ile Gly Gly Phe Gln Leu Asn Val Val Arg Lys Leu Thr Glu Lys
            115             120             125

Ile Ser Thr Pro Pro Pro Pro Ser Pro Ala Pro Val Ser Ala Ser Glu
    130             135             140

Asn Ala Lys Ala Leu Asp Leu Asn Gly Ala Val Pro Thr Gln Ser Val
145             150             155             160

Ala Ile Thr Arg Gln Glu Ser Ser Ser Arg Ser Ile Gln Thr Leu Leu
            165             170             175

Asp Arg Ala Ala Asp Asp Gly Leu Val Leu Ile His Ser Pro Arg Val
            180             185             190

Gly Leu Phe Arg Arg Ser Arg Thr Ile Lys Gly Lys Arg Ala Pro Pro
        195             200             205

Ser Cys Lys Glu Lys Gln Ile Val Lys Glu Gly Gln Val Ile Cys Tyr
    210             215             220

Ile Glu Gln Leu Gly Gly Glu Leu Pro Ile Glu Ser Asp Val Ala Gly
225             230             235             240

Glu Val Ile Arg Ile Leu Arg Glu Asp Gly Asp Pro Val Gly Tyr Gly
            245             250             255

Asp Ala Leu Val Ala Val Leu Pro Ser Phe Pro Gly Ile Glu Lys Leu
            260             265             270

Pro

<210> SEQ ID NO 159
<211> LENGTH: 273
<212> TYPE: PRT
```

<213> ORGANISM: Pyrus bretschneideri

<400> SEQUENCE: 159

```
Met Ala Ser Ser Ser Leu Gly Thr Leu Asn Ala Lys Ile Thr Asn Leu
1               5                   10                  15

Asn Phe Gly Lys Ala Arg Val Gly Val Leu Lys Ser Tyr Gly Val Arg
            20                  25                  30

Ser Trp Thr Gly Arg Lys Pro Gln Leu Tyr Ser Cys Leu Ser Ile Ser
        35                  40                  45

Arg Gln Pro Glu Lys Ala Leu His Val Arg Ser Ile Pro Ser Leu Glu
    50                  55                  60

Thr Leu Ser Ala Thr Ser Leu Glu Glu Val Pro Glu Glu Ser Gly Asp
65                  70                  75                  80

Ser Gly Pro Thr Asn Gln Leu Ile Gln Asn Phe Asp Glu Val Gln Ser
                85                  90                  95

Leu Leu Thr Ala Ile Cys Asp Thr Pro Thr Val Ala Glu Val Lys Val
            100                 105                 110

Lys Ile Gly Gly Phe Arg Leu Asn Val Val Arg Gln Pro Thr Glu Lys
        115                 120                 125

Phe Ser Thr Pro Pro Pro Ser Pro Thr Pro Val Ser Ala Ser Glu
    130                 135                 140

Asn Thr Lys Ala Leu Asp Ser Asn Gly Ala Val Pro Thr Gln Ser Val
145                 150                 155                 160

Ala Ile Thr Arg Gln Val Ser Ser Ser Arg Ser Ile Gln Thr Leu Val
            165                 170                 175

Asp Arg Ala Thr Asp Asp Gly Leu Val Leu Ile Arg Ser Pro Arg Val
            180                 185                 190

Gly Leu Phe Arg Arg Ser Arg Thr Ile Lys Gly Lys Arg Ala Pro Pro
        195                 200                 205

Ser Cys Lys Glu Lys Gln Thr Val Lys Glu Gly Gln Val Ile Cys Tyr
    210                 215                 220

Ile Glu Gln Leu Gly Gly Glu Leu Pro Ile Glu Ser Asp Val Ala Gly
225                 230                 235                 240

Glu Val Ser Arg Ile Leu Arg Glu Asp Gly Asp Pro Val Gly Tyr Gly
            245                 250                 255

Asp Ala Leu Val Ala Val Leu Pro Ser Phe Pro Gly Ile Met Lys Leu
            260                 265                 270

Gln
```

<210> SEQ ID NO 160
<211> LENGTH: 258
<212> TYPE: PRT
<213> ORGANISM: Ricinus communis

<400> SEQUENCE: 160

```
Met Glu Ser Ser Ser Ile Ala Leu Gln Cys Lys Met Tyr Gly Gln Arg
1               5                   10                  15

Leu Thr Val Gly Arg Lys Leu Met Ser Ser Ser Tyr Pro Lys Met Arg
            20                  25                  30

Arg Asn Val Met Ser Val Ser Cys Val Lys Ala Pro Glu Val Gly Ala
            35                  40                  45

Thr Ala Lys Ser Asp Ala Ala Asp Gly Ala Val Glu Lys Thr Arg Pro
    50                  55                  60

Arg Thr Ala Thr Phe Pro Ser Gly Phe Glu Ala Leu Met Leu Glu Val
65                  70                  75                  80
```

-continued

Cys Asp Glu Thr Glu Val Ala Glu Leu Lys Leu Lys Val Gly Asp Phe
                85                  90                  95

Glu Met His Leu Arg Arg Asn Val Gly Ala Thr Lys Ala Pro Leu Ser
                100                 105                 110

His Ile Ser Pro Ile Glu Pro Pro Pro Ile Pro Thr Lys Pro Met Asp
                115                 120                 125

Val Pro Ala Thr Val Ala Ala Pro Ala Ser Pro Pro Lys Pro Ser Ser
        130                 135                 140

Glu Lys Ala Thr Pro Phe Thr Asn Val Ser Phe Gly Lys Ser Ala Lys
145                 150                 155                 160

Leu Ala Ala Leu Glu Ala Ser Gly Ala Thr Gly Tyr Val Leu Val Ala
                165                 170                 175

Ser Pro Thr Val Gly Ser Phe Arg Arg Asn Arg Ser Val Lys Gly Lys
                180                 185                 190

Arg Gln Pro Pro Ile Phe Lys Glu Gly Asp Leu Ile Lys Glu Gly Gln
                195                 200                 205

Val Ile Gly Tyr Leu Asp Gln Phe Gly Thr Glu Leu Pro Val Lys Ser
        210                 215                 220

Asp Val Ala Gly Glu Val Leu Lys Leu Leu Phe Asp Asp Gly Asp Ala
225                 230                 235                 240

Val Gly Tyr Gly Asp Pro Leu Val Ala Val Leu Pro Ser Phe His Gly
                245                 250                 255

Ile Gln

<210> SEQ ID NO 161
<211> LENGTH: 293
<212> TYPE: PRT
<213> ORGANISM: Ricinus communis

<400> SEQUENCE: 161

Met Ala Ser Cys Gly Leu Gly Ala Ser Asn Ile Arg Ile Ser Lys Val
1               5                   10                  15

Asp Phe Ser Ile Ala Arg Val Gly Asn Leu Gln Gln Cys Asn Gly Arg
                20                  25                  30

Pro Asn Ser Ile Lys Ala Trp Phe Gly Arg Arg Ser Pro His Cys Ala
        35                  40                  45

Gly Val Ala Ala Ser Tyr Val Pro Lys Lys Ala Phe Ser Ile Cys Cys
        50                  55                  60

Gly Gln Thr Val Glu Thr Glu Ser Ala Thr Asn Ser Met Asp Glu Lys
65                  70                  75                  80

Glu Thr Lys Ser Ser Gly Leu Thr Ser Gln Leu Leu Pro Asn Ser Ala
                85                  90                  95

Glu Val Glu Ser Leu Ile Thr Glu Ile Cys Asn Ser Thr Ser Ile Ala
                100                 105                 110

Glu Phe Glu Leu Lys Leu Asp Gly Phe Arg Leu Tyr Val Thr Arg Asp
        115                 120                 125

Leu Thr Glu Lys Ser Lys Leu Gln Pro Leu Ser Ala Ser Ala Ser Ala
        130                 135                 140

Pro Ala Leu Ser Pro Pro Pro Ala Pro Ala Ala Ala Leu Ala Ser Val
145                 150                 155                 160

Ser Thr Asp Thr Thr Thr Ala Ala Pro Asp Leu Asn Gly Ser Val Ser
                165                 170                 175

Ser Thr Ser Arg Ala Ile Ser Lys Ser Gly Ser Phe Ser Gly Gly Val
                180                 185                 190

```
Gln Ser Ile Leu Asp Arg Ala Ala Asp Glu Gly Leu Met Ile Leu Gln
        195                 200                 205

Ser Pro Arg Val Gly Phe Phe Arg Arg Ser Arg Thr Ile Lys Gly Lys
        210                 215                 220

Arg Ala Pro Pro Ser Cys Lys Glu Lys Gln Ile Val Lys Glu Gly Gln
225                 230                 235                 240

Val Leu Cys Tyr Ile Glu Gln Leu Gly Gly Glu Leu Pro Ile Glu Ser
                245                 250                 255

Asp Val Ser Gly Glu Val Ile Lys Ile Leu Arg Glu Asp Gly Glu Pro
                260                 265                 270

Val Gly Tyr Gly Asp Ala Leu Ile Ala Ile Leu Pro Ser Phe Pro Gly
                275                 280                 285

Ile Lys Lys Leu Gln
        290

<210> SEQ ID NO 162
<211> LENGTH: 283
<212> TYPE: PRT
<213> ORGANISM: Sesamum indicum

<400> SEQUENCE: 162

Met Glu Ser Ala Ala Val Leu Arg Ser Cys His Tyr Ala Phe Thr Lys
1               5                   10                  15

Gly Ser His Phe Arg Thr Val Leu Glu Lys Pro Gly Thr Val Thr Ile
                20                  25                  30

Asn Tyr Ser Ala Phe Ser Asn Leu Ser Lys Leu Thr Val Cys Gly Gly
            35                  40                  45

Lys Leu Ser Ser Ser Thr Asn Arg His Gly Ala Ile Leu Val Ser Cys
        50                  55                  60

Val Lys Asn Ser Glu Thr Pro Val Thr Ser Lys Ser Asn Ser Asp Pro
65                  70                  75                  80

Asn Gly Ala Val Leu Glu Lys Lys Ser Pro Ser Ser Met Thr Phe Pro
                85                  90                  95

Asn Gly Phe Glu Ala Leu Leu Thr Glu Val Cys Asp Glu Thr Lys Ile
            100                 105                 110

Ala Glu Leu Lys Leu Lys Phe Gly Ala Phe Gln Ile His Met Lys Arg
        115                 120                 125

Asn Ile Asp Gly Pro Pro Val Pro Ala Ser Val Val Pro Gln Thr Thr
        130                 135                 140

Ala Pro Pro Val Pro Ser Lys Pro Ala Asn Ala Ser Ala Pro Ala Ala
145                 150                 155                 160

Leu Ser Ser Pro Pro Lys Pro Ser Ser Glu Lys Val Ser Pro Phe Thr
                165                 170                 175

Asn Val Ser Ile Glu Lys Val Ala Lys Leu Ala Ala Leu Glu Ala Ser
            180                 185                 190

Gly Ala Thr Gly Tyr Val Ile Val Ser Ser Pro Thr Val Gly Ser Phe
        195                 200                 205

Arg Arg Ala Arg Thr Leu Lys Gly Lys Lys Gln Pro Pro Ala Cys Lys
        210                 215                 220

Glu Gly Asp Val Ile Lys Glu Gly Gln Val Ile Gly Phe Leu Asp Gln
225                 230                 235                 240

Phe Gly Thr Glu Leu Pro Val Arg Ser Gly Val Ala Gly Glu Val Leu
                245                 250                 255

Lys Leu Leu Tyr Asn Asp Gly Glu Ala Val Gly Tyr Gly Asp Pro Leu
```

-continued

```
                260                 265                 270

Ile Ala Val Leu Pro Ser Phe Arg Gly Ile Asn
        275                 280

<210> SEQ ID NO 163
<211> LENGTH: 273
<212> TYPE: PRT
<213> ORGANISM: Sesamum indicum

<400> SEQUENCE: 163

Met Ala Ala Cys Gly Phe Gly Ala Ser Gly Leu Lys Ile Lys Asn Leu
1               5                   10                  15

Asp Phe Gly Ser Pro Arg Pro Lys Ser Arg Thr Leu Gln Pro Leu His
            20                  25                  30

Ser Leu Arg Thr Gln Lys Phe Val Pro Phe Asp Gly Phe Val Leu Ser
        35                  40                  45

Cys Gly Ser Lys Lys Pro Ile Phe Val Cys Arg Ser Ser Ala Ser Glu
    50                  55                  60

Ala Asp Ser Asn Ala Asn Val Glu Asp Asn Ser Glu Glu Thr Lys Ser
65                  70                  75                  80

Thr Asp Gly Thr Ser Thr Leu Val Pro Asn Gly Leu Glu Val Glu Ser
                85                  90                  95

Leu Leu Thr Val Leu Cys Asp Thr Thr Ser Ile Ala Gln Phe Glu Leu
            100                 105                 110

Lys Leu Gly Gly Phe Arg Leu Tyr Val Ser Arg Asn Leu Ala Glu Gln
        115                 120                 125

Ser Val Pro Pro Gln Pro Pro Val Pro Ala Pro Val Thr Asn Gln Thr
    130                 135                 140

Val Val Glu Ser Pro Ser Ser Asn Gly Ser Ala Ser Ser Ser Cys Leu
145                 150                 155                 160

Ala Leu Trp Lys Pro Asp Pro Tyr Ser Val Gly Val Gln Thr Leu Leu
                165                 170                 175

Asp Lys Ala Ala Asp Glu Gly Leu Ala Ile Leu Gln Ser Pro Arg Val
            180                 185                 190

Gly Tyr Phe Arg Arg Ser Arg Thr Ile Lys Gly Lys Arg Ala Pro Pro
        195                 200                 205

Ser Cys Lys Glu Lys Asp Ile Val Lys Glu Gly Gln Val Leu Cys Tyr
    210                 215                 220

Ile Glu Gln Leu Gly Gly Gln Ile Pro Val Glu Ser Asp Val Ser Gly
225                 230                 235                 240

Glu Val Val Lys Ile Leu Arg Glu Asp Gly Glu Pro Val Gly Tyr Ala
                245                 250                 255

Asp Ala Leu Ile Ala Val Leu Pro Ser Phe Pro Gly Ile Lys Lys Leu
            260                 265                 270

Gln

<210> SEQ ID NO 164
<211> LENGTH: 290
<212> TYPE: PRT
<213> ORGANISM: Solanum lycopersicum

<400> SEQUENCE: 164

Met Glu Ser Ala Ala Val Leu Arg Ser Phe His His Ser Val Gly Thr
1               5                   10                  15

Thr Ser His Val Arg Ser Val Ile Glu Met Pro Gly Val Ile Pro Thr
            20                  25                  30
```

-continued

```
Asn Asn Ile Ala Phe Ser Lys Pro Thr Lys Phe Ser Leu Lys Gly Ser
        35                  40                  45

Ser Asn Gly Ala Arg Arg Ile Ser Ser Pro Asn Lys His Gly Arg Leu
    50                  55                  60

Ile Leu Ser Cys Ala Lys Thr Ser Glu Thr Thr Val Thr Ala Lys Ser
65                  70                  75                  80

Gly Asp Gly Asn His Lys Val Pro Thr Glu Ser Ser Pro Leu Pro Thr
                85                  90                  95

Ala Thr Phe Pro Lys Gly Phe Glu Ala Leu Ile Thr Glu Val Cys Asp
                100                 105                 110

Asp Thr Glu Val Ala Glu Leu Lys Leu Lys Val Gly Asp Phe Glu Leu
            115                 120                 125

His Leu Lys Arg Asn Ile Glu Ala Pro Val Val Pro Ala Pro Val Val
    130                 135                 140

Ser Ala Pro Pro Pro Pro Pro Pro Pro Ser Ala Ser Lys Pro Ser
145                 150                 155                 160

Ile Ser Ser Thr Ala Ala Pro Ala Ala Ser Pro Gly Lys Ser Thr Ser
                165                 170                 175

Gly Lys Ile Ser Pro Phe Thr Asn Val Ala Ala Glu Lys Ser Ala Lys
            180                 185                 190

Leu Ala Ala Leu Glu Ser Thr Gly Ala Ser Gly Tyr Val Leu Val Ser
            195                 200                 205

Cys Pro Thr Val Gly Ser Phe Arg Arg Ala Arg Thr Leu Lys Gly Lys
    210                 215                 220

Lys Gln Pro Pro Ala Cys Lys Glu Gly Asp Ile Ile Lys Glu Gly Gln
225                 230                 235                 240

Ile Ile Gly Phe Leu Asp Gln Phe Gly Thr Glu Leu Pro Val Arg Ser
                245                 250                 255

Asp Ala Ala Gly Glu Val Leu Lys Ile Leu Phe Asn Asp Gly Glu Ala
                260                 265                 270

Val Gly Tyr Gly Asp Pro Leu Ile Ala Val Leu Pro Ser Phe His Gly
            275                 280                 285

Ile Asn
    290
```

<210> SEQ ID NO 165
<211> LENGTH: 274
<212> TYPE: PRT
<213> ORGANISM: Solanum lycopersicum

<400> SEQUENCE: 165

```
Met Ala Ala Cys Gly Phe Gly Ala Ser Gly Leu Lys Leu Thr Ser Leu
1               5                   10                  15

Asn Leu Gly Ser Thr Lys Pro Lys Leu Ser Val Val His Asn Leu Arg
                20                  25                  30

Thr Lys Lys Phe Val Gln Ser Asp Gly Leu Leu Leu Thr Thr Lys Ser
            35                  40                  45

Arg Lys Thr Phe Asp Cys Arg Cys Ser Thr Val Glu Ala Glu Ser Val
    50                  55                  60

Ala Ala Thr Ala Ile Pro Asn Ser Asp Asp Ser Ser Ser Lys Ile Val
65                  70                  75                  80

Ser Ser Glu Thr Ala Ser Pro Leu Thr Pro Asn Ser Tyr Glu Val Glu
                85                  90                  95

Ser Leu Leu Thr Glu Ile Cys Asp Thr Thr Ser Ile Ala Glu Val Asp
```

```
                100              105                110

Leu Lys Leu Gly Gly Phe Arg Leu Tyr Val Lys Arg Asp Leu Thr Gly
        115              120                125

Gln Ser Thr Thr Ser Leu Pro Pro Ile Ser Ser Pro Val Ser Val Ser
    130              135              140

Ser Ser Val Glu Val Ala Asp Ser Asn Gly Ser Ala Ser Ser Thr Ser
145              150                155                160

Leu Ala Ile Thr Lys Ser Ser Pro Pro Ser Asp Gly Ile Gln Thr Met
                165              170                175

Ile Glu Lys Ala Ala Asp Glu Gly Leu Val Ile Ile Gln Ser Pro Arg
            180              185                190

Val Gly Phe Phe Arg Arg Ser Arg Thr Ile Lys Gly Lys Arg Ala Pro
        195              200                205

Pro Ala Cys Lys Glu Lys Gln Gln Val Lys Glu Gly Gln Val Val Phe
    210              215                220

Tyr Ile Glu Gln Leu Gly Gly Glu Leu Pro Val Glu Ser Asp Val Ser
225              230                235                240

Gly Glu Val Ile Arg Ile Leu Arg Lys Asp Gly Asp Pro Val Gly Tyr
            245              250                255

Gly Asp Pro Leu Ile Ser Ile Leu Pro Ser Phe Pro Gly Ile Lys Lys
            260              265                270

Leu Gln

<210> SEQ ID NO 166
<211> LENGTH: 291
<212> TYPE: PRT
<213> ORGANISM: Solanum pennellii

<400> SEQUENCE: 166

Met Glu Ser Ala Ala Val Leu Arg Ser Phe His His Ser Val Gly Thr
1                 5                10                15

Thr Ser His Val Arg Ser Val Ile Glu Met Pro Gly Val Ile Pro Thr
            20              25                30

Asn Asn Ile Ala Phe Ser Lys Pro Thr Lys Phe Ser Leu Lys Gly Ser
        35              40              45

Ser Asn Gly Ala Arg Arg Ile Ser Ser Pro Asn Lys His Gly Arg Leu
    50              55              60

Ile Leu Ser Cys Ala Lys Thr Ser Glu Thr Thr Val Thr Ala Lys Ser
65              70              75                80

Gly Asp Gly Asn His Lys Val Pro Ile Glu Ser Ser Pro Leu Pro Thr
            85              90                95

Ala Thr Phe Pro Lys Gly Phe Glu Ala Leu Ile Thr Glu Val Cys Asp
            100              105                110

Asp Thr Glu Val Ala Glu Leu Lys Leu Lys Val Gly Asp Phe Glu Leu
        115              120                125

His Leu Lys Arg Asn Ile Glu Ala Pro Val Val Pro Ala Pro Val Val
        130              135                140

Ser Ala Pro Pro Pro Pro Pro Pro Ser Ala Ser Lys Pro Ser
145              150                155                160

Ile Ser Ser Thr Thr Ala Ala Pro Ala Ala Ser Pro Gly Lys Ser Thr
            165              170                175

Ser Gly Lys Ile Ser Pro Phe Thr Asn Val Ala Ala Glu Lys Ser Ala
            180              185                190

Lys Leu Ala Ala Leu Glu Ser Thr Gly Ala Ser Gly Tyr Val Leu Val
```

-continued

```
          195                 200                 205

Ser Cys Pro Thr Val Gly Ser Ser Arg Arg Ala Arg Thr Leu Lys Gly
    210                 215                 220

Lys Lys Gln Pro Pro Ala Cys Lys Glu Gly Asp Ile Ile Lys Glu Gly
225                 230                 235                 240

Gln Ile Ile Gly Phe Leu Asp Gln Phe Gly Thr Glu Leu Pro Val Arg
                245                 250                 255

Ser Asp Ala Ala Gly Glu Val Leu Lys Ile Leu Phe Asn Asp Gly Glu
                260                 265                 270

Ala Val Gly Tyr Gly Asp Pro Leu Ile Ala Val Leu Pro Ser Phe His
                275                 280                 285

Gly Ile Asn
    290

<210> SEQ ID NO 167
<211> LENGTH: 274
<212> TYPE: PRT
<213> ORGANISM: Solanum pennellii

<400> SEQUENCE: 167

Met Ala Ala Cys Gly Phe Gly Ala Ser Gly Leu Lys Leu Thr Ser Leu
1               5                 10                  15

Asn Leu Gly Ser Thr Lys Pro Lys Leu Ser Val Val His Asn Leu Arg
                20                 25                 30

Thr Lys Lys Phe Val Gln Ser Asp Gly Leu Leu Leu Thr Thr Lys Ser
                35                 40                 45

Arg Lys Thr Phe Asp Cys Arg Cys Ser Thr Val Glu Ala Glu Ser Val
    50                 55                 60

Ala Ala Thr Ala Ile Pro Asn Ser Asp Asp Ser Ser Ser Lys Ile Val
65                 70                 75                 80

Ser Ser Glu Thr Ala Ser Pro Leu Ile Pro Asn Ser Tyr Glu Val Glu
                85                 90                 95

Ser Leu Leu Thr Glu Ile Cys Asp Thr Thr Ser Ile Ala Glu Val Asp
                100                 105                 110

Leu Lys Leu Gly Glu Phe Arg Leu Tyr Val Lys Arg Asp Leu Thr Gly
                115                 120                 125

Gln Ser Thr Thr Ser Leu Pro Pro Ile Ser Ser Pro Val Ser Val Pro
    130                 135                 140

Ser Ser Val Glu Val Ala Asp Ser Asn Gly Ser Ala Ser Ser Thr Ser
145                 150                 155                 160

Leu Ala Ile Thr Lys Ser Ser Pro Pro Ser Asp Gly Ile Gln Thr Met
                165                 170                 175

Ile Glu Lys Ala Ala Asp Glu Gly Leu Val Ile Ile Gln Ser Pro Arg
                180                 185                 190

Val Gly Phe Phe Arg Arg Ser Arg Thr Ile Lys Gly Lys Arg Ala Pro
                195                 200                 205

Pro Ala Cys Lys Glu Lys Gln Gln Val Lys Glu Gly Gln Val Val Phe
    210                 215                 220

Tyr Ile Glu Gln Leu Gly Gly Glu Leu Pro Val Glu Ser Asp Val Ser
225                 230                 235                 240

Gly Glu Val Ile Arg Ile Leu Arg Lys Asp Gly Asp Pro Val Gly Tyr
                245                 250                 255

Gly Asp Pro Leu Ile Ser Ile Leu Pro Ser Phe Pro Gly Ile Lys Lys
                260                 265                 270
```

-continued

Leu Gln

<210> SEQ ID NO 168
<211> LENGTH: 289
<212> TYPE: PRT
<213> ORGANISM: Solanum tuberosum

<400> SEQUENCE: 168

Met Glu Ser Ala Ala Val Leu Arg Ser Phe His His Ser Val Gly Thr
1               5                   10                  15

Thr Ser His Val Arg Ser Val Ile Glu Met Pro Gly Val Ile Pro Thr
                20                  25                  30

Asn Ser Ile Ala Phe Ser Lys Pro Thr Lys Leu Ser Leu Lys Gly Ser
            35                  40                  45

Ser Asn Gly Ala Arg Leu Met Ser Ser Pro Asn Lys His Gly Arg Leu
        50                  55                  60

Thr Leu Ser Cys Ala Lys Thr Ser Glu Thr Thr Val Thr Ala Lys Ser
65                  70                  75                  80

Gly Asp Ser Asn Gln Lys Val Pro Thr Glu Ser Ser Pro Leu Pro Thr
                85                  90                  95

Ala Thr Phe Pro Lys Gly Phe Glu Ala Leu Ile Ile Glu Val Cys Asp
            100                 105                 110

Asp Thr Glu Val Ala Glu Leu Lys Leu Lys Val Gly Asp Phe Glu Leu
            115                 120                 125

His Leu Lys Arg Asn Ile Glu Ala Pro Val Val Pro Ala Pro Val Val
        130                 135                 140

Ser Ala Pro Pro Pro Pro Pro Ser Ala Ser Lys Thr Ser Ile Ser
145                 150                 155                 160

Ser Thr Ala Ala Ala Pro Ala Ala Ser Pro Gly Lys Ser Ser Ser Gly
                165                 170                 175

Lys Ile Ser Pro Phe Thr Asn Val Ala Ala Glu Lys Ser Ala Lys Leu
            180                 185                 190

Ala Ala Leu Glu Ser Thr Gly Ala Ser Gly Tyr Val Leu Val Ser Cys
            195                 200                 205

Pro Thr Val Gly Ser Phe Arg Arg Ala Arg Thr Leu Lys Gly Lys Lys
        210                 215                 220

Gln Pro Pro Ala Cys Lys Glu Gly Asp Ile Ile Lys Glu Gly Gln Ile
225                 230                 235                 240

Ile Gly Phe Leu Asp Gln Phe Gly Thr Glu Leu Pro Val Arg Ser Asp
                245                 250                 255

Ala Ala Gly Glu Val Leu Lys Ile Leu Phe Asn Asp Gly Glu Ala Val
            260                 265                 270

Gly Tyr Gly Asp Pro Leu Ile Ala Val Leu Pro Ser Phe Arg Gly Ile
        275                 280                 285

Asn

<210> SEQ ID NO 169
<211> LENGTH: 274
<212> TYPE: PRT
<213> ORGANISM: Solanum tuberosum

<400> SEQUENCE: 169

Met Ala Ala Cys Gly Phe Gly Ala Ser Gly Leu Lys Leu Thr Ser Leu
1               5                   10                  15

Asn Leu Gly Ser Thr Lys Pro Lys Leu Ser Val Val His Asn Leu Arg
                20                  25                  30

```
Thr Lys Lys Phe Val Gln Asn Asp Gly Leu Leu Leu Thr Thr Lys Ser
    35                  40                  45

Arg Lys Thr Phe Asp Cys Arg Cys Ser Thr Val Glu Ala Lys Pro Ala
    50                  55                  60

Ala Ala Thr Ala Ile Pro Lys Ser Asp Asp Ser Ser Ser Lys Ile Val
65                  70                  75                  80

Ser Ser Glu Thr Ala Ser Pro Leu Ile Pro Asn Ser Tyr Glu Val Glu
                85                  90                  95

Ser Leu Leu Ala Glu Ile Cys Asp Thr Thr Ser Ile Ala Glu Val Asp
                100                 105                 110

Leu Lys Leu Gly Gly Phe Arg Leu Tyr Val Lys Arg Asp Leu Thr Gly
                115                 120                 125

Gln Ser Thr Thr Ser Leu Pro Pro Ile Thr Ser Pro Val Ser Ile Pro
    130                 135                 140

Ser Ser Val Glu Val Ala Asp Ser Asn Gly Ser Ala Ser Ser Thr Ser
145                 150                 155                 160

Leu Ala Ile Thr Lys Ser Ser Pro Pro Ser Asp Gly Ile Gln Thr Met
                165                 170                 175

Ile Glu Lys Ala Ala Asp Glu Gly Leu Val Ile Ile Gln Ser Pro Arg
                180                 185                 190

Val Gly Phe Phe Arg Arg Ser Arg Thr Ile Lys Gly Lys Arg Ala Pro
                195                 200                 205

Pro Ala Cys Lys Glu Lys Gln Gln Val Lys Glu Gly Gln Val Val Phe
    210                 215                 220

Tyr Ile Glu Gln Leu Gly Gly Glu Leu Pro Val Glu Ser Asp Val Ser
225                 230                 235                 240

Gly Glu Val Ile Lys Ile Leu Arg Lys Asp Gly Asp Pro Val Gly Tyr
                245                 250                 255

Gly Asp Pro Leu Ile Ser Ile Leu Pro Ser Phe Pro Gly Ile Lys Lys
                260                 265                 270

Leu Gln
```

<210> SEQ ID NO 170
<211> LENGTH: 274
<212> TYPE: PRT
<213> ORGANISM: Spinacia oleracea

<400> SEQUENCE: 170

```
Met Glu Thr Ala Ala Phe Arg Leu Ser Ala Gly Ser Ile Ser His Ala
1               5                   10                  15

Cys Ser Ser Leu Glu Lys Pro Ser Leu Ala Ser Trp Pro Thr Val Ile
                20                  25                  30

Arg Ser His Cys Gln Ala Leu Thr Val Gly Lys Leu Ala Ser Ser Ser
        35                  40                  45

Arg Gln Ala Arg Ile Val Val Ser Cys Ala Lys Thr Pro Glu Thr Thr
    50                  55                  60

Val Ser Ser Asn Ser Asp Val Pro Val Asn Asn Arg Ser Lys Gly Ser
65                  70                  75                  80

Ile Glu Lys His Ala Leu Arg Ala Thr Phe Pro His Ala Phe Glu Ala
                85                  90                  95

Leu Leu Leu Glu Val Cys Asp Glu Thr Ser Val Ala Glu Val Gln Leu
                100                 105                 110

Lys Val Gly Asp Phe Glu Met His Leu Lys Arg Asn Val Gly Ala Val
                115                 120                 125
```

-continued

```
Asn Thr Pro Val Pro Val Ala Pro Pro Ile Pro Ser Glu Pro Met Val
    130                 135             140

Gln Ser Ala Pro Ala Ala Leu Ser Thr Ser Ala Pro Lys Pro Ser Leu
145                 150             155                 160

Glu Lys Ser Ser Leu Phe Ala Ser Ala Ser Ser Ala Ala Ser Ser Lys
                165             170             175

Leu Ala Ser Leu Glu Ala Ser Gly Ala Asp Gly Phe Glu Leu Val Thr
            180             185             190

Ser Pro Thr Val Gly Ser Phe Arg Arg Gly Arg Thr Val Lys Gly Lys
        195             200             205

Lys Gln Pro Pro Asn Cys Lys Gln Gly Asp Val Ile Lys Glu Gly Gln
    210             215             220

Val Ile Gly Tyr Ile Asp Gln Phe Gly Thr Glu Leu Pro Val Lys Ser
225             230             235             240

Asp Val Ala Gly Glu Val Leu Lys Leu Leu Phe Glu Glu Gly Glu Ala
            245             250             255

Val Gly Tyr Gly Asp Pro Leu Ile Ala Val Leu Pro Ser Phe His Gly
            260             265             270

Leu Arg

<210> SEQ ID NO 171
<211> LENGTH: 284
<212> TYPE: PRT
<213> ORGANISM: Spinacia oleracea

<400> SEQUENCE: 171

Met Ala Ser Ser Ser Leu Gly Val Ser Asn Thr Gln Ile Leu Ser Ser
1               5               10              15

Lys Leu Asn Asn Arg Arg Ser Cys Ser Leu Ala Ser Phe Pro Arg Val
            20              25              30

Ile Arg Ala Gly Asn Arg Pro Asn Ser Trp Lys Asn Ser Gly Leu Lys
        35              40              45

Met Ser Gln Ser Ser His Lys Glu Leu Ile Val Cys Arg Ala Gln Ala
    50              55              60

Ser Leu Val Thr Glu Asn Glu Pro Ala Ala Ser Ile Ile Glu Glu Gly
65              70              75              80

Glu Glu Gln Ser Asn Ser Gly Ser Val Ser Gln Leu Ile Pro Asn Ser
            85              90              95

Asp Glu Val Lys Leu Leu Val Thr Glu Ile Cys Asp Thr Thr Ser Ile
            100             105             110

Ala Glu Phe Glu Leu Lys Leu Asn Gly Phe His Leu His Val Thr Arg
        115             120             125

Ala Leu Ser Glu Gly Val Asn Pro Pro Pro Ser Leu Pro Thr Ser Gly
        130             135             140

Ser Val Ser Met Ser Ala Asn Thr Ala Val Glu Ala Pro Ser Leu Asn
145             150             155             160

Gly Pro Val Ser Pro Ser Ser Leu Ala Ile Thr Lys Ala Gly Pro Leu
            165             170             175

Asp Ile Thr His Gly Thr Leu Leu Glu Arg Ala Ala Asp Glu Gly Phe
            180             185             190

Val Ile Ile Gln Ser Pro Lys Val Gly Phe Phe Arg Arg Cys Arg Thr
        195             200             205

Ile Lys Gly Lys Arg Ala Pro Pro Ala Cys Lys Glu Lys Gln Val Val
    210             215             220
```

```
Lys Glu Gly Gln Val Ile Cys Tyr Ile Asp Gln Leu Gly Gly Glu Ile
225                 230                 235                 240

Pro Val Glu Ser Asp Val Ser Gly Glu Val Thr Lys Ile Leu Arg Gln
                245                 250                 255

Asp Gly Glu Pro Val Gly Tyr Gly Asp Ala Ile Val Ala Ile Leu Pro
                260                 265                 270

Ser Phe Pro Gly Ile Lys Lys Leu Gln Leu Asp Gly
            275                 280

<210> SEQ ID NO 172
<211> LENGTH: 287
<212> TYPE: PRT
<213> ORGANISM: Tarenaya hassleriana

<400> SEQUENCE: 172

Met Glu Ser Ser Ala Ala Leu Gly Ser Leu His Gln Thr Ile Gly Ser
1               5                   10                  15

Leu Ala Asn Ser Gln Thr Met Val Glu Asn Ser Thr Lys Val His Leu
                20                  25                  30

His Cys Gly Asn Trp Pro Val Ser Gly Asn Ser Leu Val Pro His Arg
            35                  40                  45

Arg Phe Asn Gly Lys Arg Asn Phe Thr Leu Ala Leu Ser Val Gln Ala
        50                  55                  60

Ser Lys Thr Ser Thr Thr Thr Glu Thr Gly Asp Ser Ser Asp Ala Ser
65                  70                  75                  80

Ala Ser Lys Val Lys Lys Thr Ile Gly Arg Leu Thr Phe Pro Asn Glu
                85                  90                  95

Leu Glu Ala Leu Val His Glu Val Cys Asp Asp Thr Glu Val Ala Glu
                100                 105                 110

Leu Lys Leu Lys Val Gly Asp Phe Glu Met His Leu Lys Arg Lys Ile
            115                 120                 125

Gly Glu Ile Thr Ala Pro Ala Pro Leu Thr Asp Ile Ser Pro Thr Val
        130                 135                 140

Ala Pro Pro Ile Pro Ser Glu Pro Met Asn Glu Ser Ala Pro Thr Ala
145                 150                 155                 160

Ala Pro Ile Pro Ser Lys Ala Lys Ser Ser Ser Glu Lys Ala Thr Pro
                165                 170                 175

Phe Met Asn Thr Ser Phe Gly Lys Ser Ser Lys Leu Ala Ser Leu Glu
                180                 185                 190

Ala Ser Gly Ser Asn Asn Tyr Val Leu Val Thr Ser Pro Gly Val Gly
            195                 200                 205

Thr Tyr Gln Arg Asn Arg Ala Val Lys Gly Lys Lys Gln Ala Pro Ser
        210                 215                 220

Cys Lys Glu Gly Asp Val Ile Lys Glu Gly Gln Val Ile Gly Phe Leu
225                 230                 235                 240

His Gln Leu Gly Thr Glu Leu Pro Val Lys Ser Asp Val Ala Gly Glu
                245                 250                 255

Val Leu Lys Val Leu Cys Asp Asp Gly Asp Ser Val Gly Tyr Gly Asp
                260                 265                 270

Pro Leu Val Ala Ile Leu Pro Ser Phe His Asp Ile Asn Ile Met
            275                 280                 285

<210> SEQ ID NO 173
<211> LENGTH: 271
<212> TYPE: PRT
```

<213> ORGANISM: Tarenaya hassleriana

<400> SEQUENCE: 173

```
Met Ala Ser Cys Ser Leu Gly Val Pro Lys Ile Lys Ile Ser Ala Ile
1               5                   10                  15

Asn Ile Ser Lys Gly Arg Ser Gly Asn Leu Leu Ile Pro Glu Asn Gln
            20                  25                  30

Arg Pro Arg Leu Glu Gln Lys Pro Leu Lys Tyr Val Gly Leu Arg Thr
        35                  40                  45

Thr Leu Gln Thr Val Lys Ala Val Lys Val Ser Thr Val Pro Ala Thr
    50                  55                  60

Glu Ala Asp Ala Ala Thr Asp Val Glu Glu Ala Lys Pro Ser Gly Leu
65                  70                  75                  80

Ser Ser Gln Pro Ile Pro Lys Ser Ser Glu Val Glu Ala Leu Val Thr
            85                  90                  95

Glu Ile Cys Asp Ser Thr Ser Ile Ala Glu Phe Glu Leu Lys Leu Gly
            100                 105                 110

Gly Phe Arg Leu Tyr Val Ala Arg Asn Leu Thr Asp Lys Ser Ser Pro
        115                 120                 125

Pro Pro Pro Pro Val Leu Ser Ala Val Thr Ala Ser Ala Thr Thr Glu
    130                 135                 140

Glu Phe Asp Thr Asn Gly Ser Ala Ser Ser Pro Ser Leu Ala Ile Thr
145                 150                 155                 160

Lys Ala Val Ser Ser Ser Gly Gly Gly Thr Glu Thr Leu Val Asp Arg
            165                 170                 175

Ala Ala Asp Glu Gly Leu Val Ile Leu Gln Ser Pro Lys Val Gly Phe
            180                 185                 190

Phe Arg Arg Ser Arg Thr Ile Lys Gly Lys Arg Thr Pro Pro Ser Cys
        195                 200                 205

Lys Val Lys Asp Val Val Lys Glu Gly Gln Val Leu Cys Tyr Ile Glu
    210                 215                 220

Gln Leu Gly Gly Gln Ile Pro Ile Glu Ser Asp Val Ser Gly Glu Val
225                 230                 235                 240

Val Lys Ile Leu Arg Glu Asp Gly Glu Pro Val Gly Tyr Asn Asp Ala
            245                 250                 255

Leu Ile Ala Ile Leu Pro Ser Phe Pro Gly Ile Lys Lys Leu Gln
            260                 265                 270
```

<210> SEQ ID NO 174
<211> LENGTH: 341
<212> TYPE: PRT
<213> ORGANISM: Vigna angularis

<400> SEQUENCE: 174

```
Met Gly Thr Met Ser His Met Arg Pro Ser Arg Asp Lys Gln Val Val
1               5                   10                  15

Val Pro Ile His Asn Val Arg Trp Asn Ser Lys Ser Arg Leu Phe Ile
            20                  25                  30

Gln His Leu Ala Tyr Asp Arg Lys His Ile Asn Ser His Val Lys Gly
        35                  40                  45

Asn Asn Thr Leu Val Ser Cys Ala Lys Thr Ala Glu Pro Ile Asn Thr
    50                  55                  60

Ser Lys Ser Gly Asp Ala Ser Ser Asp Ser Thr Pro Gln Gly Ser Leu
65                  70                  75                  80

Glu Lys Lys Pro Leu Gln Ala Ala Thr Phe Pro Asn Gly Phe Glu Ala
```

-continued

```
                    85              90              95
Leu Val Leu Glu Val Cys Asp Glu Thr Glu Ile Ala Glu Leu Lys Val
            100             105             110

Lys Val Ile Phe Arg Leu Val Tyr Pro Phe Val Gln Leu Glu Val Arg
            115             120             125

Tyr Phe Lys Phe Ser Ser Lys Asp Glu Lys Glu Asn Phe Arg Glu Cys
            130             135             140

Tyr Met Val Cys Leu Phe Ala Ile His Thr Leu Lys Ser Val Ala Gly
145             150             155             160

Trp Val Gly Asp Phe Glu Met His Ile Lys Arg Asn Ile Gly Ala Thr
                165             170             175

Lys Val Pro Leu Ser Asn Ile Ser Pro Thr Thr Pro Pro Ile Pro
            180             185             190

Ser Lys Pro Met Asp Glu Ser Ala Pro Gly Thr Leu Pro Pro Ser Pro
            195             200             205

Pro Lys Ser Ser Pro Glu Lys Lys Asn Ser Phe Ile Asp Ser Phe Arg
            210             215             220

Glu Lys Ser Pro Arg Met Ala Ala Leu Glu Ala Ser Gly Thr Thr Thr
225             230             235             240

Tyr Val Leu Val Pro Ser Pro Thr Val Gly Phe Phe Arg Arg Gly Arg
                245             250             255

Thr Val Lys Gly Lys Arg Gln Pro Pro Ile Cys Lys Glu Gly Asp Leu
            260             265             270

Val Lys Glu Gly Gln Ile Ile Gly Tyr Leu Asp Gln Phe Gly Thr Gly
            275             280             285

Leu Pro Val Lys Thr Asp Val Ala Gly Gln Val Leu Lys Leu Leu Val
            290             295             300

Asp Asp Gly Val Val Val Ala Gly Gly Arg Trp Gln Val Ala Glu
305             310             315             320

Ile Leu Val Ser Pro Leu Tyr Ser Arg His Val Leu Arg Val Asn Leu
                325             330             335

Thr Asn Leu Asp Ser
                340

<210> SEQ ID NO 175
<211> LENGTH: 199
<212> TYPE: PRT
<213> ORGANISM: Vigna angularis

<400> SEQUENCE: 175

Met Ala Ser Cys Ser Leu Gly Ser Pro Asn Ile Lys Val Leu Asn Leu
1               5               10              15

Tyr Phe Ser Gly Lys Asn Val Gly Leu Ser Lys Gln Val Gly Thr Arg
                20              25              30

Ser Trp Arg Arg Gln Ser Leu Gln Tyr Thr Gly Leu Val Met Ser Arg
            35              40              45

Gln Thr Asp Arg Leu Leu Ala Ser Ser Asn Asp Pro Ser Ser Glu Ile
            50              55              60

Gln Ile Ile Lys Arg Ser Glu Glu Gly Ser Glu Glu Ile Lys Ser Ser
65              70              75              80

Asp Leu Thr Ser Gln Leu Ile Pro Asn Phe Asn Glu Val Glu Phe Leu
                85              90              95

Val Thr Lys Leu Cys Asp Thr Ser Ser Ile Gly Glu Leu Glu Leu Lys
            100             105             110
```

-continued

```
Leu Ala Gly Phe His Leu Arg Val Val Arg Asp Leu Thr Lys Lys Ser
        115                 120                 125

Lys Thr Leu Pro Pro Pro Ile Pro Ala Ser Val Ser Val Asn Asn Val
        130                 135                 140

Ile Glu Thr Pro Lys Thr Asn Gly Ser Val Ser Thr Thr Ser Leu Ala
145                 150                 155                 160

Ile Ser Lys Pro Ile Ser Pro Val Glu Pro Ile Ser Ser Pro Gly Ser
                165                 170                 175

Ile Gln Lys Phe Leu Glu Arg Ala Ala Asp Glu Gly Leu Val Ile Ile
                180                 185                 190

Gln Ser Pro Lys Val Arg Ile
        195

<210> SEQ ID NO 176
<211> LENGTH: 292
<212> TYPE: PRT
<213> ORGANISM: Vigna radiata

<400> SEQUENCE: 176

Met Glu Ser Ser Ala Ala Ile Arg Ser Phe Asn Tyr Thr Met Gly Thr
1                   5                   10                  15

Met Ser His Met Arg Pro Ser Arg Asp Lys Gln Val Val Val Pro Ile
                20                  25                  30

His Asn Val Arg Trp Asn Ser Lys Ser Arg Leu Phe Ile Gln His Leu
                35                  40                  45

Ala Tyr Asp Arg Lys His Ile Asn Ser His Met Lys Gly Asn Asn Thr
        50                  55                  60

Leu Val Ser Cys Ala Lys Thr Ala Glu Pro Ile Asn Thr Ser Lys Ser
65                  70                  75                  80

Gly Asp Ala Ser Ser Asp Ser Thr Pro Gln Gly Ser Leu Glu Lys Lys
                85                  90                  95

Pro Leu Gln Ala Ala Thr Phe Pro Asn Gly Phe Glu Ala Leu Val Leu
                100                 105                 110

Glu Val Cys Asp Glu Thr Glu Ile Ala Glu Leu Lys Val Lys Val Gly
        115                 120                 125

Asp Phe Glu Met His Ile Lys Arg Asn Ile Gly Ala Thr Lys Val Pro
        130                 135                 140

Leu Ser Asn Ile Ser Pro Thr Thr Pro Pro Ile Pro Ser Lys Pro
145                 150                 155                 160

Met Asp Glu Ser Ala Pro Gly Thr Leu Pro Pro Ser Pro Lys Ser
                165                 170                 175

Ser Pro Glu Lys Lys Asn Ala Phe Ile Asp Ser Phe Arg Glu Lys Ser
                180                 185                 190

Pro Arg Met Ala Ala Leu Glu Ala Ser Gly Thr Thr Thr Tyr Val Leu
                195                 200                 205

Val Pro Ser Pro Thr Val Gly Phe Phe Arg Arg Gly Arg Thr Val Lys
        210                 215                 220

Gly Lys Arg Gln Pro Pro Ile Cys Lys Glu Gly Asp Leu Val Lys Glu
225                 230                 235                 240

Gly Gln Thr Ile Gly Tyr Leu Asp Gln Phe Gly Thr Gly Leu Pro Val
                245                 250                 255

Lys Thr Asp Val Ala Gly Gln Val Leu Lys Leu Leu Val Asp Asp Gly
                260                 265                 270

Glu Pro Val Gly Tyr Gly Asp Pro Leu Ile Ala Val Leu Pro Ser Phe
                275                 280                 285
```

His Asp Ile Lys
    290

<210> SEQ ID NO 177
<211> LENGTH: 278
<212> TYPE: PRT
<213> ORGANISM: Vigna radiata

<400> SEQUENCE: 177

Met Ala Ser Cys Ser Leu Gly Ser Pro Asn Ile Lys Val Leu Asn Leu
1               5                   10                  15

His Phe Ser Gly Lys Asn Val Gly Leu Ser Lys Gln Val Arg Thr Arg
            20                  25                  30

Ser Trp Arg Arg Gln Ser Leu Gln Tyr Thr Gly Leu Val Met Ser Arg
        35                  40                  45

Gln Ala Asp Arg Leu Leu Ala Ser Ser Asn Asp Pro Ser Ala Glu Ile
    50                  55                  60

Gln Ile Ile Lys Arg Ser Glu Glu Gly Ser Glu Glu Ile Lys Ser Ser
65                  70                  75                  80

Asp Leu Thr Ser Gln Leu Ile Pro Asn Phe Lys Glu Val Glu Phe Leu
                85                  90                  95

Val Thr Lys Leu Cys Asp Ser Ser Ser Ile Gly Glu Leu Glu Leu Lys
            100                 105                 110

Leu Ala Gly Phe His Leu His Val Val Arg Asp Leu Thr Lys Lys Asn
            115                 120                 125

Lys Thr Leu Pro Pro Pro Ile Pro Ala Ser Val Ser Val Asn Asn Val
    130                 135                 140

Ile Glu Thr Pro Lys Thr Asn Gly Ser Val Ser Thr Thr Ser Leu Ala
145                 150                 155                 160

Ile Ser Lys Pro Ile Ser Pro Val Glu Pro Ile Ser Ser Pro Gly Ser
                165                 170                 175

Ile Gln Lys Phe Leu Glu Arg Ala Ala Asp Glu Gly Leu Val Ile Ile
            180                 185                 190

Gln Ser Pro Lys Val Gly Phe Phe Arg Arg Ser Arg Thr Ile Lys Gly
            195                 200                 205

Lys Arg Ala Pro Pro Ser Cys Lys Glu Lys Gln Arg Val Glu Glu Gly
    210                 215                 220

Gln Val Ile Cys Tyr Ile Glu Gln Leu Gly Gly Gln Val Pro Ile Glu
225                 230                 235                 240

Ser Asp Val Ser Gly Glu Val Ile Lys Ile Leu Arg Lys Asp Gly Asp
                245                 250                 255

Pro Val Gly Tyr Gly Asp Ala Leu Val Ala Ile Leu Pro Ser Phe Pro
            260                 265                 270

Gly Ile Lys Lys Leu Gln
        275

<210> SEQ ID NO 178
<211> LENGTH: 288
<212> TYPE: PRT
<213> ORGANISM: Vitis vinifera

<400> SEQUENCE: 178

Met Glu Ser Val Ala Val Leu Arg Ser Val His Tyr Ser Val Gly Ala
1               5                   10                  15

Ile Ser Asn Val Arg Ser Phe Ile Glu Arg Pro Thr Met Val Pro Met
            20                  25                  30

-continued

```
Tyr Asn Ala Thr Trp Pro Thr Ser Asn Thr Leu His Val Gln Gly Leu
        35              40              45

Thr Val Gly Gly Lys Leu Ile Ser Ser Pro Ile Lys Gln Lys Gly Thr
    50              55              60

Leu Ile Ser Cys Val Lys Thr Pro Glu Thr Ala Gly Thr Ala Lys Cys
65              70              75              80

Asp Asp Gly Asn Pro Gln Gly Leu Leu Gln Lys Asp Thr Leu Pro Ser
            85              90              95

Ala Thr Phe Pro Asn Gly Phe Glu Ala Leu Ile Leu Glu Val Cys Asp
            100             105             110

Glu Thr Asp Val Ala Glu Leu Lys Leu Lys Val Gly Asp Phe Glu Met
            115             120             125

His Leu Arg Arg Asn Val Gly Val Thr Asn Pro Pro Met Pro Val Ile
        130             135             140

Ala Pro Thr Ala Pro Pro Thr Val Ser Ala Lys Pro Pro Val Glu Ser
145             150             155             160

Ala Pro Ala Ala Pro Pro Ser Leu Pro Pro Lys Pro Ser Gln Glu Lys
            165             170             175

Ile Ser Pro Phe Thr Lys Ser Leu Leu Glu Lys Pro Ser Lys Leu Arg
            180             185             190

Ala Leu Glu Ala Ser Gly Ala Asn Ala Tyr Val Leu Val Ser Ser Pro
            195             200             205

Thr Val Gly Ser Phe Arg Thr Gly Arg Thr Leu Lys Gly Lys Arg Gln
    210             215             220

Pro Pro Val Cys Lys Glu Gly Asp Val Ile Lys Glu Gly Gln Val Ile
225             230             235             240

Gly Tyr Leu Asp Gln Phe Gly Ser Glu Leu Pro Val Lys Ser Asp Thr
            245             250             255

Ala Gly Glu Val Leu Lys Val Ile Phe Asn Asp Gly Glu Ala Val Gly
            260             265             270

Tyr Gly Asp Pro Leu Val Ala Val Leu Pro Ser Phe His Gly Ile Glu
            275             280             285
```

```
<210> SEQ ID NO 179
<211> LENGTH: 274
<212> TYPE: PRT
<213> ORGANISM: Vitis vinifera

<400> SEQUENCE: 179
```

```
Met Ala Ser Cys Gly Leu Gly Ala Pro Ser Ile Lys Ile Ser Asn Leu
1               5               10              15

Asp Leu Val Arg Thr Arg Leu Gly Val Leu Gln Ser Arg Phe Ser Ile
            20              25              30

Arg Thr Ser Thr Ala Trp Thr Pro Leu Asn Asn Ser Gly Leu Val Ile
        35              40              45

Ser Gln Arg Ser Gln Lys Ala Ile Ile Leu Cys Arg Gly Ser Ser Ser
    50              55              60

Glu Ala Glu Ser Ala Val Asn Leu Glu Asp Gly Ser Glu Glu Thr Lys
65              70              75              80

Ser Ser Gly Leu Thr Ser Gln Leu Thr Pro Asn Ala Tyr Glu Val Glu
            85              90              95

Ser Leu Leu Ser Glu Ile Cys Asp Thr Thr Ser Ile Ala Glu Phe Glu
            100             105             110

Leu Lys Leu Gly Gly Phe Arg Leu Tyr Met Met Arg Asp Leu Ala Gly
```

```
                   115                 120                 125
Lys Ile Glu Pro Thr Pro Pro Pro Ser Ser Thr Pro Val Thr Val Ser
    130                 135                 140
Leu Asn Asp Glu Ala Pro Lys Leu Asn Gly Ser Ala Ser Met Ser Ser
145                 150                 155                 160
Leu Pro Ile Ser Lys Ser Ala Leu Leu Leu Gly Gln Ser Gln Thr Leu
                165                 170                 175
Leu Asp Arg Ala Ala Asp Glu Gly Leu Met Ile Leu Gln Ser Pro Lys
                180                 185                 190
Val Gly Phe Phe Arg Arg Ser Arg Thr Ile Lys Gly Lys Arg Ala Pro
                195                 200                 205
Pro Ser Cys Lys Glu Lys Gln Ile Val Lys Glu Gly Gln Val Leu Cys
    210                 215                 220
Tyr Ile Glu Gln Leu Gly Gly Glu Ile Pro Ile Glu Ser Asp Val Ser
225                 230                 235                 240
Gly Glu Val Ile Lys Ile Leu Arg Glu Asp Gly Glu Pro Val Gly Tyr
                245                 250                 255
Gly Asp Ala Leu Ile Ala Ile Leu Pro Ser Phe Pro Gly Ile Lys Lys
                260                 265                 270
Leu Gln

<210> SEQ ID NO 180
<211> LENGTH: 292
<212> TYPE: PRT
<213> ORGANISM: Ziziphus jujuba

<400> SEQUENCE: 180

Met Glu Ser Pro Ala Val Leu Arg Ser Phe Pro Cys Ser Ala Gly Ala
1               5                   10                  15
Val Ser Asn Ala Arg Ser Leu Leu Val Lys Ser Gly Val Val Pro Met
                20                  25                  30
His Asn Ala Cys Gly Pro Thr Pro Ser Gly Ser Cys Ile Gln Ser Ser
            35                  40                  45
Thr Val Ser Lys Lys Leu Ile Tyr Ser Pro Lys Met Gln Lys Thr Met
    50                  55                  60
Leu Ile Ser Cys Val Lys Thr Ser Glu Ala Lys Glu Thr Ser Lys Ser
65                  70                  75                  80
Asn Val Ser Ser Asp Ser Ile Pro Gln Gly Ser Leu Glu Lys Thr Pro
                85                  90                  95
Arg Ser Ala Thr Phe Pro Asn Gly Phe Glu Ala Leu Met Leu Glu Val
                100                 105                 110
Cys Asp Glu Thr Glu Ile Ala Glu Leu Lys Leu Lys Val Gly Asp Phe
            115                 120                 125
Glu Met His Leu Lys Arg Asn Val Gly Ala Thr Thr Thr Pro Leu Ser
    130                 135                 140
Ser Ile Ser Pro Thr Thr Pro Pro Ile Pro Ser Lys Pro Met Val
145                 150                 155                 160
Glu Ser Thr Pro Ala Ala Pro Pro Ser Pro Lys Ser Ser Ser
                165                 170                 175
Glu Lys Thr Ser Pro Phe Lys Asn Val Ala Ser Gln Lys Ile Ser Lys
                180                 185                 190
Leu Ala Ala Leu Glu Ala Ser Gly Thr Ser Gly Tyr Ile Leu Val Ser
                195                 200                 205
Ser Pro Thr Val Gly Lys Phe Gln Arg Gly Arg Thr Val Lys Glu Lys
```

-continued

```
            210                 215                 220
Arg Gln Pro Pro Ile Cys Lys Glu Gly Asp Val Ile Lys Glu Gly Gln
225                 230                 235                 240

Val Ile Gly Tyr Val Glu Gln Phe Gly Thr Glu Leu Pro Val Lys Ser
                245                 250                 255

Asp Val Gly Gly Glu Val Phe Lys Ile Leu Phe Asn Asp Glu Glu Ala
                260                 265                 270

Val Gly Tyr Gly Asp Pro Leu Val Ala Ile Leu Pro Ser Phe His Gly
                275                 280                 285

Ile Asn Ile Lys
            290
```

<210> SEQ ID NO 181
<211> LENGTH: 272
<212> TYPE: PRT
<213> ORGANISM: Ziziphus jujuba

<400> SEQUENCE: 181

```
Met Ala Ala Cys Asn Leu Gly Thr Leu Asn Ile Lys Ile Ser Asn Leu
1               5                   10                  15

Asn Phe Gly Arg Arg Ala Gly Ser Leu Gln Phe Tyr Asn Leu Arg
                20                  25                  30

Thr Ser Ala Gly Gln Arg Pro Leu Gln Tyr Ala Gly Cys Ile Ile Ser
            35                  40                  45

Arg Ser Ser Lys Arg Leu Leu Ser Val Cys Arg Gly Ser Ser Leu Glu
            50                  55                  60

Thr Leu Ser Ala Thr Thr Leu Glu Asp Ser Ser Glu Glu Asn Lys Tyr
65                  70                  75                  80

Ser Gly Ser Arg Ser Gln Leu Ile Pro Asn Phe Asp Glu Val Glu Ser
                85                  90                  95

Leu Leu Thr Lys Ile Cys Asp Thr Thr Ser Ile Ala Glu Phe Glu Leu
                100                 105                 110

Lys Leu Gly Gly Phe Arg Leu His Leu Leu Arg Asp Leu Thr Gly Lys
            115                 120                 125

Ile Ser Thr Ala Ser Ile Pro Ser Pro Val Pro Val Ser Ala Ser Thr
            130                 135                 140

Thr Ala Glu Glu Pro Ala Ser Asn Gly Ser Val Ser Ser Glu Ser Leu
145                 150                 155                 160

Ala Ile Met Lys Pro Pro Thr Ser Ser Arg Asp Ile Gln Thr Met Leu
                165                 170                 175

Asp Asn Pro Ala Asp Glu Gly Leu Val Ile Ile Arg Ser Pro Arg Val
                180                 185                 190

Gly Phe Phe Arg Arg Ser Arg Thr Ile Lys Gly Lys Arg Ala Pro Pro
            195                 200                 205

Pro Cys Gln Glu Lys Gln Val Val Glu Glu Gly Lys Val Ile Cys Phe
            210                 215                 220

Val Glu Gln Leu Gly Gly Glu Leu Pro Ile Glu Ser Asp Val Thr Gly
225                 230                 235                 240

Glu Val Ile Lys Ile Leu Val Glu Asp Gly Asp Pro Val Gly Tyr Asn
                245                 250                 255

Asp Ala Leu Ile Ala Ile Leu Pro Ser Phe Pro Gly Ile Lys Leu Gln
                260                 265                 270
```

<210> SEQ ID NO 182
<211> LENGTH: 227

<212> TYPE: PRT
<213> ORGANISM: Zostera marina

<400> SEQUENCE: 182

Met Asn Leu Asn His Ser Leu Thr Ile Phe Ser Lys Val Ser Val Ile
1               5                   10                  15

Ser Ala Thr Ser Ser Gly Asn Ala Ser Thr Gln Leu Ile Lys Pro Ala
            20                  25                  30

Phe Gln Ser Thr Lys Phe Pro Asp Glu Phe Glu Lys Leu Val Leu Asp
        35                  40                  45

Val Cys Asp Gly Thr Asp Val Ala Glu Val Lys Val Lys Val Gly Lys
    50                  55                  60

Phe Glu Met Asn Leu Lys Arg Ser Val Gly Ala Pro Lys Val Ala Ala
65              70                  75                  80

Pro Ile Ile Ser Pro Met Ile Ala Pro Pro Ile Pro Thr Glu Pro Met
                85                  90                  95

Gly Glu Ser Ala Leu Glu Ser Pro Ile Thr Gln Lys Ser Leu Pro Thr
            100                 105                 110

Val Thr Asn Asn Gln Leu Lys Asn Phe Ser Thr Val Lys Asp Leu Lys
        115                 120                 125

Leu Ala Thr Leu Glu Ala Ser Gly Glu Lys Ser Tyr Val Tyr Val Pro
    130                 135                 140

Ser Pro Thr Val Gly Ser Phe Arg His Gly Arg Thr Val Asn Gly Lys
145             150                 155                 160

Lys Lys Pro Gln Asn Phe Lys Val Gly Asp Leu Ile Lys Glu Gly His
                165                 170                 175

Ile Val Gly Tyr Leu Asp Gln Phe Gly Lys Glu Leu Pro Val Arg Ser
            180                 185                 190

Asp Val Ala Gly Glu Val Val Lys Phe Leu Tyr Gly Asp Gly Glu Ala
            195                 200                 205

Val Gly Phe Gly Asp Pro Leu Ile Ala Val Leu Pro Ser Phe Lys Gly
    210                 215                 220

Ile Asn Lys
225

<210> SEQ ID NO 183
<211> LENGTH: 294
<212> TYPE: PRT
<213> ORGANISM: Zostera marina

<400> SEQUENCE: 183

Met Ala Ser Tyr Gly Leu Gly Ala Val Leu Asn Gly Lys Leu Leu Ala
1               5                   10                  15

Thr Tyr Pro Glu Gly Asn Met Asn Asn His Gly Arg Met Gln Ile Leu
            20                  25                  30

Asn Arg His Gly Cys Gly Lys Gln Glu Ala Thr His Gly Ser Ser Leu
        35                  40                  45

Ile Phe Phe Gly Lys Lys Pro Ala Asn Phe Ser Cys Phe Leu Arg Gln
    50                  55                  60

Glu Pro Trp Arg His His Asn Arg Phe Ser Val Ile Asn Cys Ser Asn
65              70                  75                  80

Ser Gln Ile Met Ala Gln Pro Lys Asp Val Glu Leu Lys Lys Ser Ile
                85                  90                  95

Gly Glu Thr Ser Gln Leu Ile Pro Ser Ser Gln Val Glu Ser Leu Val
            100                 105                 110

```
Thr Glu Ile Cys Asp Thr Ser Ile Val Glu Phe Lys Leu Asn Leu Gly
        115                 120                 125

Gly Phe Gln Leu His Val Lys Arg Asp Val Asp Gly Asn Asp Ser Glu
        130                 135                 140

Thr Pro Pro Pro Ala Ala Phe Leu Pro Phe His Ala Gly Phe Ser Asn
145                 150                 155                 160

Gly Ile Pro His Gln Asn Gly Ser Ala Ser Ser Ser Leu Ala Ile
                165                 170                 175

Val Lys Gln Asp Ser Ser Ser Ser Gly Glu Ile Gln His Ala Ile Asp
                180                 185                 190

Ala Asn Ser Asp Glu Gly Leu Phe Met Leu Pro Ser Pro Thr Val Gly
        195                 200                 205

Leu Phe Arg Arg Cys Arg Thr Ile Lys Gly Lys Lys Thr Pro Pro Ser
        210                 215                 220

Cys Asn Glu Lys Gln Gln Val Asn Glu Gly Gln Val Leu Cys Cys Ile
225                 230                 235                 240

Glu Gln Leu Gly Thr Glu Thr Pro Ile Glu Ser Asp Val Thr Gly Glu
                245                 250                 255

Ile Val Lys Ile Leu Arg Tyr Asp Gly Glu Pro Val Gly Tyr Gly Asp
                260                 265                 270

Ser Leu Ile Ser Ile Leu Pro Ser Phe Pro Gly Ile Lys Lys Leu Gln
        275                 280                 285

Leu Pro Glu Ser Asp Tyr
    290

<210> SEQ ID NO 184
<211> LENGTH: 44
<212> TYPE: PRT
<213> ORGANISM: Artificial Sequence
<220> FEATURE:
<223> OTHER INFORMATION: Synthetic construct BADC consensus sequence
<220> FEATURE:
<221> NAME/KEY: MISC_FEATURE
<222> LOCATION: (3)..(3)
<223> OTHER INFORMATION: X = S or T or L or F or K or Y or I or V or L
<220> FEATURE:
<221> NAME/KEY: MISC_FEATURE
<222> LOCATION: (4)..(4)
<223> OTHER INFORMATION: X = F or I or L
<220> FEATURE:
<221> NAME/KEY: MISC_FEATURE
<222> LOCATION: (5)..(5)
<223> OTHER INFORMATION: X = R or Q or K
<220> FEATURE:
<221> NAME/KEY: MISC_FEATURE
<222> LOCATION: (6)..(6)
<223> OTHER INFORMATION: X = R or S or K or T or I or L or Y
<220> FEATURE:
<221> NAME/KEY: MISC_FEATURE
<222> LOCATION: (7)..(7)
<223> OTHER INFORMATION: X = N or G or A or S or C
<220> FEATURE:
<221> NAME/KEY: MISC_FEATURE
<222> LOCATION: (8)..(8)
<223> OTHER INFORMATION: X = R or I or K or T
<220> FEATURE:
<221> NAME/KEY: MISC_FEATURE
<222> LOCATION: (9)..(9)
<223> OTHER INFORMATION: X = T or K or S or V or Y or L or F
<220> FEATURE:
<221> NAME/KEY: MISC_FEATURE
<222> LOCATION: (10)..(10)
<223> OTHER INFORMATION: X = V or L or I or A or M
<220> FEATURE:
<221> NAME/KEY: MISC_FEATURE
<222> LOCATION: (13)..(13)
<223> OTHER INFORMATION: X = K or R or N or E
```

-continued

```
<220> FEATURE:
<221> NAME/KEY: MISC_FEATURE
<222> LOCATION: (14)..(14)
<223> OTHER INFORMATION: X = K or R or N or Q or C or S or F
<220> FEATURE:
<221> NAME/KEY: MISC_FEATURE
<222> LOCATION: (15)..(15)
<223> OTHER INFORMATION: X = Q or M or L or G or A or T
<220> FEATURE:
<221> NAME/KEY: MISC_FEATURE
<222> LOCATION: (16)..(16)
<223> OTHER INFORMATION: X = P or R or E or A or G or N or S
<220> FEATURE:
<221> NAME/KEY: MISC_FEATURE
<222> LOCATION: (17)..(17)
<223> OTHER INFORMATION: X = P or L or R or A or N or T or S
<220> FEATURE:
<221> NAME/KEY: MISC_FEATURE
<222> LOCATION: (18)..(18)
<223> OTHER INFORMATION: X = I or S or T or L or V or C
<220> FEATURE:
<221> NAME/KEY: MISC_FEATURE
<222> LOCATION: (19)..(19)
<223> OTHER INFORMATION: X = C or F or A or V or I
<220> FEATURE:
<221> NAME/KEY: MISC_FEATURE
<222> LOCATION: (20)..(20)
<223> OTHER INFORMATION: X = K or N or E or A or D or Q
<220> FEATURE:
<221> NAME/KEY: MISC_FEATURE
<222> LOCATION: (21)..(21)
<223> OTHER INFORMATION: X = E or V or K or D
<220> FEATURE:
<221> NAME/KEY: MISC_FEATURE
<222> LOCATION: (22)..(22)
<223> OTHER INFORMATION: X = G or N or K or R or D or M or T
<220> FEATURE:
<221> NAME/KEY: MISC_FEATURE
<222> LOCATION: (23)..(23)
<223> OTHER INFORMATION: X = D or Q or A
<220> FEATURE:
<221> NAME/KEY: MISC_FEATURE
<222> LOCATION: (24)..(24)
<223> OTHER INFORMATION: X = V or L or F or A or I or M or S or T or E
     or D or R or P or Q or K or N
<220> FEATURE:
<221> NAME/KEY: MISC_FEATURE
<222> LOCATION: (25)..(25)
<223> OTHER INFORMATION: X = I or V or G or L
<220> FEATURE:
<221> NAME/KEY: MISC_FEATURE
<222> LOCATION: (26)..(26)
<223> OTHER INFORMATION: X = K or R or Q or E
<220> FEATURE:
<221> NAME/KEY: MISC_FEATURE
<222> LOCATION: (27)..(27)
<223> OTHER INFORMATION: Xaa can be any naturally occurring amino acid
<220> FEATURE:
<221> NAME/KEY: MISC_FEATURE
<222> LOCATION: (30)..(30)
<223> OTHER INFORMATION: X = T or V or I
<220> FEATURE:
<221> NAME/KEY: MISC_FEATURE
<222> LOCATION: (31)..(31)
<223> OTHER INFORMATION: X = I or V or L
<220> FEATURE:
<221> NAME/KEY: MISC_FEATURE
<222> LOCATION: (32)..(32)
<223> OTHER INFORMATION: X = G or A or C or F
<220> FEATURE:
<221> NAME/KEY: MISC_FEATURE
<222> LOCATION: (33)..(33)
<223> OTHER INFORMATION: X = Y or F or W or C
<220> FEATURE:
<221> NAME/KEY: MISC_FEATURE
<222> LOCATION: (34)..(34)
<223> OTHER INFORMATION: X = L or V or I
<220> FEATURE:
<221> NAME/KEY: MISC_FEATURE
```

-continued

```
<222> LOCATION: (35)..(35)
<223> OTHER INFORMATION: X = D or N or H or E
<220> FEATURE:
<221> NAME/KEY: MISC_FEATURE
<222> LOCATION: (37)..(37)
<223> OTHER INFORMATION: X = F or L or I
<220> FEATURE:
<221> NAME/KEY: MISC_FEATURE
<222> LOCATION: (39)..(39)
<223> OTHER INFORMATION: X = G or T or S or K or N or A or V
<220> FEATURE:
<221> NAME/KEY: MISC_FEATURE
<222> LOCATION: (40)..(40)
<223> OTHER INFORMATION: X = E or Q or G or S or H or Y or F or V
<220> FEATURE:
<221> NAME/KEY: MISC_FEATURE
<222> LOCATION: (41)..(41)
<223> OTHER INFORMATION: X = L or N or T or V or I or M or W or Q or F
<220> FEATURE:
<221> NAME/KEY: MISC_FEATURE
<222> LOCATION: (43)..(43)
<223> OTHER INFORMATION: X = V or I or M or L
<220> FEATURE:
<221> NAME/KEY: MISC_FEATURE
<222> LOCATION: (44)..(44)
<223> OTHER INFORMATION: X = E or K or R or M or T or N

<400> SEQUENCE: 184

Val Gly Xaa Xaa Xaa Xaa Xaa Xaa Xaa Xaa Lys Gly Xaa Xaa Xaa Xaa
1               5                   10                  15

Xaa Xaa Xaa Xaa Xaa Xaa Xaa Xaa Xaa Xaa Xaa Gly Gln Xaa Xaa Xaa
            20                  25                  30

Xaa Xaa Xaa Gln Xaa Gly Xaa Xaa Xaa Pro Xaa Xaa
        35                  40
```

GENETICALLY MODIFIED PLANTS THAT EXHIBIT AN INCREASE IN SEED YIELD COMPRISING A FIRST BIOTIN ATTACHMENT DOMAIN-CONTAINING (badc) GENE HOMOZYGOUS FOR A WILD-TYPE ALLELE, A SECOND badc GENE HOMOZYGOUS FOR A MUTANT ALLELE, AND HOMOLOGS OF THE FIRST AND SECOND badc GENES

STATEMENT OF GOVERNMENT SPONSORED RESEARCH

This invention was made with government support under Contract No. DE-EE0007003 awarded by the United States Department of Energy. The government has certain rights in the invention.

FIELD OF THE INVENTION

The present invention relates generally to genetically modified plants that exhibit an increase in seed yield relative to a progenitor plant from which the genetically modified plants were derived, and more particularly to such genetically modified plants comprising: (a) a first biotin attachment domain-containing (badc) gene, occurring in its natural position within the genome of the genetically modified plant and being homozygous for a wild-type allele; (b) a second badc gene, occurring in its natural position within the genome of the genetically modified plant and being homozygous for a mutant allele; (c) one or more homologs of the first badc gene, each of the one or more homologs of the first badc gene occurring in its natural position within the genome of the genetically modified plant and being homozygous for a wild-type allele; and (d) one or more homologs of the second badc gene, each of the one or more homologs of the second bade gene occurring in its natural position within the genome of the genetically modified plant, and at least one of the homologs of the second badc gene being homozygous for a wild-type allele.

BACKGROUND OF THE INVENTION

Vegetable oils are an important renewable source of hydrocarbons for food, energy, and industrial feedstocks. As demand for this commodity increases, discovering ways to increase vegetable oil production in an oilseed crop will be an agronomic priority. With the increasing global population and the added infrastructure impact on arable land available for crop production it will be critical to increase the amount of harvestable vegetable oil from each acre of land. Vegetable oil per acre of land is determined by the yield of oilseed per acre multiplied by the oil content (usually stated as a percentage of dry seed weight). Increasing vegetable oil per acre can be accomplished in a number of ways: (1) developing new oilseed varieties which produce higher seed yield without reducing the seed oil content; (2) developing new oilseed varieties that have higher seed oil content without reducing seed yield; or (3) developing new oilseed varieties that have higher seed oil content and higher seed yield. The net impact of any of these three solutions will be to increase vegetable oil production per harvestable acre of land.

The production of oil in plants is a dynamic process involving multiple metabolic pathways including the fatty acid biosynthesis pathway, triacylglycerol (also termed "TAG") biosynthesis, and TAG degradation, and complex gene regulation systems. During the production of oil in an oilseed, the rate of fatty acid and TAG biosynthesis is high and the rate of TAG degradation is low, resulting in a net accumulation of oil. TAG degradation is an essential process for seed germination.

Genes involved in production of oil in plants include, among others, the following: (i) SUGAR-DEPENDENT1 (also termed "SDP1" or "sdp1") and SUGAR-DEPENDENT1-LIKE (also termed "SDP1-L," "sdp1-L," "SDP1-Like" or "sdp1-like") genes, which encode oil body-associated triacylglycerol lipases (Eastmond, 2006, Plant Cell, 18, 665); (ii) TRANSPARENT TESTA2 (also termed "TT2" or "tt2") genes, which encode a transcription factor that coordinates gene expression for fatty acid biosynthesis in the embryo and proanthocyanidins in the seed coat (Chen et al., Plant Physiology, 2012, 160, 1023); and (iii) Biotin/lipoyl Attachment Domain-Containing (also termed "BADC" or "badc") genes, which encode proteins that interact with the two biotin carboxyl carrier protein (also termed "BCCP") isoforms of acetyl-coA carboxylase (PCT/US2016/041386 to the University of Missouri; Salie et al., 2016, The Plant Cell, 28, 2312; Keereetaweep et al., 2018, Plant Physiology, 177, 208), which catalyzes the first committed step in fatty acid biosynthesis.

BADC proteins are understood to play a role in production of oil in plants based on biochemical and genetic analyses in *Arabidopsis thaliana* (PCT/US2016/041386; Salie et al., 2016). Salie et al. (2016) determined that *Arabidopsis* expresses three isoforms of BADC protein, designated BADC1, BADC2, and BADC3, each encoded by a separate gene, designated badc1, badc2, and badc3, respectively. The *Arabidopsis* BADC1, BADC2, and BADC3 proteins were annotated as "biotin/lipoyl attachment domain-containing protein," "biotin carboxyl carrier protein of acetyl CoA carboxylase," or "acetyl-CoA carboxylase biotin carboxyl carrier protein subunit," respectively, based on bioinformatic analysis prior to functional characterization (Accessions NP_567035.1, NP_564612.1, and NP_188190.1). As determined by Salie et al. (2016), BADC proteins resemble BCCP subunits but are not biotinylated due to mutation of a biotinylation motif. BADC proteins were shown to significantly inhibit acetyl-CoA carboxylase in both *Escherichia coli* and *Arabidopsis thaliana*. Targeted gene silencing of BADC1 in *Arabidopsis thaliana* significantly increased oil content when normalized to either mass or individual seed. Based on these observations, Salie et al. (2016) concluded that BADC proteins are ancestral BCCPs that gained a new function as negative regulators of acetyl-CoA carboxylase after initial loss of a biotinylation motif.

The precise role that BADC proteins play in the production of oil in plants remains to be determined, though.

One model for the function of BADC proteins is that they are inactive analogs of biotin carboxyl transfer proteins that lack biotin, and that their incorporation into acetyl-CoA carboxylase down-regulates activity of the acetyl-CoA carboxylase by displacing active biotin carboxyltransferase protein subunits (Keereetaweep et al., 2018). *Arabidopsis* plants homozygous for mutations in badc1, badc2, badc3, badc1 badc2, or badc1 badc3 exhibited growth and development similar to wild-type plants. The badc1 and badc2 mutants showed no significant differences in dry seed weight relative to wild-type. The badc3 mutant showed a small significant increase in dry seed weight (2.46 mg per 100 seeds compared to 2.32 mg per 100 seeds for wild-type). In contrast, the badc1 badc2 and badc1 badc3 mutants showed small significant decreases in dry seed weight. *Arabidopsis* plants homozygous for badc2 badc3, and thus only including BADC1 protein, are apparently embryonic lethal.

An alternative model for the function of BADC proteins is that they facilitate the assembly and activation of subcomplexes of BCCP, BADC, and biotin carboxylase (also termed "BC"), catalyzing bicarbonate-dependent hydrolysis of ATP, which is the first half-reaction catalyzed by acetyl-CoA carboxylase (Shivaiah et al., 2020, Plant Physiology, 182, 756). According to Shivaiah et al. (2020), although each of *Arabidopsis* BADC1, BADC2, and BADC3 can facilitate this assembly and activation, BADC2 and BADC3 appear to support catalytic activation of acetyl-CoA carboxylase to a greater extent than BADC1. Also according to Shivaiah et al. (2020), the three *Arabidopsis* BADC genes share considerable functional redundancy, and plants missing any single isoform grow normally, implying that expression of the remaining two isoforms is sufficient for growth and viability. Yet the functional redundancy is not symmetrical, as BADC2 appears to be able to replace almost all BADC3 function, but not vice versa, and plants expressing BADC1 alone are not viable through seed development.

Shivaiah et al. (2020) argues that the model of BADC as an inhibitor of acetyl-CoA carboxylase is incorrect. According to Shivaiah et al. (2020), the apparent inhibition of plant acetyl-CoA carboxylase by BADC1 in vitro may reflect replacement of more-competent BADC2 and BADC3 in complexes of acetyl-CoA carboxylase with less-competent BADC1. Shivaiah does not appear to offer an explanation for why or how BADC1 also inhibited acetyl-CoA carboxylase of *Escherichia coli*, though.

In co-pending Patent Application PCT/US2020/043063, to Yield10 Bioscience, full-length single gene homologs for SDP1, SDP1-like, TT2, and BADC proteins in *Camelina sativa*, canola, and soybean were identified as targets for reducing their expression or activity using genome editing as a means to increase oil content while minimizing the reduction in seed yield seen by most researchers using other approaches. These oilseed crops have more complex genomes than the diploid genome of *Arabidopsis*, with multiple homeologs of each gene. Thus, for example, *Camelina*, an allohexaploid, has three homeologs of SDP1 genes, each present in two copies. Using genome editing with the CRISPR/Cas9 system to knockout two copies of the three different SDP1 genes (six total copies) in *Camelina* proved very difficult, and typically only the two copies of a single homeolog of SDP1 could be inactivated. When stable homozygous plants with single homeolog knockouts of SDP1 were analyzed for seed yield and oil content, it was determined that the oil content of the seed was not negatively affected, however quite surprisingly the edited lines had a significantly higher seed yield contrary to all previous reports.

There remains a need to develop plants in which the TAG production rates are increased and TAG degradation rates during seed production are decreased without substantially impairing overall seed yield and preferably increasing overall seed yield.

BRIEF SUMMARY OF THE INVENTION

A genetically modified plant that exhibits an increase in seed yield relative to a progenitor plant from which the genetically modified plant was derived is provided. The genetically modified plant comprises: (a) a first biotin attachment domain-containing (badc) gene, occurring in its natural position within the genome of the genetically modified plant and being homozygous for a wild-type allele; (b)

a second badc gene, occurring in its natural position within the genome of the genetically modified plant and being homozygous for a mutant allele; (c) one or more homologs of the first badc gene, each of the one or more homologs of the first badc gene occurring in its natural position within the genome of the genetically modified plant and being homozygous for a wild-type allele; and (d) one or more homologs of the second badc gene, each of the one or more homologs of the second badc gene occurring in its natural position within the genome of the genetically modified plant, and at least one of the homologs of the second badc gene being homozygous for a wild-type allele. The wild-type alleles of the first badc gene, each of the one or more homologs of the first badc gene, and the at least one of the homologs of the second badc gene are identical to respective alleles of the first badc gene, each of the one or more homologs of the first badc gene, and the at least one of the homologs of the second badc gene from the progenitor plant. The mutant allele of the second badc gene does not encode a functional BADC protein and includes one or more additions, deletions, or substitutions of one or more nucleotides relative to an allele of the second badc gene from the progenitor plant. The increase in seed yield is at least 4%.

In some embodiments, the wild-type alleles of the first badc gene, each of the one or more homologs of the first badc gene, and the at least one of the homologs of the second badc gene each encode a functional BADC protein.

In some embodiments, the genetically modified plant comprises the one or more homologs of the first badc gene and the one or more homologs of the second badc gene based on one or more of polyploidy, alloploidy, autoploidy, diploidization following polyploidy, diploidization following alloploidy, or diploidization following autoploidy.

In some embodiments, the genetically modified plant is allotetraploid, allohexaploid, or allooctoploid.

In some embodiments, the genetically modified plant is homozygous for the wild-type allele of the first badc gene based on including two identical copies of a wild-type allele.

In some embodiments, the genetically modified plant is homozygous for the wild-type allele of the first badc gene based on including a first wild-type allele and a second wild-type allele that are not identical to each other.

In some embodiments, the genetically modified plant is homozygous for the mutant allele of the second badc gene based on including two copies of the mutant allele of the second badc gene that are identical.

In some embodiments, the genetically modified plant is homozygous for the mutant allele of the second badc gene based on including a first mutant allele and a second mutant allele that are not identical to each other.

In some embodiments, the one or more additions, deletions, or substitutions of one or more nucleotides comprise one or more of a frameshift mutation, an active site mutation, a nonconservative substitution mutation, or an open-reading-frame deletion mutation in the mutant allele of the second badc gene relative to the allele of the second badc gene from the progenitor plant.

In some embodiments, the first badc gene and the one or more homologs of the first badc gene encode orthologs of BADC1 of *Arabidopsis thaliana*.

In some embodiments, the second badc gene and the one or more homologs of the second badc gene encode orthologs of BADC2 of *Arabidopsis thaliana*.

In some embodiments, the second badc gene and the one or more homologs of the second badc gene encode orthologs of BADC3 of *Arabidopsis thaliana*.

In some embodiments, the increase in seed yield is at least 5%, 6%, 7%, 8%, 9%, 10%, 15%, 20%, 25%, 30%, 35%, 40%, 45%, 50%, or more.

In some embodiments, the genetically modified plant further comprises a third badc gene and one or more homologs of the third badc gene occurring in their respective natural positions within the genome of the genetically modified plant. In some of these embodiments, the third badc gene is homozygous for a wild-type allele. Also in some of these embodiments, the third badc gene is homozygous for a mutant allele. Also in some of these embodiments, the third badc gene is heterozygous for a wild-type allele and a mutant allele. Also in some embodiments, (i) if the second badc gene and the one more homologs of the second badc gene encode orthologs of BADC2 of *Arabidopsis thaliana*, then the third bade gene and the one or more homologs of the third badc gene encode orthologs of BADC3 of *Arabidopsis thaliana*, or (ii) if the second badc gene and the one more homologs of the second bade gene encode orthologs of BADC3 of *Arabidopsis thaliana*, then the third badc gene and the one more homologs of the third bade gene encode orthologs of BADC2 of *Arabidopsis thaliana*.

In some embodiments, the genetically modified plant further comprises one or more SUGAR-DEPENDENT1 (SDP1) genes, each of the SDP1 genes being homozygous for a wild-type allele.

In some embodiments, the genetically modified plant is one or more of a *Camelina* species, *Camelina sativa*, a *Brassica* species, *Brassica napus*, *Brassica rapa*, *Brassica carinata*, *Brassica juncea*, or soybean.

In some embodiments, the genetically modified plant is *Camelina sativa*. In some of these embodiments, the first badc gene and the one or more homologs of the first bade gene comprise *Camelina sativa* badc1-1, badc1-2, and badc1-3. Also in some of these embodiments, the second badc gene comprises one or more of *Camelina sativa* badc2-2 or badc2-3, and the at least one of the homologs of the second badc gene comprises *Camelina sativa* badc2-1. Also in some of these embodiments, the mutant allele includes at least one of the additions, deletions, or substitutions within the first 89 codons of the second badc gene. Also in some of these embodiments, both *Camelina sativa* badc2-2 and badc2-3 are homozygous for mutant alleles. Also in some of these embodiments, the second badc gene comprises one or more of *Camelina sativa* badc3-1 or badc3-3, and the at least one of the homologs of the second badc gene comprises *Camelina sativa* badc3-2. Also in some of these embodiments, the mutant allele includes at least one of the additions, deletions, or substitutions within the first 125 codons of the second badc gene. Also in some of these embodiments, both *Camelina sativa* badc3-1 and badc3-3 are homozygous for mutant alleles.

In some embodiments, the genetically modified plant is *Brassica napus*. In some of these embodiments, the first badc gene and the one or more homologs of the first badc gene comprise *Brassica napus* badc1-1 (previously termed badc1, as discussed below) and badc1-2 (previously termed badc2). Also in some of these embodiments, the second badc gene comprises one or more of *Brassica napus* badc3-1 (previously termed badc3), badc3-2 (previously termed badc4), badc3-3 (previously termed badc5), or badc3-4 (previously termed badc6). Also in some of these embodiments, the second bade gene comprises *Brassica napus* badc3-2. Also in some of these embodiments, the mutant allele includes at least one of the additions, deletions, or substitutions within the first 111 codons of the second badc gene. Also in some of these embodiments, both *Brassica napus* badc3-2 and badc3-3 are homozygous for mutant alleles.

In some embodiments, the genetically modified plant further exhibits an increase in seed oil content relative to the progenitor plant. In some of these embodiments, the increase in seed oil content is at least 3%, 4%, 5%, 6%, 7%, 8%, 9%, 10%, or more.

In some embodiments, the genetically modified plant further exhibits an increase in oil per plant relative to the progenitor plant. In some of these embodiments, the increase in oil per plant is at least 5%, 6%, 7%, 8%, 9%, 10%, 15%, 20%, 25%, 30%, 35%, 40%, 45%, 50%, or more.

Also provided is a method for producing the genetically modified plant that exhibits an increase in seed yield relative to a progenitor plant from which the genetically modified plant was derived. In accordance with this method, the progenitor plant comprises a first badc gene, a second badc gene, one or more homologs of the first badc gene, and one or more homologs of the second badc gene, each of the first badc gene, the second badc gene, the one or more homologs of the first badc gene, and the one or more homologs of the second bade gene being homozygous for a wild-type allele. The method comprises steps of: (1) mutating the second badc gene in cells of the progenitor plant by making one or more additions, deletions, or substitutions of one more nucleotides relative to the wild-type allele of the second badc gene that eliminate function of the BADC protein encoded by the second badc gene that is mutated, thereby obtaining a mutated plant; (2) conducting one more cycles of breeding of the mutated plant to obtain progeny of the mutated plant; (3) identifying plants of the progeny in which the second badc gene is homozygous for the mutant allele, thereby obtaining second-badc-gene homozygous mutant plants; and (4) screening the second-badc-gene homozygous mutant plants for one or more plants that have an increase in seed yield of at least 4% relative to the progenitor plant, thereby obtaining the genetically modified plant.

In some embodiments, the step of mutating the second badc gene includes introducing the one or more additions, deletions, or substitutions by genome editing. In some of these embodiments, the genome editing comprises transforming the cells of the progenitor plant with a plasmid that encodes (i) a single guide RNA that targets the second badc gene and (ii) a functional Cas enzyme molecule. Also in some of these embodiments, the transforming is by *Agrobacterium*-mediated floral dip transformation.

In some embodiments, the step of conducting one more cycles of breeding comprises conducting a first cycle of breeding of the mutated plant. In some of these embodiments, the step of conducting one or more cycles of breeding further comprises conducting one or more cycles of breeding of the progeny of the mutated plant. Also in some of these embodiments, the step of conducting one or more cycles of breeding further comprises conducting one or more cycles of breeding of the progeny of the mutated plant with progeny of the progenitor plant that comprise one or more additions, deletions, or substitutions of one more nucleotides relative to the wild-type allele of a badc gene other than the second badc gene that eliminate function of a BADC protein encoded by the other badc gene.

In some embodiments, the step of identifying plants comprises sequencing the second badc gene of the progeny of the mutated plant.

Also provided is a genetically modified plant that exhibits an increase in seed oil content relative to a progenitor plant from which the genetically modified plant was derived is provided. The genetically modified plant comprises: (a) a first badc gene, occurring in its natural position within the genome of the genetically modified plant and being homozygous for a wild-type allele; (b) a second badc gene, occurring in its natural position within the genome of the genetically modified plant and being homozygous for a mutant allele; (c) one or more homologs of the first badc gene, each of the one or more homologs of the first badc gene occurring in its natural position within the genome of the genetically modified plant and being homozygous for a wild-type allele; and (d) one or more homologs of the second badc gene, each of the one or more homologs of the second badc gene occurring in its natural position within the genome of the genetically modified plant, and at least one of the homologs of the second badc gene being homozygous for a wild-type allele. The wild-type alleles of the first badc gene, each of the one or more homologs of the first badc gene, and the at least one of the homologs of the second bade gene are identical to respective alleles of the first badc gene, each of the one or more homologs of the first bade gene, and the at least one of the homologs of the second bade gene from the progenitor plant. The mutant allele of the second badc gene does not encode a functional BADC protein and includes one or more additions, deletions, or substitutions of one or more nucleotides relative to an allele of the second badc gene from the progenitor plant. The increase in seed oil content is at least 3%.

Also provided is a method for producing the genetically modified plant that exhibits an increase in seed oil content relative to a progenitor plant from which the genetically modified plant was derived. In accordance with this method, the progenitor plant comprises a first badc gene, a second bade gene, one or more homologs of the first bade gene, and one or more homologs of the second badc gene, each of the first badc gene, the second badc gene, the one or more homologs of the first badc gene, and the one or more homologs of the second badc gene being homozygous for a wild-type allele. The method comprises steps of: (1) mutating the second badc gene in cells of the progenitor plant by making one or more additions, deletions, or substitutions of one more nucleotides relative to the wild-type allele of the second bade gene that eliminate function of the BADC protein encoded by the second badc gene that is mutated, thereby obtaining a mutated plant; (2) conducting one more cycles of breeding of the mutated plant to obtain progeny of the mutated plant, (3) identifying plants of the progeny in which the second badc gene is homozygous for the mutant allele, thereby obtaining second-bade-gene homozygous mutant plants; and (4) screening the second-badc-gene homozygous mutant plants for one or more plants that have an increase in seed oil content of at least 3% relative to the progenitor plant, thereby obtaining the genetically modified plant.

Also provided is a genetically modified plant that exhibits an increase in oil per plant relative to a progenitor plant from which the genetically modified plant was derived is provided. The genetically modified plant comprises: (a) a first badc gene, occurring in its natural position within the genome of the genetically modified plant and being homozygous for a wild-type allele; (b) a second bade gene, occurring in its natural position within the genome of the genetically modified plant and being homozygous for a mutant allele; (c) one or more homologs of the first badc gene, each of the one or more homologs of the first bade gene occurring in its natural position within the genome of the genetically modified plant and being homozygous for a wild-type allele; and (d) one or more homologs of the second bade gene, each of the one or more homologs of the second badc gene occurring in its natural position within the genome of the genetically modified plant, and at least one of the homologs of the second badc gene being homozygous for a wild-type allele. The wild-type alleles of the first badc gene, each of the one or more homologs of the first bade gene, and the at least one of the homologs of the second badc gene are identical to respective alleles of the first badc gene, each of the one or more homologs of the first bade gene, and the at least one of the homologs of the second badc gene from the progenitor plant. The mutant allele of the second badc gene does not encode a functional BADC protein and includes one or more additions, deletions, or substitutions of one or more nucleotides relative to an allele of the second badc gene from the progenitor plant. The increase in oil per plant is at least 5%.

Also provided is a method for producing the genetically modified plant that exhibits an increase in oil per plant relative to a progenitor plant from which the genetically modified plant was derived. In accordance with this method, the progenitor plant comprises a first bade gene, a second bade gene, one or more homologs of the first bade gene, and one or more homologs of the second bade gene, each of the first bade gene, the second badc gene, the one or more homologs of the first badc gene, and the one or more homologs of the second badc gene being homozygous for a wild-type allele. The method comprises steps of: (1) mutating the second badc gene in cells of the progenitor plant by making one or more additions, deletions, or substitutions of one more nucleotides relative to the wild-type allele of the second badc gene that eliminate function of the BADC protein encoded by the second badc gene that is mutated, thereby obtaining a mutated plant; (2) conducting one more cycles of breeding of the mutated plant to obtain progeny of the mutated plant; (3) identifying plants of the progeny in which the second badc gene is homozygous for the mutant allele, thereby obtaining second-badc-gene homozygous mutant plants; and (4) screening the second-badc-gene homozygous mutant plants for one or more plants that have an increase in oil per plant of at least 5% relative to the progenitor plant, thereby obtaining the genetically modified plant.

Exemplary embodiments include the following:

Embodiment 1. A genetically modified plant that exhibits an increase in seed yield relative to a progenitor plant from which the genetically modified plant was derived, the genetically modified plant comprising:

(a) a first biotin attachment domain-containing (badc) gene, occurring in its natural position within the genome of the genetically modified plant and being homozygous for a wild-type allele;

(b) a second badc gene, occurring in its natural position within the genome of the genetically modified plant and being homozygous for a mutant allele;

(c) one or more homologs of the first badc gene, each of the one or more homologs of the first badc gene occurring in its natural position within the genome of the genetically modified plant and being homozygous for a wild-type allele; and (d) one or more homologs of the second badc gene, each of the one or more homologs of the second badc gene occurring in its natural position within the genome of the genetically modified plant, and at least one of the homologs of the second badc gene being homozygous for a wild-type allele, wherein:

(i) the wild-type alleles of the first bade gene, each of the one or more homologs of the first badc gene, and the at least one of the homologs of the second badc gene are identical to respective alleles of the first badc gene, each of the one or more homologs of the first badc gene, and the at least one of the homologs of the second badc gene from the progenitor plant;

(ii) the mutant allele of the second badc gene does not encode a functional BADC protein and includes one or more additions, deletions, or substitutions of one or more nucleotides relative to an allele of the second badc gene from the progenitor plant; and (iii) the increase in seed yield is at least 4%.

Embodiment 2. The genetically modified plant of embodiment 1, wherein the wild-type alleles of the first badc gene, each of the one or more homologs of the first badc gene, and the at least one of the homologs of the second badc gene each encode a functional BADC protein.

Embodiment 3. The genetically modified plant of embodiment 1 or 2, wherein the genetically modified plant comprises the one or more homologs of the first badc gene and the one or more homologs of the second badc gene based on one or more of polyploidy, alloploidy, autoploidy, diploidization following polyploidy, diploidization following alloploidy, or diploidization following autoploidy.

Embodiment 4. The genetically modified plant of any one of embodiments 1-3, wherein the genetically modified plant is allotetraploid, allohexaploid, or allooctoploid.

Embodiment 5. The genetically modified plant of any one of embodiments 1-4, wherein the genetically modified plant is homozygous for the wild-type allele of the first badc gene based on including two identical copies of a wild-type allele.

Embodiment 6. The genetically modified plant of any one of embodiments 1-5, wherein the genetically modified plant is homozygous for the wild-type allele of the first badc gene based on including a first wild-type allele and a second wild-type allele that are not identical to each other.

Embodiment 7. The genetically modified plant of any one of embodiments 1-6, wherein the genetically modified plant is homozygous for the mutant allele of the second badc gene based on including two copies of the mutant allele of the second badc gene that are identical.

Embodiment 8. The genetically modified plant of any one of embodiments 1-7, wherein the genetically modified plant is homozygous for the mutant allele of the second badc gene based on including a first mutant allele and a second mutant allele that are not identical to each other.

Embodiment 9. The genetically modified plant of any one of embodiments 1-8, wherein the one or more additions, deletions, or substitutions of one or more nucleotides comprise one or more of a frameshift mutation, an active site mutation, a nonconservative substitution mutation, or an open-reading-frame deletion mutation in the mutant allele of the second badc gene relative to the allele of the second badc gene from the progenitor plant.

Embodiment 10. The genetically modified plant of any one of embodiments 1-9, wherein the first badc gene and the one or more homologs of the first badc gene encode orthologs of BADC1 of *Arabidopsis thaliana*.

Embodiment 11. The genetically modified plant of any one of embodiments 1-10, wherein the second badc gene and the one or more homologs of the second badc gene encode orthologs of BADC2 of *Arabidopsis thaliana*.

Embodiment 12. The genetically modified plant of any one of embodiments 1-10, wherein the second badc gene and the one or more homologs of the second badc gene encode orthologs of BADC3 of *Arabidopsis thaliana*.

Embodiment 13. The genetically modified plant of any one of embodiments 1-12, wherein the increase in seed yield is at least 5%, 6%, 7%, 8%, 9%, 10%, 15%, 20%, 25%, 30%, 35%, 40%, 45%, 50%, or more.

Embodiment 14. The genetically modified plant of any one of embodiments 1-13, further comprising a third badc gene and one or more homologs of the third badc gene occurring in their respective natural positions within the genome of the genetically modified plant.

Embodiment 15. The genetically modified plant of embodiment 14, wherein the third badc gene is homozygous for a wild-type allele.

Embodiment 16. The genetically modified plant of embodiment 14, wherein the third badc gene is homozygous for a mutant allele.

Embodiment 17 The genetically modified plant of embodiment 14, wherein the third badc gene is heterozygous for a wild-type allele and a mutant allele.

Embodiment 18. The genetically modified plant of embodiment 14, wherein:

(i) if the second badc gene and the one more homologs of the second badc gene encode orthologs of BADC2 of *Arabidopsis thaliana*, then the third badc gene and the one or more homologs of the third badc gene encode orthologs of BADC3 of *Arabidopsis thaliana*, or (ii) if the second badc gene and the one more homologs of the second badc gene encode orthologs of BADC3 of *Arabidopsis thaliana*, then the third badc gene and the one more homologs of the third badc gene encode orthologs of BADC2 of *Arabidopsis thaliana*.

Embodiment 19. The genetically modified plant of any one of embodiments 1-18, further comprising one or more SUGAR-DEPENDENT1 (SDP1) genes, each of the SDP1 genes being homozygous for a wild-type allele.

Embodiment 20. The genetically modified plant of any one of embodiments 1-19, wherein the genetically modified plant is one or more of a *Camelina* species, *Camelina sativa*, a *Brassica* species, *Brassica napus, Brassica rapa, Brassica carinata, Brassica juncea*, or soybean.

Embodiment 21. The genetically modified plant of any one of embodiments 1-19, wherein the genetically modified plant is *Camelina sativa*.

Embodiment 22. The genetically modified plant of embodiment 21, wherein the first badc gene and the one or more homologs of the first badc gene comprise *Camelina sativa* badc1-1, badc1-2, and badc1-3.

Embodiment 23. The genetically modified plant of embodiment 21 or 22, wherein the second badc gene comprises one or more of *Camelina sativa* badc2-2 or badc2-3, and the at least one of the homologs of the second badc gene comprises *Camelina sativa* badc2-1.

Embodiment 24. The genetically modified plant of embodiment 23, wherein the mutant allele includes at least one of the additions, deletions, or substitutions within the first 89 codons of the second badc gene.

Embodiment 25. The genetically modified plant of embodiment 23 or 24, wherein both *Camelina sativa* badc2-2 and badc2-3 are homozygous for mutant alleles.

Embodiment 26. The genetically modified plant of embodiment 21 or 22, wherein the second badc gene comprises one or more of *Camelina sativa* badc3-1 or badc3-3, and the at least one of the homologs of the second badc gene comprises *Camelina sativa* badc3-2.

Embodiment 27. The genetically modified plant of embodiment 26, wherein the mutant allele includes at least one of the additions, deletions, or substitutions within the first 125 codons of the second badc gene.

Embodiment 28. The genetically modified plant of embodiment 26 or 27, wherein both *Camelina sativa* badc3-1 and badc3-3 are homozygous for mutant alleles.

Embodiment 29. The genetically modified plant of any one of embodiments 1-19, wherein the genetically modified plant is *Brassica napus*.

Embodiment 30. The genetically modified plant of embodiment 29, wherein the first badc gene and the one or more homologs of the first badc gene comprise *Brassica napus* badc1-1 and badc1-2.

Embodiment 31. The genetically modified plant of embodiment 29 or 30, wherein the second badc gene comprises one or more of *Brassica napus* badc3-1, badc3-2, badc3-3, or badc3-4.

Embodiment 32. The genetically modified plant of embodiment 29 or 30, wherein the second badc gene comprises *Brassica napus* badc3-2.

Embodiment 33. The genetically modified plant of embodiment 32, wherein the mutant allele includes at least one of the additions, deletions, or substitutions within the first 111 codons of the second badc gene.

Embodiment 34. The genetically modified plant of embodiment 33, wherein both *Brassica napus* badc3-2 and badc3-3 are homozygous for mutant alleles.

Embodiment 35. The genetically modified plant of any one of embodiments 1-34, wherein the genetically modified plant further exhibits an increase in seed oil content relative to the progenitor plant.

Embodiment 36. The genetically modified plant of embodiment 35, wherein the increase in seed oil content is at least 3%, 4%, 5%, 6%, 7%, 8%, 9%, 10%, or more.

Embodiment 37. The genetically modified plant of any one of embodiments 1-36, wherein the genetically modified plant further exhibits an increase in oil per plant relative to the progenitor plant.

Embodiment 38. The genetically modified plant of embodiment 37, wherein the increase in oil per plant is at least 5%, 6%, 7%, 8%, 9%, 10%, 15%, 20%, 25%, 30%, 35%, 40%, 45%, 50%, or more.

Embodiment 39. A method for producing the genetically modified plant of any one of embodiments 1-38 from a progenitor plant comprising a first badc gene, a second badc gene, one or more homologs of the first badc gene, and one or more homologs of the second badc gene, each of the first badc gene, the second badc gene, the one or more homologs of the first badc gene, and the one or more homologs of the second badc gene being homozygous for a wild-type allele, the method comprising steps of:

(1) mutating the second badc gene in cells of the progenitor plant by making one or more additions, deletions, or substitutions of one more nucleotides relative to the wild-type allele of the second badc gene that eliminate function of the BADC protein encoded by the second badc gene that is mutated, thereby obtaining a mutated plant;

(2) conducting one more cycles of breeding of the mutated plant to obtain progeny of the mutated plant;

(3) identifying plants of the progeny in which the second badc gene is homozygous for the mutant allele, thereby obtaining second-badc-gene homozygous mutant plants; and (4) screening the second-badc-gene homozygous mutant plants for one or more plants that have an increase in seed yield of at least 4% relative to the progenitor plant, thereby obtaining the genetically modified plant.

Embodiment 40. The method of embodiment 39, wherein the step of mutating the second badc gene includes introducing the one or more additions, deletions, or substitutions by genome editing.

Embodiment 41. The method of embodiment 40, wherein the genome editing comprises transforming the cells of the progenitor plant with a plasmid that encodes (i) a single guide RNA that targets the second badc gene and (ii) a functional Cas enzyme molecule.

Embodiment 42. The method of embodiment 41, wherein the transforming is by *Agrobacterium*-mediated floral dip transformation.

Embodiment 43. The method of any one of embodiments 39-42, wherein the step of conducting one more cycles of breeding comprises conducting a first cycle of breeding of the mutated plant.

Embodiment 44. The method of embodiment 43, wherein the step of conducting one or more cycles of breeding further comprises conducting one or more cycles of breeding of the progeny of the mutated plant.

Embodiment 45. The method of embodiment 43 or 44, wherein the step of conducting one or more cycles of breeding further comprises conducting one or more cycles of breeding of the progeny of the mutated plant with progeny of the progenitor plant that comprise one or more additions, deletions, or substitutions of one more nucleotides relative to the wild-type allele of a badc gene other than the second badc gene that eliminate function of a BADC protein encoded by the other badc gene.

Embodiment 46. The method of any one of embodiments 39-45, wherein the step of identifying plants comprises sequencing the second badc gene of the progeny of the mutated plant.

DETAILED DESCRIPTION OF THE INVENTION

Figure 1:
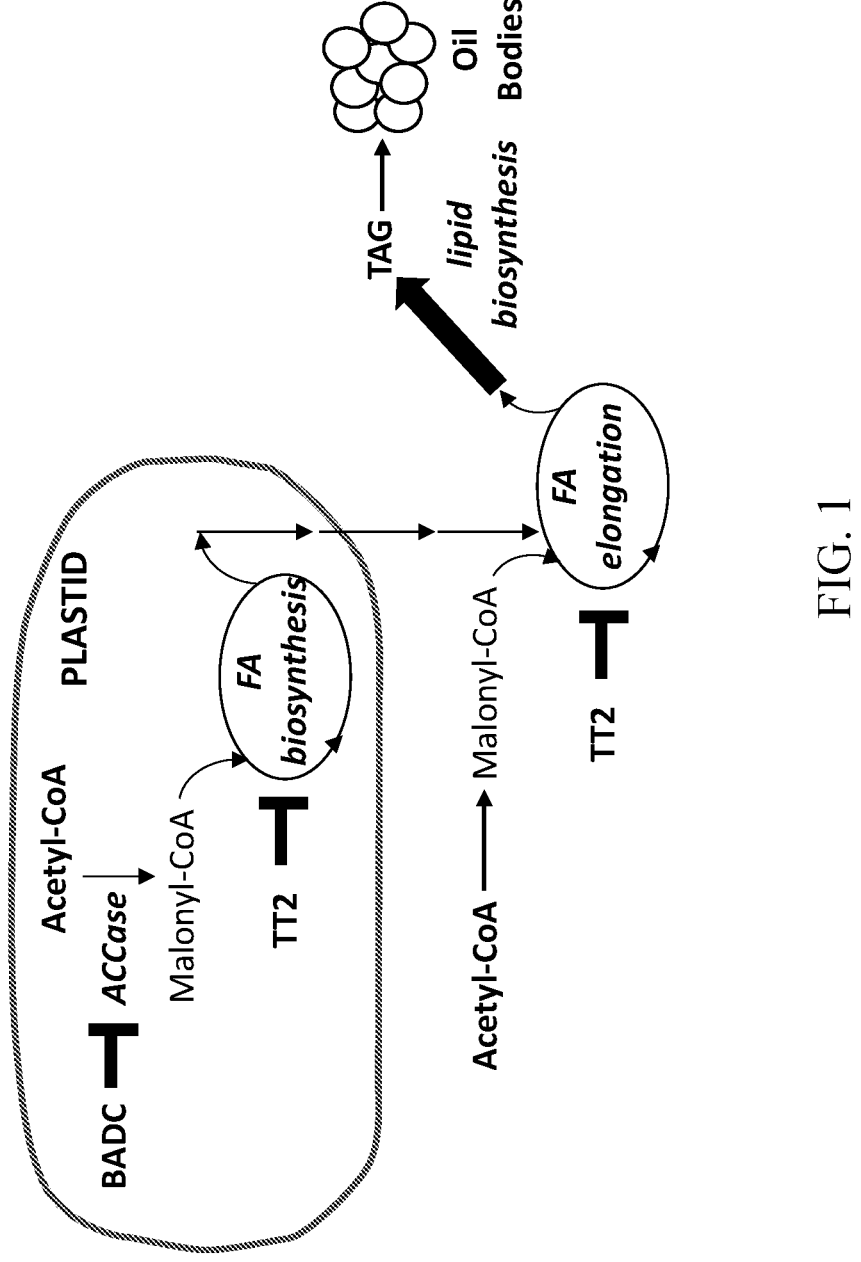
FIG. 1 illustrates a simplified pathway for lipid biosynthesis in oilseeds. Abbreviations are as follows. BADC, Biotin/lipoyl Attachment Domain Containing protein; ACCase, acetyl-CoA carboxylase.

Herein we describe improvements of TAG accumulation in plants by modulating the activity of the badc gene. Preferably these modifications are accomplished without introducing DNA sequences from a different species. Preferred methods for modulating the activity of the genes include genome editing and cis-genic approaches, including cis-genic systems expressing RNA inhibitors of expression of the target genes such as RNAi or anti-sense.

We have identified full-length single gene orthologs of *Arabidopsis* BADC1, BADC2, and BADC3 proteins in *Camelina sativa*, and of *Arabidopsis* BADC1 and BADC3 in canola (also termed *Brassica napus*) and *Glycine max*, as targets for reducing their expression or activity using genome editing as a means to increase oil content while minimizing the reduction in seed yield. These oilseed crops have more complex genomes than the diploid genome of *Arabidopsis*, with multiple homeologs of each badc gene. Thus, for example, *Camelina*, an allohexaploid, has three homeologs of each of its three badc genes, namely badc1-1, badc1-2, and badc1-3, encoding its orthologs of *Arabidopsis* BADC1, badc2-1, badc2-2, and badc2-3, encoding its orthologs of *Arabidopsis* BADC2, and badc3-1, badc3-2, and badc3-3, encoding its orthologs of *Arabidopsis* BADC3, each present in two copies. Canola, an allotetraploid, has six bade genes, namely badc1-1 and badc1-2, encoding its orthologs of *Arabidopsis* BADC1, and badc3-1, badc3-2, badc3-3, and badc3-4, encoding its orthologs of *Arabidopsis* BADC3. We previously referred to canola's badc1-1, badc1-2, badc3-1, badc3-2, badc3-3, and badc3-4 as badc1, badc2, badc3, badc4, badc5, and badc6, respectively, in our U.S. Provisional Application No. 63/064,796. *Glycine max* cultivar Williams 82 has four badc genes, namely badc1-1 and badc1-2, encoding its orthologs of *Arabidopsis* BADC1, and badc3-1 and badc3-2, encoding its orthologs of *Arabidopsis* BADC3.

As discussed below, using the same type of analysis, orthologs of *Arabidopsis* BADC1, BADC2, and BADC3 proteins can be readily identified in other oilseed plants, including other *Brassica* species such as *Brassica juncea, Brassica carinata* and *Brassica rappa*, and in flax, pennycress, safflower, sunflower and sesame.

Surprisingly, using genome editing with the CRISPR/Cas9 system to knockout multiple badc genes in *Camelina* and canola proved difficult. In *Camelina*, in our initial efforts to generate lines including null mutations in each homeolog of each of ortholog of *Arabidopsis* BADC1, BADC2, and BADC3, we were able to generate null segregant lines of two of three homeologs of badc2 and badc3, namely badc2-2, badc2-3, badc3-1, and badc3-3, but not of the remaining homeologs of badc2 or badc3, namely badc2-1 or badc3-2, and not of any homeologs of badc1. Similarly, in canola were able to generate null segregant lines of three of four homeologs of *Arabidopsis* BADC3, namely badc3-1, badc3-2, and badc3-3, but not of the remaining one, badc3-4, nor in either of the two homeologs of *Arabidopsis* BADC1. This was surprising because *Arabidopsis* plants homozygous for mutations in badc1, badc2, badc3, badc1 badc2, or badc1 badc3 exhibited growth and development similar to wild-type plants (Keereetaweep et al., 2018). As noted above, according to Shivaiah et al. (2020), the three *Arabidopsis* BADC genes share considerable functional redundancy, and plants missing any single isoform grow normally, implying that expression of the remaining two isoforms is sufficient for growth and viability. Also, in *Arabidopsis* BADC2 appears to be able to replace almost all BADC3 function, but not vice versa, and *Arabidopsis* plants expressing BADC1 alone are not viable through seed development. In contrast, our results suggest that in plants with complex genomes, including multiple homeologs of two or more BADC proteins, there may be little or no functional redundancy between particular BADC homeologs, let alone between BADC orthologs.

Also surprisingly, many of the *Camelina* and canola badc null segregant lines exhibited increased seed yields, as well as increased seed oil content and/or oil per plant. Our results suggest direct and efficient approaches for editing specific badc genes of plants with complex genomes to obtain null segregant lines that exhibit improved oil production based on higher seed oil content and higher seed yield.

I. Definitions

The following terms, unless otherwise indicated, will be understood to have the following meanings:

The term "plant" includes whole plant, mature plants, seeds, shoots and seedlings, and parts, propagation material, plant organ tissue, protoplasts, callus and other cultures, for example cell cultures, derived from plants belonging to the plant subkingdom Embryophyta, and all other species of groups of plant cells giving functional or structural units, also belonging to the plant subkingdom Embryophyta. The term "mature plants" refers to plants at any developmental stage beyond the seedling. The term "seedlings" refers to young, immature plants at an early developmental stage. The terms "crops" and "plants" are used interchangeably.

As used herein a "genetically modified plant" refers to non-naturally occurring plants or crops engineered as described throughout herein.

As used herein a "control plant" means a plant that has not been modified as described in the present disclosure to impart an enhanced trait or altered phenotype. A control plant is used to identify and select a modified plant that has an enhanced trait or altered phenotype. For instance, a control plant can be a plant that has not been modified or has not been genome edited to express or to inhibit its endogenous gene product. A suitable control plant can be a non-transgenic or non-edited plant of the parental line used to generate a transgenic plant, for example, a wild-type plant devoid of a recombinant DNA or a genome edit. A suitable control plant can also be a transgenic plant that contains recombinant DNA that imparts other traits, for example, a transgenic plant having enhanced herbicide tolerance. A suitable control plant can in some cases be a progeny of a hemizygous transgenic plant line that does not contain the recombinant DNA, known as a negative segregant, a null segregant, or a negative isogenic line.

As used herein the term "seed oil content" refers to amount of oil per mature seed weight and is typically expressed as a percentage.

As used herein the term "seed yield" refers to weight of seeds produced per plant and is typically expressed in grams per plant.

As used herein the term "oil yield" refers to weight of oil produced per plant and is typically expressed as grams per plant.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct," which are used interchangeably, refers to any gene that is not a native gene, comprising regulatory and coding sequences that are not found together in nature. A "Cis-genic gene" is a chimeric gene where the DNA sequences making up the gene are from the same plant species or a sexually compatible plant species where the cis-genic gene is deployed in the same species from which the DNA sequences were obtained. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

As used herein "gene" includes protein coding regions of the specific genes and the regulatory sequences both 5' and 3' which control the expression of the gene.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for increased expression in a host cell, it is desirable to design the nucleic acid fragment such that its frequency of codon usage approaches the frequency of preferred codon usage of the host cell.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity). When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percent sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percent sequence identity" means the value determined by comparing two aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percent sequence identity.

"Homeologs" are pluralities of genes (e.g. two, three, or more genes) that originated by speciation and were brought back together in the same genome by allopolyploidization (Glover et al., 2016, Trends Plant Sci., 21, 609).

"Polyploidy" is a heritable condition of an organism having more than two complete sets of chromosomes (Woodhouse et al., 2009, Nature Education, 2, 1). For example, a "tetraploid" has four sets of chromosomes. A "hexaploid" has six sets of chromosomes.

"Allopolyploidy" is a type of whole-genome duplication by hybridization followed by genome doubling (Glover et al., 2016). Allopolyploidy typically occurs between two related species, and results in the merging of the genomes of two divergent species into one genome. For example, an "allotetraploid" is an alloploid that has four sets of chromosomes. An "allohexaploid" is a hexaploid that has six sets of chromosomes.

"Autopolyploidy" is a type of whole-genome duplication based on doubling of a genome within one species.

"Diploidization" of a polyploid is a process that involves genomic reorganization, restructuring, and functional alternations in association with polyploidy, generally resulting in restoration of a secondary diploid-like behavior of a polyploid genome (del Pozo et al., 2015, Journal Experimental Botany, 66, 6991). Most polyploid plants have lost their polyploidy over time through diploidization (del Pozo et al., 2015).

II. Preferred Embodiments

As noted above, a genetically modified plant that exhibits an increase in seed yield relative to a progenitor plant from which the genetically modified plant was derived is provided.

The genetically modified plant comprises a first biotin attachment domain-containing (badc) gene, occurring in its natural position within the genome of the genetically modified plant and being homozygous for a wild-type allele. The wild-type allele of the first badc gene is identical to an allele of the first badc gene from the progenitor plant.

In some embodiments, the wild-type alleles of the first badc gene, each of the one or more homologs of the first badc gene, and the at least one of the homologs of the second bade gene each encode a functional BADC protein. As noted above, BADC proteins interact with the two biotin carboxyl carrier protein (also termed "BCCP") isoforms of acetyl-coA carboxylase. Accordingly, in some embodiments the wild-type alleles of the first badc gene, each of the one or more homologs of the first bade gene, and the at least one of the homologs of the second badc gene each encode a functional BADC protein based on each of the BADC proteins being able to interact with the two BCCP isoforms of acetyl-coA carboxylase to a similar extent and/or the same extent as respective BADC proteins of the progenitor plant.

The genetically modified plant also comprises a second badc gene, occurring in its natural position within the genome of the genetically modified plant and being homozygous for a mutant allele. The mutant allele of the second badc gene does not encode a functional BADC protein and includes one or more additions, deletions, or substitutions of one or more nucleotides relative to an allele of the second bade gene from the progenitor plant.

The genetically modified plant also comprises one or more homologs of the first badc gene, each of the one or more homologs of the first badc gene occurring in its natural position within the genome of the genetically modified plant and being homozygous for a wild-type allele. Each of the one or more homologs of the first badc gene is identical to respective alleles of each of the one or more homologs of the first bade gene from the progenitor plant.

The genetically modified plant also comprises one or more homologs of the second bade gene, each of the one or more homologs of the second badc gene occurring in its natural position within the genome of the genetically modified plant, and at least one of the homologs of the second bade gene being homozygous for a wild-type allele. At least one of the homologs of the second badc gene is identical to an allele of the at least one of the homologs of the second badc gene from the progenitor plant.

In some embodiments, the genetically modified plant comprises the one or more homologs of the first badc gene and the one or more homologs of the second badc gene based on one or more of polyploidy, alloploidy, autoploidy, diploidization following polyploidy, diploidization following alloploidy, or diploidization following autoploidy. In some embodiments, the genetically modified plant is allotetraploid, allohexaploid, or allooctoploid.

The increase in seed yield is at least 4%. As noted above, we found that many of the edited lines had higher seed yield. In some embodiments, the increase in seed yield is at least 5%, 6%, 7%, 8%, 9%, 10%, 15%, 20%, 25%, 30%, 35%, 40%, 45%, 50%, or more.

As noted above, the first badc gene is homozygous for the wild-type allele. In some embodiments, the genetically modified plant is homozygous for the wild-type allele of the first badc gene based on including two identical copies of a wild-type allele. The identical wild-type alleles may be derived, for example, from a single wild-type allele of a progenitor plant. In some embodiments, the genetically modified plant is homozygous for the wild-type allele of the first badc gene based on including a first wild-type allele and a second wild-type allele that are not identical to each other. The non-identical wild-type alleles may differ, for example, based on differences in the nucleotide sequences of the non-identical alleles that are sufficiently minor as to have no corresponding phenotype with respect to function of the BADC protein expressed from these alleles.

As also noted above, the second badc gene is homozygous for the mutant allele. In some embodiments, the genetically modified plant is homozygous for the mutant allele of the second badc gene based on including two copies of the mutant allele of the second badc gene that are identical. The identical mutant alleles may be based, for example, on breeding the genetically modified plant to homozygosity with respect to a particular mutant allele. In some embodiments, the genetically modified plant is homozygous for the mutant allele of the second badc gene based on including a first mutant allele and a second mutant allele that are not identical to each other. The non-identical mutant alleles may differ, for example, based on having different additions, deletions, and/or substitutions of one or more nucleotides relative to each other, with the additions, deletions, and/or substitutions of each being sufficiently severe to cause a loss of function of the BADC protein encoded by each.

In some embodiments, the one or more additions, deletions, or substitutions of one or more nucleotides comprise one or more of a frameshift mutation, an active site mutation, a nonconservative substitution mutation, or an open-reading-frame deletion mutation in the mutant allele of the second badc gene relative to the allele of the second bade gene from the progenitor plant.

In some embodiments, the first badc gene and the one or more homologs of the first badc gene encode orthologs of BADC1 of *Arabidopsis thaliana*. Such genes include *Camelina sativa* badc1-1, badc1-2, and badc1-3. Such genes also include *Brassica napus* badc1 and badc2.

In some embodiments, the second badc gene and the one or more homologs of the second badc gene encode orthologs of BADC2 of *Arabidopsis thaliana*. Such genes include *Camelina sativa* badc2-1, badc2-2, and badc2-3.

In some embodiments, the second badc gene and the one or more homologs of the second badc gene encode orthologs of BADC3 of *Arabidopsis thaliana*. Such genes include *Camelina sativa* badc3-1, badc3-2, and badc3-3. Such genes also include *Brassica napus* badc3-1, badc3-2, badc3-3, and badc3-4.

In some embodiments, the genetically modified plant further comprises a third bade gene and one or more homologs of the third bade gene occurring in their respective natural positions within the genome of the genetically modified plant. In some of these embodiments, the third badc gene is homozygous for a wild-type allele. Also in some of these embodiments, the third badc gene is homozygous for a mutant allele. Also in some of these embodiments, the third badc gene is heterozygous for a wild-type allele and a mutant allele. Also in some embodiments, (i) if the second badc gene and the one more homologs of the second badc gene encode orthologs of BADC2 of *Arabidopsis thaliana*, then the third bade gene and the one or more homologs of the third badc gene encode orthologs of BADC3 of *Arabidopsis thaliana*, or (ii) if the second bade gene and the one more homologs of the second bade gene encode orthologs of BADC3 of *Arabidopsis thaliana*, then the third badc gene and the one more homologs of the third bade gene encode orthologs of BADC2 of *Arabidopsis thaliana*.

In some embodiments, the genetically modified plant further comprises one or more SUGAR-DEPENDENT1 (SDP1) genes, each of the SDP1 genes being homozygous for a wild-type allele. As noted above, SUGAR-DEPENDENT1 (also termed "SDP1" or "sdp1") genes encode oil body-associated triacylglycerol lipases. Also as noted, in co-pending Patent Application PCT/US2020/043063, to Yield10 Bioscience, full-length single gene homologs for SDP1, among other genes, in *Camelina sativa*, canola, and soybean were identified as targets for reducing their expression or activity using genome editing as a means to increase oil content while minimizing the reduction in seed yield seen by most researchers using other approaches. As will be appreciated, although SDP1 can be targeted for reduced expression or activity, genetically modified plants also can be developed in which each SDP1 gene is homozygous for a wild-type allele.

In some embodiments, the genetically modified plant is one or more of a *Camelina* species, *Camelina sativa*, a *Brassica* species, *Brassica napus, Brassica rapa, Brassica carinata, Brassica juncea*, or soybean.

In some embodiments, the genetically modified plant is *Camelina sativa*. In some of these embodiments, the first badc gene and the one or more homologs of the first badc gene comprise *Camelina sativa* badc1-1, badc1-2, and badc1-3. Also in some of these embodiments, the second badc gene comprises one or more of *Camelina sativa* badc2-2 or badc2-3, and the at least one of the homologs of the second badc gene comprises *Camelina sativa* badc2-1. Also in some of these embodiments, the mutant allele includes at least one of the additions, deletions, or substitutions within the first 89 codons of the second badc gene. Also in some of these embodiments, both *Camelina sativa* badc2-2 and badc2-3 are homozygous for mutant alleles. Also in some of these embodiments, the second badc gene comprises one or more of *Camelina sativa* badc3-1 or badc3-3, and the at least one of the homologs of the second badc gene comprises *Camelina sativa* badc3-2. Also in some of these embodiments, the mutant allele includes at least one of the additions, deletions, or substitutions within the first 125 codons of the second badc gene. Also in some of these embodiments, both *Camelina sativa* badc3-1 and badc3-3 are homozygous for mutant alleles.

In some embodiments, the genetically modified plant is *Brassica napus*. In some of these embodiments, the first badc gene and the one or more homologs of the first badc gene comprise *Brassica napus* badc1 and badc2. Also in some of these embodiments, the second badc gene comprises one or more of *Brassica napus* badc3-1, badc3-2, badc3-3, or badc3-4. Also in some of these embodiments, the second badc gene comprises *Brassica napus* badc3-2. Also in some of these embodiments, the mutant allele includes at least one of the additions, deletions, or substitutions within the first 111 codons of the second badc gene. Also in some of these embodiments, both *Brassica napus* badc3-2 and badc3-3 are homozygous for mutant alleles.

In some embodiments, the genetically modified plant further exhibits an increase in seed oil content relative to the progenitor plant. In some of these embodiments, the increase in seed oil content is at least 3%, 4%, 5%, 6%, 7%, 8%, 9%, 10%, or more.

In some embodiments, the genetically modified plant further exhibits an increase in oil per plant relative to the progenitor plant. In some of these embodiments, the increase in oil per plant is at least 5%, 6%, 7%, 8%, 9%, 10%, 15%, 20%, 25%, 30%, 35%, 40%, 45%, 50%, or more.

Also provided is a genetically modified plant that exhibits an increase in seed oil content relative to a progenitor plant from which the genetically modified plant was derived is provided. The genetically modified plant comprises: (a) a first badc gene, occurring in its natural position within the genome of the genetically modified plant and being homozygous for a wild-type allele: (b) a second badc gene, occurring in its natural position within the genome of the genetically modified plant and being homozygous for a mutant allele; (c) one or more homologs of the first badc gene, each of the one or more homologs of the first badc gene occurring in its natural position within the genome of the genetically modified plant and being homozygous for a wild-type allele; and (d) one or more homologs of the second badc gene, each of the one or more homologs of the second badc gene occurring in its natural position within the genome of the genetically modified plant, and at least one of the homologs of the second badc gene being homozygous for a wild-type allele. The wild-type alleles of the first badc gene, each of the one or more homologs of the first badc gene, and the at least one of the homologs of the second badc gene are identical to respective alleles of the first bade gene, each of the one or more homologs of the first badc gene, and the at least one of the homologs of the second bade gene from the progenitor plant. The mutant allele of the second badc gene does not encode a functional BADC protein and includes one or more additions, deletions, or substitutions of one or more nucleotides relative to an allele of the second badc gene from the progenitor plant. The increase in seed oil content is at least 3%.

The genetically modified plant can be as described above. For example, in some embodiments the wild-type alleles of the first bade gene, each of the one or more homologs of the first badc gene, and the at least one of the homologs of the second bade gene each encode a functional BADC protein. Also for example, in some embodiments the genetically modified plant comprises the one or more homologs of the first badc gene and the one or more homologs of the second badc gene based on one or more of polyploidy, alloploidy, autoploidy, diploidization following polyploidy, diploidization following alloploidy, or diploidization following autoploidy.

Also provided is a genetically modified plant that exhibits an increase in oil per plant relative to a progenitor plant from which the genetically modified plant was derived is provided. The genetically modified plant comprises: (a) a first badc gene, occurring in its natural position within the genome of the genetically modified plant and being homozygous for a wild-type allele: (b) a second badc gene, occurring in its natural position within the genome of the geneti-
cally modified plant and being homozygous for a mutant
allele; (c) one or more homologs of the first badc gene, each
of the one or more homologs of the first badc gene occurring
in its natural position within the genome of the genetically
modified plant and being homozygous for a wild-type allele;
and (d) one or more homologs of the second bade gene, each
of the one or more homologs of the second badc gene
occurring in its natural position within the genome of the
genetically modified plant, and at least one of the homologs
of the second badc gene being homozygous for a wild-type
allele. The wild-type alleles of the first badc gene, each of
the one or more homologs of the first badc gene, and the at
least one of the homologs of the second badc gene are
identical to respective alleles of the first badc gene, each of
the one or more homologs of the first badc gene, and the at
least one of the homologs of the second bade gene from the
progenitor plant. The mutant allele of the second badc gene
does not encode a functional BADC protein and includes
one or more additions, deletions, or substitutions of one or
more nucleotides relative to an allele of the second bade
gene from the progenitor plant. The increase in oil per plant
is at least 5%.

The genetically modified plant also can be as described
above. For example, in some embodiments the wild-type
alleles of the first badc gene, each of the one or more
homologs of the first bade gene, and the at least one of the
homologs of the second badc gene each encode a functional
BADC protein. Also for example, in some embodiments the
genetically modified plant comprises the one or more
homologs of the first badc gene and the one or more
homologs of the second badc gene based on one or more of
polyploidy, alloploidy, autoploidy, diploidization following
polyploidy, diploidization following alloploidy, or dip-
loidization following autoploidy.

Also provided is a method for producing the genetically
modified plant that exhibits an increase in seed yield relative
to a progenitor plant from which the genetically modified
plant was derived. In accordance with this method, the
progenitor plant comprises a first bade gene, a second bade
gene, one or more homologs of the first badc gene, and one
or more homologs of the second badc gene, each of the first
badc gene, the second bade gene, the one or more homologs
of the first bade gene, and the one or more homologs of the
second badc gene being homozygous for a wild-type allele.
The method comprises a step of: (1) mutating the second
badc gene in cells of the progenitor plant by making one or
more additions, deletions, or substitutions of one more
nucleotides relative to the wild-type allele of the second
badc gene that eliminate function of the BADC protein
encoded by the second bade gene that is mutated, thereby
obtaining a mutated plant; (2) conducting one more cycles of
breeding of the mutated plant to obtain progeny of the
mutated plant; (3) identifying plants of the progeny in which
the second badc gene is homozygous for the mutant allele,
thereby obtaining second-badc-gene homozygous mutant
plants; and (4) screening the second-badc-gene homozygous
mutant plants for one or more plants that have an increase in
seed yield of at least 4% relative to the progenitor plant,
thereby obtaining the genetically modified plant.

The steps of (1) mutating the second badc gene, (2)
conducting one more cycles of breeding of the mutated
plant, (3) identifying plants of the progeny in which the
second badc gene is homozygous for the mutant allele, and
(4) screening the second-badc-gene homozygous mutant
plants can be carried out as described below.

In some embodiments, the step of mutating the second
badc gene includes introducing the one or more additions,
deletions, or substitutions by genome editing. In some of
these embodiments, the genome editing comprises trans-
forming the cells of the progenitor plant with a plasmid that
encodes (i) a single guide RNA that targets the second bade
gene and (ii) a functional Cas enzyme molecule. Also in
some of these embodiments, the transforming is by *Agro-
bacterium*-mediated floral dip transformation.

In some embodiments, the step of conducting one more
cycles of breeding comprises conducting a first cycle of
breeding of the mutated plant. In some of these embodi-
ments, the step of conducting one or more cycles of breeding
further comprises conducting one or more cycles of breeding
of the progeny of the mutated plant. Also in some of these
embodiments, the step of conducting one or more cycles of
breeding further comprises conducting one or more cycles of
breeding of the progeny of the mutated plant with progeny
of the progenitor plant that comprise one or more additions,
deletions, or substitutions of one more nucleotides relative
to the wild-type allele of a badc gene other than the second
badc gene that eliminate function of a BADC protein
encoded by the other badc gene.

In some embodiments, the step of identifying plants
comprises sequencing the second badc gene of the progeny
of the mutated plant.

Also provided is a method for producing the genetically
modified plant that exhibits an increase in seed oil content
relative to a progenitor plant from which the genetically
modified plant was derived. In accordance with this method,
the progenitor plant comprises a first bade gene, a second
badc gene, one or more homologs of the first badc gene, and
one or more homologs of the second bade gene, each of the
first badc gene, the second bade gene, the one or more
homologs of the first badc gene, and the one or more
homologs of the second badc gene being homozygous for a
wild-type allele. The method comprises steps of: (1) mutat-
ing the second bade gene in cells of the progenitor plant by
making one or more additions, deletions, or substitutions of
one more nucleotides relative to the wild-type allele of the
second badc gene that eliminate function of the BADC
protein encoded by the second badc gene that is mutated,
thereby obtaining a mutated plant; (2) conducting one more
cycles of breeding of the mutated plant to obtain progeny of
the mutated plant; (3) identifying plants of the progeny in
which the second badc gene is homozygous for the mutant
allele, thereby obtaining second-badc-gene homozygous
mutant plants; and (4) screening the second-bade-gene
homozygous mutant plants for one or more plants that have
an increase in seed oil content of at least 3% relative to the
progenitor plant, thereby obtaining the genetically modified
plant.

Also provided is a method for producing the genetically
modified plant that exhibits an increase in oil per plant
relative to a progenitor plant from which the genetically
modified plant was derived. In accordance with this method,
the progenitor plant comprises a first bade gene, a second
badc gene, one or more homologs of the first badc gene, and
one or more homologs of the second bade gene, each of the
first badc gene, the second badc gene, the one or more
homologs of the first badc gene, and the one or more
homologs of the second badc gene being homozygous for a
wild-type allele. The method comprises steps of: (1) mutat-
ing the second bade gene in cells of the progenitor plant by
making one or more additions, deletions, or substitutions of
one more nucleotides relative to the wild-type allele of the
second badc gene that eliminate function of the BADC protein encoded by the second badc gene that is mutated, thereby obtaining a mutated plant; (2) conducting one more cycles of breeding of the mutated plant to obtain progeny of the mutated plant; (3) identifying plants of the progeny in which the second badc gene is homozygous for the mutant allele, thereby obtaining second-badc-gene homozygous mutant plants; and (4) screening the second-bade-gene homozygous mutant plants for one or more plants that have an increase in oil per plant of at least 5% relative to the progenitor plant, thereby obtaining the genetically modified plant.

III. Genetic Modification of Plants

Methods of Plant Transformation

Known transformations methods can be used to genetically modify a plant with respect to one or more gene sequences of the invention using transgenic, cis-genic, or genome editing methods.

Vectors

Several plant transformation vector options are available, including those described in *Gene Transfer to Plants,* 1995, Potrykus et al., eds., Springer-Verlag Berlin Heidelberg N.Y., *Transgenic Plants: A Production System for Industrial and Pharmaceutical Proteins,* 1996, Owen et al., eds., John Wiley & Sons Ltd. Eng, and *Methods in Plant Molecular Biology: A Laboratory Course Manual,* 1995, Maliga et al., eds., Cold Spring Laboratory Press, New York. Plant transformation vectors generally include one or more coding sequences of interest under the transcriptional control of 5' and 3' regulatory sequences, including a promoter, a transcription termination and/or polyadenylation signal, and a selectable or screenable marker gene.

Many vectors are available for transformation using *Agrobacterium tumefaciens*. These typically carry at least one T-DNA sequence and include vectors such as pBIN19. Typical vectors suitable for *Agrobacterium* transformation include the binary vectors pCIB200 and pCIB2001, as well as the binary vector pCIB 10 and hygromycin selection derivatives thereof (see, for example, U.S. Pat. No. 5,639, 949).

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. The choice of vector for transformation techniques that do not rely on *Agrobacterium* depends largely on the preferred selection for the species being transformed. Typical vectors suitable for non-*Agrobacterium* transformation include pCIB3064, pSOG 19, and pSOG35. (See, for example, U.S. Pat. No. 5,639,949). Alternatively, DNA fragments containing the transgene and the necessary regulatory elements for expression of the transgene can be excised from a plasmid and delivered to the plant cell using microprojectile bombardment-mediated, or alternatively, nanotube-mediated methods.

Protocols

Transformation protocols as well as protocols for introducing nucleotide sequences into plants may vary depending on the type of plant or plant cell targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad Sci. USA* 83:5602-5606), *Agrobacterium*-mediated transformation (Townsend et al., U.S. Pat. No. 5,563, 055; Zhao et al. WO US98/01268), direct gene transfer (Paszkowski et al. (1984) EMBO J. 3:2717-2722), and ballistic particle acceleration (see, for example, Sanford et al., U.S. Pat. No. 4,945,050; Tomes et al. (1995) *Plant Cell, Tissue, and Organ Culture: Fundamental Methods,* ed. Gamborg and Phillips (Springer-Verlag, Berlin); and McCabe et al. *Biotechnology* 6:923-926 (1988)). Also see Weissinger et al. *Ann. Rev. Genet.* 22:421-477 (1988); Sanford et al. Particulate Science and Technology 5:27-37 (1987) (onion); Christou et al. *Plant Physiol.* 87:671-674 (1988) (soybean); McCabe et al. (1988) BioTechnology 6:923-926 (soybean); Finer and McMullen *In Vitro Cell Dev. Biol.* 27P:175-182 (1991) (soybean); Singh et al. *Theor. Appl. Genet.* 96:319-324 (1998)(soybean); Dafta et al. (1990) *Biotechnology* 8:736-740 (rice); Klein et al. *Proc. Natl. Acad. Sci. USA* 85:4305-4309 (1988) (maize); Klein et al. *Biotechnology* 6:559-563 (1988) (maize); Tomes, U.S. Pat. No. 5,240,855; Buising et al., U.S. Pat. Nos. 5,322,783 and 5,324,646; Tomes et al. (1995) in Plant Cell, Tissue, and Organ Culture: Fundamental Methods, ed. Gamborg (Springer-Verlag, Berlin) (maize); Klein et al. Plant Physiol. 91:440-444 (1988) (maize); Fromm et al. *Biotechnology* 8:833-839 (1990) (maize); Hooykaas-Van Slogteren et al. *Nature* 311:763-764 (1984); Bowen et al., U.S. Pat. No. 5,736,369 (cereals); Bytebier et al. *Proc. Natl. Acad. Sci. USA* 84:5345-5349 (1987) (Liliaceae); De Wet et al. in The Experimental Manipulation of Ovule Tissues, ed. Chapman et al. (Longman, N.Y.), pp. 197-209 (1985) (pollen); Kaeppler et al. *Plant Cell Reports* 9:415-418 (1990) and Kaeppler et al. *Theor. Appl. Genet.* 84:560-566 (1992) (whisker-mediated transformation); D'Halluin et al. *Plant Cell* 4:1495-1505 (1992) (electroporation); Li et al. *Plant Cell Reports* 12:250-255 (1993) and Christou and Ford Annals of Botany 75:407-413 (1995) (rice); Osjoda et al. *Nature Biotechnology* 14:745-750 (1996) (maize via *Agrobacterium tumefaciens*). References for protoplast transformation and/or gene gun for Agrisoma technology are described in WO 2010/037209. Methods for transforming plant protoplasts are available including transformation using polyethylene glycol (PEG), electroporation, and calcium phosphate precipitation (see for example Potrykus et al., 1985, Mol. Gen. Genet., 199, 183-188; Potrykus et al., 1985, Plant Molecular Biology Reporter, 3, 117-128). Methods for plant regeneration from protoplasts have also been described [Evans et al., in Handbook of Plant Cell Culture, Vol 1, (Macmillan Publishing Co., New York, 1983); Vasil, I K in Cell Culture and Somatic Cell Genetics (Academic, Oro, 1984)].

Transformation protocols as well as protocols for introducing nucleotide sequences into plants may vary depending on the type of plant or plant cell, i.e., monocot or dicot, targeted for transformation.

Suitable methods of introducing nucleotide sequences into plant cells and subsequent insertion into the plant genome are described in US 2010/0229256 A1 to Somleva & Ali and US 2012/0060413 to Somleva et al.

The transformed cells are grown into plants in accordance with conventional techniques (see, for example, McCormick et al., 1986, *Plant Cell Rep.* 5: 81-84). These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

Procedures for in planta transformation can be simple. Tissue culture manipulations and possible somaclonal variations are avoided and only a short time is required to obtain transgenic plants. However, the frequency of transformants in the progeny of such inoculated plants is relatively low and variable. At present, there are very few species that can be routinely transformed in the absence of a tissue culture-based regeneration system. Stable *Arabidopsis* transformants can be obtained by several in planta methods including vacuum infiltration (Clough & Bent, 1998, *The Plant J.* 16: 735-743), transformation of germinating seeds (Feldmann & Marks, 1987, *Mol. Gen. Genet.* 208: 1-9), floral dip (Clough and Bent, 1998, *Plant J.* 16: 735-743), and floral spray (Chung et al., 2000, *Transgenic Res.* 9: 471-476). Other plants that have successfully been transformed by in planta methods include rapeseed and radish (vacuum infiltration, Ian and Hong, 2001, Transgenic Res., 10: 363-371; Desfeux et al., 2000, *Plant Physiol.* 123: 895-904), *Medicago truncatula* (vacuum infiltration, Trieu et al., 2000, *Plant J.* 22: 531-541), *camelina* (floral dip, WO/2009/117555 to Nguyen et al.), and wheat (floral dip, Zale et al., 2009, *Plant Cell Rep.* 28: 903-913). In planta methods have also been used for transformation of germ cells in maize (pollen, Wang et al. 2001. *Acta Botanica Sin.*, 43, 275-279; Zhang et al., 2005, *Euphytica*, 144, 11-22; pistils, Chumakov et al. 2006, *Russian J. Genetics*, 42, 893-897; Mamontova et al. 2010, *Russian J. Genetics.* 46, 501-504) and Sorghum (pollen, Wang et al. 2007, *Biotechnol. Appl. Biochem.*, 48, 79-83).

Selection

Following transformation by any one of the methods described above, the following procedures can be used to obtain a transformed plant expressing the transgenes: select the plant cells that have been transformed on a selective medium; regenerate the plant cells that have been transformed to produce differentiated plants; select transformed plants expressing the DNA construct for introducing the targeted insertion of the DNA sequence elements producing the desired level of desired polypeptide(s) in the desired tissue and cellular location.

The cells that have been transformed may be grown into plants in accordance with conventional techniques (see, for example, McCormick et al. *Plant Cell Reports* 5:81-84 (1986)). These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

Transgenic plants can be produced using conventional techniques to express any genes of interest in plants or plant cells (*Methods in Molecular Biology*, 2005, vol. 286, Transgenic Plants: Methods and Protocols, Pena L., ed., Humana Press, Inc. Totowa, NJ; Shyamkumar Barampuram and Zhanyuan J. Zhang, Recent Advances in Plant Transformation, in James A. Birchler (ed.), *Plant Chromosome Engineering: Methods and Protocols, Methods in Molecular Biology, vol.* 701, Springer Science+Business Media). Typically, gene transfer, or transformation, is carried out using explants capable of regeneration to produce complete, fertile plants. Generally, a DNA or an RNA molecule to be introduced into the organism is part of a transformation vector. A large number of such vector systems known in the art may be used, such as plasmids. The components of the expression system can be modified, e.g., to increase expression of the introduced nucleic acids. For example, truncated sequences, nucleotide substitutions or other modifications may be employed. Expression systems known in the art may be used to transform virtually any plant cell under suitable conditions. A transgene comprising a DNA molecule encoding a gene of interest is preferably stably transformed and integrated into the genome of the host cells. Transformed cells are preferably regenerated into whole fertile plants. Detailed description of transformation techniques are within the knowledge of those skilled in the art.

Plant promoters can be selected to control the expression of the transgene in different plant tissues or organelles for all of which methods are known to those skilled in the art (Gasser & Fraley, 1989, *Science* 244: 1293-1299). In one embodiment, promoters are selected from those of eukaryotic or synthetic origin that are known to yield high levels of expression in plants and algae. In a preferred embodiment, promoters are selected from those that are known to provide high levels of expression in monocots.

Constitutive promoters include, for example, the core promoter of the Rsyn7 promoter and other constitutive promoters disclosed in WO 99/43838 and U.S. Pat. No. 6,072,050, the core CaMV 35S promoter (Odell et al., 1985, *Nature* 313: 810-812), rice actin (McElroy et al., 1990, *Plant Cell* 2: 163-171), ubiquitin (Christensen et al., 1989, *Plant Mol. Biol.* 12: 619-632; Christensen et al., 1992, *Plant Mol. Biol.* 18: 675-689), pEMU (Last et al., 1991, *Theor. Appl. Genet.* 81: 581-588), MAS (Velten et al., 1984, *EMBO J.* 3: 2723-2730), and ALS promoter (U.S. Pat. No. 5,659,026). Other constitutive promoters are described in U.S. Pat. Nos. 5,608,149; 5,608,144; 5,604,121; 5,569,597; 5,466,785; 5,399,680; 5,268,463; and 5,608,142.

"Tissue-preferred" promoters can be used to target gene expression within a particular tissue. Compared to chemically inducible systems, developmentally and spatially regulated stimuli are less dependent on penetration of external factors into plant cells. Tissue-preferred promoters include those described by Van Ex et al., 2009, *Plant Cell Rep.* 28: 1509-1520; Yamamoto et al., 1997, *Plant J.* 12: 255-265; Kawamata et al., 1997, *Plant Cell Physiol.* 38: 792-803; Hansen et al., 1997, *Mol. Gen. Genet.* 254: 337-343; Russell et al., 1997, *Transgenic Res.* 6: 157-168; Rinehart et al., 1996, *Plant Physiol.* 112: 1331-1341; Van Camp et al., 1996, *Plant Physiol.* 112: 525-535; Canevascini et al., 1996, *Plant Physiol.* 112: 513-524; Yamamoto et al., 1994, *Plant Cell Physiol.* 35: 773-778; Lam, 1994, *Results Probl. Cell Differ.* 20: 181-196, Orozco et al., 1993, *Plant Mol. Biol.* 23: 1129-1138; Matsuoka et al., 1993, *Proc. Natl. Acad. Sci. USA* 90: 9586-9590, and Guevara-Garcia et al., 1993, *Plant J.* 4: 495-505. Such promoters can be modified, if necessary, for weak expression.

Any of the described promoters can be used to control the expression of one or more of the genes of the invention, their homologs and/or orthologs as well as any other genes of interest in a defined spatiotemporal manner.

Expression Cassettes

Nucleic acid sequences intended for expression in transgenic plants are first assembled in expression cassettes behind a suitable promoter active in plants. The expression cassettes may also include any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be transferred to the plant transformation vectors described infra.

A variety of transcriptional terminators are available for use in expression cassettes. These are responsible for the termination of transcription beyond the transgene and the correct polyadenylation of the transcripts. Appropriate transcriptional terminators are those that are known to function in plants and include the CaMV 35S terminator, the tm1 terminator, the nopaline synthase terminator and the pea rbcS E9 terminator. These are used in both monocotyledonous and dicotyledonous plants.

Individual plants within a population of transgenic plants that express a recombinant gene(s) may have different levels of gene expression. The variable gene expression is due to multiple factors including multiple copies of the recombinant gene, chromatin effects, and gene suppression. Accordingly, a phenotype of the transgenic plant may be measured as a percentage of individual plants within a population. The yield of a plant can be measured simply by weighing. The yield of seed from a plant can also be determined by weighing. The increase in seed weight from a plant can be due to a number of factors, an increase in the number or size of the seed pods, an increase in the number of seed or an increase in the number of seed per plant. In the laboratory or greenhouse seed yield is usually reported as the weight of seed produced per plant and in a commercial crop production setting yield is usually expressed as weight per acre or weight per hectare.

A recombinant DNA construct including a plant-expressible gene or other DNA of interest is inserted into the genome of a plant by a suitable method. Suitable methods include, for example, Agrobacterium tumefaciens-mediated DNA transfer, direct DNA transfer, liposome-mediated DNA transfer, electroporation, co-cultivation, diffusion, particle bombardment, microinjection, gene gun, calcium phosphate coprecipitation, viral vectors, and other techniques. Suitable plant transformation vectors include those derived from a Ti plasmid of Agrobacterium tumefaciens. In addition to plant transformation vectors derived from the Ti or root-inducing (Ri) plasmids of Agrobacterium, alternative methods can be used to insert DNA constructs into plant cells. A transgenic plant can be produced by selection of transformed seeds or by selection of transformed plant cells and subsequent regeneration.

In one embodiment, the transgenic plants are grown (e.g., on soil) and harvested. In one embodiment, above ground tissue is harvested separately from below ground tissue. Suitable above ground tissues include shoots, stems, leaves, flowers, grain, and seed. Exemplary below ground tissues include roots and root hairs. In one embodiment, whole plants are harvested and the above ground tissue is subsequently separated from the below ground tissue.

Genetic constructs may encode a selectable marker to enable selection of transformation events. There are many methods that have been described for the selection of transformed plants [for review see (Miki et al., *Journal of Biotechnology,* 2004, 107, 193-232) and references incorporated within]. Selectable marker genes that have been used extensively in plants include the neomycin phosphotransferase gene nptII (U.S. Pat. Nos. 5,034,322, 5,530,196), hygromycin resistance gene (U.S. Pat. No. 5,668,298, Waldron et al., (1985), *Plant Mol Biol,* 5:103-108; Zhijian et al., (1995), *Plant Sci,* 108:219-227), the bar gene encoding resistance to phosphinothricin (U.S. Pat. No. 5,276,268), the expression of aminoglycoside 3′-adenyltransferase (aad4) to confer spectinomycin resistance (U.S. Pat. No. 5,073,675), the use of inhibition resistant 5-enolpyruvyl-3-phosphoshikimate synthetase (U.S. Pat. No. 4,535,060) and methods for producing glyphosate tolerant plants (U.S. Pat. Nos. 5,463, 175; 7,045,684). Other suitable selectable markers include, but are not limited to, genes encoding resistance to chloramphenicol (Herrera Estrella et al., (1983), *EMBO J,* 2:987-992), methotrexate (Herrera Estrella et al., (1983), *Nature,* 303:209-213; Meijer et al, (1991), *Plant Mol Biol,* 16:807-820); streptomycin (Jones et al., (1987), *Mol Gen Genet,* 210:86-91); bleomycin (Hille et al., (1990), *Plant Mol Biol,* 7:171-176); sulfonamide (Guerineau et al., (1990), *Plant Mol Biol,* 15:127-136); bromoxynil (Stalker et al., (1988), *Science,* 242:419-423); glyphosate (Shaw et al., (1986), *Science,* 233:478-481); phosphinothricin (DeBlock et al., (1987), *EMBO J,* 6:2513-2518).

Methods of plant selection that do not use antibiotics or herbicides as a selective agent have been previously described and include expression of glucosamine-6-phosphate deaminase to inactive glucosamine in plant selection medium (U.S. Pat. No. 6,444,878) and a positive/negative system that utilizes D-amino acids (Erikson et al., *Nat Biotechnol,* 2004, 22, 455-8). European Patent Publication No. EP 0 530 129 A1 describes a positive selection system which enables the transformed plants to outgrow the non-transformed lines by expressing a transgene encoding an enzyme that activates an inactive compound added to the growth media. U.S. Pat. No. 5,767,378 describes the use of mannose or xylose for the positive selection of transgenic plants.

Methods for positive selection using sorbitol dehydrogenase to convert sorbitol to fructose for plant growth have also been described (WO 2010/102293). Screenable marker genes include the beta-glucuronidase gene (Jefferson et al., 1987, *EMBO J.* 6: 3901-3907; U.S. Pat. No. 5,268,463) and native or modified green fluorescent protein gene (Cubitt et al., 1995, *Trends Biochem. Sci.* 20: 448-455; Pan et al., 1996, *Plant Physiol.* 112: 893-900).

Transformation events can also be selected through visualization of fluorescent proteins such as the fluorescent proteins from the nonbioluminescent Anthozoa species which include DsRed, a red fluorescent protein from the Discosoma genus of coral (Matz et al. (1999), Nat Biotechnol 17: 969-73). An improved version of the DsRed protein has been developed (Bevis and Glick (2002), Nat Biotech 20: 83-87) for reducing aggregation of the protein.

Visual selection can also be performed with the yellow fluorescent proteins (YFP) including the variant with accelerated maturation of the signal (Nagai, T. et al. (2002), Nat Biotech 20: 87-90), the blue fluorescent protein, the cyan fluorescent protein, and the green fluorescent protein (Sheen et al. (1995), Plant J 8: 777-84; Davis and Vierstra (1998), Plant Molecular Biology 36: 521-528). A summary of fluorescent proteins can be found in Tzfira et al. (Tzfira et al. (2005), Plant Molecular Biology 57: 503-516) and Verkhusha and Lukyanov (Verkhusha, V. V. and K. A. Lukyanov (2004), Nat Biotech 22, 289-296) whose references are incorporated in entirety. Improved versions of many of the fluorescent proteins have been made for various applications. It will be apparent to those skilled in the art how to use the improved versions of these proteins or combinations of these proteins for selection of transformants.

The plants modified for enhanced performance may be combined or stacked with input traits by crossing or plant breeding. Useful input traits include herbicide resistance and insect tolerance, for example a plant that is tolerant to the herbicide glyphosate and that produces the *Bacillus thuringiensis* (BT) toxin. Glyphosate is a herbicide that prevents the production of aromatic amino acids in plants by inhibiting the enzyme 5-enolpyruvylshikimate-3-phosphate synthase (EPSP synthase). The overexpression of EPSP synthase in a crop of interest allows the application of glyphosate as a weed killer without killing the modified plant (Suh, et al., J. M Plant Mol. Biol. 1993, 22, 195-205). BT toxin is a protein that is lethal to many insects providing the plant that produces it protection against pests (Barton, et al. Plant Physiol. 1987, 85, 1103-1109). Other useful herbicide tolerance traits include but are not limited to tolerance to Dicamba by expression of the dicamba monoxygenase gene (Behrens et al, 2007, Science, 316, 1185), tolerance to 2,4-D and 2,4-D choline by expression of a bacterial aad-1 gene that encodes for an aryloxyalkanoate dioxygenase enzyme (Wright et al., Proceedings of the National Academy of Sciences, 2010, 107, 20240), glufosinate tolerance by expression of the bialophos resistance gene (bar) or the pat gene encoding the enzyme phosphinotricin acetyl transferase (Droge et al., Planta, 1992, 187, 142), as well as genes encoding a modified 4-hydroxyphenylpyruvate dioxygenase (HPPD) that provides tolerance to the herbicides mesotrione, isoxaflutole, and tembotrione (Siehl et al., Plant Physiol, 2014, 166, 1162). The plants modified for enhanced yield by reducing the expression of the transcription factor genes or transcription factor gene combinations may be combined or stacked with other genes which improve plant performance.

Genome Editing

Genome editing can also be used to accomplish genetic modification of plants according to the invention. An advantage of using genome editing technologies is that the regulatory body in the United States views genome editing as an advanced plant breeding tool and may not regulate the technologies. Recent advances in genome editing technologies provide an opportunity to precisely remove genes, edit control sequences, introduce frame shift mutations, etc., to significantly alter the expression levels of targeted genes and/or the activities of the proteins encoded thereby. Plants engineered using this approach may be defined as non-regulated by USDA-APHIS providing the opportunity to continually improve the plants. Given the timelines and costs associated with achieving regulatory approval for transgenic plants this approach enables a single regulatory filing instead of having to continuously file for regulatory approval for each subsequent genetic modification to improve the plants.

Genome editing can be accomplished by using Clustered Regularly Interspaced Short Palindromic Repeats (CRISPR/Cas9) or CRISPR/Cpf1. The use of this technology in genome editing is well described in the art (Fauser et al, 2014, The Plant Journal, Vol 79, p 348-359; Belhaj, K., 2013, Plant Methods 9, 39; Khandagale & Nadal, 2016, Plant Biotechnol Rep 10, 327). In short, CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). At least two classes (Class I and II) and six types (Types 1-VI) of Cas proteins have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). The Type II CRISPR/Cas is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA: tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Cas9 is thus the hallmark protein of the Type II CRISPR-Cas system, and a large monomeric DNA nuclease guided to a DNA target sequence adjacent to the PAM (protospacer adjacent motif) sequence motif by a complex of two noncoding RNAs. CRISPR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms.

For applications in eukaryotic organisms, codon optimized versions of Cas9, which is originally from the bacterium *Streptococcus pyogenes*, have been used. The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is 20 bp. In plants, sgRNAs have been expressed using plant RNA polymerase Ill promoters, such as U6 and U3. Cas9 expression plasmids for use in the methods of the invention can be constructed as described in the art.

The Cas9 enzyme and sgRNA can introduced to the cells to be edited using multiple methods. Genetic transformation of an expression construct encoding the sgRNA and the Cas9 enzyme (FIG. 3) can be used to edit the cells. Subsequent removal of the transgenes encoding the sgRNA and the Cas9 enzyme can be achieved through segregation yielding plants with only the genome edit. Alternatively, the sgRNA can be synthesized in vitro and introduced into cells, often in the form of Ribonucleoprotein complexes (RNPs) that contain Cas9 protein to promote cleavage of the target genomic DNA at the "guide target sequence".

Various other methods can be used for gene editing, by using transcription activator-like effector nucleases (TALENs), clustered Regularly Interspaced Short Palindromic Repeats (CRISPR/Cas9) or zinc-finger nucleases (ZFN) techniques (as described in Belhaj et al, 2013, Plant Methods, vol 9, p 39, Chen et al, 2014 Methods Volume 69, Issue 1, p 2-8).

EXAMPLES

Example 1. Identification of the *Camelina* Orthologs of the *Arabidopsis* BADC Genes BADC encodes the Biotin/lipoyl Attachment Domain Containing protein. BADC protein has been proposed to be a negative regulator of acetyl-CoA carboxylase (ACCase, Salie et al., Plant Cell, 2016, 28, 2312), the first committed step in de novo fatty acid biosynthesis (FIG. 1). BADC protein also has been proposed, alternatively, to facilitate the assembly and activation of BCCP-BADC-BC subcomplexes catalyzing bicarbonate-dependent hydrolysis of ATP, which is the first half-reaction catalyzed by acetyl-CoA carboxylase (Shivaiah et al., 2020, Plant Physiology, 182, 756). In any case, one or more of the *Camelina* BADC homeologs can be edited into *Camelina* lines. With reference to PCT/US2016/041386 to University of Missouri (published as WO 2017/039834), the one or more BADC homeolog edits may serve to increase carbon flow into fatty acid biosynthesis further increasing oil content.

The *Camelina* genome was searched for BADC orthologs using the *Arabidopsis* BADC protein sequences as BLAST queries. Since *Camelina* is an allohexaploid containing three subgenomes (for review see Malik et al., 2018, Plant Cell Rep, 37, 1367), three orthologs for each of the *Arabidopsis* BADC genes are expected. Nine BADC genes were identified in the *Camelina* genome and are listed in TABLE 1. These include three orthologs each to the *Arabidopsis* AtBADC1 gene (CsBADC1-1 located on chromosome 4, CsBADC1-2 located on chromosome 6, and CsBADC1-3 located on chromosome 9), AtBADC2 gene (CsBADC2-1 on chromosome 17, CsBADC2-2 on chromosome 14, and CsBADC2-3 on chromosome 3), and AtBADC3 gene (CsBADC3-1 on chromosome 15, CsBADC3-2 on chromosome 19, and CsBADC3-3 on chromosome 1) (TABLE 1). Guide sequences for constructing editing constructs to edit the BADC genes are shown in TABLE 2.

DNA sequencing was performed on the nine BADC genes of *Camelina sativa* germplasm WT43 and compared to the sequences for *Camelina sativa* germplasm. DH55. The DH55 and WT43 BADC genes were found to be identical with the exception of CsBADC2-2, which differed by a single base pair. The one base pair difference in the DNA sequence of DH55 BADC2-2 (SEQ ID NO: 18) and WT43 (SEQ ID NO: 33) is however a silent mutation such that the DH55 BADC2-2 protein is identical to the WT43 BADC2-2 protein.

TABLE 2

Guide sequences for editing BADC genes in Camelina.

| Guide name | Target Gene | Guide target[1] | | | |
|---|---|---|---|---|---|
| | | Chromo-some # | Strand | Guide target sequence (5' to 3') | PAM |
| CsC1-69 | CsBADC1-1 | 4 | − | GGTTGTTGTCGAAGT | AGG |
| | CsBADC1-2 | 6 | | TTTAG | |
| | CsBADC1-3 | 9 | | (SEQ ID NO: 24) | |
| CsC2-33 | CsBADC2-1 | 17 | + | GCTCATTCCCAAGTC | AGG |
| | CsBADC2-2 | 14 | | CTCTG | |
| | CsBADC2-3 | 3 | | (SEQ ID NO: 25) | |

TABLE 1

BADC Genes in *Arabidopsis* and *Camelina*.

| *Arabidopsis* gene (*Arabidopsis* gene locus) | Target Gene (Chromosome location; SEQ ID NO) | GenBank mRNA Accession* | GenBank Protein Accession | DH55 LOC No. | GenBank annotation | CDS Size (bp) |
|---|---|---|---|---|---|---|
| AtBADC1 (AT3G56130) | CsBADC1-1 (Ch 4; SEQ ID NO: 14) | XM_010506195.2 | XP_010504497.1 | LOC104781505 | BCCP-like | 831 |
| | CsBADC1-2 (Ch 6; SEQ ID NO: 15) | XM_010517912.2 | XP_010516214.1 | LOC104791905 | BCCP-like | 831 |
| | CsBADC1-3 (Ch 9; SEQ ID NO: 16) | XM_010429119.2 | XP_010427421.1 | LOC104712265 | BCCP-like | 831 |
| AtBADC2 (AT1GS2670) | CsBADC2-1 (Ch 17; SEQ ID NO: 17) | XM_010481479.2 | XP_010479781.1 | LOC104758587 | BCCP | 831 |
| | CsBADC2-2 (Ch 14; SEQ ID NO: 18) | XM_010463810.2 | XP_010462112.1 | LOC104742768 | BCCP, X1 | 810 |
| | CsBADC2-3 (Ch 3; SEQ ID NO: 19) | XM_010502574.2 | XP_010500876.1 | LOC104778185 | BCCP, X1 | 810 |
| AtBADC3 (AT3G15690) | CsBADC3-1 (Ch 15; SEQ ID NO: 20) | XM_010467246.2 | XP_010465548.1 | LOC104745878 | BCCP | 792 |
| | CsBADC3-2 (Ch 19: SEQ ID NO: 21) | XM_010489100.2 | XP_010487402.1 | LOC104765401 | BCCP | 792 |
| | CsBADC3-3 (Ch 1: SEQ ID NO: 22) | XM_010505032.2 | XP_010503334.1 | LOC104780528 | BCCP | 792 |

*GenBank sequence data is from Camelina line DH55 mRNA.

Abbreviation: Ch, chromosome.

TABLE 2-continued

Guide sequences for editing BADC genes in Camelina.

| | | | | Guide target[1] | |
| | | | | Guide target | |
| Guide name | Target Gene | Chromo- some # | Strand | sequence (5' to 3') | PAM |
|---|---|---|---|---|---|
| CsC3- 52 | CsBADC3-1 CsBADC3-2 CsBADC3-3 | 15 19 1 | – | GATCCCTTGCTACAT ATAGG (SEQ ID NO: 26) | CGG |

Figure 3:
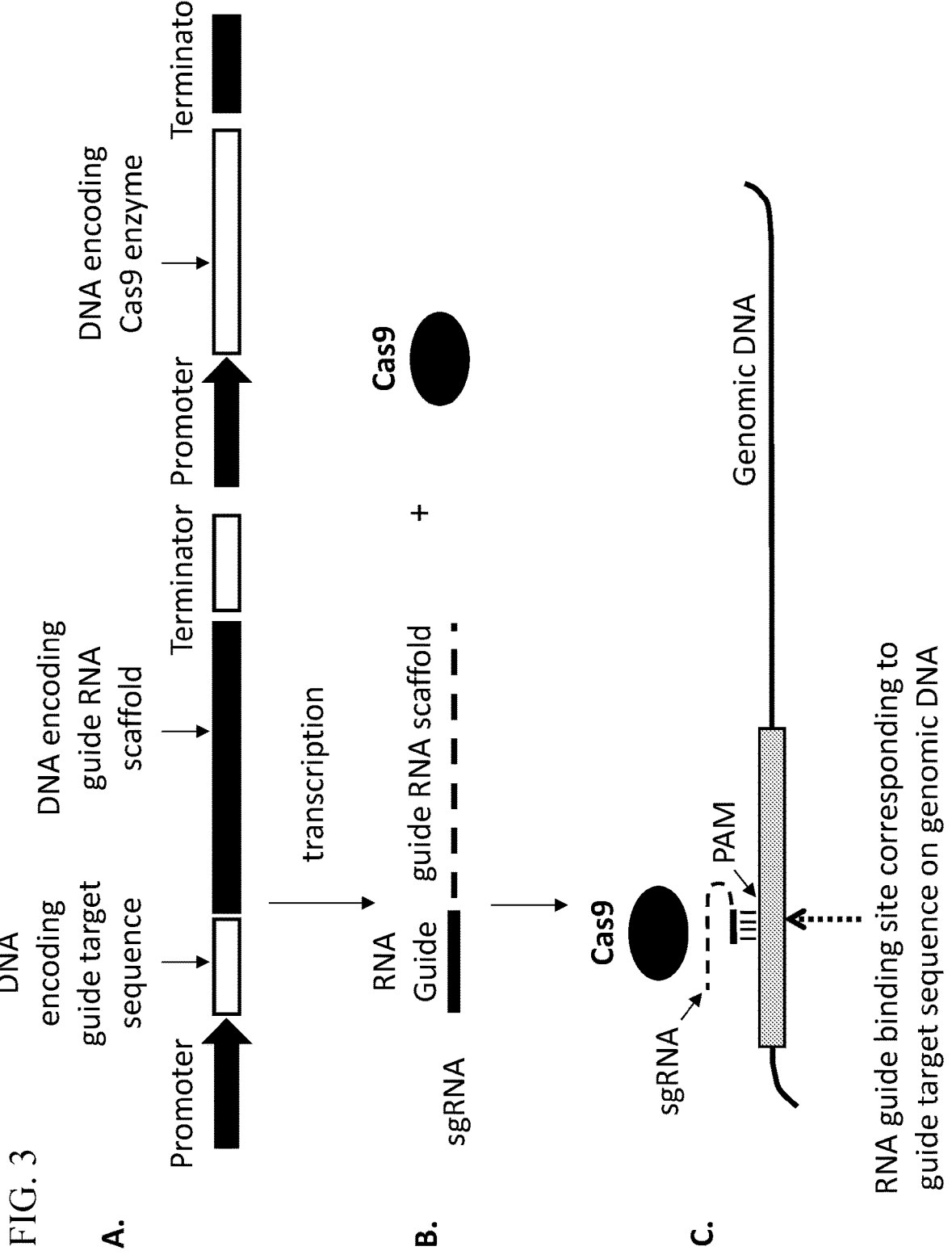
FIG. 3 illustrates the genetic elements transformed into plants to achieve Cas9 mediated genome editing. (A) Separate cassettes for expression of a DNA molecule encoding a single guide RNA (sgRNA) and a gene encoding the Cas9 enzyme. The expression cassette for the sgRNA is composed of DNA encoding a guide target sequence, targeted to the gene of interest in the *Camelina* genome, fused to DNA encoding a guide RNA scaffold. The DNA encoding the guide portion of the sgRNA is often identical to the "guide target sequence" of the genomic DNA to be cut, however several mismatches, depending on their position, can be tolerated and still promote double stranded DNA cleavage. (B) A sgRNA and Cas9 enzyme are produced. (C) Pairing of the sgRNA to genomic DNA at the target site, which lies adjacent to a protospacer adjacent motif (PAM) site, an additional requirement for target recognition. A double stranded DNA break will occur at a position within the Guide target site.

[1]An sgRNA is composed of DNA encoding a guide target sequence, targeted to the gene of interest in the Camelina genome, fused to DNA encoding a guide RNA scaffold (FIG. 3). Pairing of the sgRNA to genomic DNA at the target site requires an adjacent protospacer adjacent motif (PAM) site, an additional require- ment for target recognition. The adjacent PAM sequence is listed in the table.

Figure 2:
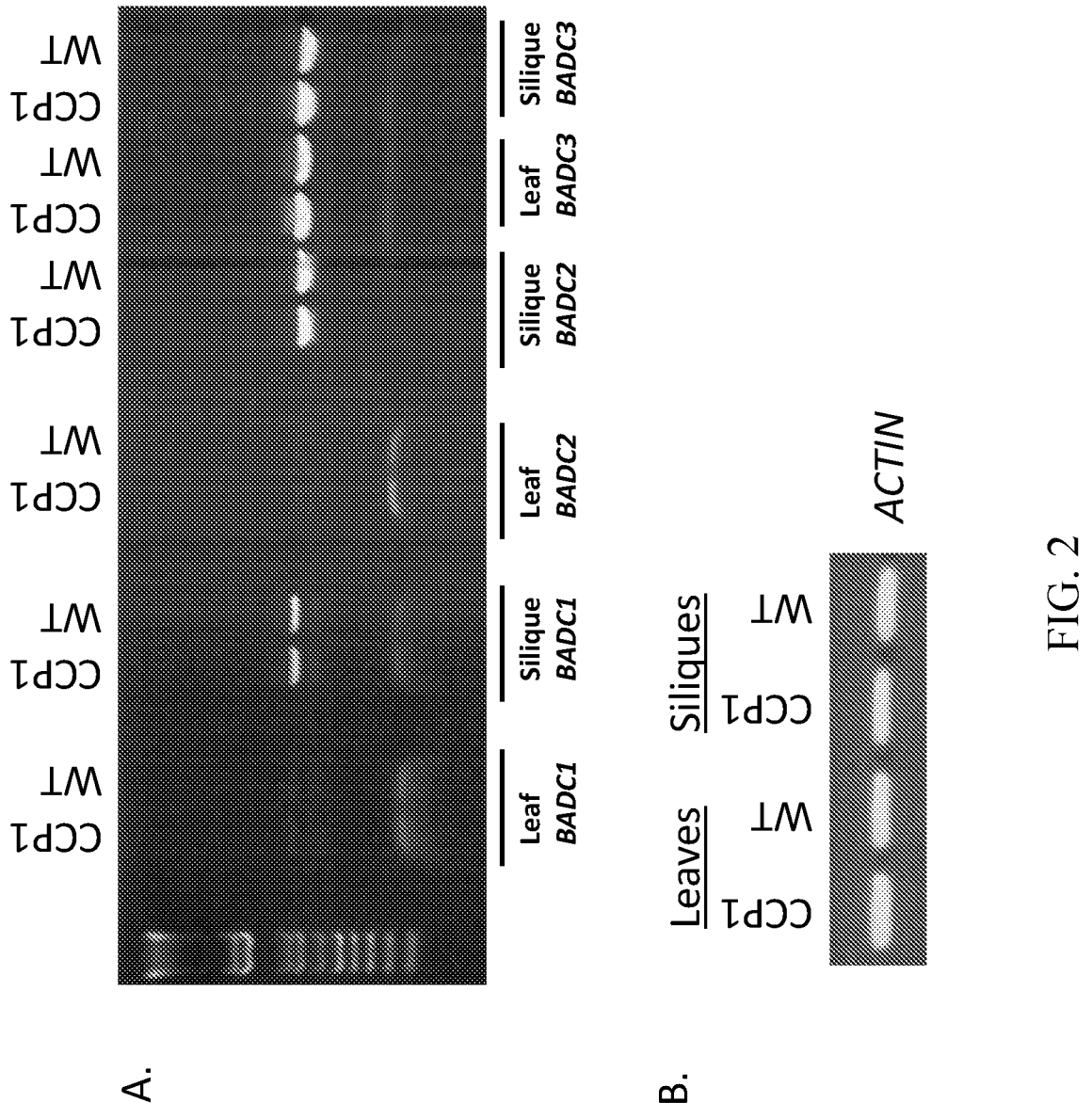
FIG. 2 illustrates expression profiles of CsBADC1, CsBADC2, and CsBADC3 genes in *Camelina sativa*. (A) Agarose gel from electrophoresis of RT-PCR reactions with primers specific for BADC1, BADC2, or BADC3. Samples of cDNA were obtained from a *C. sativa* genotype WT43 expressing the CCP1 gene (labeled CCP1, WO 2015/103074) and a wild-type plant from *C. sativa* genotype WT43 (labeled WT). (B) Agarose gel from electrophoresis of RT-PCR reactions with primers specific for the actin gene as a control. Samples of cDNA were obtained from a *C. sativa* genotype WT43 expressing the CCP1 gene (labeled CCP1, WO 2015/103074) and a wild-type plant from *C. sativa* genotype WT43 (labeled WT).

RT-PCR experiments were performed on wild-type WT43 line and a transgenic plant with a yield enhancement trait, CCP1 (WO 2015/103074), to determine the expression of the BADC1, BADC2, and BADC3 in leaf or developing silique tissues. RT-PCR was performed with Q5 high fidelity enzyme with one μL of cDNA from each tissue and primers specific for each gene. 25 μL of each sample was loaded on an agarose gel and resolved by electrophoresis. FIG. 2 shows the differences in expression profiles of the genes. CsBADC1 and CsBADC2 are primarily expressed in the developing silique tissue and not in the leaves whereas BADC3 is expressed in both the leaf and silique tissue. For reference, RNA seq expression data are available for Camelina sativa based on development of a transcriptome atlas for twelve developmental stages of the plant (Kagale et al., 2016, The Plant Journal, 88, 879).

Lines containing the badc1, badc2, and/or badc3 edits can be constructed to increase seed yield and seed oil content in Camelina. The badc edits are designed to reduce or elimi- nate the activity of the encoded enzyme.

Example 2. Genome Editing of the Camelina sativa Badc Genes Encoding Biotin/Lipoyl Attachment Domain Containing Proteins The large-seeded C. sativa germplasm 10CS0043 (abbre- viated WT43) that was obtained from a breeding program at Agriculture and Agri-Food Canada was used for genome editing of the badc1, badc2, and/or badc3 gene targets. To create mutations in the badc genes, genetic constructs were designed that would generate a single guide RNA (sgRNA) within the plant cell and produce a functional Cas9 enzyme molecule. FIG. 3 shows the genetic elements required for editing and how they interact with genomic DNA to achieve an edit. Genetic construct pMBXS1200 (FIG. 4; SEQ ID NO: 11), a binary vector containing expression cassettes to produce sgRNAs to simultaneously target editing of the badc1, badc2, and badc3 genes, a plant-codon optimized Cas9 (pcoCas9, Li et al., 2013. Nature Biotechnology, 31, 688), and the DsRed gene, which encodes a red fluorescent protein from the Discosoma genus of coral (Matz et al., 1999, Nat Biotechnol 17, 969), was constructed. DsRed expression can be used to distinguish transformed T1 seeds from untransformed seeds using a fluorescence microscope or by shining light of the correct wavelength on the seeds and viewing through the appropriate filter.

Construct pMBXS1200 (FIG. 4) was transformed into Camelina using Agrobacterium-mediated floral dip transfor- mation procedures (Lu and Kang, 2008, Plant Cell Rep, 27, 273) as follows.

In preparation for plant transformation experiments, seeds of Camelina sativa germplasm 10CS0043 (abbreviated WT43, obtained from Agriculture and Agri-Food Canada) were sown directly into 4 inch (10 cm) pots filled with soil in the greenhouse. Growth conditions were maintained at 24° C. during the day and 18° C. during the night. Plants were grown until flowering. Plants with a number of unopened flower buds were used in "floral dip" transforma- tions.

Agrobacterium strain GV3101 (pMP90) was transformed with plasmid pMBXS1200 using electroporation. A single colony of GV3101 (pMP90) containing the construct of interest was obtained from a freshly streaked plate and was inoculated into 5 mL LB medium. After overnight growth at 28° C., 2 mL of culture was transferred to a 500-mL flask containing 300 mL of LB and incubated overnight at 28° C. Cells were pelleted by centrifugation (4,000 rpm, 20 min), and diluted to an OD600 of ~0.8-1.0 with infiltration medium containing 5% sucrose and 0.05% (v/v) Silwet-L77 (Lehle Seeds, Round Rock, TX, USA). Plants of Camelina sativa germplasm WT43 were transformed by "floral dip" using the pMBXS1200 (FIG. 4) transformation construct as follows. Pots containing plants at the flowering stage were placed inside a 460 mm height vacuum desiccator (Bel-Art, Pequannock, NJ, USA). Inflorescences were immersed into the Agrobacterium inoculum contained in a 500-ml beaker. A vacuum (85 kPa) was applied and held for 5 min. Plants were removed from the desiccator and were covered with plastic bags in the dark for 24 h at room temperature. Plants were removed from the bags and returned to normal growth conditions within the greenhouse for seed formation (T1 generation of seed).

T1 seeds were screened by monitoring the expression of DsRed, a marker on the T-DNA in plasmid vector pMBXS1200 (FIG. 4) allowing the identification of trans- genic seeds. DsRed expression in the seed was visualized by fluorescent microscopy using a Nikon AZ100 microscope with a TRITC-HQ(RHOD)2 filter module (HQ545/30X, Q570LP, HQ610/75M) as previously described (Malik et al., 2015, Plant Biotechnology Journal, 13, 675).

T1 generation DsRed+ seeds were selected and planted in soil. Plantlets were grown in a greenhouse under supple- mental lighting. Tissue was harvested from plants with 3-4 leaves and Amplicon sequencing was used to identify edited lines. Amplicon sequencing allows a survey of the different types of edits in a plant (i.e. deletions, insertions) as well as a determination of the number of alleles of the target gene that are edited. A fee for service provider was used to perform Amplicon sequencing work.

After confirmation of edits in T1 lines, select lines were advanced by growing the plants to produce second genera- tion seed. The segregation of the transformed T-DNA sequences (includes expression cassettes for the DsRed marker gene, Cas9 enzyme, and sgRNA) from the edited line was monitored with loss of the visible DsRed marker forming E2 seeds (second generation edited seeds that have lost the T-DNA but may retain the edit). Amplicon sequenc- ing was performed to verify that the edit was retained in the E2 DsRed-lines. At this point in line development, edits were not yet homozygous and often required at least one additional cycle of breeding to achieve a homozygous edit.

E2 lines were allowed to produce E3 seeds that were planted in the greenhouse to generate E3 lines. Tissue from E3 lines was harvested and edits were characterized by Amplicon sequencing. In the E3 generation different edits were obtained (TABLE 3). Although some editing of the badc1 gene was observed in early generations, this edit was lost in generation of later lines. Some lines were found to have increased oil per seed (mgs per seed) and increased seed oil content in bulk E4 seeds (% seed weight) (TABLE 3).

Lines from TABLE 3 that were homozygous for edits, and also had one edit on both homologous chromosomes, were chosen to propagate further to produce seeds for additional greenhouse studies and for field trials and are shown in TABLE 4. Sequences of edits were determined by Amplicon sequencing which was performed through a contract vendor. All edits in TABLE 4 were deletions that resulted in a truncated protein with the exception of edits on chromosome 14 of badc2, which removed 3 base pairs such that one amino acid was removed from the protein.

TABLE 3

Summary of badc1, badc2, and badc3 edits in select Camelina generation E3 lines producing E4 seed.

| | Summary of Edits in Tissue from E3 lines[1] | | | | | | | | | % increase oil per E4 seed (mg per seed) | % increase 1000 E4 seed weight | % increase E4 seed oil content (% seed weight) | % increase # E4 seeds produced per E3 plant | % increase total oil produced per E3 plant | % increase total E4 seed yield produced per E3 plant (grams) |
|---|---|---|---|---|---|---|---|---|---|---|---|---|---|---|---|
| | badc1 Ch | | | badc2 Ch | | | badc3 Ch | | | | | | | | |
| E3 Line | 4 | 6 | 9 | 3 | 14 | 17 | 1 | 15 | 19 | | | | | | |
| Wild-type | — | — | — | — | — | — | — | — | — | 0 | 0 | 0 | 0 | 0 | 0 |
| 18-3590 | — | — | — | X | X | — | — | — | — | 4.6 | 6.5 | −1.5 | 5.4 | 10.9 | 12.6 |
| 18-3592* | — | — | — | X | X | — | — | — | — | 15.6 | 10.4 | 7.5 | −4.7 | 13.4 | 5.6 |
| 18-3604* | — | — | — | X | X | — | — | — | — | 33.5 | 36.7 | −0.4 | −32.1 | −7.3 | −6.9 |
| 18-3640* | — | — | — | X | X | — | — | — | — | 26.0 | 14.2 | 3.8 | −17.2 | −1.6 | −5.1 |
| 18-3696* | — | — | — | X | X | — | — | — | — | 12.6 | 7.7 | 3.0 | 7.8 | 19.9 | 16.5 |
| 18-3697* | — | — | — | X | X | — | — | — | — | 18.3 | 11.6 | 3.2 | −4.3 | 10.6 | 7.2 |
| 18-3565 | — | — | — | X | X | — | — | — | — | 16.4 | 1.81 | 6.2 | −13.6 | −6.3 | −11.7 |
| 19-2310 | — | — | — | — | — | — | X | X | — | −6.76 | −8.81 | 0.35 | 0.75 | −7.78 | −8.10 |
| 19-2341 | — | — | — | — | — | — | X | X | — | 0.01 | −2.35 | 4.05 | −3.74 | −2.17 | −5.98 |
| 19-2308 | — | — | — | x | — | — | X | X | — | −4.38 | −5.35 | −0.43 | 8.76 | 2.52 | 2.97 |
| 19-2309 | — | — | — | x | — | — | X | X | — | −7.62 | −9.27 | −0.67 | 13.95 | 2.71 | 3.41 |
| 19-2345 | — | — | — | x | — | — | X | X | — | −5.24 | −2.12 | −4.68 | −15.00 | −20.68 | −16.78 |
| 19-2307* | — | — | — | X | — | — | X | X | — | −7.66 | −9.04 | 0.20 | 12.30 | 2.37 | 2.17 |
| 19-2311* | — | — | — | X | — | — | X | X | — | −5.20 | −3.27 | −4.10 | 2.85 | −4.57 | −0.49 |
| 19-2315 | — | — | — | X | — | — | X | X | — | −1.95 | −3.50 | −0.80 | 12.00 | 7.24 | 8.10 |
| 19-2316 | — | — | — | X | — | — | X | X | — | −0.19 | −1.42 | 1.17 | 5.78 | 5.51 | 4.29 |
| 19-2320 | — | — | — | — | — | — | — | X | x | −1.53 | −4.42 | −1.45 | −10.91 | −16.06 | −14.83 |
| 19-2334 | — | — | — | — | — | — | — | X | x | −4.37 | −7.43 | 2.96 | 6.80 | 1.82 | −1.11 |
| 19-2337 | — | — | — | — | — | — | — | X | x | −6.20 | −6.04 | 0.58 | 0.80 | −4.72 | −5.27 |

[1]Symbol "X" denotes complete editing of the chromosomal allele of the gene; "x" denotes incomplete editing of the chromosomal allele of the gene; "—" denotes the wild-type sequence of the chromosomal allele of the gene; *denotes lines containing edits with two different sequences that will segregate.
Abbreviations: Ch, chromosome.

TABLE 4

Summary of badc2 and badc3 edits in select Camelina generation E4 lines.

| E3 Parent Line (TABLE 3) | E4 Line | Badc1 Ch | | | badc2 Ch | | | badc3 Ch | | | Sequence of Edited Region[2] |
|---|---|---|---|---|---|---|---|---|---|---|---|
| | | 4 | 6 | 9 | 3 | 14 | 17 | 1 | 15 | 19 | |
| Wild-type | Wild-type | | | | | | | | | | Wild-type badc2 Ch3 GCTCATTCCCAAGTCCTCTGAGG (SEQ ID NO: 1) Wild-type badc2 Ch14 GCTCATTCCCAAGTCCTCTGAGG (SEQ ID NO: 2) Wild-type badc3 Ch1 CCGCCTATATGTAGCAAGGGATCT (SEQ ID NO: 3) Wild-type badc3 Ch15 |

TABLE 4-continued

Summary of badc2 and badc3
edits in select Camelina generation E4 lines.

| E3 Parent Line (TABLE 3) | E4 Line | Badc1 Ch | | | badc2 Ch | | | badc3 Ch | | | Sequence of Edited Region[2] |
|---|---|---|---|---|---|---|---|---|---|---|---|
| | | 4 | 6 | 9 | 3 | 14 | 17 | 1 | 15 | 19 | |
| | | | | | | | | | | | CCGCCTATATGTAGCAAGGGATCT (SEQ ID NO: 4) |
| 18-3590 | 19-4925 | | | | X | X | | | | | badc2 Ch3 (2 base pair deletion forms truncated protein) GCTCATTCCCAAGTC--CTGAGG (SEQ ID NO: 5) badc2 Ch14 (3 base pair deletion removes 1 amino acid from protein) GCTCATTCCCAAGT---CTGAGG (SEQ ID NO: 6) |
| | 19-4931 | | | | X | X | | | | | badc2 Ch3 (2 base pair deletion forms truncated protein) GCTCATTCCCAAGTC--CTGAGG (SEQ ID NO: 5) badc2 Ch14 (3 base pair deletion removes 1 amino acid from protein) GCTCATTCCCAAGT---CTGAGG (SEQ ID NO: 6) |
| 18-3565 | 19-4935 | | | | X | X | | | | | badc2 Ch3 (10 base pair deletion forms truncated protein) GCTCATT----------CTGAGG (SEQ ID NO: 7) badc2 Ch14 (3 base pair deletion removes 1 amino acid from protein) GCTCATTCCCAAGT---CTGAGG (SEQ ID NO: 6) |
| | 19-4938 | | | | X | X | | | | | badc2 Ch3 (10 base pair deletion forms truncated protein) GCTCATT----------CTGAGG (SEQ ID NO: 7) badc2 Ch14 (3 base pair deletion removes 1 amino acid from protein) GCTCATTCCCAAGT---CTGAGG (SEQ ID NO: 6) |
| 19-2341 | 19-4973 | | | | | | | X | X | | badc3 Ch1 (4 base pair deletion forms truncated protein) CCGCCT----GTAGCAAGGGATC (SEQ ID NO: 8) badc3 Ch15 (22 base pair deletion forms truncated protein) C--------------------T (nucleotides 8-9 of SEQ ID NO: 9) |
| | 19-4974 | | | | | | | X | X | | badc3 Ch1 (4 base pair deletion forms truncated protein) CCGCCT----GTAGCAAGGGATC (SEQ ID NO: 8) badc3 Ch15 (22 base pair deletion forms truncated protein) C--------------------T (nucleotides 8-9 of SEQ ID NO: 9) |
| 19-2316 | 19-4997 | | | | X | | | X | X | | badc2 Ch3 (5 base pair deletion forms truncated protein) GCTCATTCCCAAG-----TGAGG (SEQ ID NO: 10) badc3 Ch1 (4 base pair deletion forms truncated protein) CCGCCT----GTAGCAAGGGATC (SEQ ID NO: 8) badc3 Ch15 (22 base pair deletion forms truncated protein) C--------------------T (nucleotides 8-9 of SEQ ID NO: 9) |

TABLE 4-continued

Summary of badc2 and badc3
edits in select Camelina generation E4 lines.

| E3 Parent Line (TABLE 3) | E4 Line | Badc1 Ch 4 | 6 | 9 | badc2 Ch 3 | 14 | 17 | badc3 Ch 1 | 15 | 19 | Sequence of Edited Region[2] |
|---|---|---|---|---|---|---|---|---|---|---|---|
| | 19-5000 | | X | | | X | X | | | | badc2 Ch3 (5 base pair deletion forms truncated protein) GCTCATTCCCAAG-----TGAGG (SEQ ID NO: 10) badc3 Ch1 (4 base pair deletion forms truncated protein) CCGCCT----GTAGCAAGGGATC (SEQ ID NO: 8) badc3 Ch15 (22 base pair deletion forms truncated protein) C--------------------T (nucleotides 8-9 of SEQ ID NO: 9) |
| 19-2334 | 19-5007 | | | | | | | | X | | badc3 Ch15 (22 base pair deletion forms truncated protein) C--------------------T (nucleotides 8-9 of SEQ ID NO: 9) |
| | 19-5008 | | | | | | | | X | | badc3 Ch15 (22 base pair deletion forms truncated protein) C--------------------T (nucleotides 8-9 of SEQ ID NO: 9) |

[1]Symbol "X" denotes complete homozygous editing of the chromosomal allele of the gene.
[2]For edited lines with deletions, the missing bases are designated with an "-".
Only sequences of edited genes are shown.
Abbreviations: Ch, chromosome.

Figure 4:
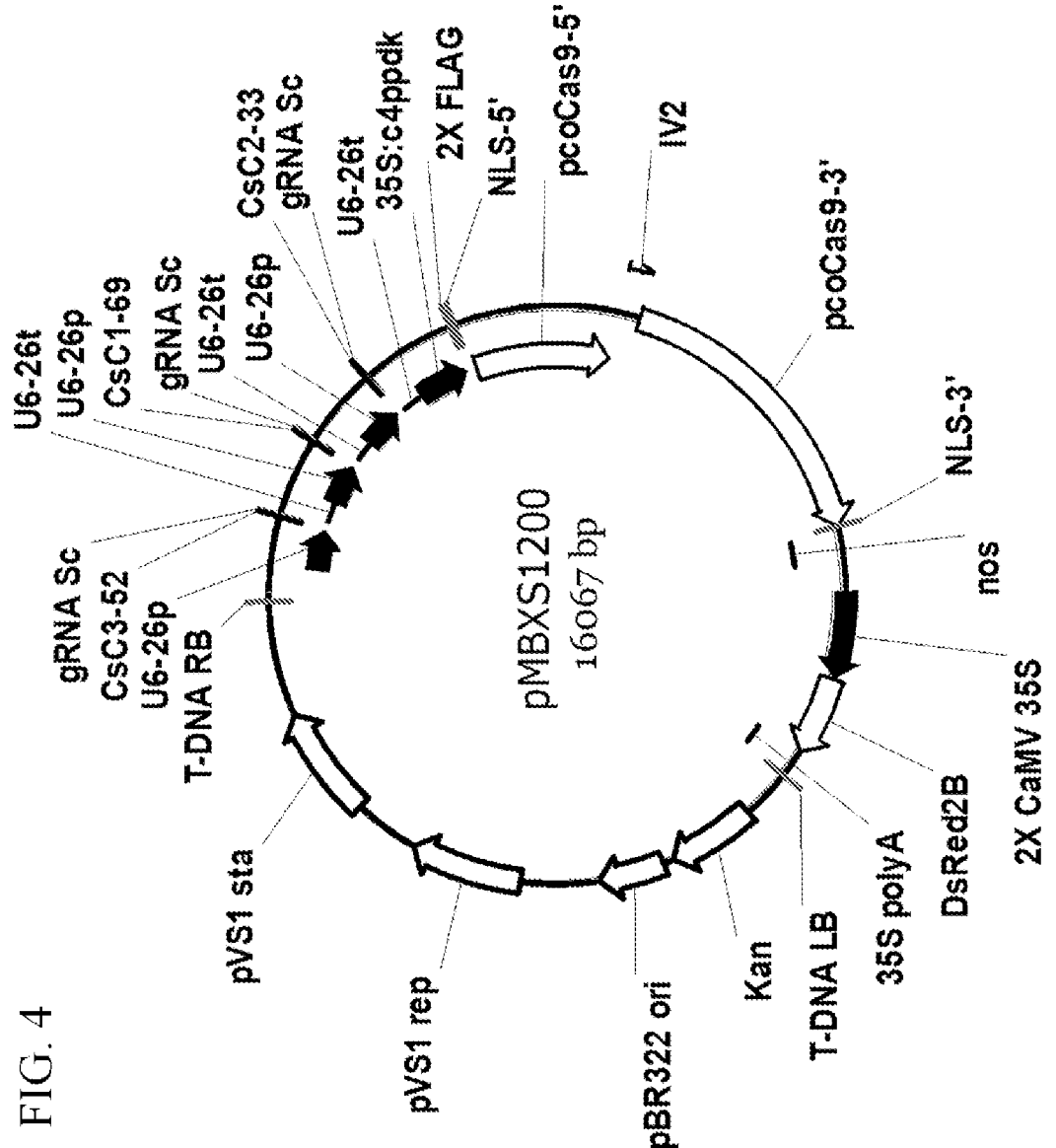
FIG. 4 illustrates the plasmid map of a binary vector pMBXS1200 (SEQ ID NO. 11) for Cas9 mediated genome editing of the nine *Camelina* BADC genes (CsBADC1-1, CsBADC1-2, CsBADC1-3, CsBADC2-1, CsBADC2-2, CsBADC2-3, CsBADC3-1, CsBADC3-2, and CsBADC3-3). Important genetic elements within the vector are as follows: U6-26p, a DNA fragment encoding the polymerase III promoter from the *Arabidopsis* U6-26 small nuclear RNA gene; Guide CsC3-52 (SEQ ID NO: 26), DNA encoding a 20 bp guide target sequence to edit CsBADC3-1, CsBADC3-2 and CsBADC3-3; gRNA Sc, DNA fragment encoding a Guide RNA scaffold encoding a crRNA-tracrRNA hybrid engineered from the *Streptococcus pyogenes* CRISPR locus (the DNA encoding the guide target sequence and gRNASc, when expressed together, form a functional sgRNA sequence); U6-26t, a DNA fragment encoding the terminator from the *Arabidopsis* U6-26 snRNA gene; Guide CsC1-69 (SEQ ID NO: 24), DNA encoding a 20 bp guide target sequence to edit CsBADC1-1, CsBADC1-2 and CsBADC1-3; Guide CsC2-33 (SEQ ID NO: 25), DNA encoding a 20 bp guide target sequence to edit CsBADC2-1, CsBADC2-2, and CsBADC2-3; 35S:C4PPDK promoter (Chiu et al., 1996, Curr. Biol., 6, 325); 2X Flag, a fragment encoding a FLAG polypeptide protein tag (Li et al., 2013, Nature Biotechnology, 31, 688) created by artificial design (Hopp et al., 1988, Bio/Technology, 6, 1204); NLS-5', a nuclear localization sequence encoding the peptide MAPKKKRK VGIHGVPAA (SEQ ID) NO: 23) (WO 2016114972) attached to the 5' end of Cas9; pcoCas9-5', DNA fragment encoding the 5' part of a Cas9 (CRISPR associated protein 9) from *Streptococcus pyogenes* codon-optimized for expression in plants (pcoCas9, Li et al., 2013, Nature Biotechnology, 31, 688); IV2, a DNA sequence encoding the second intron (IV2) of the nuclear photosynthetic gene ST-LS1 from *Solanum tuberosum* (Vancanneyt et al., 1990, Molecular and General Genetics, 220, 245); pco-Cas9-3', DNA fragment encoding the 3' part of Cas9 (the 5' fragment and the 3' fragment of pcoCas9 together form the complete Cas9 protein coding sequence); NLS-3', DNA fragment encoding the nuclear localization sequence of nucleoplasmin, a protein involved in chromatin assembly and histone storage in the *Xenopus* oocyte and egg (Dingwall et al., 1988, Journal of Cell Biology, 1988, 107, 841), attached to the 3' end of Cas9; nos, a termination sequence. An expression cassette for the DsRed protein driven by the 2X CaMV 35S promoter provides a visual selection of transgenic seeds.

The results in TABLES 3 and 4 suggest that it is difficult to obtain a line with edits in all three bade genes (badc1, badc2, and badc3) in *Camelina* transformed with genetic construct pMBXS1200 (FIG. 4). In addition, we were not able to obtain edits of badc1, badc2, or badc3 where all three homeologs of the gene were edited. While some level of badc1 gene edits (less than 2% editing) were obtained in earlier generations upon transformation of *Camelina* with genetic construct pMBXS1200 (FIG. 4), these edits were lost in later generations. Certain combinations of edits obtained provided an advantage for increasing the amount of oil produced per plant. Edits in the badc2 gene on chromosomes 3 and 14 gave the highest increases in total oil per plant. Four lines (18-3590, 18-3592, 18-3696, and 18-3697) gave increases of at least 10% in oil produced per plant, with line 18-3696 giving a 19.9% increase. These same four lines (18-3590, 18-3592, 18-3696, and 18-3697) gave some of the highest increases in seed yield per plant, with line 18-3696 giving a 16.5% increase in seed yield. These four lines also gave increases in oil produced per seed (mg/seed) and 1000 seed weight with up to 18.3% increase in oil per seed and up to 11.6% increase in oil per seed observed for line 18-3697. Thus the identification of combinations of badc edits to increase seed yield and/or oil content is important.

Example 3. Genome Editing of the *Camelina sativa* Badc1 Gene Encoding Biotin/Lipoyl Attachment Domain Containing Proteins While some editing of badc1 was obtained in early generations with genetic construct pMBXS1200, these edits were lost to segregation in later generations. Additional attempts to edit the badc1 genes were made by redesigning the guide RNA targeting badc1 (TABLE 5) and focusing on only editing the badc1 gene.

TABLE 5

Redesigned guide sequence
for editing BADC1 genes in Camelina.

| Guide name | Target Gene | Strand | Guide target sequence (5' to 3') | PAM |
|---|---|---|---|---|
| C1-29A | CsBADC1-2 CsBADC1-3 | + | GTACTTCTTGTGTACCACGG (SEQ ID NO: 27) | TGG |
| C1-29B | CsBADC1-1 | + | GTACTTCTTGCGTTCCACGG (SEQ ID NO: 28) | TGG |
| C1-66 | CsBADC1-1 CsBADC1-2 CsBADC1-3 | − | GATATATCCTCCACAGGAAT (SEQ ID NO: 29) | GGG |

[1]An sgRNA is composed of DNA encoding a guide target sequence, targeted to the gene of interest in the Camelina genome, fused to DNA encoding a guide RNA scaffold (FIG. 3).

Pairing of the sgRNA to genomic DNA at the target site requires an adjacent protospacer adjacent motif (PAM) site, an additional requirement for target recognition. The adjacent PAM sequence in the genomic DNA is listed in the table.

Figure 5:
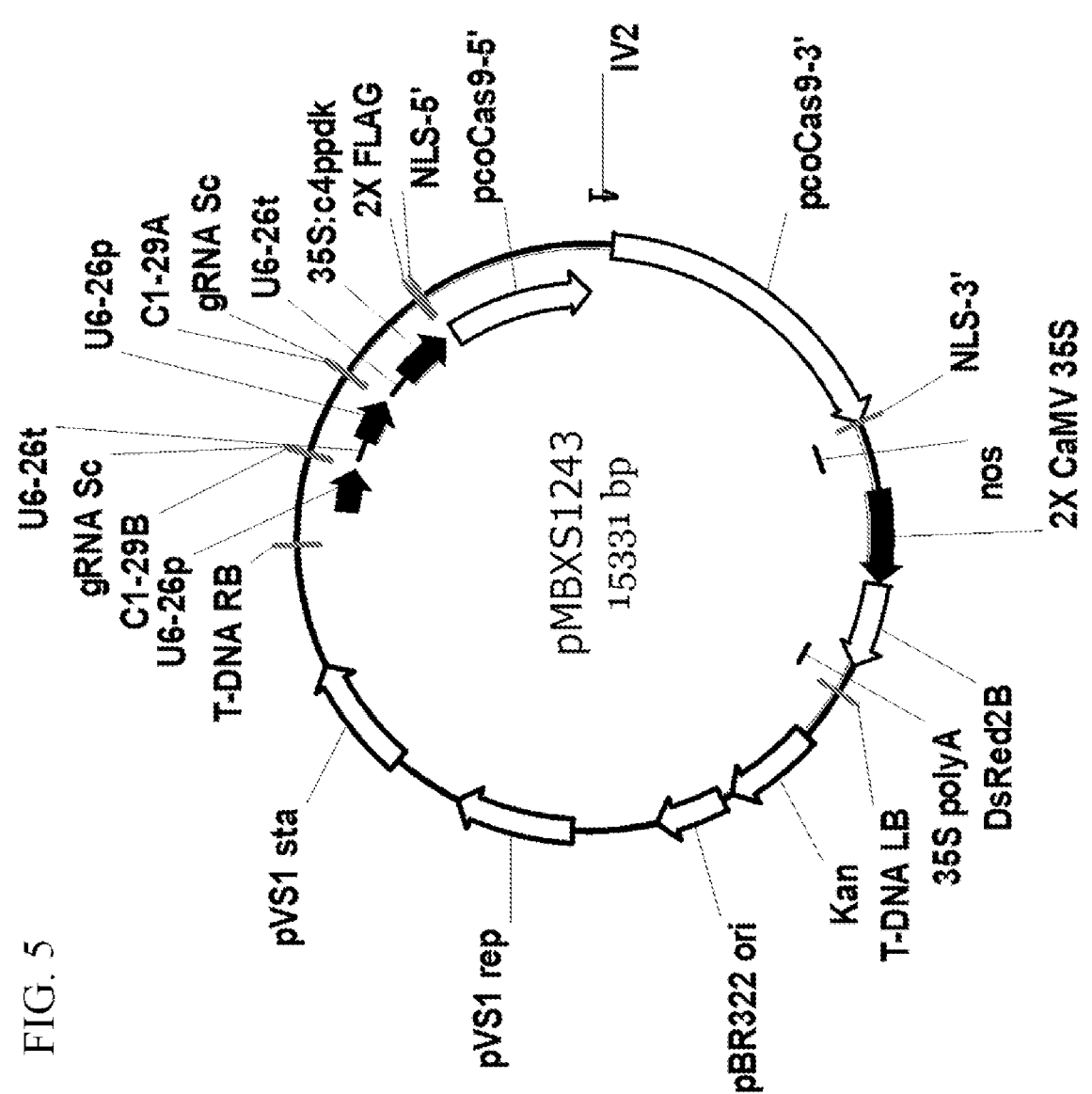
FIG. 5 illustrates the plasmid map of a binary vector pMBXS1243 (SEQ ID NO. 12) for Cas9 mediated genome editing of the three *Camelina* BADC1 genes (CsBADC1-1, CsBADC1-2, CsBADC1-3). Important genetic elements within the vector are as follows: U6-26p, a DNA fragment encoding the polymerase III promoter from the *Arabidopsis* U6-26 small nuclear RNA gene: Guide C1-29B (SEQ ID NO: 28), DNA encoding a 20 bp guide target sequence to edit the CsBADC1-1 gene; gRNA Sc, DNA fragment encoding a Guide RNA scaffold encoding a crRNA-tracrRNA hybrid engineered from the *Streptococcus pyogenes* CRISPR locus (the DNA encoding the guide target sequence and gRNASc, when expressed together, form a functional sgRNA sequence); U6-26t, a DNA fragment encoding the terminator from the *Arabidopsis* U6-26 snRNA gene; Guide C1-29A (SEQ ID NO: 27), DNA encoding a 20 bp guide target sequence to edit CsBADC1-2 and CsBADC1-3 genes; 35S:C4PPDK promoter (Chiu et al., 1996, Curr. Biol., 6, 325); 2X Flag, a fragment encoding a FLAG polypeptide protein tag (Li et al., 2013, Nature Biotechnology, 31, 688) created by artificial design (Hopp et al., 1988, Bio/Technology, 6, 1204); NLS-5', a nuclear localization sequence encoding the peptide MAPKKKRKVGIHGVPAA (SEQ ID NO: 23) (WO 2016114972) attached to the 5' end of Cas9; pcoCas9-5', DNA fragment encoding the 5' part of a Cas9 (CRISPR associated protein 9) from *Streptococcus pyogenes* codon-optimized for expression in plants (pcoCas9, Li et al., 2013, Nature Biotechnology, 31, 688); IV2, a DNA sequence encoding the second intron (IV2) of the nuclear photosynthetic gene ST-LS1 from *Solanum tuberosum* (Vancanneyt et al., 1990, Molecular and General Genetics, 220, 245); pcoCas9-3', DNA fragment encoding the 3' part of Cas9 (the 5' fragment and the 3' fragment of pcoCas9 together form the complete Cas9 protein coding sequence); NLS-3', DNA fragment encoding the nuclear localization sequence of nucleoplasmin, a protein involved in chromatin assembly and histone storage in the *Xenopus* oocyte and egg (Dingwall et al., 1988, Journal of Cell Biology, 1988, 107, 841), attached to the 3' end of Cas9; nos, a termination sequence. An expression cassette for the DsRed protein driven by the 2X CaMV 35S promoter provides a visual selection of transgenic seeds.

*Camelina* WT43 was transformed with pMBXS1243 (FIG. 5), using the *Camelina* transformation procedures described above, and T1 lines were obtained. Six out of 33

T1 lines with a high percentage of edits (greater than 40% in each chromosome of the three BADC1 genes) as determined by Amplicon sequencing, were obtained and advanced to the E2 generation in the greenhouse to remove the T-DNA insert by segregation (see above). Removal of the T-DNA insert was determined by monitoring the loss of the visual DsRed marker in seeds and performing PCR with primer sets spanning the entire plasmid. Lines that were homozygous for edits, on one chromosome or all three chromosomes were chosen to propagate further to produce seeds for field trials and are shown in TABLE 6. Sequences of edits were determined by Amplicon sequencing which was performed through a contract vendor. All edits in TABLE 6 were either 1 bp insertions or 1 to 5 bp deletions that resulted in a truncated protein.

TABLE 6

| Summary of badc1 edits in select Camelina generation E2 lines. | | | | | |
|---|---|---|---|---|---|
| T1 Parent Line | E2 Line | Summary of Edits[1] Badc1 Ch 4 | 6 | 9 | Sequence of Edited Region[2] |
| Wild-type | Wild-type | | | | Wild-type badc1 Ch4 GTACTTCTTGCGTTCCACGG (SEQ ID NO: 28) Wild-type badc1 Ch6 GTACTTCTTGTGTACCACGG (SEQ ID NO: 27) Wild-type badc1 Ch9 GTACTTCTTGTGTACCACGG (SEQ ID NO: 27) |
| 20-3483 | 20-4573 | | X | | badc1 Ch6 (1 base pair insertion forms truncated protein) GTACTTCTTGTGTACCAACGG (SEQ ID NO: 34) |
| 20-3484 | 20-4644 | X | | | badc1 Ch4 (1 base pair insertion forms truncated protein) GTACTTCTTGCGTTCCAACGG (SEQ ID NO: 35) |
| 20-3493 | 20-4724[3] | X | X | X | badc1 Ch4 (1 base pair insertion forms truncated protein) GTACTTCTTGCGTTCCAACGG (SEQ ID NO: 36) GTACTTCTTGCGTTCCAGCGG (SEQ ID NO: 37) badc1 Ch6 (5 base pair deletion forms truncated protein) GTACTTCTTGTGTA-----G (SEQ ID NO: 38) badc1 Ch9 (1 base pair insertion forms truncated protein) GTACTTCTTGTGTACCAGCGG (SEQ ID NO: 39) GTACTTCTTGTGTACCATCGG (SEQ ID NO: 40) |
| | 20-4757 | x | X | X | badc1 Ch4 (1 base pair insertion forms truncated protein) GTACTTCTTGCGTTCCACCGG (SEQ ID NO: 41) badc1 Ch6 (1 base pair insertion forms truncated protein) GTACTTCTTGTGTACCAACGG (SEQ ID NO: 42) badc1 Ch9 (1 base pair insertion forms truncated protein) GTACTTCTTGTGTACCATCGG (SEQ ID NO: 43) |
| | 20-4781 | X | X | X | badc1 Ch4 (1 base pair insertion forms truncated protein) GTACTTCTTGCGTTCCAACGG (SEQ ID NO: 44) badc1 Ch6 (1 base pair insertion forms truncated protein) GTACTTCTTGTGTACCAGCGG (SEQ ID NO: 45) badc1 Ch9 (2 base pair deletion forms truncated protein) GTACTTCTTGTGTACC--GG (SEQ ID NO: 46) |
| | 20-4799 | X | X | X | badc1 Ch4 (1 base pair insertion forms truncated protein) |

TABLE 6-continued

Summary of badc1 edits in select Camelina generation E2 lines.

| T1 Parent Line | E2 Line | Summary of Edits[1] Badc1 Ch 4 | 6 | 9 | Sequence of Edited Region[2] |
|---|---|---|---|---|---|
| | | | | | GTACTTCTTGCGTTCCAACGG (SEQ ID NO: 47) |
| | | | | | badc1 Ch6 (1 base pair deletion forms truncated protein) GTACTTCTTGTGTACC-CGG (SEQ ID NO: 48) |
| | | | | | badc1 Ch9 (1 base pair deletion forms truncated protein) GTACTTCTTGTGTACC-CGG (SEQ ID NO: 49) |
| | 20-4806[3] | X | X | X | badc1 Ch4 (1 base pair deletion forms truncated protein) GTACTTCTTGCGTTCC-CGG (SEQ ID NO: 50) |
| | | | | | badc1 Ch6 (1 base pair insertion forms truncated protein) GTACTTCTTGTGTACCAACGG (SEQ ID NO: 51) GTACTTCTTGTGTACCATCGG (SEQ ID NO: 52) |
| | | | | | badc1 Ch9 (1 base pair insertion forms truncated protein) GTACTTCTTGTGTACCAACGG (SEQ ID NO: 53) |
| | 20-4816[3] | X | X | X | badc1 Ch4 (1 base pair insertion forms truncated protein) GTACTTCTTGCGTTCCATCGG (SEQ ID NO: 54) |
| | | | | | badc1 Ch6 (1 base pair insertion forms truncated protein) GTACTTCTTGTGTACCAACGG (SEQ ID NO: 55) |
| | | | | | badc1 Ch9 (1 base pair insertion forms truncated protein) GTACTTCTTGTGTACCATCGG (SEQ ID NO: 56) GTACTTCTTGTGTACCAACGG (SEQ ID NO: 57) |
| | 20-4822[3] | X | X | x | badc1 Ch4 (1 base pair insertion forms truncated protein) GTACTTCTTGCGTTCCAGCGG (SEQ ID NO: 58) |
| | | | | | badc1 Ch6 (1 base pair insertion forms truncated protein) GTACTTCTTGTGTACCATCGG (SEQ ID NO: 59) |
| | | | | | badc1 Ch9 (1 base pair insertion or 2 base pair deletion forms truncated protein) GTACTTCTTGTGTACCATCGG (SEQ ID NO: 60) GTACTTCTTGTGTACCA--GG (SEQ ID NO: 61) |

[1]Symbol "X" denotes complete homozygous editing of the chromosomal allele of the gene.
[2]For edited lines with deletions, the missing bases are designated with an "-". Only sequences of edited genes are shown.
Abbreviations: Ch, chromosome.
[3]Lines that have two different types of edits on the homologous chromosomes.

Example 4. Crossing Edited *Camelina* Lines

Crossing of edited *Camelina* lines is being conducted.

To stack the BADC1 gene edits with BADC2 gene edits and BADC1 with BADC3 gene edits, manual crosses (TABLE 7) were performed between select parental lines described in TABLE 4 and TABLE 6.

The stacking of edits obtained by crossing will be confirmed by Amplicon sequencing in the F1 plants. F1 lines are advanced to develop lines with homozygous edits in all three genes of BADC1 and two out of three edited genes of BADC2. Additional F1 lines are advanced to develop lines with homozygous edits in all three genes of BADC1 and two out of three edited genes of BADC3. F2 seeds are harvested and plants are grown in flats and genotyped by Amplicon sequencing to identify lines that are homozygous for all five genes (one out of 1024 plants is expected to have five genes edited in a homozygous state). If homozygous edits for all five genes are not obtained in F2 stage, another generation of advancement and screening to obtain homozygous edits is performed.

TABLE 7

| F1 hybrids generated between Camelina lines edited for all three genes of BADC1 | | | | |
|---|---|---|---|---|
| Description of stacked edits | Crosses of Parental lines | Female parent | Male parent | # of F1 seeds obtained |
| BADC2 × BADC1 | 19-4935 × 20-4757 | 20-6196 (derived from E4 line 19-4935) | 20-6190 (derived from E2 line 20-4757) | 91 |
| BADC1 × BADC2 | 20-4781 × 19-4935 | 20-6193 (derived from E2 line 20-4781) | 20-6197 (derived from E4 line 19-4935) | 58 |
| BADC2 × BADC1 | 19-4935 × 20-4799 | 20-6197 (derived from E4 line 19-4935) | 20-6195 (derived from E2 line 20-4799) | 97 |
| BADC1 × BADC2 | 20-4816 × 19-4935 | 20-6178 (derived from E2 line 20-4816) | 20-6197 (derived from E4 line 19-4935) | 40 |
| BADC3 × BADC1 | 19-4973 × 20-4757 | 20-6198 (derived from E4 line 19-4973) | 20-6190 (derived from E2 line 20-4757) | 10 |
| BADC1 × BADC3 | 20-4781 × 19-4973 | 20-6192 (derived from E2 line 20-4781) | 20-6198 (derived from E4 line 19-4973) | 62 |
| BADC1 × BADC3 | 20-4799 × 19-4973 | 20-6195 (derived from E2 line | 20-6199 (derived from E4 line | 52 |

TABLE 7-continued

| F1 hybrids generated between Camelina lines edited for all three genes of BADC1 | | | | |
|---|---|---|---|---|
| Description of stacked edits | Crosses of Parental lines | Female parent | Male parent | # of F1 seeds obtained |
| | | from E2 line 20-4816) | from E4 line 19-4973) | |

Example 5. Identification of the *Brassica napus* Orthologs of *Arabidopsis* BADC Genes The *Brassica napus* (canola) genome from cultivar Darmor-bzh was searched for BADC orthologs using the *Arabidopsis* BADC protein sequences as BLAST queries (TABLE 8). *B. napus* (2n=38, AACC) is an allotetraploid crop that originated through natural hybridization of its progenitor species, *B. rapa* (2n=20, AA) and *B. oleracea* (2n=18, CC). There is a high level of collinearity between the A and C genomes of *B. napus* (Parkin et al. 2005, Genetics 171: 765-781). Six BADC genes were identified in the genomes and are listed in TABLE 8. These include two *B. napus* orthologs to the *Arabidopsis* BADC1 gene (At-BADC1), which are designated BnBADC1-1 and BnBADC1-2, and four orthologs to the AtBADC3 gene, designated BnBADC3-1, BnBADC3-2, BnBADC3-3, and BnBADC3-4. No orthologs to the *Arabidopsis* BADC2 genes were identified. The badc genes were also sequenced from *B. napus* cultivar DH12075. Sequence information for the BADC genes from the *B. napus* cultivar DH12075 also is shown in TABLE 8.

TABLE 8

| BADC Genes in *Arabidopsis* and *Brassica napus*. | | | | | | |
|---|---|---|---|---|---|---|
| *Arabidopsis* | | *B. napus* | *B. napus* cultivar Darmor-bzh | | *B. napus* cultivar DH12075 | |
| BADC gene | | ortholog | Gene[1] | Protein size | Gene | Protein |
| AtBADC1 | AT3G56130 | BnBADC1-1 | BnaA09g35590D | 270 aa | SEQ ID NO: 62 | SEQ ID NO: 68 270 aa |
| | | BnBADC1-2 | BnaC08g27030D | 258 aa | SEQ ID NO: 63 | SEQ ID NO: 69 258 aa |
| AtBADC2 | AT1G52670 | No candidate ortholog for AtBADC2 was found in *B.napus* | | | | |
| AtBADC3 | AT3G15690 | BnBADC3-1 | BnaA01g28580D | 249 aa | SEQ ID NO: 64 | SEQ ID NO: 70 249 aa |
| | | BnBADC3-2 | BnaA05g23850D | 253 aa | SEQ ID NO: 65 | SEQ ID NO: 71 253 aa |
| | | BnBADC3-3 | BnaC05g37660D | 254 aa | SEQ ID NO: 66 | SEQ ID NO: 72 256 aa |
| | | BnBADC3-4 | BnaC01g35870D | 254 aa | SEQ ID NO: 67 | SEQ ID NO: 73 254 aa |

[1]Darmor-bzh genes were obtained from website: genoscope.cns.fr/brassicanapus/.
[2]Abbreviations: aa, amino acids

TABLE 7-continued

| F1 hybrids generated between Camelina lines edited for all three genes of BADC1 | | | | |
|---|---|---|---|---|
| Description of stacked edits | Crosses of Parental lines | Female parent | Male parent | # of F1 seeds obtained |
| | | 20-4799) | 19-4973) | |
| BADC1 × BADC3 | 20-4816 × 19-4973 | 20-6113 (derived | 20-6198 (derived | 63 |

Example 6. Editing BADC Genes in Canola

Figure 6:
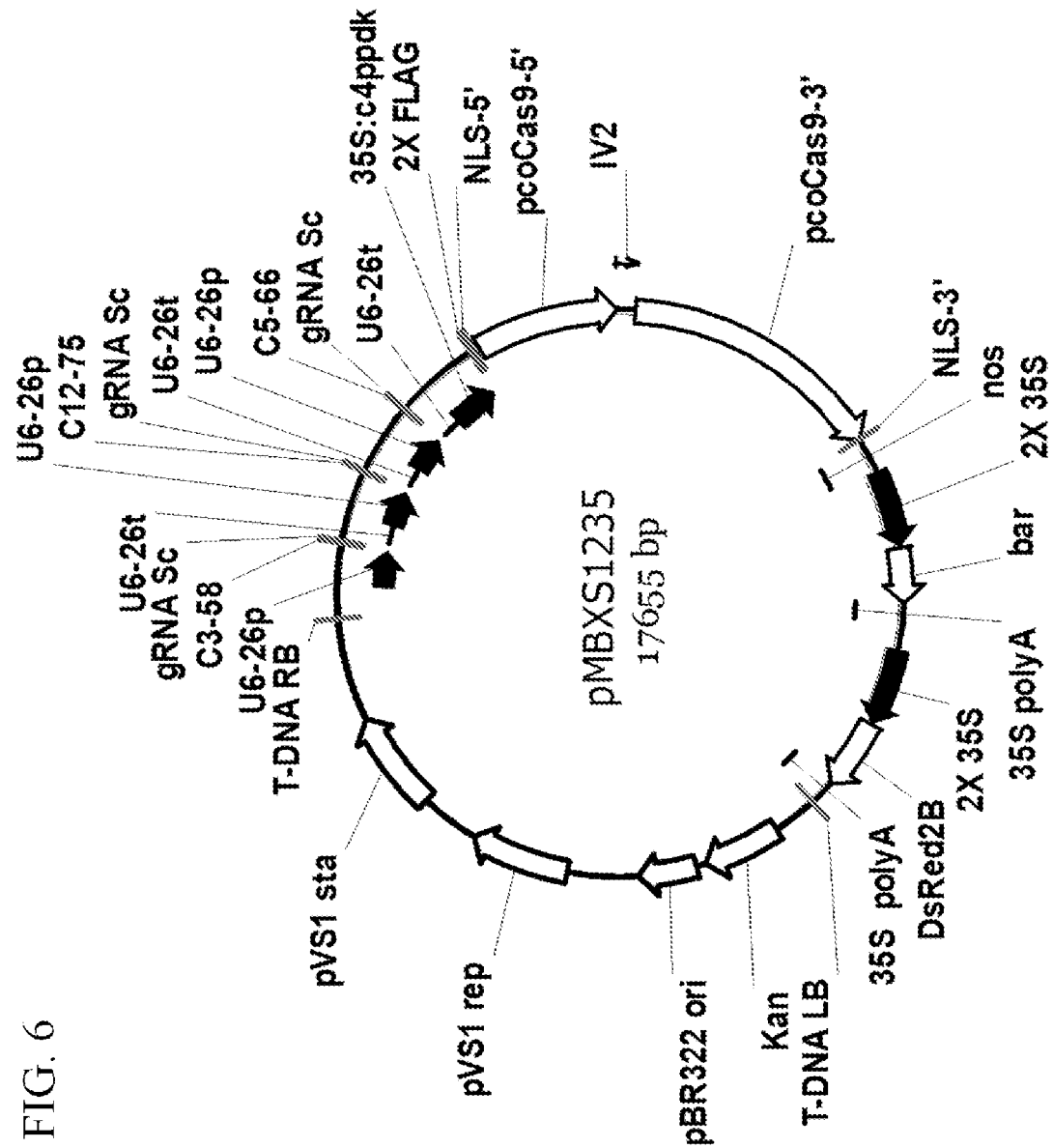
FIG. 6 illustrates the plasmid map of a binary vector pMBXS1235 (SEQ ID NO: 13), for Cas9 mediated genome editing of the six *Brassica napus* BADC genes (BnBADC1-1, BnBADC1-2, BnBADC3-1, BnBADC3-2, BnBADC3-3, BnBADC3-4). Important genetic elements within the vector are as follows: U6-26p, a DNA fragment encoding the polymerase III promoter from the *Arabidopsis* U6-26 small nuclear RNA gene; Guide C3-58 (SEQ ID NO: 31), DNA encoding a 20 bp guide target sequence to edit BnBADC3-1, BnBADC3-2 and BnBADC3-4 genes; gRNA Sc, DNA fragment encoding a Guide RNA scaffold encoding a crRNA-tracrRNA hybrid engineered from the *Streptococcus pyogenes* CRISPR locus (the DNA encoding the guide target sequence and gRNASc, when expressed together, form a functional sgRNA sequence); U6-26t, a DNA fragment encoding the terminator from the *Arabidopsis* U6-26 snRNA gene; Guide C12-75 (SEQ ID NO: 30), DNA encoding a 20 bp guide target sequence to edit BnBADC1-1 and BnBADC1-2 genes; Guide C5-66 (SEQ ID NO: 32), DNA encoding a 20 bp guide target sequence to edit BnBADC3-3; 35S:C4PPDK promoter (Chiu et al., 1996, Curr. Biol., 6, 325); 2X Flag, a fragment encoding a FLAG polypeptide protein tag (Li et al., 2013, Nature Biotechnology, 31, 688) created by artificial design (Hopp et al., 1988, Bio/Technology, 6, 1204); NLS-5', a nuclear localization sequence encoding the peptide MAPKKKRKVGIHGVPAA (SEQ ID NO: 23) (WO 2016114972) attached to the 5' end of Cas9; pcoCas9-5', DNA fragment encoding the 5' part of a Cas9 (CRISPR associated protein 9) from *Streptococcus pyogenes* codon-optimized for expression in plants (pcoCas9, Li et al., 2013, Nature Biotechnology, 31, 688); IV2, a DNA sequence encoding the second intron (IV2) of the nuclear photosynthetic gene ST-LS1 from *Solanum tuberosum* (Vancanneyt et al., 1990, Molecular and General Genetics, 220, 245); pcoCas9-3', DNA fragment encoding the 3' part of Cas9 (the 5' fragment and the 3' fragment of pcoCas9 together form the complete Cas9 protein coding sequence); NLS-3', DNA fragment encoding the nuclear localization sequence of nucleoplasmin, a protein involved in chromatin assembly and histone storage in the *Xenopus* oocyte and egg (Dingwall et al., 1988, Journal of Cell Biology, 1988, 107, 841), attached to the 3' end of Cas9; nos, a termination sequence. An expression cassette for the bar gene, driven by the 2X CaMV 35S promoter, provides selection of transgenic plants on phosphinothricin or LibertyLink. An expression cassette for the DsRed protein, driven by the 2X CaMV 35S promoter, provides a visual selection of transgenic plants.
Figure 7:
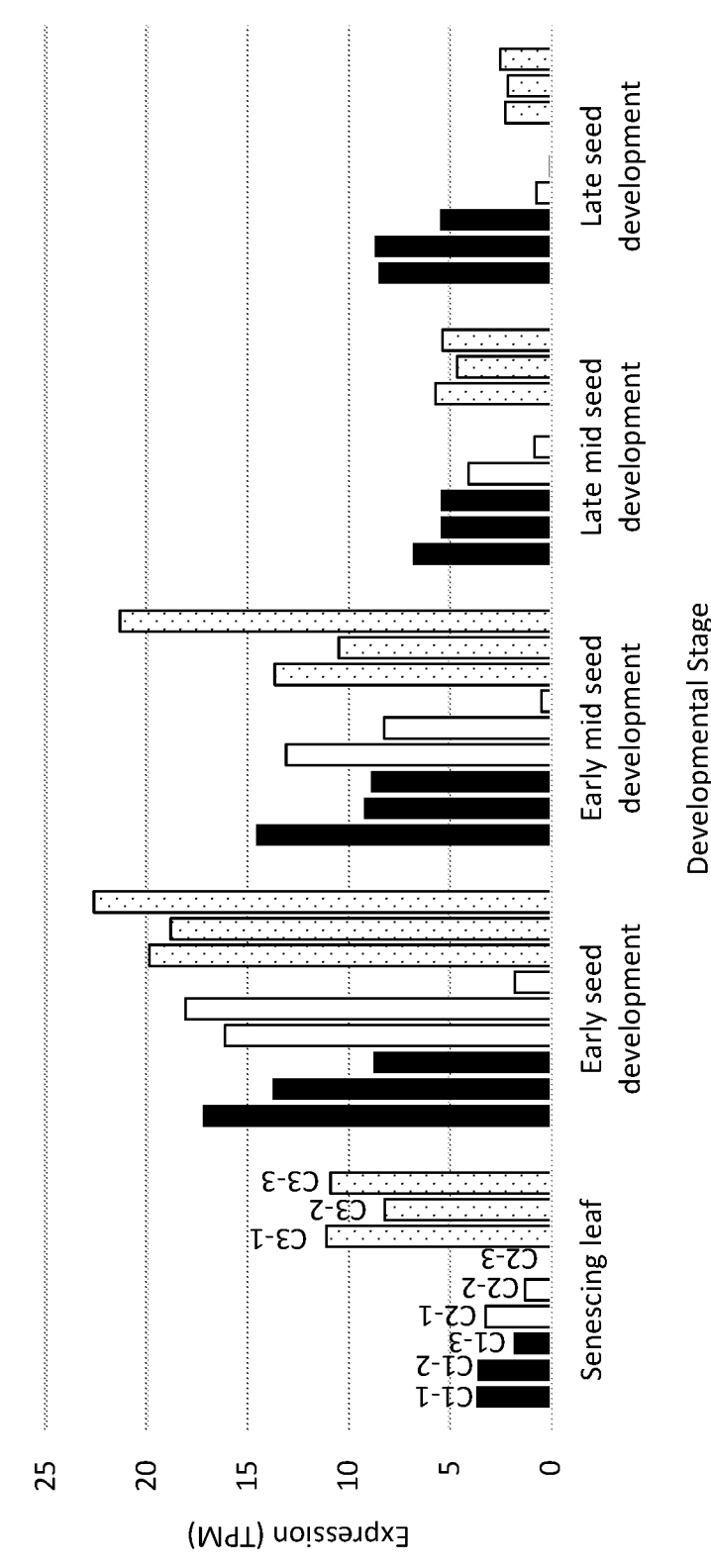
FIG. 7 illustrates the predicted expression of BADC genes in *Camelina sativa* at multiple stages of development of line DH55 (line used as *C. sativa* reference genome) as determined by RNA-Seq (Kagale et al., 2016, The Plant Journal, 88, 879). The homeologs of each gene are shown in numerical order from left to right. Units of expression are shown in Transcripts Per Million (TPM).

Guide sequences for constructing editing constructs to edit the canola BADC genes were designed and are shown in TABLE 9. A genetic construct containing these guide RNAs was produced to create mutations in the BnBADC genes. Plasmid pMBXS1235 (FIG. 6, SEQ ID NO: 13) was designed that would both generate single guide RNAs (sgRNAs) within the plant cell to target the BnBADC genes and produce a functional Cas9 enzyme molecule. FIG. 3 shows the genetic elements required for editing and how they interact with genomic DNA to achieve an edit. Genetic construct pMBXS1235 (FIG. 6; SEQ ID NO: 13), a binary vector containing expression cassettes to produce sgRNAs to target the six *B. napus* badc-genes (BnBADC1-1, BnBADC1-2, BnBADC3-1, BnBADC3-2, BnBADC3-3 and BnBADC3-4), a plant-codon optimized Cas9 (pcoCas9, Li et al., 2013. Nature Biotechnology, 31, 688), the DsRed gene, which encodes a red fluorescent protein from the *Discosoma* genus of coral (Matz et al., 1999, Nat Biotechnol 17, 969), and the bar gene for selection of transformed plants, was constructed.

TABLE 9

Guide sequences for
editing the *Brassica napus* BADC genes

| Guide name | Target Gene | Strand | Guide target sequence (5' to 3') | PAM |
|---|---|---|---|---|
| C12-75 | BnBADC1-1 BnBADC1-2 | − | GATTTGTTCATGGGC TCAGA (SEQ ID NO: 30) | AGG |
| C3-58 | BnBADC3-1 BnBADC3-2 BnBADC3-4 | + | GCTCGTTCCCAAGCC CTCTG (SEQ ID NO: 31) | AGG |
| C5-66 | BnBADC3-3 | + | GCTTGTTCCCAAGCC CTCTG (SEQ ID NO 32) | AGG |

[1]An sgRNA is composed of DNA encoding a guide target sequence, targeted to the gene of interest in the Camelina genome, fused to DNA encoding a guide RNA scaffold (FIG. 3). Pairing of the sgRNA to genomic DNA at the target site requires an adjacent protospacer adjacent motif (PAM) site, an additional requirement for target recognition. The adjacent PAM sequence in the genomic DNA is listed in the table.

*Brassica napus* line DH12075 was edited using the following procedure. The binary editing construct, pMBXS1235 (FIG. 6), was delivered into the plant cells affected by leaf painting with LibertyLink indicated the presence of the T-DNA containing the Cas9 expression and guide RNA expression cassettes. Leaf tissue from T0 plants was screened for genome editing by Amplicon sequencing. Plants containing genome edits in the BADC1-1, BADC1-2, BADC3-1, BADC3-2, BADC3-3 and BADC3-4 loci were isolated. T1 (first generation) seeds were harvested and germinated in soil. The segregating T1 plants were screened for the absence of the herbicide resistant marker, bar, through leaf painting with LibertyLink indicating removal of the T-DNA via segregation such that T1 (bar resistant plants that still contain T-DNA) and E1 (bar sensitive plants that have lost T-DNA but still retain the edit) were identified. The bar sensitive E1 plants were also confirmed by PCR for the absence of the bar gene. E2 seeds (second generation seeds) from E1 marker-free plants were analyzed for oil content. The marker negative E2 plants were further advanced through one additional generation to generate E3 seeds.

A summary of select edited lines that were isolated is given in TABLE 10. While some editing was observed in the BnBADC1-1, BnBADC1-2, and BnBADC3-4 genes in earlier generations, no lines with stable edits in these genes were obtained in later generations. The data in TABLE 10 suggests that certain combinations of edits provided an advantage in the E2 generation and increased the amount of oil produced per plant by both increasing the seed yield and the percent oil content (% seed weight, TABLE 10). The best lines had edits in the BnBADC3-2 and/or BnBADC3-3 genes, both orthologs of AtBADC3 (TABLE 8). Up to 54% increase in oil was obtained in the best line (line 19-3023), with lines 19-2959 and 19-2987 producing 30% and 22% increase in total oil produced per plant, respectively. An exception was line 19-2950 edited in the BnBADC3-2 gene which provided no advantage. Thus the identification of combinations of badc edits to increase seed yield and/or oil content in canola is important.

TABLE 10

Summary of BADC edits in select heterozygous canola E1 generation lines producing E2 seeds

| E1 Line Number | Summary of Edits in Tissue from E1 lines[1] BADC gene | | | | | | % increase oil per E2 seed (mg per seed) | % increase 200 E2 seed weight | % increase E2 seed oil content (% seed weight) | % increase # E2 seeds per plant | % increase total oil produced per E1 plant | % increase total E2 seed yield per E1 plant (grams) |
|---|---|---|---|---|---|---|---|---|---|---|---|---|
| | 1-1 | 1-2 | 3-1 | 3-2 | 3-3 | 3-4 | | | | | | |
| Wild-type | — | — | — | — | — | — | 0 | 0 | 0 | 0 | 0 | 0 |
| 19-2950 | — | — | — | X | — | — | −9.1 | 6.9 | −8.1 | −6.5 | −36.9 | −35.2 |
| 19-2958 | — | — | X | X | X | — | −23.0 | −20.2 | −15.3 | 25.3 | −38.0 | −31.1 |
| 19-2959 | — | — | — | X | X | — | −7.0 | −2.9 | 8.4 | 3.0 | 30.1 | 12.9 |
| 19-2987 | — | — | — | X | — | — | −14.4 | −12.3 | 4.9 | 14.0 | 22.1 | 9.4 |
| 19-3023 | — | — | — | X | — | — | −19.3 | −18.7 | 9.5 | 23.0 | 54.0 | 32.5 |

[1]Symbol "X" denotes complete homozygous editing of the chromosomal allele of the gene, "x" denotes incomplete heterozygous editing of the chromosomal allele of the gene, and "—" denotes the wild-type sequence of the chromosomal allele of the gene.
Abbreviations: Ch, chromosome.

with an *Agrobacterium*-mediated cotyledonary petiole transformation method. The initial steps of selecting the transformed plants involved tissue culture selection on phosphinothricin (2 mg/L and 5 mg/L L-PPT) containing media. The next step of selection was screening the T0 generation plants with LibertyLink herbicide through leaf painting to select the transformed plants after planting them in soil. Plants not Lines from TABLE 10 were chosen to propagate further to produce seeds for additional greenhouse studies and for field trials and are shown in TABLE 11. Amplicon sequencing was performed through a contract vendor to determine the nature of edits and to identify homozygous edits (TABLE 11).

TABLE 11

Summary of BADC edits in select canola E2 generation lines producing E3 seeds

| E1 Parental Line Number | E2 Line Number | \multicolumn{6}{Summary of Edits in Tissue from E2 lines[1] BADC gene} | | | | | | Change in Edited Lines[2] | % increase total E3 seed yield produced per E2 plant (grams) |
|---|---|---|---|---|---|---|---|---|---|
| | | 1-1 | 1-2 | 3-1 | 3-2 | 3-3 | 3-4 | | |
| Wild-type | Wild-type | — | — | — | — | — | — | None | 0 |
| 19-2950 | 19-5194 | — | — | — | X | — | — | BnBADC3-2, edited GC deletion and C mutated to T, 88 amino acid truncated protein | 1.0 |
| | 19-5195 | — | — | — | X | — | — | BnBADC3-2, edited GC deletion and C mutated to T, 88 amino acid truncated protein | −0.7 |
| | 19-5196 | — | — | — | X | — | — | BnBADC3-2, edited T insertion, 91 amino acid truncated protein | −13.0 |
| 19-2958 | 19-5202 | — | — | X | X | X | — | BnBADC3-1, edited T insertion, 92 amino acid truncated protein BnBADC3-2, edited T insertion, 91 amino acid truncated protein BnBADC3-3, edited A deletion, 99 amino acid truncated protein | −3.1 |
| | 19-5203 | — | — | X | X | X | — | BnBADC3-1, edited T insertion, 92 amino acid truncated protein BnBADC3-2, edited T insertion, 91 amino acid truncated protein BnBADC3-3, edited A deletion, 99 amino acid truncated proteins | −53.9 |
| | 19-5204 | — | — | X | X | X | — | BnBADC3-1, edited T insertion, 92 amino acid truncated protein BnBADC3-2, edited T insertion, 91 amino acid truncated protein BnBADC3-3, edited A deletion, 99 amino acid truncated proteins | −2.6 |
| | 19-5205 | — | — | X | X | X | — | BnBADC3-1, edited T insertion, 92 amino acid truncated protein BnBADC3-2, edited T insertion, 91 amino acid truncated protein BnBADC3-3, edited A deletion, 99 amino acid truncated proteins | 0.3 |
| 19-2959 | 19-5210 | — | — | — | X | X | — | BnBADC3-2, edited GC deletion and C mutated to T, 88 amino acid truncated protein BnBADC3-3, edited A deletion, 99 amino acid truncated proteins | 6.5 |
| | 19-5211 | — | — | — | X | X | — | BnBADC3-2, edited T insertion, 91 amino acid truncated protein BnBADC3-3, edited A deletion, 99 amino acid truncated proteins | 3.2 |
| | 19-5212 | — | — | — | X | X | — | BnBADC3-2, edited GC deletion and C mutated to T, 88 amino acid truncated protein BnBADC3-3, edited A insertion, 94 amino acid truncated proteins | 0.6 |
| 19-2987 | 19-5218 | — | — | — | X | — | — | BnBADC3-2, edited T deletion, 110 amino acid truncated protein | 10.3 |
| | 19-5219 | — | — | — | X | — | — | BnBADC3-2, edited T deletion, 110 amino acid truncated protein | 15.6 |
| | 19-5220 | — | — | — | X | — | — | BnBADC3-2, edited T deletion, 110 amino acid truncated protein | −5.9 |
| | 19-5221 | — | — | — | X | — | — | BnBADC3-2, edited T deletion, 110 amino acid truncated protein | 5.9 |
| 19-3023 | 19-5226 | — | — | — | X | — | — | BnBADC3-2, edited CT deletion, 90 amino acid truncated protein | 11.5 |
| | 19-5227 | — | — | — | X | — | — | BnBADC3-2, edited CT deletion, 90 amino acid truncated protein | 2.5 |
| | 19-5228 | — | — | — | X | — | — | BnBADC3-2, edited CT deletion, 90 amino acid truncated protein | 5.5 |
| | 19-5229 | — | — | — | X | — | — | BnBADC3-2, edited CT deletion, 90 amino acid truncated protein | −8.2 |

TABLE 11-continued

| Summary of BADC edits in select canola E2 generation lines producing E3 seeds | | | | | | | | | |
|---|---|---|---|---|---|---|---|---|---|
| E1 Parental Line | E2 Line | Summary of Edits in Tissue from E2 lines[1] BADC gene | | | | | | Change in Edited Lines[2] | % increase total E3 seed yield produced per E2 plant (grams) |
| Number | Number | 1-1 | 1-2 | 3-1 | 3-2 | 3-3 | 3-4 | | |

[1]Symbol "X" denotes complete homozygous editing of the chromosomal allele of the gene, "x" denotes incomplete heterozygous editing of the chromosomal allele of the gene, and "—" denotes the wild-type sequence of the chromosomal allele of the gene.
[2]For edited lines, only sequences of edited genes are shown.
Abbreviations: Ch, chromosome.

Example 7. Growth of E3 Canola Lines in Greenhouse

Select E3 edited canola lines were grown in a greenhouse in 6 inch (15 cm) pots in a randomized complete block design (n=17). Plants were harvested at maturity and E4 seed yield and oil content was determined. A 4.2% and 4.8% increase in the bulk seed oil content (% of seed weight) was observed in E3 lines E5210 and E521, respectively, compared to the oil content in the wild-type control line (TABLE 12). In addition, an increased seed yield of 14.3% and 17.6% was observed in E3 lines E5210 and E5211, respectively, compared to the wild-type control line. Both lines E5210 and E5211 also have an increase in their thousand seed weight (7.6% for E5210; 5.2% for E5211; TABLE 13) and fatty acid content per seed (expressed as fatty acid methyl ester [FAME] detected in individual seed upon methanolysis reaction followed by gas chromatographic analysis (TABLE 13)). Both lines E5210 and E5211 have edits in BADC3-2 and BADC3-3 genes suggesting that these edits are preferential for increasing seed oil content, seed yield, thousand seed weight, and individual seed fatty acid content in canola.

TABLE 12

| Results from greenhouse growth of homozygous canola E3 generation BADC edited lines (n = 13). | | | | | | | | | | | |
|---|---|---|---|---|---|---|---|---|---|---|---|
| | | Summary of Edits in Tissue from E2 lines[1] | | | | | | Percent Oil % | | Seed Yield % | |
| Parental | | BADC gene | | | | | | | | | |
| E2 line | E3 Line | 1-1 | 1-2 | 3-1 | 3-2 | 3-3 | 3-4 | Increase | T-Test | Increase | T-Test |
| 19-5211 | E5211 | — | — | — | X | X | — | 4.8 | 0.046* | 17.6 | 0.002* |
| 19-5210 | E5210 | — | — | — | X | X | — | 4.2 | 0.078 | 14.3 | 0.007* |
| 19-5194 | E5194 | — | — | — | X | — | — | 2.6 | 0.167 | 8.4 | 0.119 |
| 19-5226 | E5226 | — | — | — | X | — | — | -4.2 | 0.039* | -3.6 | 0.294 |
| 19-5219 | E5219 | — | — | — | X | — | — | -5.4 | 0.014 | -0.6 | 0.464 |
| 19-5204 | E5204 | — | — | X | X | X | — | -6.8 | 0.004* | -3.7 | 0.296 |
| Wild-type | Wild-type | — | — | — | — | — | — | — | — | — | — |

[1]Symbol "X" denotes complete homozygous editing of the chromosomal allele of the gene, "x" denotes incomplete heterozygous editing of the chromosomal allele of the gene, and "—" denotes the wild-type sequence of the chromosomal allele of the gene.
*indicates significance by Student T test, p < 0.05

TABLE 13

| Results from greenhouse growth of homozygous canola E3 generation BADC edited lines (n = 13). | | | | | | | | | | | |
|---|---|---|---|---|---|---|---|---|---|---|---|
| | | Summary of Edits in Tissue from E2 lines[1] | | | | | | Thousand Seed Weight % | | FAME[2] per seed % | |
| Parental | | BADC gene | | | | | | | | | |
| E2 line | E3 Line | 1-1 | 1-2 | 3-1 | 3-2 | 3-3 | 3-4 | Increase | T-Test | Increase | T-Test |
| 19-5211 | E5211 | — | — | — | X | X | — | 5.2 | 0.000* | 8.0 | 0.0555 |
| 19-5210 | E5210 | — | — | — | X | X | — | 7.6 | 0.000* | 11.7 | 0.0138 |
| 19-5194 | E5194 | — | — | — | X | — | — | -0.9 | 0.278 | 6.71 | 0.1163 |
| 19-5226 | E5226 | — | — | — | X | — | — | -8.9 | 0.000* | -11.3 | 0.0114 |
| 19-5219 | E5219 | — | — | — | X | — | — | -4.0 | 0.005* | -8.4 | 0.0363 |

TABLE 13-continued

| | | | Summary of Edits in Tissue from E2 lines[1] | | | | | | Thousand Seed Weight | | FAME[2] per seed | |
|---|---|---|---|---|---|---|---|---|---|---|---|---|
| Parental | | | BADC gene | | | | | | % | | % | |
| E2 line | E3 Line | 1-1 | 1-2 | 3-1 | 3-2 | 3-3 | 3-4 | | Increase | T-Test | Increase | T-Test |
| 19-5204 | E5204 | — | — | X | X | X | — | | −6.6 | 0.000* | −11.5 | 0.0090 |
| Wild-type | Wild-type | — | — | — | — | — | — | | — | — | — | — |

Results from greenhouse growth of homozygous canola E3 generation BADC edited lines (n = 13).

[1]Symbol "X" denotes complete homozygous editing of the chromosomal allele of the gene, "x" denotes incomplete heterozygous editing of the chromosomal allele of the gene, and "—" denotes the wild-type sequence of the chromosomal allele of the gene.
*Indicates significance by Student T test, $p < 0.05$
[2]Amount of fatty acids in individual seed, expressed as fatty acid methyl ester (FAME) detected in individual seed upon methanolysis reaction followed by gas chromatographic analysis.

Figure 8:
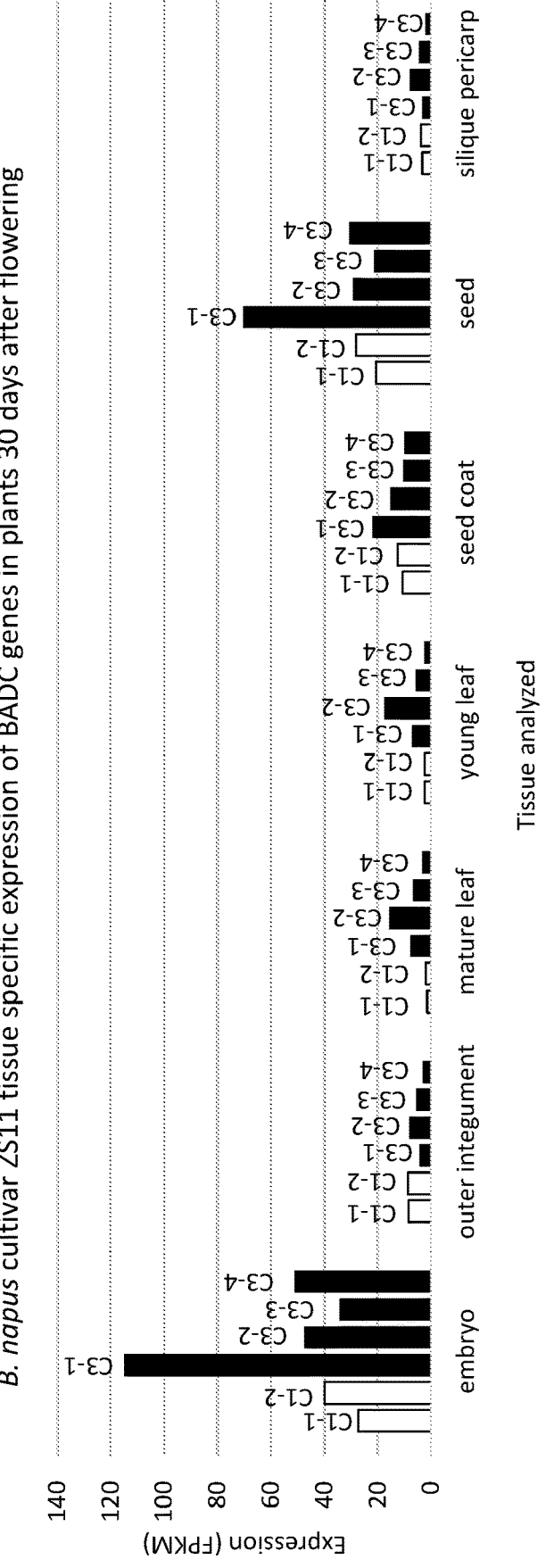
FIG. 8 illustrates the predicted expression of BADC genes in *Brassica napus* at multiple stages of development as determined from an eFP browser containing expression data for *B. napus* cultivar ZS11 (Chao et al., 2020, International Journal of Molecular Sciences, 21, 5831). In the study of Chao et al. various tissues were harvested from plants 30 days after flowering. The homeologs of each gene are shown in numerical order from left to right. Units of expression are shown in Fragments Per Kilobase Million (FPKM).

The best combination of edits obtained in the study shown in TABLES 12 and 13 resulted in inactivation of the BADC3-2 and BADC3-3 genes. The expression profile of these genes was compared using data from an eFP browser containing expression data for *B. napus* cultivar ZS11 (Chao et al., 2020, International Journal of Molecular Sciences, 21, 5831). The study of Chao et al. used various tissues of harvested plants 30 days after flowering. FIG. 8 shows that in embryo and seed, the highest measured transcript was for BADC3-1, which reduced yield and oil content in line E5204 (TABLE 12) when edited. BADC3-2 and BADC3-3 had lower levels of expression and their combined editing resulted in lines with higher seed oil content and an increase in seed yield.

Example 8. Field Trials of BADC Edited Canola Lines

Field trials of select BADC edited canola lines are in progress.

Select canola lines that contained homozygous edits (TABLE 12) and wild-type controls were planted in the Spring of 2021 in small scale replicated field plots in Bozeman, Mont. Plots were replicated 4 times.

Seed from plots will be harvested and analyzed for yield and seed oil content.

Example 9. Identification of the *Glycine max* Orthologs of the *Arabidopsis* BADC Genes The *Glycine max* (soybean) genome from cultivar Williams 82 was searched for BADC orthologs using the *Arabidopsis* BADC protein sequences as BLAST queries. Four BADC genes were identified and are listed in TABLE 14. These include two *Glycine max* orthologs to the *Arabidopsis* BADC1 gene (AtBADC1), which are designated GmBADC1-1 and GmBADC1-2, and two orthologs to the AtBADC3 gene, designated GmBADC3-1 and GmBADC3-2. No orthologs to the *Arabidopsis* BADC2 genes were identified.

TABLE 14

BADC Genes in *Arabidopsis* and *Glycine max*[1].

| *Arabidopsis* BADC gene | | *Glycine max* ortholog | *Glycine max* cultivar Williams 82 | |
|---|---|---|---|---|
| | | | Gene ID[1] | Protein Accession number and size |
| AtBADC1 | AT3G56130 | GmBADC1-1 | Glyma11G233700 (SEQ ID NO: 74) | XP_ 006590336.1 (SEQ ID NO: 75) 291aa |
| | | GmBADC1-2 | Glyma18G023300 (SEQ ID NO: 76) | NP_001241051.1 (SEQ ID NO: 77) 291aa |
| AtBADC2 | AT1G52670 | No candidate ortholog for AtBADC2 was found in *G. max* | | |
| AtBADC3 | AT3G15690 | GmBADC3-1 | Glyma13G363500 (SEQ ID NO: 78) | XP_003543673.1 (SEQ ID NO: 79) 298 aa |
| | | GmBADC3-2 | Glyma15G010300 (SEQ ID NO: 80) | XP_006597130.2 (SEQ ID NO: 81) 276 aa |

Figure 9:
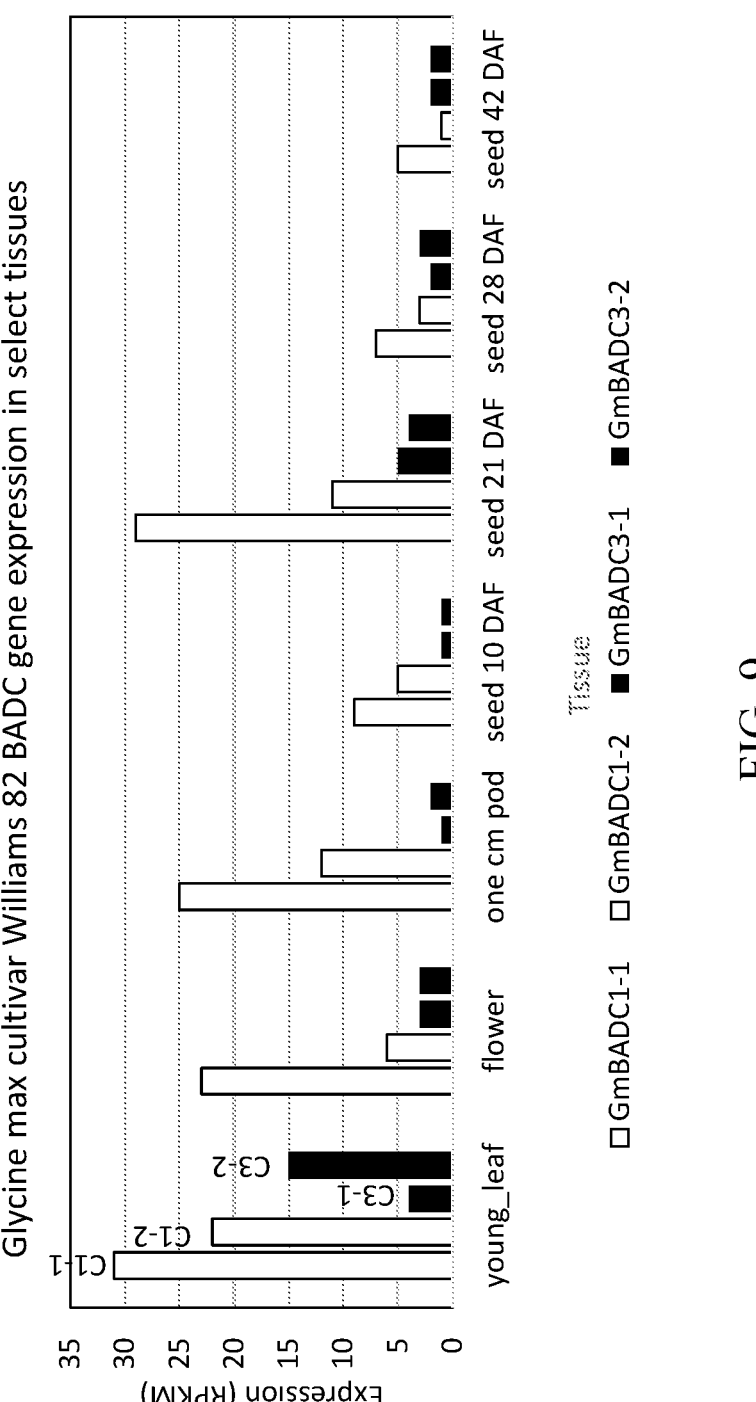
FIG. 9 illustrates the predicted expression of BADC genes in *Glycine max* in select tissues and developmental stages. Expression data were obtained from the RNA-SEQ Atlas of *Glycine max* (Severin et al., 2010, BMC Plant Biology, 10, 1-16). The homeologs of each gene are shown in numerical order from left to right. Units of expression are shown in Reads Per Kilobase Million (RPKM).

[1]Gene sequences of *Glycine max* BADC genes were obtained from GenBank (NCBI—National Center for Biotechnology Information).
[2]Abbreviations: aa, amino acids The expression patterns of the GmBADC genes in select tissues and developmental stages were obtained from the RNA-SEQ Atlas of *Glycine max* (Severin et al., 2010, BMC Plant Biology, 10, 1-16) and are shown in FIG. 9.

Specific vectors or DNA fragments can be constructed to edit the soybean BADC genes. These constructs will contain the following expression cassettes. (a) an expression cassette for the Cas9 gene that contains a promoter functional in soybean, the Cas9 gene that includes nuclear localization sequences on the 5' and 3' end of the gene, and a terminator; (b) one or more expression cassettes for a guide RNA(s) that consists of a promoter, the guide target sequence with about 20 bp homology upstream of a PAM sequence with the consensus sequence of "NGG", a gRNA scaffold sequence necessary for Cas9 binding, and a poly T-termination sequence (the promoter for gRNAs is preferably a U6 promoter functional in the crop to be transformed); (c) an expression cassette for a selectable marker that can be used for the specific crop for selection of transformants. For *Agrobacterium*-mediated transformation, these expression cassettes can be cloned into one or more binary vectors for transformation of the appropriate explant of the crop. For stable transformation by particle bombardment or protoplast transformation, expression cassettes can be introduced as a DNA fragment(s) or can be localized on one or more simple plasmid vectors. For both methods, soybean plants can be screened for edits using Next Generation Sequencing methods. After the edits are obtained, the expression cassettes described above can be removed by segregation using conventional breeding methods for soybean.

For transient expression of expression cassettes in protoplasts, the expression cassettes described above for the Cas9 and the gRNA can be introduced as one or more DNA fragments or can be localized on one or more simple vectors. An expression cassette for a selectable marker is not required. Protoplast cultures or alternatively, callus cultures derived from the protoplast cultures, can be screened for edits using Next Generation Sequencing methods, and protoplast or callus cultures with the edits can be regenerated into plants.

For editing using ribonucleoprotein complexes or RNPs, purified Cas9 enzyme can be mixed with one or more gRNAs to form a complex of the Cas9 enzyme and the gRNAs which can then be introduced directly to protoplasts. Protoplast cultures or alternatively, callus cultures derived from the protoplast cultures, can be screened for edits using Next Generation Sequencing methods, and protoplast or callus cultures with the edits can be regenerated into plants.

It will be apparent to those skilled in the art that Cas9 can be replaced with other nucleases with the required guide RNAs or DNAs to achieve editing of the BADC genes.

For transformation of soybean, a biolistic method can be employed. The transformation, selection, and plant regeneration protocol for soybean is adapted from Simmonds (2003) (Simmonds, 2003, Genetic Transformation of Soybean with Biolistics. In: Jackson J F, Linskens H F (eds) *Genetic Transformation of Plants*. Springer Verlag, Berlin, pp 159-174) and requires expression cassettes for the Cas9 enzyme, the gRNA(s), and a selectable marker, such as the hygromycin resistance marker. These expression cassettes can be co-localized on one plasmid or isolated DNA fragment, or alternatively, two separate plasmids or isolated DNA fragments containing the expression cassettes can be co-bombarded.

The purified DNA fragment(s) are introduced into embryogenic cultures of soybean *Glycine max* cultivars X5 and Westag97 via biolistics, to obtain transgenic plants. The transformation, selection, and plant regeneration of soybean is performed as follows.

Induction and Maintenance of Proliferative Embryogenic Cultures: Immature pods, containing 3-5 mm long embryos, are harvested from host plants grown at 28/24° C. (day/night), 15-h photoperiod at a light intensity of 300-400 μmol $m^{-2} s^{-1}$. Pods are sterilized for 30 s in 70% ethanol followed by 15 min in 1% sodium hypochlorite [with 1-2 drops of Tween 20 (Sigma, Oakville, ON, Canada)] and three rinses in sterile water. The embryonic axis is excised and explants are cultured with the abaxial surface in contact with the induction medium [MS salts, B5 vitamins (Gamborg O L, Miller R A, Ojima K. Exp Cell Res 50:151-158), 3% sucrose, 0.5 mg/L BA, pH 5.8), 1.25-3.5% glucose (concentration varies with genotype), 20 mg/l 2,4-D, pH 5.7]. The explants, maintained at 20° C. at a 20-h photoperiod under cool white fluorescent lights at 35-75 μmol $m^{-2} s^{-1}$, are sub-cultured four times at 2-week intervals. Embryogenic clusters, observed after 3-8 weeks of culture depending on the genotype, are transferred to 125-ml Erlenmeyer flasks containing 30 ml of embryo proliferation medium containing 5 mM asparagine, 1-2.4% sucrose (concentration is genotype dependent), 10 mg/l 2,4-D, pH 5.0 and cultured as above at 35-60 μmol $m^{-2} s^{-1}$ of light on a rotary shaker at 125 rpm. Embryogenic tissue (30-60 mg) is selected, using an inverted microscope, for subculture every 4-5 weeks.

Transformation: Cultures are bombarded 3 days after subculture. The embryogenic clusters are blotted on sterile Whatman filter paper to remove the liquid medium, placed inside a 10×30-mm Petri dish on a 2×2 $cm^2$ tissue holder (PeCap, 1 005 μm pore size, Band SH Thompson and Co. Ltd. Scarborough, ON, Canada) and covered with a second tissue holder that is then gently pressed down to hold the clusters in place. Immediately before the first bombardment, the tissue is air dried in the laminar air flow hood with the Petri dish cover off for no longer than 5 min. The tissue is turned over, dried as before, bombarded on the second side and returned to the culture flask. The bombardment conditions used for the Biolistic PDS-1000/He Particle Delivery System are as follows: 737 mm Hg chamber vacuum pressure, 13 mm distance between rupture disc (Bio-Rad Laboratories Ltd., Mississauga, ON, Canada) and macrocarrier. The first bombardment uses 900 psi rupture discs and a microcarrier flight distance of 8.2 cm, and the second bombardment uses 1100 psi rupture discs and 11.4 cm microcarrier flight distance. DNA precipitation onto 1.0 μm diameter gold particles is carried out as follows: 2.5 μl of 100 ng/μl of insert DNA (Cas9 and gRNA(s) expression cassettes) and 2.5 μl of 100 ng/μl selectable marker DNA (cassette for hygromycin selection) are added to 3 mg gold particles suspended in 50 μl sterile $dH_2O$ and vortexed for 10 sec; 50 μl of 2.5 M $CaCl_2$ is added, vortexed for 5 sec, followed by the addition of 20 μl of 0.1 M spermidine which is also vortexed for 5 sec. The gold is then allowed to settle to the bottom of the microfuge tube (5-10 min) and the supernatant fluid is removed. The gold/DNA is resuspended in 200 μl of 100% ethanol, allowed to settle and the supernatant fluid is removed. The ethanol wash is repeated and the supernatant fluid is removed. The sediment is resuspended in 120 μl of 100% ethanol and aliquots of 8 μl are added to each macrocarrier. The gold is resuspended before each aliquot is removed. The macrocarriers are placed under vacuum to ensure complete evaporation of ethanol (about 5 min).

Selection: The bombarded tissue is cultured on embryo proliferation medium described above for 12 days prior to subculture to selection medium (embryo proliferation medium containing 55 mg/l hygromycin added to autoclaved media). The tissue is sub-cultured 5 days later and weekly for the following 9 weeks. Green colonies (putative transgenic events) are transferred to a well containing 1 ml of selection media in a 24-well multi-well plate that is maintained on a flask shaker as above. The media in multi-well dishes is replaced with fresh media every 2 weeks until the colonies are approx. 2-4 mm in diameter with proliferative embryos, at which time they are transferred to 125 ml Erlenmeyer flasks containing 30 ml of selection medium. A portion of the proembryos from transgenic events is harvested to examine gene expression by RT-PCR.

Plant regeneration: Maturation of embryos is carried out, without selection, at conditions described for embryo induction. Embryogenic clusters are cultured on Petri dishes containing maturation medium (MS salts, B5 vitamins, 6% maltose, 0.2% gelrite gellan gum (Sigma), 750 mg/l $MgCl_2$, pH 5.7) with 0.5% activated charcoal for 5-7 days and without activated charcoal for the following 3 weeks. Embryos (10-15 per event) with apical meristems are selected under a dissection microscope and cultured on a similar medium containing 0.6% phytagar (Gibco, Burlington, ON, Canada) as the solidifying agent, without the additional $MgCl_2$, for another 2-3 weeks or until the embryos become pale yellow in color. A portion of the embryos from transgenic events after varying times on gelrite are harvested to examine gene expression by RT-PCR.

Mature embryos are desiccated by transferring embryos from each event to empty Petri dish bottoms that are placed inside Magenta boxes (Sigma) containing several layers of sterile Whatman filter paper flooded with sterile water, for 100% relative humidity. The Magenta boxes are covered and maintained in darkness at 20° C. for 5-7 days. The embryos are germinated on solid B5 medium containing 2% sucrose, 0.2% gelrite and 0.075% $MgCl_2$ in Petri plates, in a chamber at 20° C., 20-h photoperiod under cool white fluorescent lights at 35-75 µmol m$^{-2}$ s$^{-1}$. Germinated embryos with unifoliate or trifoliate leaves are planted in artificial soil (Sunshine Mix No. 3, SunGro Horticulture Inc., Bellevue, WA, USA), and covered with a transparent plastic lid to maintain high humidity. The flats are placed in a controlled growth cabinet at 26/24° C. (day/night), 18 h photoperiod at a light intensity of 150 µmol m$^{-2}$ s$^{-1}$. At the 2-3 trifoliate stage (2-3 weeks), the plantlets with strong roots are transplanted to pots containing a 3:1:1:1 mix of ASB Original Grower Mix (a peat-based mix from Greenworld, ON, Canada):soil:sand:perlite and grown at 18-h photoperiod at a light intensity of 300-400 µmol m$^{-2}$ s$^{-1}$.

T1 seeds are harvested and planted in soil and grown in a controlled growth cabinet at 26/24° C. (day/night), 18 h photoperiod at a light intensity of 300-400 µmol m$^{-2}$ s$^{-1}$. Plants are grown to maturity and T2 seed is harvested.

Plant tissue from the T1 and T2 generations are screened for edits using Next Generation Sequencing by extracting genomic DNA from leaf tissue and performing PCR reactions using primers that bind to regions of genomic DNA about 100 base pairs away from the gRNA binding site. Sequencing analysis is performed on the crude PCR mixture using a Next-Generation sequencing technology and automated sequencing assembly offered by a vendor. Plants with INDELS are identified. The sequence of the edits is analyzed and edits that insert 1 base or that delete 1, 2, 4, 5, 7, 8 or more bases are selected. These INDELS will create a reading frame shift likely creating a truncated protein. Lines with the best INDELS are allowed to grow in a greenhouse to maturity prior to seed harvest. If required, lines can be grown another generation to obtain homogenous edits. Promising soybean lines are evaluated for their total seed yield, oil content, and thousand seed weight.

The expression levels of BADC genes in various tissues of soybean is determined. Transcript levels of leaves, stem tissues, and seeds at different developmental stages are determined by RT-PCR using a gene such as β-actin as a reference. Total RNA is isolated from the different tissues using the RNeasy Plant Mini Kit (Qiagen, Valencia, CA, USA) according to the manufacturer's protocol. DNase treatment and column purification are performed and RNA quality is assessed using an Agilent 2100 Bioanalyzer (Agilent Technologies, Santa Clara, CA, USA) according to the manufacturer's instructions. The RT-PCR analysis is performed with 50 ng of total RNA using a One Step RT-PCR Kit (Qiagen, Valencia, CA, USA). Lines with reduced expression of BADC are evaluated.

Example 10. Identification of Orthologs of *Arabidopsis* BADC Genes in Other Plants Genetically modified plants as described herein can be produced from progenitor plants of additional types of plants, including other oilseed plants, that include at least two orthologs of each of at least two of the *Arabidopsis* BADC genes.

BADC genes of additional types of plants can be identified as described in PCT/US2016/041386 to University of Missouri (published as WO 2017/039834). As taught by PCT/US2016/041386, the three BADC isoforms of *Arabidopsis thaliana* share many characteristics of two biotin carboxyl carrier protein (BCCP) isoforms of *Arabidopsis thaliana*. Specifically, BADC isoforms contain a canonical plastid target peptide and are predicted to be localized in plastids. Also, the BADC isoforms share 24 to 29% amino acid identity with the BCCP isoforms. In addition, structural predictions indicate that the BADC and BCCP isoforms share a similar beta sheet secondary structure with a characteristic "thumb motif." The BADC isoforms lack a canonical biotinylation motif present in BCCP though.

Also as taught by PCT/US2016/041386, BADC proteins can be identified based on a 44-amino acid consensus sequence, corresponding to SEQ ID NO. 184 herein, as determined by multiple sequence alignment of the three BADC isoforms of *Arabidopsis thaliana* and BADC orthologs identified from other plants and from algae. The consensus sequence corresponds to amino acids 201 to 244 of *Arabidopsis thaliana* BADC1 of SEQ ID NO: 84. The consensus sequence includes identical amino acids at positions 1, 2, 11, 12, 28, 29, 36, 38, and 42, and variable residues at the remaining positions.

TABLE 15 lists BADC orthologs from various additional oilseed plants and other plants as disclosed in PCT/US2016/041386.

Using the analysis described above for *Camelina sativa*, *Brassica napus* (canola), and *Glycine max*, and with reference to the teachings of PCT/US2016/041386, genes encoding orthologs of *Arabidopsis* BADC1, BADC2, and BADC3 proteins can be readily identified in other oilseed plants, including other *Brassica* species such as *Brassica juncea*, *Brassica carinata*, and *Brassica rappa*, and flax, pennycress, safflower, sunflower and, sesame.

Plants that include at least two orthologs of each of at least two of the *Arabidopsis* BADC genes, for example based on polyploidy, alloploidy, autoploidy, diploidization following polyploidy, diploidization following alloploidy, or diploidization following autoploidy, can be genetically modified as described herein to produce additional plants with increased seed yield, seed oil content, and/or oil per plant.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "YTEN-63059WO-Sequence-Listing_ST25.txt", created Aug. 11, 2021, file size of 376,832 bytes, is hereby incorporated by reference.

TABLE 15

Orthologs of *Arabidopsis* BADC1, BADC2, and BADC3 identified in various additional oilseed plants and other plants.

| Species | Category | BCCP1 | BCCP2 | BADC1 | BADC2 | BADC3 |
|---|---|---|---|---|---|---|
| *Amborella trichopoda* | Flowering Plants | XP_011621081.1 | N/A | XP_011627066.1 (SEQ ID NO: 82) | N/A | XP_011627066.1 (SEQ ID NO: 83) |
| *Arabidopsis thaliana* | Eudicots | NP_197143.1 | NP_568316.1 | NP_567035.1 (SEQ ID NO: 84) | NP_564612.1 (SEQ ID NO: 85) | NP_188190.1 (SEQ ID NO: 86) |
| *Arabis alpina* | Eudicots | KFK25879.1 | KFK25777.1 | KFK34856.1 (SEQ ID NO: 87) | N/A | KFK38917.1 (SEQ ID NO: 88) |
| *Arachis duranensis* | Eudicots | XP_015962701.1 | XP_015946097.1 | XP_015944188.1 (SEQ ID NO: 89) | N/A | XP_015933506.1 (SEQ ID NO: 90) |
| *Arachis ipaensis* | Eudicots | XP_016194346.1 | XP_016181644.1 | XP_016181047.1 (SEQ ID NO: 91) | N/A | XP_016170604.1 (SEQ ID NO: 92) |
| *Beta vulgaris* subsp. *vulgaris* | Eudicots | XP_010679318.1 | N/A | XP_010692910.1 (SEQ ID NO: 93) | N/A | XP_010691182.1 (SEQ ID NO: 94) |
| *Brassica oleracea* var. *oleracea* | Eudicots | XP_013625183.1 | XP_013621850.1 | XP_013605292.1 (SEQ ID NO: 95) | N/A | XP_013585896.1 (SEQ ID NO: 96) |
| *Brassica rapa* | Eudicots | XP_009131537.1 | XP_009131471.1 | XP_009116310.1 (SEQ ID NO: 97) | N/A | XP_009115305.1 (SEQ ID NO: 98) |
| *Cajanus cajan* | Eudicots | KYP60383.1 | N/A | KYP44948.1 (SEQ ID NO: 99) | N/A | KYP59593.1 (SEQ ID NO: 100) |
| *Capsella rubella* | Eudicots | XP_006286538.1 | XP_006288243.1 | N/A | XP_006305526.1 (SEQ ID NO: 101) | XP_006298142.2 (SEQ ID NO: 102) |
| *Capsicum annuum* | Eudicots | XP_016573862.1 | N/A | XP_016575440.1 (SEQ ID NO: 103) | N/A | XP_016578500.1 (SEQ ID NO: 104) |
| *Cicer arietinum* | Eudicots | XP_012569122.1 | N/A | XP_004500525.1 (SEQ ID NO: 105) | N/A | XP_004486692.1 (SEQ ID NO: 106) |
| *Citrus clementina* | Eudicots | N/A | XP_006431277.1 | XP_006435833.1 (SEQ ID NO: 107) | N/A | XP_006427204.1 (SEQ ID NO: 108) |
| *Citrus sinensis* | Eudicots | N/A | XP_006482733.1 | XP_006486239.1 (SEQ ID NO: 109) | N/A | XP_006465373.1 (SEQ ID NO: 110) |
| *Cucumis melo* | Eudicots | N/A | XP_008456473.1 | XP_008441486.1 (SEQ ID NO: 111) | N/A | XP_008461084.2 (SEQ ID NO: 112) |
| *Cucumis sativus* | Eudicots | N/A | XP_004137199.1 | XP_011656420.1 (SEQ ID NO: 113) | N/A | XP_004135840.1 (SEQ ID NO: 114) |
| *Daucus carota* subsp. *sativus* | Eudicots | KZM82431.1 | N/A | KZM80059.1 (SEQ ID NO: 115) | N/A | KZM88409.1 (SEQ ID NO: 116) |
| *Dorcoceras hygrometricum* | Eudicots | KZV23283.1 | N/A | KZV16809.1 (SEQ ID NO: 117) | N/A | N/A |
| *Elaeis guineensis* | Monocots | XP_010936329.1 | N/A | XP_010938420.1 (SEQ ID NO: 118) | N/A | XP_010921048.1 (SEQ ID NO: 119) |
| *Erythranthe guttata* | Eudicots | XP_012834625.1 | XP_012844390.1 | XP_012858601.1 (SEQ ID NO: 120) | N/A | XP_012856758.1 (SEQ ID NO: 121) |
| *Eucalyptus grandis* | Eudicots | XP_010038361.1 | XP_010032526.1 | XP_010067567.3 (SEQ ID NO: 122) | N/A | XP_010033940.1 (SEQ ID NO: 123) |
| *Fragaria vesca* subsp. *vesca* | Eudicots | N/A | XP_004304236.1 | XP_004307696.1 (SEQ ID NO: 124) | N/A | XP_004302964.1 (SEQ ID NO: 125) |
| *Genlisea aurea* | Eudicots | EPS63946.1 | N/A | N/A | EPS63437.1 (SEQ ID NO: 126) | N/A |
| *Glycine soja* | Eudicots | KHN13569.1 | N/A | KHN04794.1 (SEQ ID NO: 127) | N/A | KHN44161.1 (SEQ ID NO: 128) |
| *Gossypium arboreum* | Eudicots | KHG03380.1 | KHG02691.1 | N/A | KHG02291.1 (SEQ ID NO: 129) | N/A |
| *Gossypium hirsutum* | Eudicots | XP_016683408.1 | XP_016752201.1 | XP_016724217.2 (SEQ ID NO: 130) | N/A | N/A |
| *Gossypium raimondii* | Eudicots | XP_012451021.1 | N/A | XP_012462883.1 (SEQ ID NO: 131) | N/A | XP_012454990.1 (SEQ ID NO: 132) |
| *Jatropha curcas* | Eudicots | XP_012085783.1 | XP_012084810.1 | XP_012086589.1 (SEQ ID NO: 133) | N/A | XP_012073227.1 (SEQ ID NO: 134) |
| *Klebsormidium flaccidum* | Green Plants | N/A | GAQ84037.1 | N/A | N/A | GAQ80014.1 (SEQ ID NO: 135) |
| *Malus domestica* | Eudicots | N/A | XP_008379410.1 | XP_008374383.2 (SEQ ID NO: 136) | N/A | N/A |
| *Marchantia polymorpha* subsp. *polymorpha* | Liverworts | OAE20385,1 | N/A | N/A | N/A | OAE28621.1 (SEQ ID NO: 137) |
| *Musa acuminata* subsp. *malaccensis* | Monocots | XP_009394324.1 | N/A | XP_009418932.1 (SEQ ID NO: 138) | N/A | N/A |
| *Nelumbo nucifera* | Eudicots | XP_010259375.1 | N/A | XP_010250846.1 (SEQ ID NO: 139) | N/A | XP_010254348.1 (SEQ ID NO: 140) |
| *Nicotiana sylvestris* | Eudicots | XP_009759359.1 | N/A | XP_009785832.1 (SEQ ID NO: 141) | XP_009787427.1 (SEQ ID NO: 142) | N/A |
| *Nicotiana tabacum* | Eudicots | XP_016465895.1 | XP_016481002.1 | XP_016473105.1 (SEQ ID NO: 143) | N/A | XP_016514334.1 (SEQ ID NO: 144) |
| *Phaseolus vulgaris* | Eudicots | XP_007139713.1 | N/A | XP_007163588.1 (SEQ ID NO: 145) | N/A | XP_007150717.1 (SEQ ID NO: 146) |
| *Phoenix dactylifera* | Monocots | XP_008805110.1 | N/A | XP_008789922.1 (SEQ ID NO: 147) | N/A | XP_008809725.1 (SEQ ID NO: 148) |
| *Populus euphratica* | Eudicots | XP_011013398.1 | XP_011013434.1 | XP_011004753.1 (SEQ ID NO: 149) | N/A | XP_011040023.1 (SEQ ID NO: 150) |

TABLE 15-continued

Orthologs of *Arabidopsis* BADC1, BADC2, and BADC3 identified in various additional oilseed plants and other plants.

| Species | Category | BCCP1 | BCCP2 | BADC1 | BADC2 | BADC3 |
|---|---|---|---|---|---|---|
| *Populus trichocarpa* | Eudicots | N/A | XP_002305399.1 | XP_002311250.1 (SEQ ID NO: 151) | N/A | XP_002299605.2 (SEQ ID NO: 152) |
| *Prunus mume* | Eudicots | XP_008240458.1 | N/A | XP_008233825.1 (SEQ ID NO: 153) | XP_008228653.1 (SEQ ID NO: 154) | N/A |
| *Prunus persica* | Eudicots | XP_007204703.1 | XP_007215770.1 | XP_007218764.2 (SEQ ID NO: 155) | XP_007215787.1 (SEQ ID NO: 156) | N/A |
| *Pyrus* x *bretschneideri* | Eudicots | N/A | XP_009360536.1 | XP_009369234.1 (SEQ ID NO: 157) | XP_009349124.1 (SEQ ID NO: 158) | XP_009348645.1 (SEQ ID NO: 159) |
| *Ricinus communis* | Eudicots | XP_015572257.1 | XP_002526099.1 | XP_002520803.1 (SEQ ID NO: 160) | N/A | XP_015573743.1 (SEQ ID NO: 161) |
| *Sesamum indicum* | Eudicots | N/A | XP_011072842.1 | XP_011084859.1 (SEQ ID NO: 162) | N/A | XP_011072247.1 (SEQ ID NO: 163) |
| *Solanum lycopersicum* | Eudicots | NP_001234322.1 | N/A | XP_004240889.1 (SEQ ID NO: 164) | N/A | XP_004241703.1 (SEQ ID NO: 165) |
| *Solanum pennellii* | Eudicots | XP_015076155.1 | N/A | XP_015080112.1 (SEQ ID NO: 166) | N/A | XP_015079819.1 (SEQ ID NO: 167) |
| *Solanum tuberosum* | Eudicots | XP_006345777.1 | N/A | XP_006353414.1 (SEQ ID NO: 168) | N/A | XP_006356200.1 (SEQ ID NO: 169) |
| *Spinacia oleracea* | Eudicots | KNA11791.1 | N/A | KNA11168.1 (SEQ ID NO: 170) | N/A | KNA24821.1 (SEQ ID NO: 171) |
| *Tarenaya hassleriana* | Eudicots | XP_010558581.1 | XP_010551815.1 | XP_010534633.1 (SEQ ID NO: 172) | XP_010535127.1 (SEQ ID NO: 173) | N/A |
| *Vigna angularis* | Eudicots | N/A | KOM56589.1 | KOM39631.1 (SEQ ID NO: 174) | N/A | KOM44575.1 (SEQ ID NO: 175) |
| *Vigna radiata* var. *radiata* | Eudicots | N/A | XP_014523207.1 | XP_014494474.1 (SEQ ID NO: 176) | N/A | XP_014498647.1 (SEQ ID NO: 177) |
| *Vitis vinifera* | Eudicots | XP_010649227.1 | XP_002284374.1 | XP_002278151.2 (SEQ ID NO: 178) | N/A | XP_002285378.1 (SEQ ID NO: 179) |
| *Ziziphus jujuba* | Eudicots | XP_015875754.1 | XP_015879793.1 | XP_015877502.1 (SEQ ID NO: 180) | N/A | XP_015868335.1 (SEQ ID NO: 181) |
| *Zostera marina* | Monocots | N/A | KMZ60645.1 | KMZ56653.1 (SEQ ID NO: 182) | KMZ55983.1 (SEQ ID NO: 183) | N/A |

What is claimed is:

1. A genetically modified plant that exhibits an increase in seed yield relative to a progenitor plant from which the genetically modified plant was derived, the genetically modified plant comprising:

(a) a first biotin attachment domain-containing (badc) gene, occurring in its natural position within the genome of the genetically modified plant and being homozygous for a wild-type allele;

(b) a second badc gene, occurring in its natural position within the genome of the genetically modified plant and being homozygous for a mutant allele;

(c) one or more homologs of the first badc gene, each of the one or more homologs of the first badc gene occurring in its natural position within the genome of the genetically modified plant and being homozygous for a wild-type allele; and (d) one or more homologs of the second badc gene, each of the one or more homologs of the second badc gene occurring in its natural position within the genome of the genetically modified plant, and at least one of the homologs of the second badc gene being homozygous for a wild-type allele, wherein:

(i) the wild-type alleles of the first badc gene, each of the one or more homologs of the first badc gene, and the at least one of the homologs of the second badc gene are identical to respective alleles of the first badc gene, each of the one or more homologs of the first badc gene, and the at least one of the homologs of the second badc gene from the progenitor plant;

(ii) the mutant allele of the second badc gene does not encode a functional BADC protein and includes one or more additions, deletions, or substitutions of one or more nucleotides relative to an allele of the second badc gene from the progenitor plant;

(iii) the increase in seed yield is at least 4%;

(iv) the genetically modified plant is *Brassica napus*; and (v) the first badc gene or the one or more homologs of the first badc gene comprise *Brassica napus* badc1-1 of SEQ ID NO: 62 or badc1-2 of SEQ ID NO: 63.

2. A genetically modified plant that exhibits an increase in seed yield relative to a progenitor plant from which the genetically modified plant was derived, the genetically modified plant comprising:

(a) a first biotin attachment domain-containing (badc) gene, occurring in its natural position within the genome of the genetically modified plant and being homozygous for a wild-type allele;

(b) a second badc gene, occurring in its natural position within the genome of the genetically modified plant and being homozygous for a mutant allele;

(c) one or more homologs of the first badc gene, each of the one or more homologs of the first badc gene occurring in its natural position within the genome of the genetically modified plant and being homozygous for a wild-type allele; and (d) one or more homologs of the second badc gene, each of the one or more homologs of the second badc gene occurring in its natural position within the genome of the genetically modified plant, and at least one of the homologs of the second badc gene being homozygous for a wild-type allele, wherein:

(i) the wild-type alleles of the first badc gene, each of the one or more homologs of the first badc gene, and the at least one of the homologs of the second badc gene are identical to respective alleles of the first badc gene, each of the one or more homologs of the first badc gene, and the at least one of the homologs of the second badc gene from the progenitor plant;

(ii) the mutant allele of the second badc gene does not encode a functional BADC protein and includes one or more additions, deletions, or substitutions of one or more nucleotides relative to an allele of the second badc gene from the progenitor plant;

(iii) the increase in seed yield is at least 4%;

(iv) the genetically modified plant is *Brassica napus*; and (v) the second badc gene or the one or more homologs of the second badc gene comprises one or more of *Brassica napus* badc3-1 of SEQ ID NO: 64, badc3-2 of SEQ ID NO: 65, badc3-3 of SEQ ID NO: 66, or badc3-4 of SEQ ID NO: 67.

3. The genetically modified plant of claim 1, wherein the second badc gene comprises *Brassica napus* badc3-2 of SEQ ID NO: 65.

4. The genetically modified plant of claim 3, wherein the mutant allele includes at least one of the additions, deletions, or substitutions within the first 111 codons of the second badc gene.

5. The genetically modified plant of claim 4, wherein both *Brassica napus* badc3-2 of SEQ ID NO: 65 and badc3-3 of SEQ ID NO: 66 are homozygous for mutant alleles.

6. A genetically modified plant that exhibits an increase in seed yield relative to a progenitor plant from which the genetically modified plant was derived, the genetically modified plant comprising:

(a) a first biotin attachment domain-containing (badc) gene, occurring in its natural position within the genome of the genetically modified plant and being homozygous for a wild-type allele;

(b) a second badc gene, occurring in its natural position within the genome of the genetically modified plant and being homozygous for a mutant allele;

(c) one or more homologs of the first badc gene, each of the one or more homologs of the first badc gene occurring in its natural position within the genome of the genetically modified plant and being homozygous for a wild-type allele; and (d) one or more homologs of the second badc gene, each of the one or more homologs of the second badc gene occurring in its natural position within the genome of the genetically modified plant, and at least one of the homologs of the second badc gene being homozygous for a wild-type allele, wherein:

(i) the wild-type alleles of the first badc gene, each of the one or more homologs of the first badc gene, and the at least one of the homologs of the second badc gene are identical to respective alleles of the first badc gene, each of the one or more homologs of the first badc gene, and the at least one of the homologs of the second badc gene from the progenitor plant;

(ii) the mutant allele of the second badc gene does not encode a functional BADC protein and includes one or more additions, deletions, or substitutions of one or more nucleotides relative to an allele of the second badc gene from the progenitor plant;

(iii) the increase in seed yield is at least 4%;

(iv) the genetically modified plant is *Brassica napus;*

(v) the first badc gene and the one or more homologs of the first badc gene, each being homozygous for a wild-type allele, are *Brassica napus* badc1-1 of SEQ ID NO: 62and badc1-2 of SEQ ID NO: 63;

(vi) the second badc gene, being homozygous for a mutant allele, is *Brassica napus* badc3-2 of SEQ ID NO: 65;

(vii) the at least one homolog of the second badc gene, being homozygous for a wild-type allele, are *Brassica napus* badc3-1 of SEQ ID NO: 64 and badc3-4 of SEQ ID NO: 67; and (viii) a remaining homolog of the second badc gene, being homozygous for a mutant allele, is *Brassica napus* badc3-3 of SEQ ID NO: 66.

7. A method for producing the genetically modified plant of claim 6 from a progenitor plant comprising a first badc gene, a second badc gene, one or more homologs of the first badc gene, and one or more homologs of the second badc gene, each of the first badc gene, the second badc gene, the one or more homologs of the first badc gene, and the one or more homologs of the second badc gene being homozygous for a wild-type allele, the method comprising steps of:

(1) mutating the second badc gene in cells of the progenitor plant by making one or more additions, deletions, or substitutions of one more nucleotides relative to the wild-type allele of the second badc gene that eliminate function of the BADC protein encoded by the second badc gene that is mutated, thereby obtaining a mutated plant;

(2) conducting one more cycles of breeding of the mutated plant to obtain progeny of the mutated plant;

(3) identifying plants of the progeny in which the second badc gene is homozygous for the mutant allele, thereby obtaining second-badc-gene homozygous mutant plants; and (4) screening the second-badc-gene homozygous mutant plants for one or more plants that have an increase in seed yield of at least 4% relative to the progenitor plant, thereby obtaining the genetically modified plant, wherein:

(i) the first badc gene and the one or more homologs of the first badc gene, each being homozygous for a wild-type allele, are *Brassica napus* badc1-1 of SEQ ID NO: 62 and badc1-2 of SEQ ID NO: 63;

(ii) the second badc gene, being homozygous for a mutant allele, is *Brassica napus* badc3-2 of SEQ ID NO: 65;

(iii) the at least one homolog of the second badc gene, being homozygous for a wild-type allele, are *Brassica napus* badc3-1 of SEQ ID NO: 64 and badc3-4 of SEQ ID NO: 67; and (iv) a remaining homolog of the second badc gene, being homozygous for a mutant allele, is *Brassica napus* badc3-3 of SEQ ID NO: 66.

8. The genetically modified plant of claim 1, wherein the second badc gene or the one or more homologs of the second badc gene comprises one or more of *Brassica napus* badc3-1 of SEQ ID NO: 64, badc3-2 of SEQ ID NO: 65, badc3-3 of SEQ ID NO: 66, or badc3-4 of SEQ ID NO: 67.

9. The genetically modified plant of claim 2, wherein the second badc gene comprises *Brassica napus* badc3-2 of SEQ ID NO: 65.

10. The genetically modified plant of claim 9, wherein the mutant allele includes at least one of the additions, deletions, or substitutions within the first 111 codons of the second badc gene.

11. The genetically modified plant of claim 10, wherein both *Brassica napus* badc3-2 of SEQ ID NO: 65 and badc3-3 of SEQ ID NO: 66 are homozygous for mutant alleles.

* * * * *